United States Patent
Wang et al.

(10) Patent No.: US 10,253,018 B2
(45) Date of Patent: Apr. 9, 2019

(54) APOPTOSIS SIGNAL-REGULATING KINASE 1 INHIBITORS AND METHODS OF USE THEREOF

(71) Applicant: ENANTA PHARMACEUTICALS, INC., Watertown, MA (US)

(72) Inventors: Guoqiang Wang, Belmont, MA (US); Brett Granger, Sudbury, MA (US); Ruichao Shen, Belmont, MA (US); Yong He, Lexington, MA (US); Xuechao Xing, Wilmington, MA (US); Jun Ma, Belmont, MA (US); Jiang Long, Wayland, MA (US); Jing He, Somerville, MA (US); Bin Wang, Brighton, MA (US); Yat Sun Or, Watertown, MA (US)

(73) Assignee: ENANTA PHARMACEUTICALS, INC., Watertown, MA (US)

( * ) Notice: Subject to any disclaimer, the term of this patent is extended or adjusted under 35 U.S.C. 154(b) by 0 days.

(21) Appl. No.: 15/988,763

(22) Filed: May 24, 2018

(65) Prior Publication Data
US 2018/0362501 A1 Dec. 20, 2018

Related U.S. Application Data

(60) Provisional application No. 62/510,955, filed on May 25, 2017.

(51) Int. Cl.
C07D 401/14 (2006.01)
C07D 401/04 (2006.01)
C07D 491/107 (2006.01)
C07D 498/08 (2006.01)

(52) U.S. Cl.
CPC ......... *C07D 401/14* (2013.01); *C07D 401/04* (2013.01); *C07D 491/107* (2013.01); *C07D 498/08* (2013.01)

(58) Field of Classification Search
CPC .......................... C07D 401/14; C07D 401/04; C07D 491/107; C07D 498/08
USPC ..................................... 514/210.21
See application file for complete search history.

(56) References Cited

U.S. PATENT DOCUMENTS

| | | |
|---|---|---|
| 6,534,651 B2 | 3/2003 | Jagtap et al. |
| 8,378,108 B2 | 2/2013 | Corkey et al. |
| 9,254,284 B2 | 2/2016 | Notte |
| 2009/0318425 A1 | 12/2009 | Chang et al. |
| 2011/0009410 A1 | 1/2011 | Corkey et al. |
| 2013/0203731 A1 | 8/2013 | Chang et al. |
| 2013/0210810 A1 | 8/2013 | Singh et al. |
| 2014/0018370 A1 | 1/2014 | Corkey et al. |
| 2014/0249135 A1 | 9/2014 | Burger et al. |
| 2014/0329850 A1 | 11/2014 | Chang |
| 2015/0005280 A1 | 1/2015 | Sasmal et al. |

FOREIGN PATENT DOCUMENTS

| | | |
|---|---|---|
| CN | 107793400 A | 3/2018 |
| WO | 2005009470 A1 | 2/2005 |
| WO | 2005103288 A1 | 11/2005 |
| WO | 2007000339 A1 | 1/2007 |
| WO | 2008016131 A1 | 2/2008 |
| WO | 2008082579 A1 | 7/2008 |
| WO | 2009027283 A1 | 3/2009 |
| WO | 2009123986 A1 | 10/2009 |
| WO | 2010008843 A1 | 1/2010 |
| WO | 2011008709 A1 | 1/2011 |
| WO | 2011041293 A1 | 4/2011 |

(Continued)

OTHER PUBLICATIONS

Gibson, et al., "Structure-based drug design of novel ASK1 inhibitors using an integrated lead optimization strategy," Bioorganic & Medicinal Chemistry Letters, pp. 1-5, 2017.
Monastyrskyi, et al., "Discovery of 2-arylquinazoline derivatives as a new class of ASK1 inhibitors," Bioorganic & Medicinal Chemistry Letters, 28:400-404, 2018.

(Continued)

*Primary Examiner* — Kristin A Vajda
(74) *Attorney, Agent, or Firm* — Edgar W. Harlan; Carolyn S. Elmore, Esq.; Elmore Patent Law Group, P.C.

(57) ABSTRACT

The present invention discloses compounds of Formula (I), or pharmaceutically acceptable salts, ester, stereoisomer, tautomer, solvate, hydrate, or combination thereof:

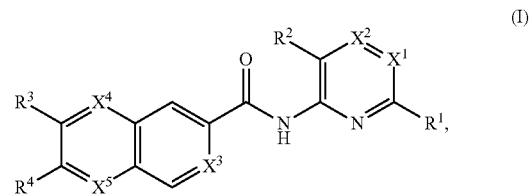

which inhibit the Apoptosis signal-regulating kinase 1 (ASK-1), which associated with autoimmune disorders, neurodegenerative disorders, inflammatory diseases, chronic kidney disease, cardiovascular disease. The present invention further relates to pharmaceutical compositions comprising the aforementioned compounds for administration to a subject suffering from ASK-1 related disease. The invention also relates to methods of treating an ASK-1 related disease in a subject by administering a pharmaceutical composition comprising the compounds of the present invention. The present invention specifically relates to methods of treating ASK-1 associated with hepatic steatosis, including non-alcoholic fatty liver disease (NAFLD) and non-alcohol steatohepatitis disease (NASH).

26 Claims, No Drawings

(56) References Cited

FOREIGN PATENT DOCUMENTS

| WO | 2011097079 A1 | 8/2011 |
| WO | 2012003387 A3 | 1/2012 |
| WO | 2012011548 A1 | 1/2012 |
| WO | 2012080735 A1 | 6/2012 |
| WO | 2013112741 A1 | 8/2013 |
| WO | 2014100541 A1 | 6/2014 |
| WO | 2015095059 A1 | 6/2015 |
| WO | 2016049069 A1 | 3/2016 |
| WO | 2016049070 A1 | 3/2016 |
| WO | 2016105453 A1 | 6/2016 |
| WO | 2016106384 A1 | 6/2016 |
| WO | 2018090869 A1 | 5/2018 |
| WO | 2018133856 A1 | 7/2018 |
| WO | 2018133866 A1 | 7/2018 |
| WO | 2018148204 A1 | 8/2018 |
| WO | 2018149284 A1 | 8/2018 |
| WO | 2018151830 A1 | 8/2018 |
| WO | 2018157857 A1 | 9/2018 |

OTHER PUBLICATIONS

Lovering, et al., "Rational approach to highly potent and selective apoptosis signal regulating kinase 1 (ASK1) inhibitors," European Journal of Medicinal Chemistry, 145:606-621, 2018.

Loomba, et al., "The ASK1 Inhibitor Selonsertib in Patients with Nonalcoholic Steatohepatitis: A Randomized, Phase 2 Trial," Hepatology 67(2):549-559, 2018.

Volynets, et al., "Identification of 3H-Naphtho[1,2,3-de]quinoline-2,7-diones as Inhibitors of Apoptosis Signal-Regulating Kinase 1 (ASK1)," Journal of Medicinal Chemistry, 54:2680-2686, 2011.

Volynets, et al., "Rational design of apoptosis signal-regulating kinase 1 inhibitors: Discovering novel structural scaffold," European Journal of Medicinal Chemistry 61:104-115, 2013.

Terao, et al., "Design and biological evaluation of imidazo[1,2-a]pyridines as novel and potent ASK1 inhibitors," Bioorganic & Medicinal Chemistry Letters, 22:7326-7329, 2012.

U.S. Appl. No. 15/979,128, filed May 14, 2018.
U.S. Appl. No. 15/988,806, filed May 24, 2018.
U.S. Appl. No. 15/988,783, filed May 24, 2018.
U.S. Appl. No. 16/113,611, filed Aug. 27, 2018.

APOPTOSIS SIGNAL-REGULATING KINASE 1 INHIBITORS AND METHODS OF USE THEREOF

RELATED APPLICATIONS

This application claims the benefit of U.S. Provisional Application No. 62/510,955, filed on May 25, 2017. The entire teachings of the above applications are incorporated herein by reference.

TECHNICAL FIELD

The present invention relates generally to compounds and pharmaceutical compositions useful as ASK-1 inhibitors. Specifically, the present invention relates to compounds useful as inhibitors of ASK-1 and methods for their preparation and use.

BACKGROUND OF THE INVENTION

Apoptosis signal-regulating kinase 1 (ASK-1) is a member of the mitogen-activated protein kinase kinase kinase (MAPKKK, MAP3K) family, which when activated phosphorylates downstream MAP kinase kinases (MAPKK, MAP2K), which in turn activate MAP kinases (MAPK). MAPKs elicit a response by phosphorylating cellular substrates, thus regulating the activity of transcription factors that ultimately control gene expression. Specifically ASK-1, also known as MAPKKK5, phosphorylates MAPKK4/MAPKK7 or MAPKK3/MAPKK6, which subsequently phosphorylates and activates the c-Jun N-terminal protein kinase (JNK) and p38 MAPKs, respectively (H. Ichijo, et al., *Cell Comm. Signal* 2009, 7, 1-10; K. Takeda, et al., *Annu. Rev. Pharmacol. Toxicol.* 2008, 48, 199-225; H. Nagai, et al., *J. Biochem. Mol. Biol.* 2007, 40, 1-6). Activation of the JNK and p38 pathways triggers a downstream stress response such as apoptosis, inflammation, or differentiation (H. Ichijo, et al., *Science* 1997, 275, 90-94; K. Takeda, et al., *J. Biol. Chem.* 2000, 275, 9805-9813; K. Tobiume, et al., *EMBO Rep.* 2001, 2, 222-228; K. Sayama et al., *J. Biol. Chem.* 2001, 276, 999-1004).

The activity of ASK-1 is regulated by thioredoxin (Trx), which binds to the N-terminal end of ASK-1 (M. Saitoh, et al., *EMBO J.* 1998, 17, 2596-2606). ASK-1 is activated succeeding autophosphorylation at Thr838 in response to environmental stimuli including oxidative stress, lipopolysaccharides (LPS), reactive oxygen species (ROS), endoplasmic reticulum (ER) stress, an increase in cellular calcium ion concentrations, Fas ligand, and various cytokines such as tumor necrosis factor (TNF) (H. Nishitoh, et al., *Genes Dev.* 2002, 16, 1345-1355; K. Takeda, et al., *EMBO Rep.* 2004, 5, 161-166; A. Matsuzawa, et al., *Nat. Immunol.* 2005, 6, 587-592).

ASK-1 has been associated with autoimmune disorders, neurodegenerative disorders, inflammatory diseases, chronic kidney disease, cardiovascular disease, metabolic disorders, and acute and chronic liver diseases (R. Hayakawa, et al., *Proc. Jpn. Acad., Ser. B* 2012, 88, 434-453).

More specifically, ASK-1 has been associated with hepatic steatosis, including non-alcoholic fatty liver disease (NAFLD) and non-alcohol steatohepatitis (NASH). In a mouse model, high fat diets have caused induction of hepatic steatosis, ultimately causing fat accumulation and fatty acid oxidation. This led to the generation of ROS which caused hepatocyte dysfunction and death (S. K. Mantena, et al., *Free Radic. Biol. Med.* 2008, 44, 1259-1272; S. K. Mantena, et al., *Biochem. J.* 2009, 417, 183-193). Moreover, TNF was shown to be critical for apoptosis of hepatocytes through the ASK-1-JNK pathway, and TNF deficient mice showed reduced hepatic steatosis and fibrosis (W. Zhang, et al., *Biochem. Biophys. Res. Commun.* 2010, 391, 1731-1736).

Small molecule compounds which act as ASK-1 inhibitors have been disclosed in the following publications: WO 2008/016131, WO 2009/027283, WO 2009/0318425, WO 2009/123986, US 2009/0318425, WO 2011/041293, WO 2011/097079, US 2011/0009410, G. P. Volynets, et al., *J. Med. Chem.* 2011, 54, 2680-2686, WO 2012/003387, WO 2012/011548, WO 2012/080735, Y. Terao, et al., *Bioorg. Med. Chem. Lett.* 2012, 22, 7326-7329, WO 2013/112741, G. P. Volynets, et al., *Eur. J. Med. Chem.* 2013, 16, 104-115, US 2014/0018370, WO 2014/100541, WO 2015/095059, WO 2016/049069, WO 2016/049070.

There is a need for the development of ASK-1 inhibitors for the treatment and prevention of disease. The present invention has identified compounds which inhibit ASK-1 as well as methods of using these compounds to treat disease.

SUMMARY OF THE INVENTION

In one aspect, the invention provides compounds represented by Formula I, or a pharmaceutically acceptable salt or ester thereof:

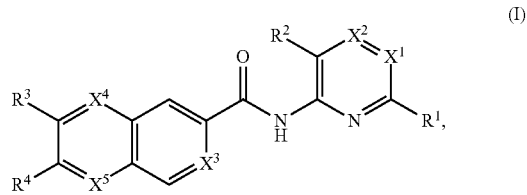

(I)

wherein;

$X^1$, $X^2$, $X^4$, and $X^5$ are each independently $C(R^9)$ or N;
$X^3$ is $C(R^{10})$ or N, in which $R^{10}$ is selected from the group consisting of hydrogen, optionally substituted —$C_1$-$C_8$ alkyl, optionally substituted —$C_1$-$C_8$ alkoxy and halogen;
$R^1$ is selected from

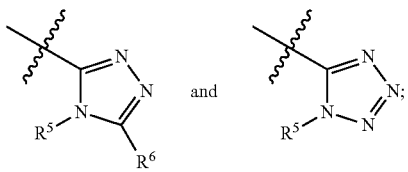

and $R^5$ is selected from the group consisting of:
1) Hydrogen;
2) Substituted or unsubstituted —$C_1$-$C_8$ alkyl;
3) Substituted or unsubstituted —$C_2$-$C_8$ alkenyl;
4) Substituted or unsubstituted —$C_2$-$C_8$ alkynyl;
5) Substituted or unsubstituted —$C_3$-$C_8$ cycloalkyl;
6) Substituted or unsubstituted aryl;
7) Substituted or unsubstituted arylalkyl;
8) Substituted or unsubstituted 3- to 8 membered heterocycloalkyl;
9) Substituted or unsubstituted heteroaryl; and
10) Substituted or unsubstituted heteroarylalkyl;

$R^2$, $R^6$, and $R^9$ are each independently selected from the group consisting of:
1) Hydrogen;
2) Halogen;
3) —$NO_2$;
4) Cyano;
5) Substituted or unsubstituted —$C_1$-$C_8$ alkyl;
6) Substituted or unsubstituted —$C_2$-$C_8$ alkenyl;
7) Substituted or unsubstituted —$C_2$-$C_8$ alkynyl;
8) Substituted or unsubstituted —$C_3$-$C_8$ cycloalkyl;
9) Substituted or unsubstituted aryl;
10) Substituted or unsubstituted arylalkyl;
11) Substituted or unsubstituted 3- to 8-membered heterocycloalkyl;
12) Substituted or unsubstituted heteroaryl;
13) Substituted or unsubstituted heteroarylalkyl;
14) —$N(R^7)(R^8)$;
15) —$S(O)_2N(R^7)(R^8)$;
16) —$N(R^7)C(O)R^8$; and
17) —$N(R^7)S(O)_2R^8$;

$R^3$ and $R^4$ are each independently selected from the group consisting of:
1) Hydrogen;
2) Halo;
3) Substituted or unsubstituted —$C_1$-$C_8$ alkyl;
4) Substituted or unsubstituted —$C_2$-$C_8$ alkenyl;
5) Substituted or unsubstituted —$C_2$-$C_8$ alkynyl;
6) Substituted or unsubstituted —$C_3$-$C_8$ cycloalkyl;
7) Substituted or unsubstituted aryl;
8) Substituted or unsubstituted arylalkyl;
9) Substituted or unsubstituted 3- to 8-membered heterocycloalkyl;
10) Substituted or unsubstituted 3- to 8-membered heterocycloalkyl-alkyl;
11) Substituted or unsubstituted heteroaryl;
12) Substituted or unsubstituted heteroarylalkyl;
13) —$N(R^7)(R^8)$; and
14) —$OR^7$;

$R^7$ and $R^8$ are independently selected from the group consisting of hydrogen, —$C_1$-$C_8$ alkyl, —$C_1$-$C_8$ alkenyl, —$C_1$-$C_8$ alkynyl, —$C_3$-$C_8$ cycloalkyl, aryl, heterocycloalkyl, heteroaryl, and heteroarylalkyl, wherein each —$C_1$-$C_8$ alkyl, —$C_1$-$C_8$ alkenyl, —$C_1$-$C_8$ alkynyl, —$C_3$-$C_8$ cycloalkyl, aryl, heterocycloalkyl, heteroaryl, and heteroarylalkyl is optionally substituted with 1-3 substituents selected from halo, alkyl, —$C_3$-$C_5$ cycloalkyl, alkylamino, dialkylamino, alkylC(O)NH—, arylC(O)NH, heteroarylC(O)NH—, —CN, alkoxy, —$CF_3$, aryl, and heteroaryl; alternatively, $R^7$ and $R^8$ are taken together with the nitrogen atom to which they are attached to form an optionally substituted heterocyclic.

In another embodiment, the present invention provides a pharmaceutical composition comprising a compound or combination of compounds of the present invention, or a pharmaceutically acceptable salt or ester thereof, in combination with a pharmaceutically acceptable carrier or excipient.

In another embodiment, the present invention provides a method for the prevention or treatment of an ASK-1 mediated disease or condition. The method comprises administering a therapeutically effective amount of a compound of Formula (I). The present invention also provides the use of a compound of Formula (I) for the preparation of a medicament for the prevention or treatment of an ASK-1 mediated disease or condition. Such diseases include autoimmune disorders, neurodegenerative disorders, inflammatory diseases, chronic kidney disease, cardiovascular disease, metabolic disorders, and acute and chronic liver diseases.

DETAILED DESCRIPTION OF THE INVENTION

A first embodiment of the invention is a compound represented by Formula I as described above, or a pharmaceutically acceptable salt or ester thereof.

In certain embodiments, the present invention relates to compounds of Formula I, or a pharmaceutically acceptable salt or ester thereof, wherein $R^5$ is selected from the groups below:

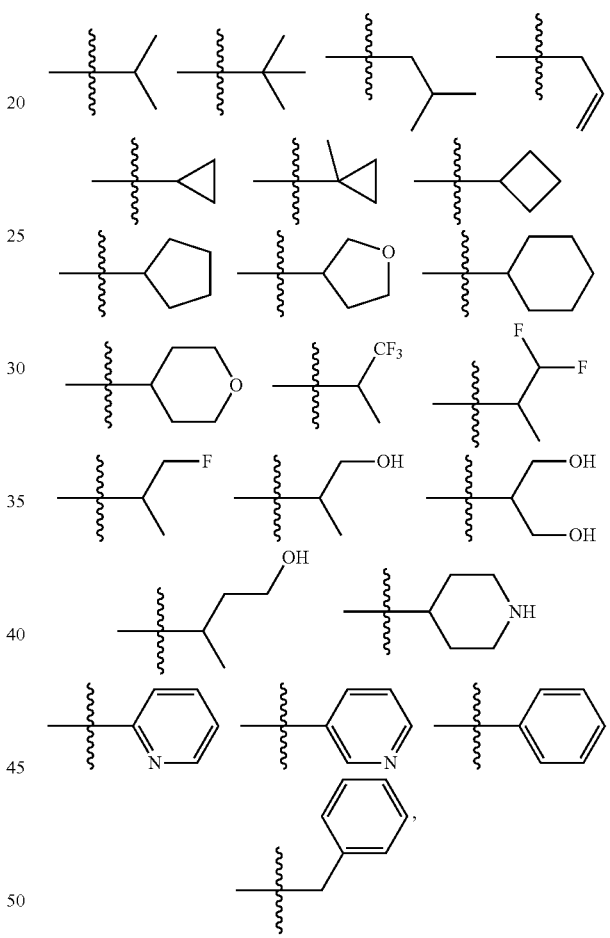

wherein each of the above shown groups is optionally substituted. Preferably, $R^5$ is selected from

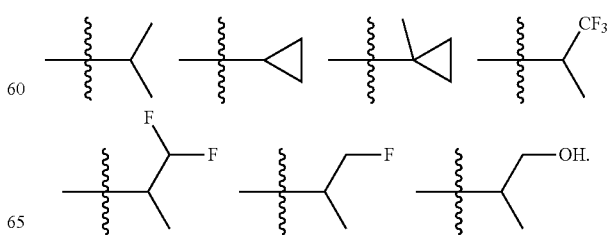

In certain embodiments, the present invention relates to compounds of Formula I, or a pharmaceutically acceptable salt or ester thereof, wherein $R^2$ is hydrogen or halogen.

In certain embodiments, the present invention relates to compounds of Formula I, or a pharmaceutically acceptable salt or ester thereof, wherein $R^6$ is hydrogen or halogen.

In certain embodiments, the present invention relates to compounds of Formula I, or a pharmaceutically acceptable salt or ester thereof, wherein both $R^2$ and $R^6$ are hydrogen.

In certain embodiments, the present invention relates to compounds of Formula I, or a pharmaceutically acceptable salt or ester thereof, wherein $R^3$ is selected from the groups below:

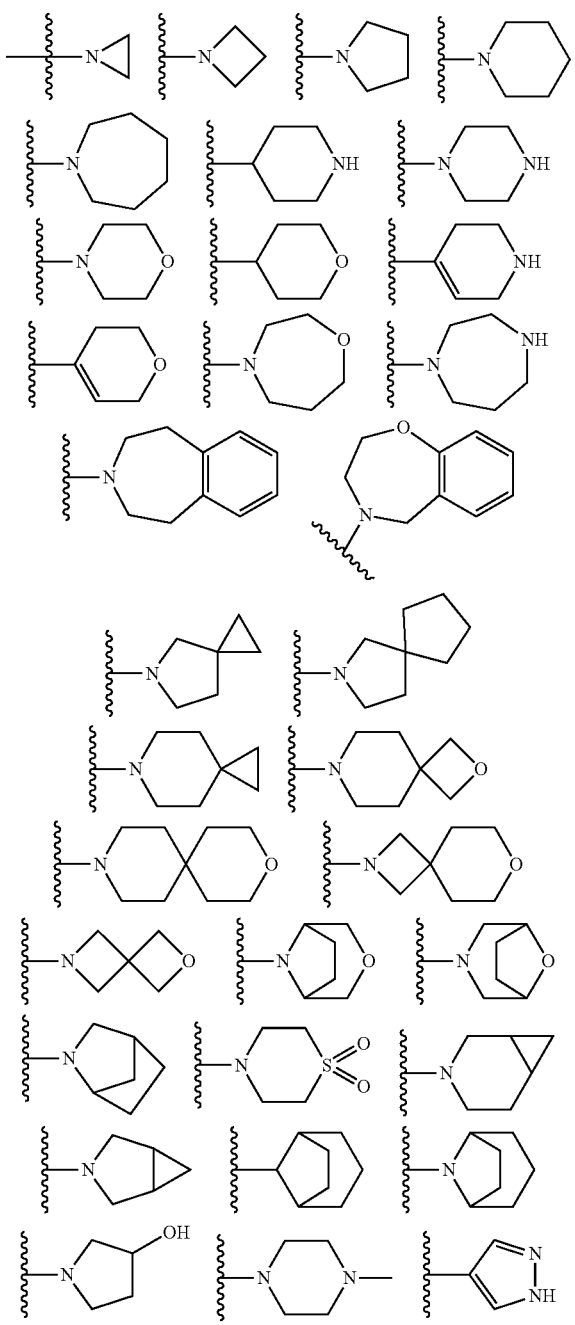

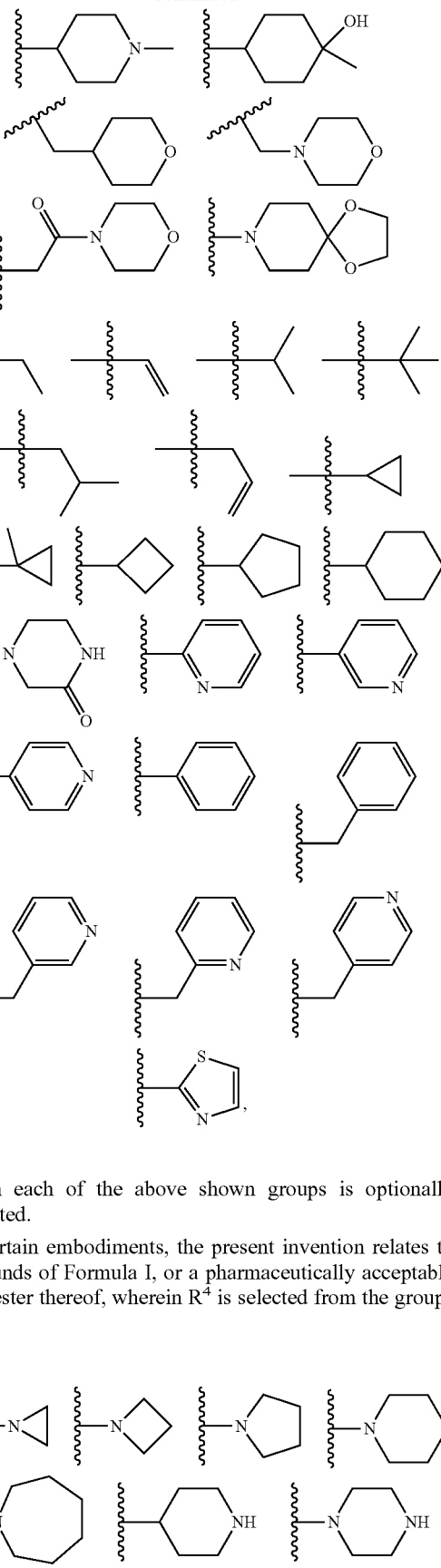

wherein each of the above shown groups is optionally substituted.

In certain embodiments, the present invention relates to compounds of Formula I, or a pharmaceutically acceptable salt or ester thereof, wherein $R^4$ is selected from the groups below:

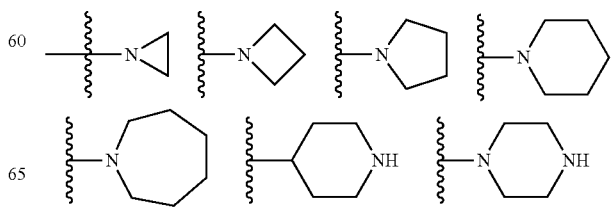

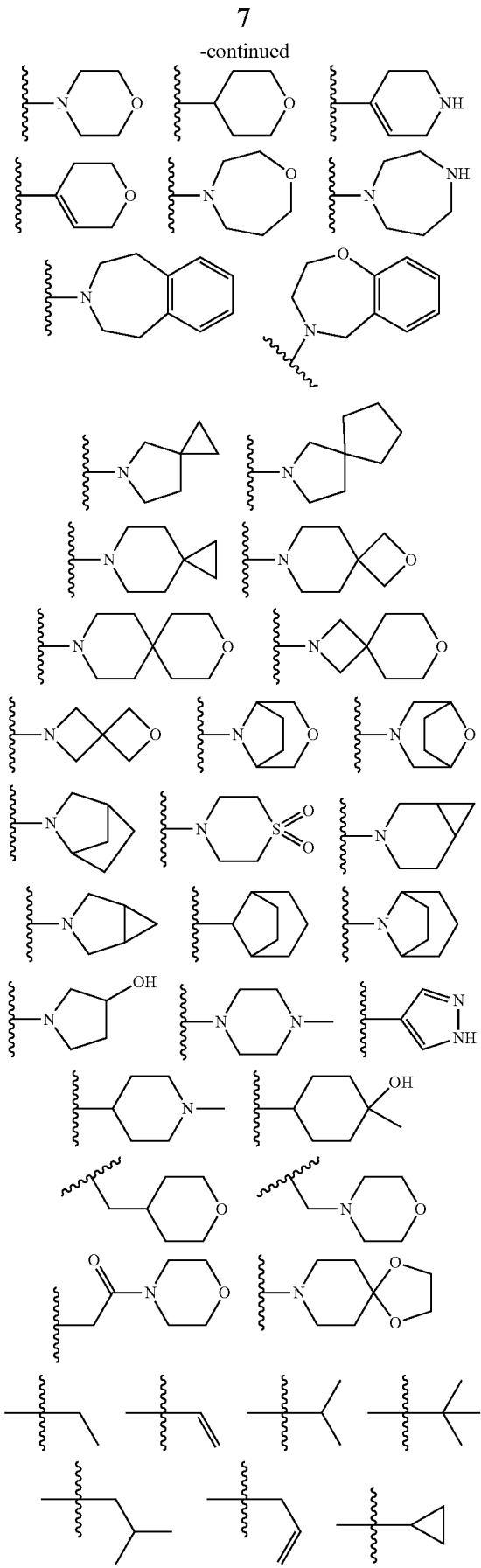
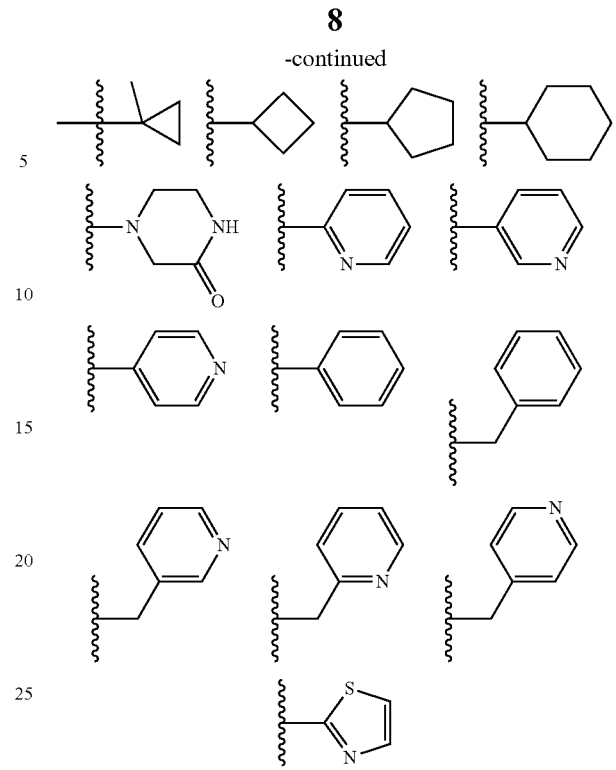

wherein each of the above shown groups is optionally substituted.

In certain embodiments, the present invention relates to compounds of Formula I, or a pharmaceutically acceptable salt or ester thereof, wherein $X^3$ is selected from C—H, C—F, and N.

In certain embodiments, the compound of Formula I is represented by one of Formulas IIa~IIh, or a pharmaceutically acceptable salt or ester thereof:

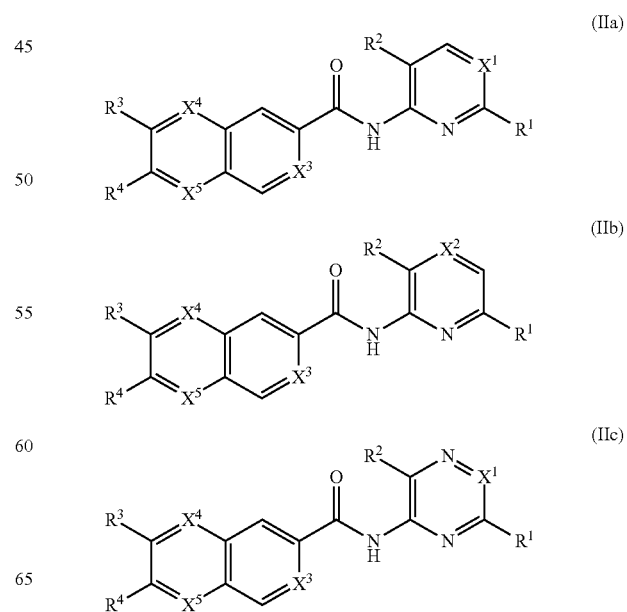

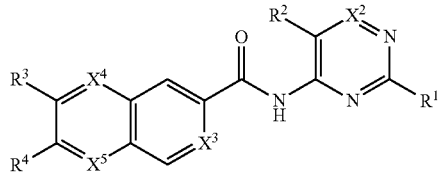
(IId)

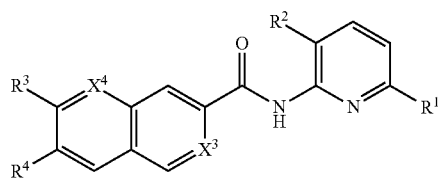
(IIe)

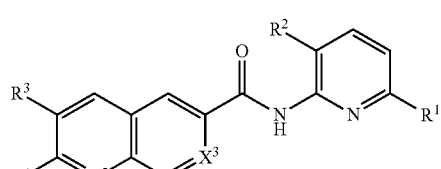
(IIf)

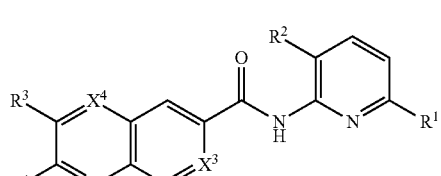
(IIg)

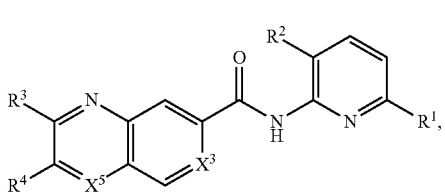
(IIh)

wherein $R^1$, $R^2$, $R^3$, $R^4$, $X^1$, $X^2$, $X^3$, $X^4$, and $X^5$ are as previously defined.

In certain embodiments, the compound of Formula I is represented by Formula IIIa, IIIb, IIIc, or IIId, or a pharmaceutically acceptable salt or ester thereof:

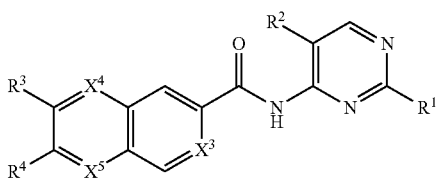
(IIIa)

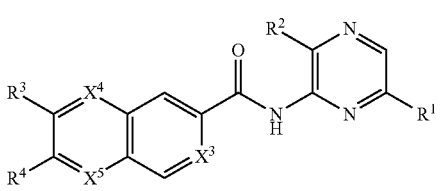
(IIIb)

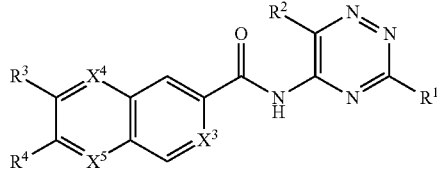
(IIIc)

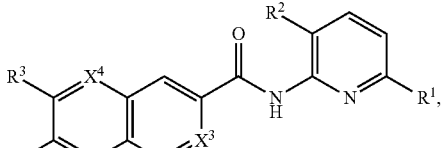
(IIId)

wherein $R^1$, $R^2$, $R^3$, $R^4$, $X^3$, $X^4$, and $X^5$ are as previously defined.

In certain embodiments, the compound of Formula I is represented by Formular IIIe, IIIf, IIIg, or IIIh, or a pharmaceutically acceptable salt or ester thereof:

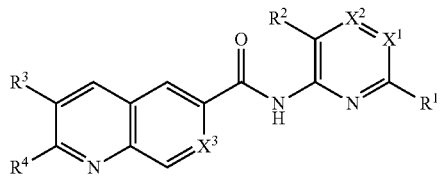
(IIIe)

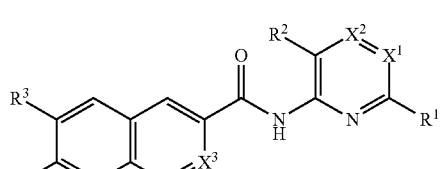
(IIIf)

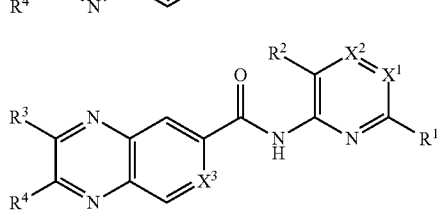
(IIIg)

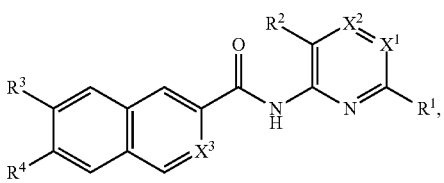
(IIIh)

wherein $R^1$, $R^2$, $R^3$, $R^4$, $X^1$, $X^2$, and $X^3$ are as previously defined.

In another embodiment of the invention, the compound of Formula I is represented by Formula IV or a pharmaceutically acceptable salt or ester thereof:

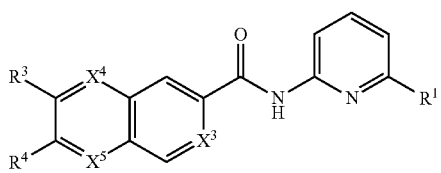
(IV)

wherein $R^1$, $R^3$, $R^4$, $X^3$, $X^4$, and $X^5$ are as previously defined.

In another embodiment of the invention, the compound of Formula I is represented by Formula V or a pharmaceutically acceptable salt or ester thereof:

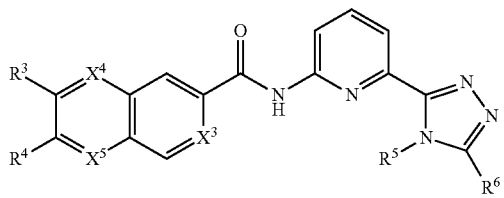
(V)

wherein $R^3$, $R^4$, $R^5$, $R^6$, $X^3$, $X^4$, and $X^5$ are as previously defined.

In another embodiment of the invention, the compound of Formula I is represented by Formula VI or a pharmaceutically acceptable salt or ester thereof:

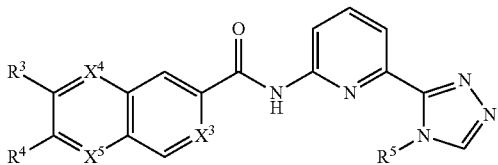
(VI)

wherein $R^3$, $R^4$, $R^5$, $X^3$, $X^4$, and $X^5$ are as previously defined.

In another embodiment of the invention, the compound of Formula I is represented by Formula VII or a pharmaceutically acceptable salt or ester thereof:

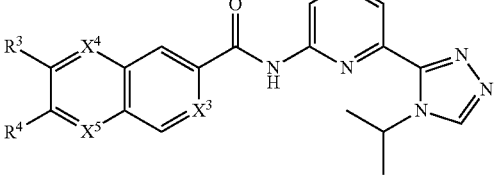
(VII)

wherein $R^3$, $R^4$, $X^3$, $X^4$, and $X^5$ are as previously defined.

In another embodiment of the invention, the compound of Formula I is represented by Formula VIII or a pharmaceutically acceptable salt or ester thereof:

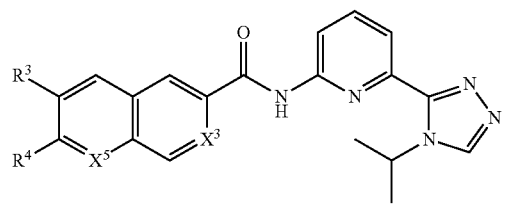
(VIII)

wherein $R^3$, $R^4$, $X^3$, and $X^5$ are as previously defined.

In another embodiment of the invention, the compound of Formula I is represented by Formula IX or a pharmaceutically acceptable salt or ester thereof:

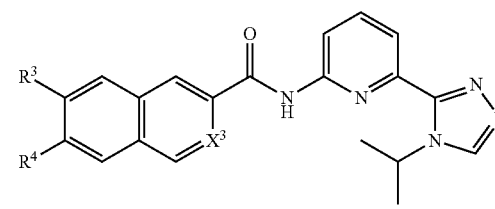
(IX)

wherein $R^3$, $R^4$, and $X^3$ are as previously defined.

Representative compounds of the invention include, but are not limited to, the following compounds (compound 1 to compound 180 in Table 1) according to Formula IX, and pharmaceutically acceptable salts thereof, wherein $R^3$, $R^4$, and $X^3$ are delineated for each compound in Table 1.

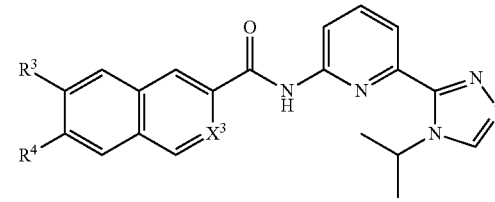
(IX)

TABLE 1

| Compound | $R^3$ | $R^4$ | $X^3$ |
|---|---|---|---|
| 1 | H | H | C—H |
| 2 | H | —Cl | C—H |

TABLE 1-continued
| Compound | R³ | R⁴ | X³ |
|---|---|---|---|
| 3 | H | —Br | C—H |
| 4 | H | 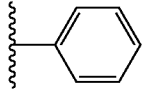 phenyl | C—H |
| 5 | H | —OMe | C—H |
| 6 | H | —O*i*-Pr | C—H |
| 7 | H | —NHMe | C—H |
| 8 | H | —NH*i*-Pr | C—H |
| 9 | H | 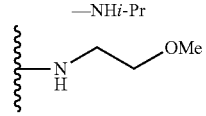 —NH-CH₂CH₂-OMe | C—H |
| 10 | H | 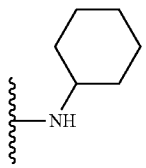 —NH-cyclohexyl | C—H |
| 11 | H | —N(CH₃)₂ | C—H |
| 12 | H | 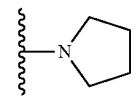 [SMILES: *N1CCCC1] pyrrolidinyl | C—H |
| 13 | H | 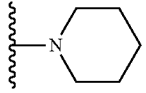 piperidinyl | C—H |
| 14 | H | 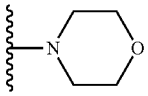 morpholinyl | C—H |
| 15 | H | 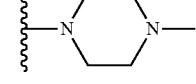 N-methylpiperazinyl | C—H |
| 16 | H | 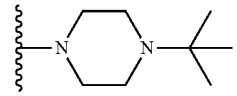 N-tert-butylpiperazinyl | C—H |
| 17 | H | 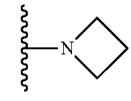 azetidinyl | C—H |
| 18 | H |  2-oxa-6-azaspiro[3.3]heptanyl | C—H |
| 19 | H | 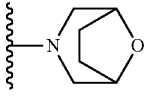 8-oxa-3-azabicyclo[3.2.1]octanyl | C—H |
| 20 | H | —N(Et)Bn | C—H |
| 21 | H | H | C—H |
| 22 | —Cl | H | C—H |
| 23 | —Br | H | C—H |

TABLE 1-continued
| Compound | R³ | R⁴ | X³ |
|---|---|---|---|
| 24 | 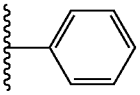 | H | C—H |
| 25 | —OMe | H | C—H |
| 26 | —O$i$-Pr | H | C—H |
| 27 | —NHMe | H | C—H |
| 28 | —NH$i$-Pr | H | C—H |
| 29 | 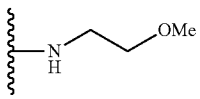 [SMILES: *NCCOC] | H | C—H |
| 30 | 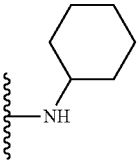 [SMILES: *NC1CCCCC1] | H | C—H |
| 31 | —N(CH$_3$)$_2$ | H | C—H |
| 32 | 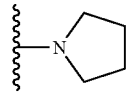 | H | C—H |
| 33 | 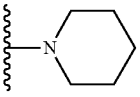 | H | C—H |
| 34 | 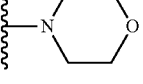 | H | C—H |
| 35 | 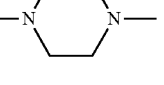 | H | C—H |
| 36 | 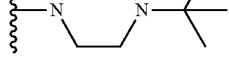 | H | C—H |
| 37 | 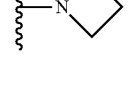 | H | C—H |
| 38 |  | H | C—H |
| 39 | 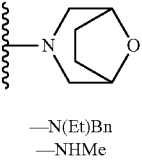 | H | C—H |
| 40 | —N(Et)Bn | H | C—H |
| 41 | —NHMe | —OMe | C—H |
| 42 | —NHMe | —O$i$-Pr | C—H |
| 43 | —NH$i$-Pr | —OMe | C—H |
| 44 | —NH$i$-Pr | —O$i$-Pr | C—H |

TABLE 1-continued

| Compound | R³ | R⁴ | X³ |
|---|---|---|---|
| 45 | cyclohexyl-NH- | —OMe | C—H |
| 46 | cyclohexyl-NH- | —Oi-Pr | C—H |
| 47 | pyrrolidin-1-yl | —OMe | C—H |
| 48 | pyrrolidin-1-yl | —Oi-Pr | C—H |
| 49 | piperidin-1-yl | —OMe | C—H |
| 50 | piperidin-1-yl | —Oi-Pr | C—H |
| 51 | morpholin-4-yl | —OMe | C—H |
| 52 | morpholin-4-yl | —Oi-Pr | C—H |
| 53 | —NHMe | —NHMe | C—H |
| 54 | —NHMe | —NHi-Pr | C—H |
| 55 | —NHi-Pr | —NHMe | C—H |
| 56 | —NHi-Pr | —NHi-Pr | C—H |
| 57 | piperidin-1-yl | —NHMe | C—H |
| 58 | piperidin-1-yl | —NHi-Pr | C—H |
| 59 | morpholin-4-yl | —NHMe | C—H |
| 60 | morpholin-4-yl | —NHi-Pr | C—H |
| 61 | H | H | C—F |

TABLE 1-continued
| Compound | R³ | R⁴ | X³ |
|---|---|---|---|
| 62 | H | —Cl | C—F |
| 63 | H | —Br | C—F |
| 64 | H | 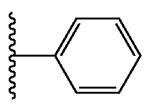 | C—F |
| 65 | H | —OMe | C—F |
| 66 | H | —O$i$-Pr | C—F |
| 67 | H | —NHMe | C—F |
| 68 | H | —NH$i$-Pr | C—F |
| 69 | H | 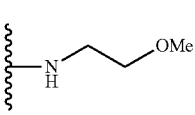 | C—F |
| 70 | H | 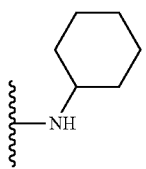 | C—F |
| 71 | H | —N(CH$_3$)$_2$ | C—F |
| 72 | H | 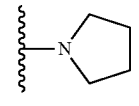 | C—F |
| 73 | H | 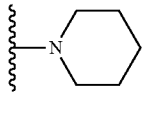 | C—F |
| 74 | H | 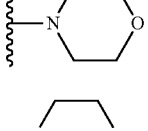 | C—F |
| 75 | H | 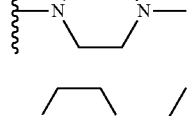 | C—F |
| 76 | H | 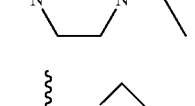 | C—F |
| 77 | H | 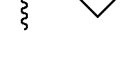 | C—F |
| 78 | H | 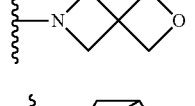 | C—F |
| 79 | H | 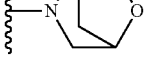 | C—F |
| 80 | H | —N(Et)Bn | C—F |
| 81 | H | H | C—F |
| 82 | —Cl | H | C—F |
| 83 | —Br | H | C—F |

TABLE 1-continued
| Compound | R³ | R⁴ | X³ |
|---|---|---|---|
| 84 | 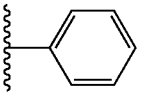 | H | C—F |
| 85 | —OMe | H | C—F |
| 86 | —O*i*-Pr | H | C—F |
| 87 | —NHMe | H | C—F |
| 88 | —NH*i*-Pr | H | C—F |
| 89 | 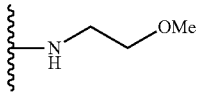 | H | C—F |
| 90 | 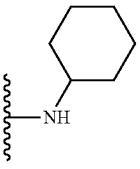 [SMILES: *NC1CCCCC1] | H | C—F |
| 91 | —N(CH₃)₂ | H | C—F |
| 92 | 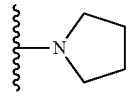 | H | C—F |
| 93 | 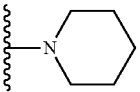 | H | C—F |
| 94 | 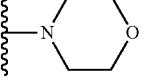 | H | C—F |
| 95 | 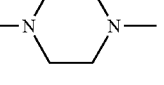 | H | C—F |
| 96 | 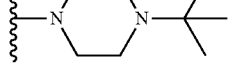 | H | C—F |
| 97 | 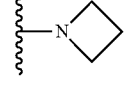 | H | C—F |
| 98 |  | H | C—F |
| 99 | 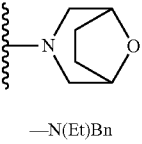 | H | C—F |
| 100 | —N(Et)Bn | H | C—F |
| 101 | —NHMe | —OMe | C—F |
| 102 | —NHMe | —O*i*-Pr | C—F |
| 103 | —NH*i*-Pr | —OMe | C—F |
| 104 | —NH*i*-Pr | —O*i*-Pr | C—F |

TABLE 1-continued

| Compound | R³ | R⁴ | X³ |
|---|---|---|---|
| 105 | cyclohexyl-NH- | —OMe | C—F |
| 106 | cyclohexyl-NH- | —Oi-Pr | C—F |
| 107 | pyrrolidin-1-yl | —OMe | C—F |
| 108 | pyrrolidin-1-yl | —Oi-Pr | C—F |
| 109 | piperidin-1-yl | —OMe | C—F |
| 110 | piperidin-1-yl | —Oi-Pr | C—F |
| 111 | morpholin-4-yl | —OMe | C—F |
| 112 | morpholin-4-yl | —Oi-Pr | C—F |
| 113 | —NHMe | —NHMe | C—F |
| 114 | —NHMe | —NHi-Pr | C—F |
| 115 | —NHi-Pr | —NHMe | C—F |
| 116 | —NHi-Pr | —NHi-Pr | C—F |
| 117 | piperidin-1-yl | —NHMe | C—F |
| 118 | piperidin-1-yl | —NHi-Pr | C—F |
| 119 | morpholin-4-yl | —NHMe | C—F |
| 120 | morpholin-4-yl | —NHi-Pr | C—F |
| 121 | H | H | N |

TABLE 1-continued
| Compound | R³ | R⁴ | X³ |
|---|---|---|---|
| 122 | H | —Cl | N |
| 123 | H | —Br | N |
| 124 | H | 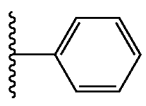 | N |
| 125 | H | —OMe | N |
| 126 | H | —O*i*-Pr | N |
| 127 | H | —NHMe | N |
| 128 | H | —NH*i*-Pr | N |
| 129 | H | 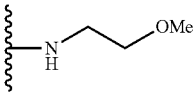 | N |
| 130 | H | 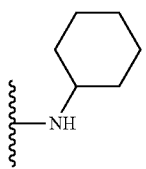 | N |
| 131 | H | —N(CH₃)₂ | N |
| 132 | H | 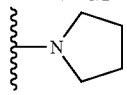 | N |
| 133 | H | 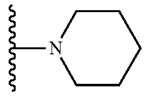 | N |
| 134 | H | 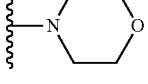 | N |
| 135 | H | 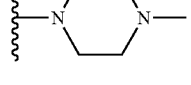 | N |
| 136 | H | 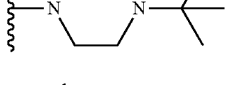 | N |
| 137 | H | 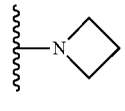 | N |
| 138 | H |  | N |
| 139 | H | 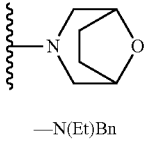 | N |
| 140 | H | —N(Et)Bn | N |
| 141 | H | H | N |
| 142 | —Cl | H | N |
| 143 | —Br | H | N |

TABLE 1-continued
| Compound | R³ | R⁴ | X³ |
|---|---|---|---|
| 144 | 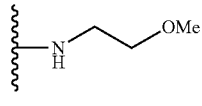 [SMILES: *NCCOC] | H | N |
| 145 | —OMe | H | N |
| 146 | —O*i*-Pr | H | N |
| 147 | —NHMe | H | N |
| 148 | —NH*i*-Pr | H | N |
| 149 | 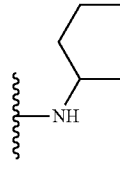 | H | N |
| 150 | 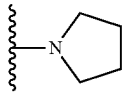 | H | N |
| 151 | —N(CH₃)₂ | H | N |
| 152 | 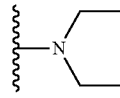 | H | N |
| 153 | 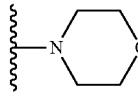 | H | N |
| 154 | 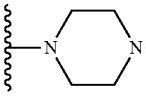 | H | N |
| 155 | 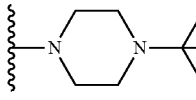 | H | N |
| 156 | 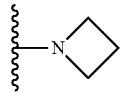 | H | N |
| 157 | 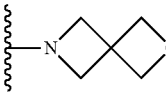 | H | N |
| 158 | 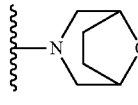 | H | N |
| 159 |  | H | N |
| 160 | —N(Et)Bn | H | N |
| 161 | —NHMe | —OMe | N |
| 162 | —NHMe | —O*i*-Pr | N |
| 163 | —NH*i*-Pr | —OMe | N |
| 164 | —NH*i*-Pr | —O*i*-Pr | N |

TABLE 1-continued

| Compound | R³ | R⁴ | X³ |
|---|---|---|---|
| 165 | cyclohexyl-NH- | —OMe | N |
| 166 | cyclohexyl-NH- | —Oi-Pr | N |
| 167 | pyrrolidin-1-yl | —OMe | N |
| 168 | pyrrolidin-1-yl | —Oi-Pr | N |
| 169 | piperidin-1-yl | —OMe | N |
| 170 | piperidin-1-yl | —Oi-Pr | N |
| 171 | morpholin-4-yl | —OMe | N |
| 172 | morpholin-4-yl | —Oi-Pr | N |
| 173 | —NHMe | —NHMe | N |
| 174 | —NHMe | —NHi-Pr | N |
| 175 | —NHi-Pr | —NHMe | N |
| 176 | —NHi-Pr | —NHi-Pr | N |
| 177 | piperidin-1-yl | —NHMe | N |
| 178 | piperidin-1-yl | —NHi-Pr | N |
| 179 | morpholin-4-yl | —NHMe | N |
| 180 | morpholin-4-yl | —NHi-Pr | N |

In another embodiment of the invention, the compound of Formula I is represented by Formula X or a pharmaceutically acceptable salt or ester or thereof:

(X)
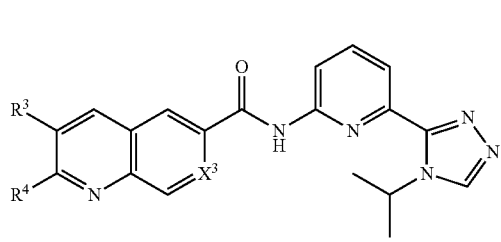

wherein $R^3$, $R^4$, and $X^3$ are as previously defined.

Representative compounds of the invention include, but are not limited to, the following compounds (compound 181 to compound 360 in Table 2) according to Formula X, and pharmaceutically acceptable salts thereof, wherein $R^3$, $R^4$, and $X^3$ are delineated for each compound in Table 2.

(X)
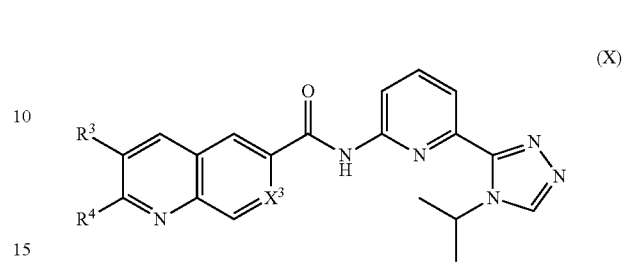

TABLE 2

| Compound | $R^3$ | $R^4$ | $X^3$ |
|---|---|---|---|
| 181 | H | H | C—H |
| 182 | H | —Cl | C—H |
| 183 | H | —Br | C—H |
| 184 | H | 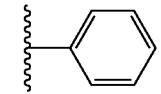 [SMILES: *c1ccccc1] | C—H |
| 185 | H | —OMe | C—H |
| 186 | H | —Oi-Pr | C—H |
| 187 | H | —NHMe | C—H |
| 188 | H | —NHi-Pr | C—H |
| 189 | H | 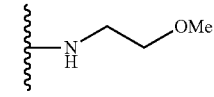 [SMILES: *NCCOC] | C—H |
| 190 | H | 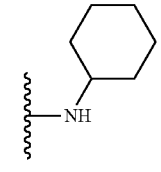 [SMILES: *NC1CCCCC1] | C—H |
| 191 | H | —N(CH$_3$)$_2$ | C—H |
| 192 | H | 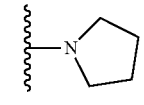 | C—H |
| 193 | H | 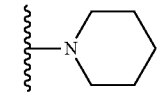 | C—H |
| 194 | H | 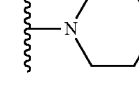 | C—H |
| 195 | H | 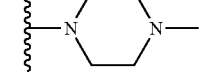 | C—H |

TABLE 2-continued
| Compound | R³ | R⁴ | X³ |
|---|---|---|---|
| 196 | H | 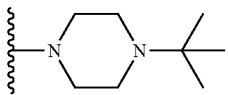 | C—H |
| 197 | H | 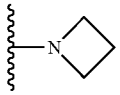 [SMILES: *N1CCC1] | C—H |
| 198 | H |  | C—H |
| 199 | H | 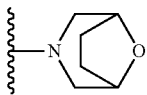 | C—H |
| 200 | H | —N(Et)Bn | C—H |
| 201 | H | H | C—H |
| 202 | —Cl | H | C—H |
| 203 | —Br | H | C—H |
| 204 | 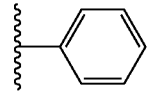 [SMILES: *c1ccccc1] | H | C—H |
| 205 | —OMe | H | C—H |
| 206 | —Oi-Pr | H | C—H |
| 207 | —NHMe | H | C—H |
| 208 | —NHi-Pr | H | C—H |
| 209 | 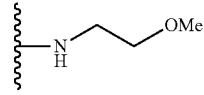 [SMILES: *NCCOC] | H | C—H |
| 210 | 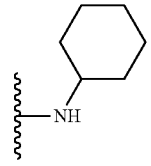 [SMILES: *NC1CCCCC1] | H | C—H |
| 211 | —N(CH₃)₂ | H | C—H |
| 212 | 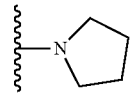 [SMILES: *N1CCCC1] | H | C—H |
| 213 | 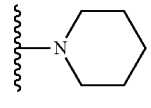 | H | C—H |
| 214 | 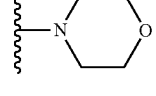 | H | C—H |
| 215 | 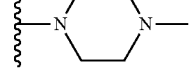 | H | C—H |

TABLE 2-continued

| Compound | R³ | R⁴ | X³ |
|---|---|---|---|
| 216 | N-piperazine-N-tBu | H | C—H |
| 217 | N-azetidine | H | C—H |
| 218 | N-azetidine-spiro-oxetane | H | C—H |
| 219 | N-bicyclic oxa-azabicycle | H | C—H |
| 220 | —N(Et)Bn | H | C—H |
| 221 | —NHMe | —OMe | C—H |
| 222 | —NHMe | —Oi-Pr | C—H |
| 223 | —NHi-Pr | —OMe | C—H |
| 224 | —NHi-Pr | —Oi-Pr | C—H |
| 225 | NH-cyclohexyl | —OMe | C—H |
| 226 | NH-cyclohexyl | —Oi-Pr | C—H |
| 227 | N-pyrrolidine | —OMe | C—H |
| 228 | N-pyrrolidine | —Oi-Pr | C—H |
| 229 | N-piperidine | —OMe | C—H |
| 230 | N-piperidine | —Oi-Pr | C—H |
| 231 | N-morpholine | —OMe | C—H |
| 232 | N-morpholine | —Oi-Pr | C—H |

TABLE 2-continued
| Compound | R³ | R⁴ | X³ |
|---|---|---|---|
| 233 | —NHMe | —NHMe | C—H |
| 234 | —NHMe | —NHi-Pr | C—H |
| 235 | —NHi-Pr | —NHMe | C—H |
| 236 | —NHi-Pr | —NHi-Pr | C—H |
| 237 | 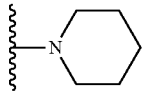 | —NHMe | C—H |
| 238 | 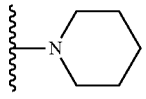 | —NHi-Pr | C—H |
| 239 | 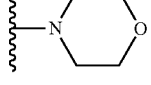 | —NHMe | C—H |
| 240 | 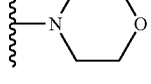 | —NHi-Pr | C—H |
| 241 | H | H | C—F |
| 242 | H | —Cl | C—F |
| 243 | H | —Br | C—F |
| 244 | H | 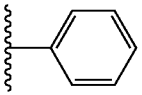 | C—F |
| 245 | H | —OMe | C—F |
| 246 | H | —Oi-Pr | C—F |
| 247 | H | —NHMe | C—F |
| 248 | H | —NHi-Pr | C—F |
| 249 | H | 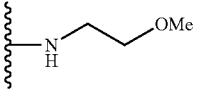 | C—F |
| 250 | H | 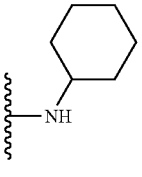 [SMILES: *NC1CCCCC1] | C—F |
| 251 | H | —N(CH₃)₂ | C—F |
| 252 | H | 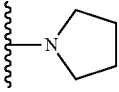 [SMILES: *N1CCCC1] | C—F |
| 253 | H | 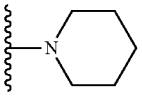 | C—F |
| 254 | H | 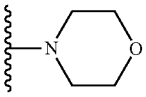 | C—F |

TABLE 2-continued
| Compound | R³ | R⁴ | X³ |
|---|---|---|---|
| 255 | H | 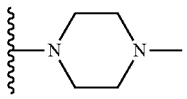 [SMILES: *N1CCN(C)CC1] N-methylpiperazinyl | C—F |
| 256 | H | 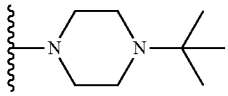 N-tert-butylpiperazinyl | C—F |
| 257 | H | 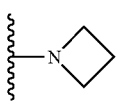 azetidinyl | C—F |
| 258 | H |  2-oxa-6-azaspiro[3.3]heptyl | C—F |
| 259 | H | 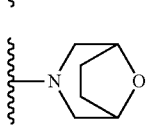 8-oxa-3-azabicyclo[3.2.1]octyl | C—F |
| 260 | H | —N(Et)Bn | C—F |
| 261 | H | H | C—F |
| 262 | —Cl | H | C—F |
| 263 | —Br | H | C—F |
| 264 | 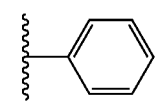 phenyl | H | C—F |
| 265 | —OMe | H | C—F |
| 266 | —Oi-Pr | H | C—F |
| 267 | —NHMe | H | C—F |
| 268 | —NHi-Pr | H | C—F |
| 269 | 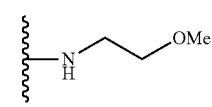 [SMILES: *NCCOC] —NH-CH₂CH₂-OMe | H | C—F |
| 270 | 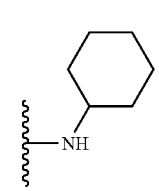 [SMILES: *NC1CCCCC1] cyclohexyl-NH— | H | C—F |
| 271 | —N(CH₃)₂ | H | C—F |
| 272 | 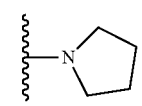 [SMILES: *N1CCCC1] pyrrolidinyl | H | C—F |
| 273 | 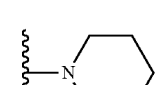 piperidinyl | H | C—F |
| 274 | 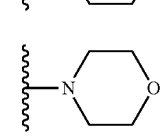 morpholinyl | H | C—F |

TABLE 2-continued
| Compound | R³ | R⁴ | X³ |
|---|---|---|---|
| 275 | 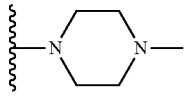 | H | C—F |
| 276 | 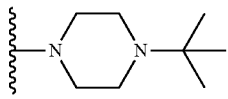 [SMILES: *N1CCN(C(C)(C)C)CC1] | H | C—F |
| 277 | 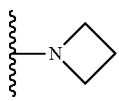 | H | C—F |
| 278 |  | H | C—F |
| 279 | 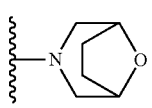 | H | C—F |
| 280 | —N(Et)Bn | H | C—F |
| 281 | —NHMe | —OMe | C—F |
| 282 | —NHMe | —Oi-Pr | C—F |
| 283 | —NHi-Pr | —OMe | C—F |
| 284 | —NHi-Pr | —Oi-Pr | C—F |
| 285 | 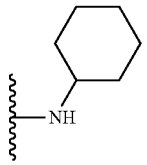 | —OMe | C—F |
| 286 | 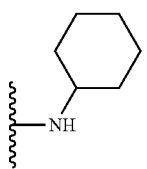 [SMILES: *NC1CCCCC1] | —Oi-Pr | C—F |
| 287 | 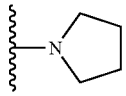 | —OMe | C—F |
| 288 | 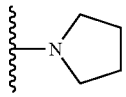 | —Oi-Pr | C—F |
| 289 | 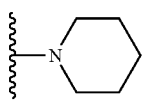 | —OMe | C—F |
| 290 | 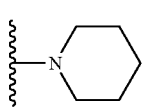 | —Oi-Pr | C—F |
| 291 | 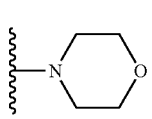 | —OMe | C—F |

TABLE 2-continued
| Compound | R³ | R⁴ | X³ |
|---|---|---|---|
| 292 | 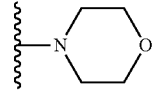 | —Oi-Pr | C—F |
| 293 | —NHMe | —NHMe | C—F |
| 294 | —NHMe | —NHi-Pr | C—F |
| 295 | —NHi-Pr | —NHMe | C—F |
| 296 | —NHi-Pr | —NHi-Pr | C—F |
| 297 | 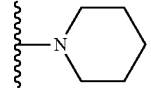 | —NHMe | C—F |
| 298 | 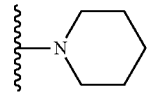 | —NHi-Pr | C—F |
| 299 | 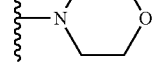 | —NHMe | C—F |
| 300 | 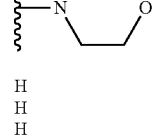 | —NHi-Pr | C—F |
| 301 | H | H | N |
| 302 | H | —Cl | N |
| 303 | H | —Br | N |
| 304 | H | 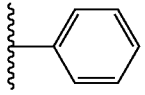 | N |
| 305 | H | —OMe | N |
| 306 | H | —Oi-Pr | N |
| 307 | H | —NHMe | N |
| 308 | H | —NHi-Pr | N |
| 309 | H | 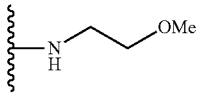 [SMILES: *NCCOC] | N |
| 310 | H | 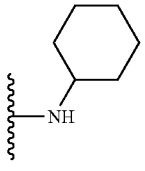 [SMILES: *NC1CCCCC1] | N |
| 311 | H | —N(CH₃)₂ | N |
| 312 | H | 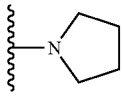 | N |
| 313 | H | 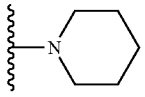 | N |
| 314 | H | 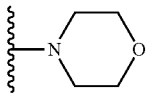 | N |

TABLE 2-continued
| Compound | R³ | R⁴ | X³ |
|---|---|---|---|
| 315 | H | 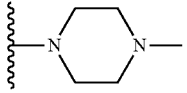 | N |
| 316 | H | 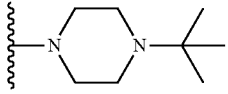 [SMILES: *N1CCN(C(C)(C)C)CC1] | N |
| 317 | H | 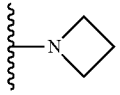 [SMILES: *N1CCC1] | N |
| 318 | H |  | N |
| 319 | H | 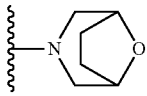 | N |
| 320 | H | —N(Et)Bn | N |
| 321 | H | H | N |
| 322 | —Cl | H | N |
| 323 | —Br | H | N |
| 324 | 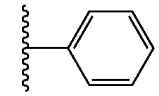 [SMILES: *c1ccccc1] | H | N |
| 325 | —OMe | H | N |
| 326 | —Oi-Pr | H | N |
| 327 | —NHMe | H | N |
| 328 | —NHi-Pr | H | N |
| 329 | 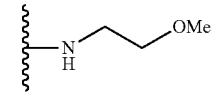 [SMILES: *NCCOC] | H | N |
| 330 | 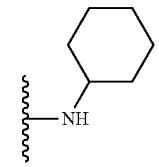 [SMILES: *NC1CCCCC1] | H | N |
| 331 | —N(CH₃)₂ | H | N |
| 332 | 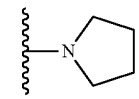 | H | N |
| 333 | 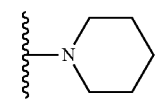 | H | N |
| 334 | 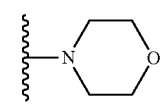 | H | N |

TABLE 2-continued
| Compound | R³ | R⁴ | X³ |
|---|---|---|---|
| 335 | 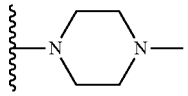 | H | N |
| 336 | 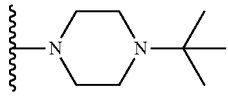 | H | N |
| 337 | 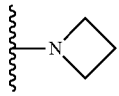 [SMILES: *N1CCC1] | H | N |
| 338 | 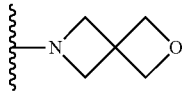 [SMILES: *N1CC2(COC2)C1] | H | N |
| 339 | 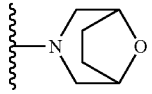 | H | N |
| 340 | —N(Et)Bn | H | N |
| 341 | —NHMe | —OMe | N |
| 342 | —NHMe | —Oi-Pr | N |
| 343 | —NHi-Pr | —OMe | N |
| 344 | —NHi-Pr | —Oi-Pr | N |
| 345 | 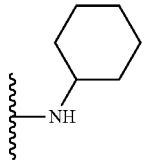 | —OMe | N |
| 346 | 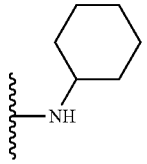 [SMILES: *NC1CCCCC1] | —Oi-Pr | N |
| 347 | 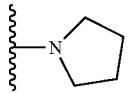 [SMILES: *N1CCCC1] | —OMe | N |
| 348 | 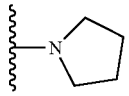 | —Oi-Pr | N |
| 349 | 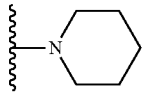 | —OMe | N |
| 350 | 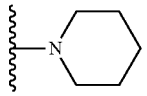 | —Oi-Pr | N |
| 351 | 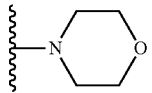 | —OMe | N |

TABLE 2-continued

| Compound | R³ | R⁴ | X³ |
|---|---|---|---|
| 352 | 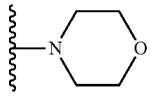 | —Oi-Pr | N |
| 353 | —NHMe | —NHMe | N |
| 354 | —NHMe | —NHi-Pr | N |
| 355 | —NHi-Pr | —NHMe | N |
| 356 | —NHi-Pr | —NHi-Pr | N |
| 357 | 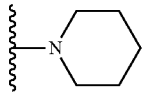 | —NHMe | N |
| 358 | 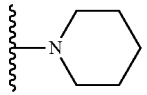 | —NHi-Pr | N |
| 359 | 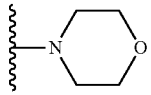 | —NHMe | N |
| 360 | 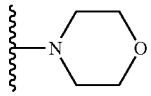 | —NHi-Pr | N |

In certain embodiments, the compound of Formula I is represented by Formula XI or a pharmaceutically acceptable salt or ester thereof:

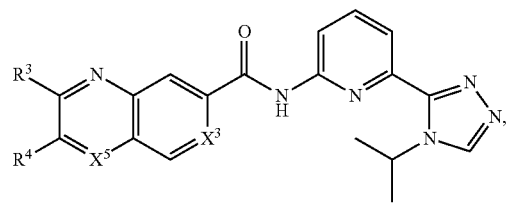

(XI)

wherein R³, R⁴, X³, and X⁵ are as previously defined.

In certain embodiments, the compound of Formula I is represented by Formula XII or a pharmaceutically acceptable salt or ester thereof:

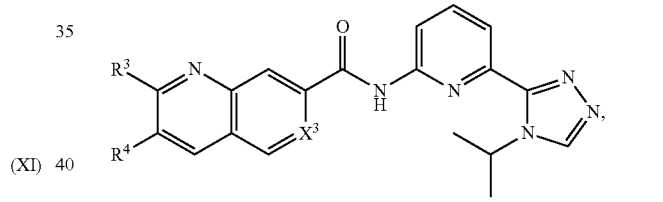

(XII)

wherein R³, R⁴, and X³ are as previously defined.

Representative compounds of the invention include, but are not limited to, the following compounds (compound 361 to compound 540 in Table 3) according to Formula XII, and pharmaceutically acceptable salts thereof, wherein R³, R⁴, and X³ are delineated for each compound in Table 3.

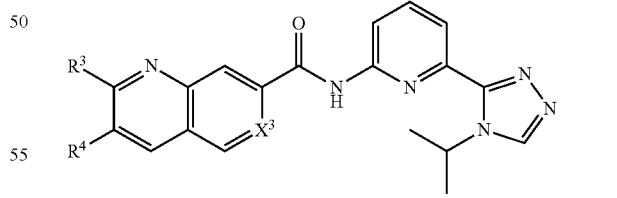

(XII)

TABLE 3

| Compound | R³ | R⁴ | X³ |
|---|---|---|---|
| 361 | H | H | C—H |
| 362 | H | —Cl | C—H |
| 363 | H | —Br | C—H |

TABLE 3-continued
| Compound | R³ | R⁴ | X³ |
|---|---|---|---|
| 364 | H | 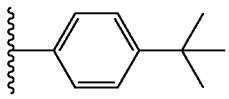 [SMILES: *c1ccc(C(C)(C)C)cc1] | C—H |
| 365 | H | —OMe | C—H |
| 366 | H | —Oi-Pr | C—H |
| 367 | H | —NHMe | C—H |
| 368 | H | —NH-Pr | C—H |
| 369 | H | 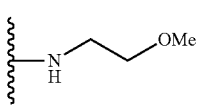 [SMILES: *NCCOC] | C—H |
| 370 | H | 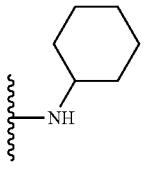 [SMILES: *NC1CCCCC1] | C—H |
| 371 | H | —N(CH₃)₂ | C—H |
| 372 | H | 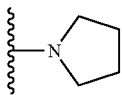 | C—H |
| 373 | H | 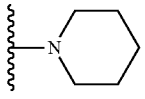 | C—H |
| 374 | H | 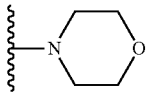 | C—H |
| 375 | H | 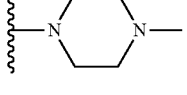 | C—H |
| 376 | H | 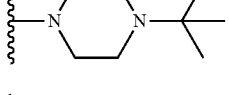 | C—H |
| 377 | H | 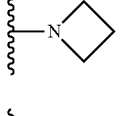 | C—H |
| 378 | H | 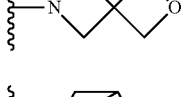 | C—H |
| 379 | H | 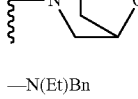 | C—H |
| 380 | H | —N(Et)Bn | C—H |
| 381 | H | H | C—H |
| 382 | —Cl | H | C—H |
| 383 | —Br | H | C—H |

TABLE 3-continued

| Compound | R³ | R⁴ | X³ |
|---|---|---|---|
| 384 | phenyl | H | C—H |
| 385 | —OMe | H | C—H |
| 386 | —Oi-Pr | H | C—H |
| 387 | —NHMe | H | C—H |
| 388 | —NHi-Pr | H | C—H |
| 389 | —NH-CH₂CH₂-OMe | H | C—H |
| 390 | cyclohexyl-NH— | H | C—H |
| 391 | —N(CH₃)₂ | H | C—H |
| 392 | 2-(methoxymethyl)pyrrolidin-1-yl | H | C—H |
| 393 | piperidin-1-yl | H | C—H |
| 394 | morpholin-4-yl | H | C—H |
| 395 | 4-methylpiperazin-1-yl | H | C—H |
| 396 | 4-tert-butylpiperazin-1-yl | H | C—H |
| 397 | azetidin-1-yl | H | C—H |
| 398 | 2-oxa-6-azaspiro[3.3]heptan-6-yl | H | C—H |
| 399 | 8-oxa-3-azabicyclo[3.2.1]octan-3-yl | H | C—H |
| 400 | —N(Et)Bn | H | C—H |
| 401 | —NHMe | —OMe | C—H |
| 402 | —NHMe | —Oi-Pr | C—H |
| 403 | —NHi-Pr | —OMe | C—H |
| 404 | —NHi-Pr | —Oi-Pr | C—H |

TABLE 3-continued

| Compound | R³ | R⁴ | X³ |
|---|---|---|---|
| 405 | cyclohexyl-NH- | —OMe | C—H |
| 406 | cyclohexyl-NH- | —Oi-Pr | C—H |
| 407 | pyrrolidin-1-yl | —OMe | C—H |
| 408 | pyrrolidin-1-yl | —Oi-Pr | C—H |
| 409 | piperidin-1-yl | —OMe | C—H |
| 410 | piperidin-1-yl | —Oi-Pr | C—H |
| 411 | morpholin-4-yl | —OMe | C—H |
| 412 | morpholin-4-yl | —Oi-Pr | C—H |
| 413 | —NHMe | —NHMe | C—H |
| 414 | —NHMe | —NHi-Pr | C—H |
| 415 | —NHi-Pr | —NHMe | C—H |
| 416 | —NHi-Pr | —NHi-Pr | C—H |
| 417 | piperidin-1-yl | —NHMe | C—H |
| 418 | piperidin-1-yl | —NHi-Pr | C—H |
| 419 | morpholin-4-yl | —NHMe | C—H |
| 420 | morpholin-4-yl | —NHi-Pr | C—H |

TABLE 3-continued

| Compound | R³ | R⁴ | X³ |
| --- | --- | --- | --- |
| 421 | H | H | C—F |
| 422 | H | —Cl | C—F |
| 423 | H | —Br | C—F |
| 424 | H | phenyl | C—F |
| 425 | H | —OMe | C—F |
| 426 | H | —Oi-Pr | C—F |
| 427 | H | —NHMe | C—F |
| 428 | H | —NHi-Pr | C—F |
| 429 | H | —NH-CH₂CH₂-OMe | C—F |
| 430 | H | —NH-cyclohexyl | C—F |
| 431 | H | —N(CH₃)₂ | C—F |
| 432 | H | pyrrolidin-1-yl | C—F |
| 433 | H | piperidin-1-yl | C—F |
| 434 | H | morpholin-4-yl | C—F |
| 435 | H | 4-methylpiperazin-1-yl | C—F |
| 436 | H | 4-tert-butylpiperazin-1-yl | C—F |
| 437 | H | azetidin-1-yl | C—F |
| 438 | H | 2-oxa-6-azaspiro[3.3]heptan-6-yl | C—F |
| 439 | H | 8-oxa-3-azabicyclo[3.2.1]octan-3-yl | C—F |
| 440 | H | —N(Et)Bn | C—F |
| 441 | H | H | C—F |
| 442 | —Cl | H | C—F |

TABLE 3-continued
| Compound | R³ | R⁴ | X³ |
|---|---|---|---|
| 443 | —Br | H | C—F |
| 444 | 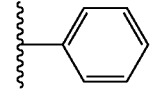 [SMILES: *c1ccccc1] | H | C—F |
| 445 | —OMe | H | C—F |
| 446 | —Oi-Pr | H | C—F |
| 447 | —NHMe | H | C—F |
| 448 | —NHi-Pr | H | C—F |
| 449 | 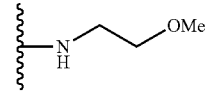 [SMILES: *NCCOC] | H | C—F |
| 450 | 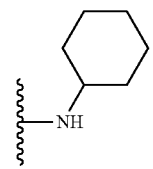 [SMILES: *NC1CCCCC1] | H | C—F |
| 451 | —N(CH₃)₂ | H | C—F |
| 452 | 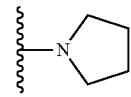 [SMILES: *N1CCCC1] | H | C—F |
| 453 | 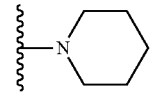 [SMILES: *N1CCCCC1] | H | C—F |
| 454 | 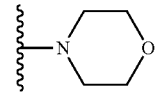 | H | C—F |
| 455 | 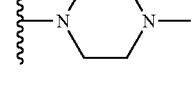 | H | C—F |
| 456 | 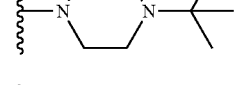 | H | C—F |
| 457 | 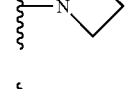 | H | C—F |
| 458 |  | H | C—F |
| 459 | 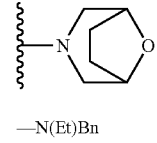 | H | C—F |
| 460 | —N(Et)Bn | H | C—F |
| 461 | —NHMe | —OMe | C—F |
| 462 | —NHMe | —Oi-Pr | C—F |
| 463 | —NHi-Pr | —OMe | C—F |
| 464 | —NHi-Pr | —Oi-Pr | C—F |

TABLE 3-continued

| Compound | R³ | R⁴ | X³ |
|---|---|---|---|
| 465 | cyclohexyl-NH- | —OMe | C—F |
| 466 | cyclohexyl-NH- | —Oi-Pr | C—F |
| 467 | pyrrolidin-1-yl | —OMe | C—F |
| 468 | pyrrolidin-1-yl | —Oi-Pr | C—F |
| 469 | piperidin-1-yl | —OMe | C—F |
| 470 | piperidin-1-yl | —Oi-Pr | C—F |
| 471 | morpholin-4-yl | —OMe | C—F |
| 472 | morpholin-4-yl | —Oi-Pr | C—F |
| 473 | —NHMe | —NHMe | C—F |
| 474 | —NHMe | —NHi-Pr | C—F |
| 475 | —NHi-Pr | —NHMe | C—F |
| 476 | —NHi-Pr | —NHi-Pr | C—F |
| 477 | piperidin-1-yl | —NHMe | C—F |
| 478 | piperidin-1-yl | —NHi-Pr | C—F |
| 479 | morpholin-4-yl | —NHMe | C—F |
| 480 | morpholin-4-yl | —NHi-Pr | C—F |

TABLE 3-continued
| Compound | R³ | R⁴ | X³ |
|---|---|---|---|
| 481 | H | H | N |
| 482 | H | —Cl | N |
| 483 | H | —Br | N |
| 484 | H | 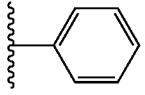 | N |
| 485 | H | —OMe | N |
| 486 | H | —Oi-Pr | N |
| 487 | H | —NHMe | N |
| 488 | H | —NHi-Pr | N |
| 489 | H | 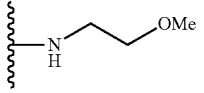 [SMILES: *NCCOC] | N |
| 490 | H | 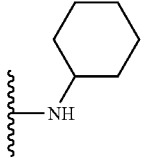 [SMILES: *NC1CCCCC1] | N |
| 491 | H | —N(CH₃)₂ | N |
| 492 | H | 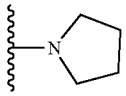 | N |
| 493 | H | 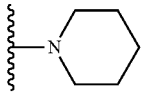 | N |
| 494 | H | 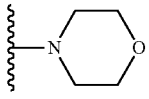 | N |
| 495 | H | 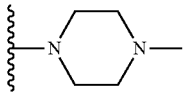 | N |
| 496 | H | 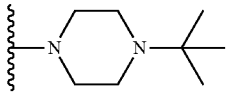 | N |
| 497 | H | 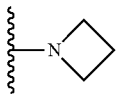 | N |
| 498 | H |  | N |
| 499 | H | 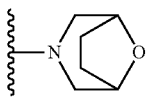 | N |
| 500 | H | —N(Et)Bn | N |
| 501 | H | H | N |
| 502 | —Cl | H | N |
| 503 | —Br | H | N |

TABLE 3-continued
| Compound | R³ | R⁴ | X³ |
|---|---|---|---|
| 504 | 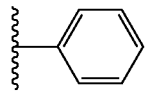 [SMILES: *c1ccccc1] | H | N |
| 505 | —OMe | H | N |
| 506 | —Oi-Pr | H | N |
| 507 | —NHMe | H | N |
| 508 | —NHi-Pr | H | N |
| 509 | 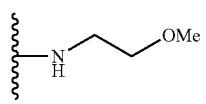 [SMILES: *NCCOC] | H | N |
| 510 | 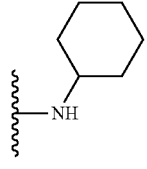 [SMILES: *NC1CCCCC1] | H | N |
| 511 | —N(CH₃)₂ | H | N |
| 512 | 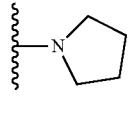 [SMILES: *N1CCCC1] | H | N |
| 513 | 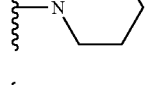 | H | N |
| 514 | 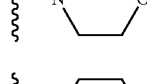 | H | N |
| 515 | 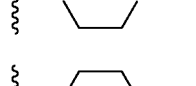 | H | N |
| 516 | 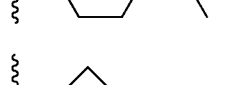 | H | N |
| 517 | 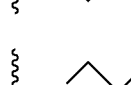 | H | N |
| 518 | 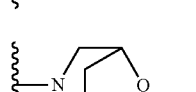 | H | N |
| 519 | 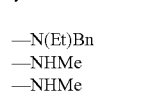 | H | N |
| 520 | —N(Et)Bn | H | N |
| 521 | —NHMe | —OMe | N |
| 522 | —NHMe | —Oi-Pr | N |
| 523 | —NHi-Pr | —OMe | N |
| 524 | —NHi-Pr | —Oi-Pr | N |

TABLE 3-continued

| Compound | R³ | R⁴ | X³ |
|---|---|---|---|
| 525 | cyclohexyl-NH- | —OMe | N |
| 526 | cyclohexyl-NH- | —Oi-Pr | N |
| 527 | pyrrolidin-1-yl | —OMe | N |
| 528 | pyrrolidin-1-yl | —Oi-Pr | N |
| 529 | piperidin-1-yl | —OMe | N |
| 530 | piperidin-1-yl | —Oi-Pr | N |
| 531 | morpholin-4-yl | —OMe | N |
| 532 | morpholin-4-yl | —Oi-Pr | N |
| 533 | —NHMe | —NHMe | N |
| 534 | —NHMe | —NHi-Pr | N |
| 535 | —NHi-Pr | —NHMe | N |
| 536 | —NHi-Pr | —NHi-Pr | N |
| 537 | piperidin-1-yl | —NHMe | N |
| 538 | piperidin-1-yl | —NHi-Pr | N |
| 539 | morpholin-4-yl | —NHMe | N |
| 540 | morpholin-4-yl | —NHi-Pr | N |

In another embodiment of the invention, the compound of Formula I is represented by Formula XIII or a pharmaceutically acceptable salt or ester thereof:

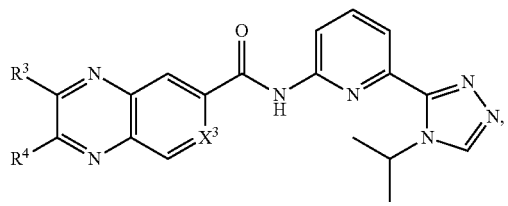
(XIII)

wherein $R^3$, $R^4$, and $X^3$ are as previously defined.

Representative compounds of the invention include, but are not limited to, the following compounds (compound 541 to compound 720 in Table 4) according to Formula XIII, and pharmaceutically acceptable salts thereof, wherein $R^3$, $R^4$, and $X^3$ are delineated for each compound in Table 4.

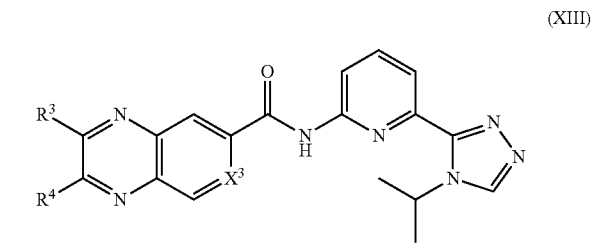
(XIII)

TABLE 4

| Compound | $R^3$ | $R^4$ | $X^3$ |
|---|---|---|---|
| 541 | H | H | C—H |
| 542 | H | —Cl | C—H |
| 543 | H | —Br | C—H |
| 544 | H | phenyl | C—H |
| 545 | H | —OMe | C—H |
| 546 | H | —Oi-Pr | C—H |
| 547 | H | —NHMe | C—H |
| 548 | H | —NHi-Pr | C—H |
| 549 | H | —NH-CH₂CH₂-OMe | C—H |
| 550 | H | —NH-cyclohexyl | C—H |
| 551 | H | —N(CH₃)₂ | C—H |
| 552 | H | pyrrolidin-1-yl | C—H |
| 553 | H | piperidin-1-yl | C—H |
| 554 | H | morpholin-4-yl | C—H |
| 555 | H | 4-methylpiperazin-1-yl | C—H |

TABLE 4-continued
| Compound | R³ | R⁴ | X³ |
|---|---|---|---|
| 556 | H | 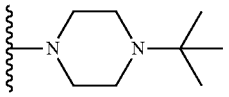 N-piperazine-tBu | C—H |
| 557 | H | 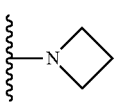 azetidinyl | C—H |
| 558 | H |  2-oxa-6-azaspiro[3.3]heptanyl | C—H |
| 559 | H | 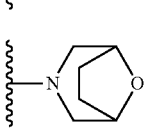 8-oxa-3-azabicyclo[3.2.1]octanyl | C—H |
| 560 | H | —N(Et)Bn | C—H |
| 561 | H | H | C—H |
| 562 | —Cl | H | C—H |
| 563 | —Br | H | C—H |
| 564 | 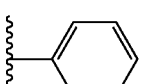 phenyl | H | C—H |
| 565 | —OMe | H | C—H |
| 566 | —Oi-Pr | H | C—H |
| 567 | —NHMe | H | C—H |
| 568 | —NHi-Pr | H | C—H |
| 569 | 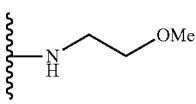 [SMILES: *NCCOC] —NH-CH₂CH₂-OMe | H | C—H |
| 570 | 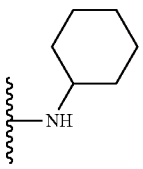 cyclohexyl-NH | H | C—H |
| 571 | —N(CH₃)₂ | H | C—H |
| 572 | 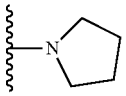 pyrrolidinyl | H | C—H |
| 573 | 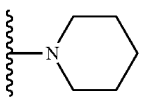 piperidinyl | H | C—H |
| 574 | 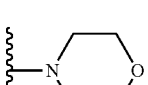 morpholinyl | H | C—H |
| 575 | 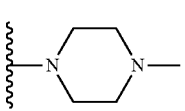 N-methylpiperazinyl | H | C—H |

TABLE 4-continued

| Compound | R³ | R⁴ | X³ |
|---|---|---|---|
| 576 | N-piperazine-N-t-Bu | H | C—H |
| 577 | N-azetidine | H | C—H |
| 578 | N-azetidine-spiro-oxetane | H | C—H |
| 579 | N-oxabicyclic | H | C—H |
| 580 | —N(Et)Bn | H | C—H |
| 581 | —NHMe | —OMe | C—H |
| 582 | —NHMe | —Oi-Pr | C—H |
| 583 | —NHi-Pr | —OMe | C—H |
| 584 | —NHi-Pr | —Oi-Pr | C—H |
| 585 | NH-cyclohexyl | —OMe | C—H |
| 586 | NH-cyclohexyl | —Oi-Pr | C—H |
| 587 | N-pyrrolidine | —OMe | C—H |
| 588 | N-pyrrolidine | —Oi-Pr | C—H |
| 589 | N-piperidine | —OMe | C—H |
| 590 | N-piperidine | —Oi-Pr | C—H |
| 591 | N-morpholine | —OMe | C—H |
| 592 | N-morpholine | —Oi-Pr | C—H |

TABLE 4-continued
| Compound | R³ | R⁴ | X³ |
|---|---|---|---|
| 593 | —NHMe | —NHMe | C—H |
| 594 | —NHMe | —NHi-Pr | C—H |
| 595 | —NHi-Pr | —NHMe | C—H |
| 596 | —NHi-Pr | —NHi-Pr | C—H |
| 597 | 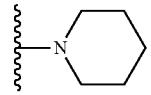 | —NHMe | C—H |
| 598 | 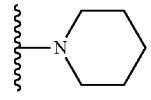 | —NHi-Pr | C—H |
| 599 | 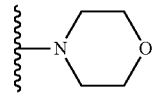 | —NHMe | C—H |
| 600 | 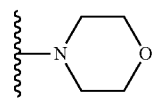 | —NHi-Pr | C—H |
| 601 | H | H | C—F |
| 602 | H | —Cl | C—F |
| 603 | H | —Br | C—F |
| 604 | H | 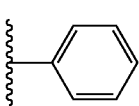 | C—F |
| 605 | H | —OMe | C—F |
| 606 | H | —Oi-Pr | C—F |
| 607 | H | —NHMe | C—F |
| 608 | H | —NHi-Pr | C—F |
| 609 | H | 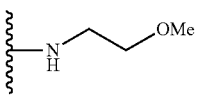 [SMILES: *NCCOC] | C—F |
| 610 | H | 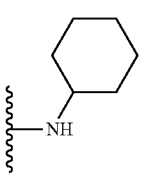 | C—F |
| 611 | H | —N(CH₃)₂ | C—F |
| 612 | H | 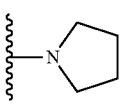 | C—F |
| 613 | H | 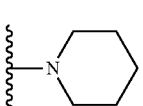 | C—F |
| 614 | H | 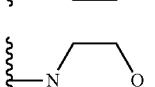 | C—F |
| 615 | H | 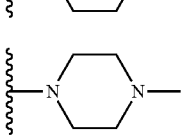 | C—F |

TABLE 4-continued

| Compound | R³ | R⁴ | X³ |
|---|---|---|---|
| 616 | H | N-piperazine-N-t-Bu | C—F |
| 617 | H | N-azetidinyl | C—F |
| 618 | H | 2-oxa-6-azaspiro[3.3]heptan-6-yl | C—F |
| 619 | H | 8-oxa-3-azabicyclo[3.2.1]octan-3-yl | C—F |
| 620 | H | —N(Et)Bn | C—F |
| 621 | H | H | C—F |
| 622 | —Cl | H | C—F |
| 623 | —Br | H | C—F |
| 624 | phenyl | H | C—F |
| 625 | —OMe | H | C—F |
| 626 | —Oi-Pr | H | C—F |
| 627 | —NHMe | H | C—F |
| 628 | —NHi-Pr | H | C—F |
| 629 | —NH-CH₂CH₂-OMe | H | C—F |
| 630 | —NH-cyclohexyl | H | C—F |
| 631 | —N(CH₃)₂ | H | C—F |
| 632 | N-pyrrolidinyl | H | C—F |
| 633 | N-piperidinyl | H | C—F |
| 634 | N-morpholinyl | H | C—F |
| 635 | N-(4-methylpiperazinyl) | H | C—F |

TABLE 4-continued
| Compound | R³ | R⁴ | X³ |
|---|---|---|---|
| 636 | 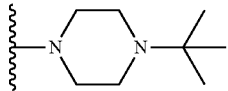 | H | C—F |
| 637 | 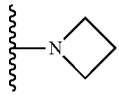 | H | C—F |
| 638 |  | H | C—F |
| 639 | 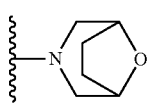 | H | C—F |
| 640 | —N(Et)Bn | H | C—F |
| 641 | —NHMe | —OMe | C—F |
| 642 | —NHMe | —Oi-Pr | C—F |
| 643 | —NHi-Pr | —OMe | C—F |
| 644 | —NHi-Pr | —Oi-Pr | C—F |
| 645 | 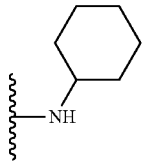 [SMILES: *NC1CCCCC1] | —OMe | C—F |
| 646 | 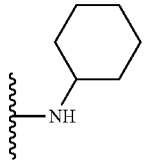 [SMILES: *NC1CCCCC1] | —Oi-Pr | C—F |
| 647 | 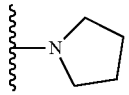 [SMILES: *N1CCCC1] | —OMe | C—F |
| 648 | 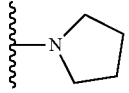 | —Oi-Pr | C—F |
| 649 | 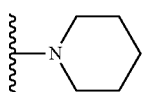 | —OMe | C—F |
| 650 | 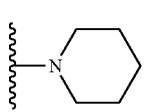 | —Oi-Pr | C—F |
| 651 | 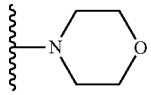 | —OMe | C—F |
| 652 | 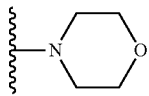 | —Oi-Pr | C—F |

TABLE 4-continued
| Compound | R³ | R⁴ | X³ |
|---|---|---|---|
| 653 | —NHMe | —NHMe | C—F |
| 654 | —NHMe | —NHi-Pr | C—F |
| 655 | —NHi-Pr | —NHMe | C—F |
| 656 | —NHi-Pr | —NHi-Pr | C—F |
| 657 | 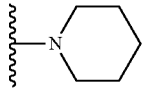 | —NHMe | C—F |
| 658 | 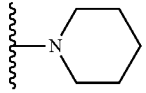 | —NHi-Pr | C—F |
| 659 | 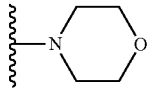 | —NHMe | C—F |
| 660 | 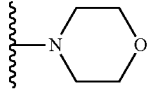 | —NHi-Pr | C—F |
| 661 | H | H | N |
| 662 | H | —Cl | N |
| 663 | H | —Br | N |
| 664 | H | 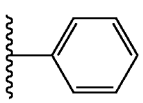 [SMILES: *c1ccccc1] | N |
| 665 | H | —OMe | N |
| 666 | H | —Oi-Pr | N |
| 667 | H | —NHMe | N |
| 668 | H | —NHi-Pr | N |
| 669 | H | 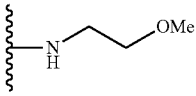 [SMILES: *NCCOC] | N |
| 670 | H | 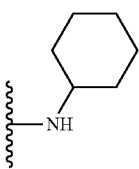 | N |
| 671 | H | —N(CH₃)₂ | N |
| 672 | H | 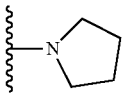 | N |
| 673 | H | 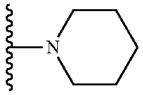 | N |
| 674 | H | 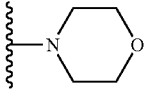 | N |
| 675 | H | 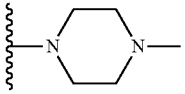 [SMILES: *N1CCN(C)CC1] | N |

TABLE 4-continued
| Compound | R³ | R⁴ | X³ |
|---|---|---|---|
| 676 | H | 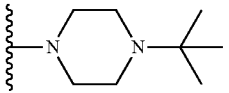 | N |
| 677 | H | 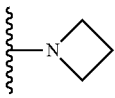 | N |
| 678 | H | 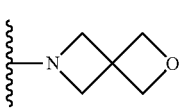 [SMILES: *N1CC2(COC2)C1] | N |
| 679 | H | 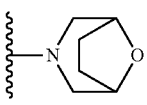 | N |
| 680 | H | —N(Et)Bn | N |
| 681 | H | H | N |
| 682 | —Cl | H | N |
| 683 | —Br | H | N |
| 684 | 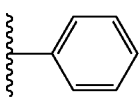 | H | N |
| 685 | —OMe | H | N |
| 686 | —Oi-Pr | H | N |
| 687 | —NHMe | H | N |
| 688 | —NHi-Pr | H | N |
| 689 | 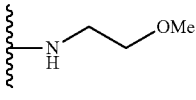 | H | N |
| 690 | 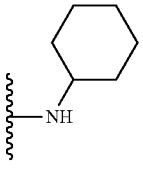 | H | N |
| 691 | —N(CH₃)₂ | H | N |
| 692 | 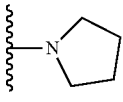 | H | N |
| 693 | 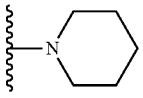 | H | N |
| 694 | 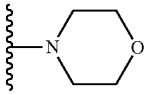 | H | N |
| 695 |  | H | N |

TABLE 4-continued

| Compound | R³ | R⁴ | X³ |
|---|---|---|---|
| 696 | N-piperazine-tBu | H | N |
| 697 | N-azetidine | H | N |
| 698 | N-azetidine-spiro-oxetane | H | N |
| 699 | N-8-oxa-bicyclic | H | N |
| 700 | —N(Et)Bn | H | N |
| 701 | —NHMe | —OMe | N |
| 702 | —NHMe | —Oi-Pr | N |
| 703 | —NHi-Pr | —OMe | N |
| 704 | —NHi-Pr | —Oi-Pr | N |
| 705 | NH-cyclohexyl | —OMe | N |
| 706 | NH-cyclohexyl | —Oi-Pr | N |
| 707 | N-pyrrolidine | —OMe | N |
| 708 | N-pyrrolidine | —Oi-Pr | N |
| 709 | N-piperidine | —OMe | N |
| 710 | N-piperidine | —Oi-Pr | N |
| 711 | N-morpholine | —OMe | N |
| 712 | N-morpholine | —Oi-Pr | N |

TABLE 4-continued

| Compound | R³ | R⁴ | X³ |
|---|---|---|---|
| 713 | —NHMe | —NHMe | N |
| 714 | —NHMe | —NHi-Pr | N |
| 715 | —NHi-Pr | —NHMe | N |
| 716 | —NHi-Pr | —NHi-Pr | N |
| 717 | piperidinyl | —NHMe | N |
| 718 | piperidinyl | —NHi-Pr | N |
| 719 | morpholinyl | —NHMe | N |
| 720 | morpholinyl | —NHi-Pr | N |

In certain embodiments, the compound of Formula I is represented by Formula XIV or a pharmaceutically acceptable salt or ester thereof:

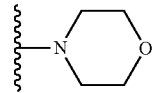

(XIV)

wherein R³, R⁴, R⁵, X³, X⁴, and X⁵ are as previously defined.

In certain embodiments, the compound of Formula I is represented by Formula XV or a pharmaceutically acceptable salt or ester thereof:

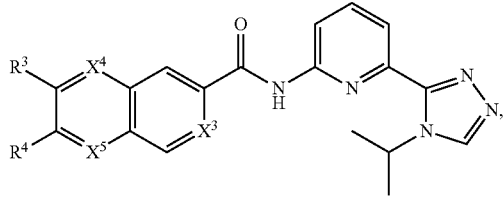

(XV)

wherein R³, R⁴, X³, X⁴, and X⁵ are as previously defined.

In certain embodiments, the compound of Formula I is represented by Formula XVI or a pharmaceutically acceptable salt or ester thereof:

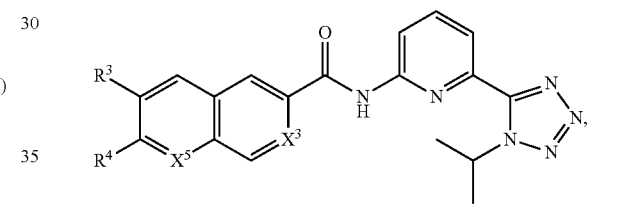

(XVI)

wherein R³, R⁴, X³, and X⁵ are as previously defined.

In certain embodiments, the compound of Formula I is represented by Formula XVII or a pharmaceutically acceptable salt or ester thereof:

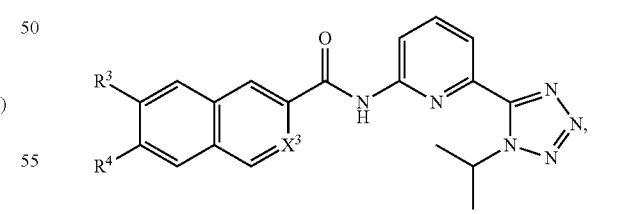

(XVII)

wherein R³, R⁴, and X³ are as previously defined.

Representative compounds of the invention include, but are not limited to, the following compounds (compound 721 to compound 900 in Table 5) according to Formula XVII, and pharmaceutically acceptable salts thereof, wherein R³, R⁴, and X³ are delineated for each compound in Table 5.

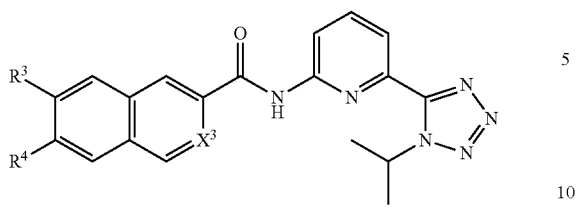
(XVII)
TABLE 5
| Compound | R³ | R⁴ | X³ |
| --- | --- | --- | --- |
| 721 | H | H | C—H |
| 722 | H | —Cl | C—H |
| 723 | H | —Br | C—H |
| 724 | H | phenyl | C—H |
| 725 | H | —OMe | C—H |
| 726 | H | —Oi-Pr | C—H |
| 727 | H | —NHMe | C—H |
| 728 | H | —NH-Pr | C—H |
| 729 | H | —NH-CH₂CH₂-OMe | C—H |
| 730 | H | —NH-cyclohexyl | C—H |
| 731 | H | —N(CH₃)₂ | C—H |
| 732 | H | pyrrolidin-1-yl | C—H |
| 733 | H | piperidin-1-yl | C—H |
| 734 | H | morpholin-4-yl | C—H |
| 735 | H | 4-methylpiperazin-1-yl | C—H |
| 736 | H | 4-tert-butylpiperazin-1-yl | C—H |
| 737 | H | azetidin-1-yl | C—H |

TABLE 5-continued
| Compound | R³ | R⁴ | X³ |
|---|---|---|---|
| 738 | H |  | C—H |
| 739 | H | 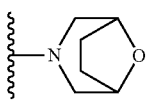 | C—H |
| 740 | H | —N(Et)Bn | C—H |
| 741 | H | H | C—H |
| 742 | —Cl | H | C—H |
| 743 | —Br | H | C—H |
| 744 | 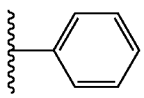 [SMILES: *c1ccccc1] | H | C—H |
| 745 | —OMe | H | C—H |
| 746 | —Oi-Pr | H | C—H |
| 747 | —NHMe | H | C—H |
| 748 | —NHi-Pr | H | C—H |
| 749 | 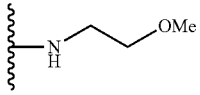 | H | C—H |
| 750 | 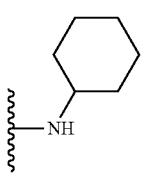 [SMILES: *NC1CCCCC1] | H | C—H |
| 751 | —N(CH₃)₂ | H | C—H |
| 752 | 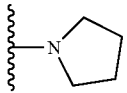 [SMILES: *N1CCCC1] | H | C—H |
| 753 | 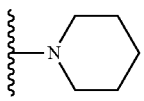 | H | C—H |
| 754 | 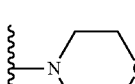 | H | C—H |
| 755 | 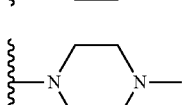 | H | C—H |
| 756 | 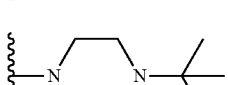 | H | C—H |
| 757 | 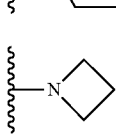 | H | C—H |

TABLE 5-continued
| Compound | R³ | R⁴ | X³ |
|---|---|---|---|
| 758 |  | H | C—H |
| 759 | 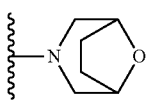 | H | C—H |
| 760 | —N(Et)Bn | H | C—H |
| 761 | —NHMe | —OMe | C—H |
| 762 | —NHMe | —Oi-Pr | C—H |
| 763 | —NH—NHi-Pr | —OMe | C—H |
| 764 | —NHi-Pr | —Oi-Pr | C—H |
| 765 | 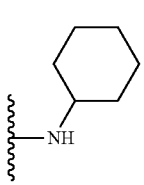 [SMILES: *NC1CCCCC1] | —OMe | C—H |
| 766 | 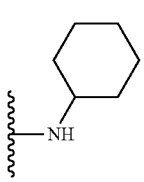 | —Oi-Pr | C—H |
| 767 | 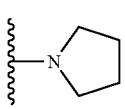 [SMILES: *N1CCCC1] | —OMe | C—H |
| 768 | 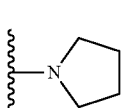 | —Oi-Pr | C—H |
| 769 | 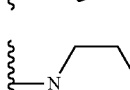 | —OMe | C—H |
| 770 | 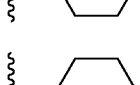 | —Oi-Pr | C—H |
| 771 | 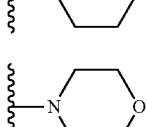 | —OMe | C—H |
| 772 | 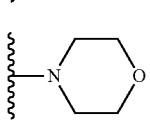 | —Oi-Pr | C—H |
| 773 | —NHMe | —NHMe | C—H |
| 774 | —NHMe | —NHi-Pr | C—H |
| 775 | —NHi-Pr | —NHMe | C—H |
| 776 | —NHi-Pr | —NHi-Pr | C—H |
| 777 | 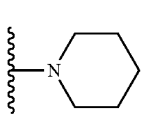 | —NHMe | C—H |

TABLE 5-continued
| Compound | R³ | R⁴ | X³ |
|---|---|---|---|
| 778 | 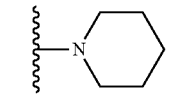 [SMILES: *N1CCCCC1] | —NHi-Pr | C—H |
| 779 | —NHMe | | C—H |
| 780 | 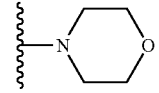 | —NHi-Pr | C—H |
| 781 | H | H | C—F |
| 782 | H | —Cl | C—F |
| 783 | H | —Br | C—F |
| 784 | H | 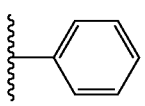 [SMILES: *c1ccccc1] | C—F |
| 785 | H | —OMe | C—F |
| 786 | H | —Oi-Pr | C—F |
| 787 | H | —NHMe | C—F |
| 788 | H | —NHi-Pr | C—F |
| 789 | H | 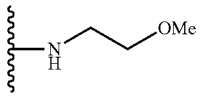 [SMILES: *NCCOC] | C—F |
| 790 | H | 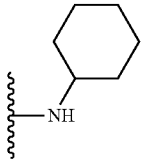 [SMILES: *NC1CCCCC1] | C—F |
| 791 | H | —N(CH₃)₂ | C—F |
| 792 | H | 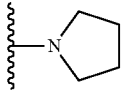 | C—F |
| 793 | H | 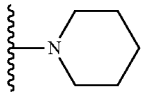 | C—F |
| 794 | H | 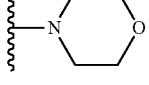 | C—F |
| 795 | H | 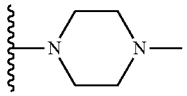 | C—F |
| 796 | H | 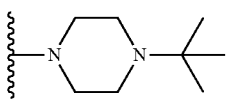 | C—F |
| 797 | H | 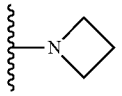 | C—F |

TABLE 5-continued
| Compound | R³ | R⁴ | X³ |
|---|---|---|---|
| 798 | H |  2-oxa-6-azaspiro[3.3]heptane | C—F |
| 799 | H | 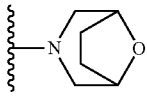 8-oxa-3-azabicyclo[3.2.1]octane | C—F |
| 800 | H | —N(Et)Bn | C—F |
| 801 | H | H | C—F |
| 802 | —Cl | H | C—F |
| 803 | —Br | H | C—F |
| 804 | 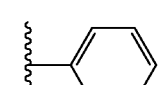 phenyl | H | C—F |
| 805 | —OMe | H | C—F |
| 806 | —Oi-Pr | H | C—F |
| 807 | —NHMe | H | C—F |
| 808 | —NHi-Pr | H | C—F |
| 809 | 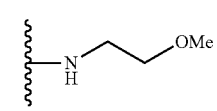 [SMILES: *NCCOC] —NHCH₂CH₂OMe | H | C—F |
| 810 | 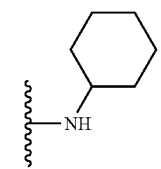 [SMILES: *NC1CCCCC1] cyclohexylamino | H | C—F |
| 811 | —N(CH₃)₂ | H | C—F |
| 812 | 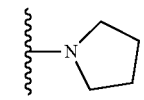 pyrrolidinyl | H | C—F |
| 813 | 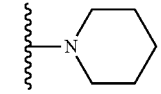 [SMILES: *N1CCCCC1] piperidinyl | H | C—F |
| 814 | 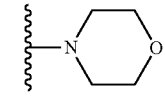 [SMILES: *N1CCOCC1] morpholinyl | H | C—F |
| 815 | 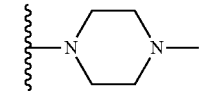 4-methylpiperazinyl | H | C—F |
| 816 | 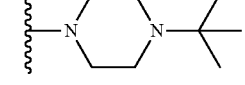 4-tert-butylpiperazinyl | H | C—F |
| 817 | 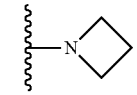 [SMILES: *N1CCC1] azetidinyl | H | C—F |

TABLE 5-continued
| Compound | R³ | R⁴ | X³ |
|---|---|---|---|
| 818 | 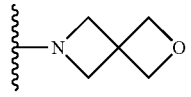 [SMILES: *N1CC2(COC2)C1] | H | C—F |
| 819 | 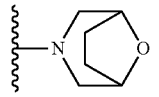 [SMILES: *N1CC2CCC(C1)O2] | H | C—F |
| 820 | —N(Et)Bn | H | C—F |
| 821 | —NHMe | —OMe | C—F |
| 822 | —NHMe | —Oi-Pr | C—F |
| 823 | —NHi-Pr | —OMe | C—F |
| 824 | —NHi-Pr | —Oi-Pr | C—F |
| 825 | 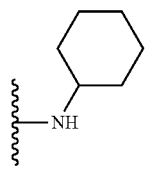 [SMILES: *NC1CCCCC1] | —OMe | C—F |
| 826 | 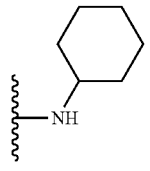 [SMILES: *NC1CCCCC1] | —Oi-Pr | C—F |
| 827 | 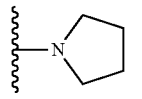 [SMILES: *N1CCCC1] | —OMe | C—F |
| 828 | 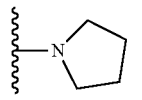 | —Oi-Pr | C—F |
| 829 | 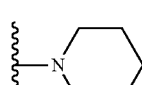 | —OMe | C—F |
| 830 | 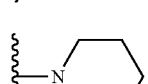 | —Oi-Pr | C—F |
| 831 | 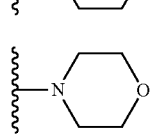 | —OMe | C—F |
| 832 | 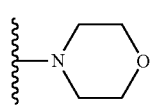 | —Oi-Pr | C—F |
| 833 | —NHMe | —NHMe | C—F |
| 834 | —NHMe | —NHi-Pr | C—F |
| 835 | —NHi-Pr | —NHMe | C—F |
| 836 | —NHi-Pr | —NHi-Pr | C—F |
| 837 | 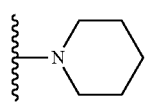 | —NHMe | C—F |

TABLE 5-continued
| Compound | R³ | R⁴ | X³ |
|---|---|---|---|
| 838 | 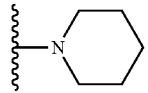 | —NHi-Pr | C—F |
| 839 | 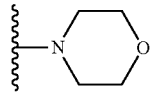 | —NHMe | C—F |
| 840 | 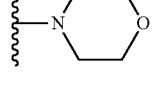 | —NHi-Pr | C—F |
| 841 | H | H | N |
| 842 | H | —Cl | N |
| 843 | H | —Br | N |
| 844 | H | 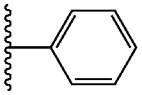 | N |
| 845 | H | —OMe | N |
| 846 | H | —Oi-Pr | N |
| 847 | H | —NHMe | N |
| 848 | H | —NHi-Pr | N |
| 849 | H | 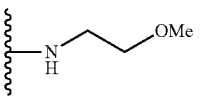 | N |
| 850 | H | 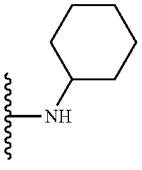 [SMILES: *NC1CCCCC1] | N |
| 851 | H | —N(CH₃)₂ | N |
| 852 | H | 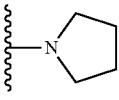 | N |
| 853 | H | 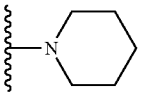 | N |
| 854 | H | 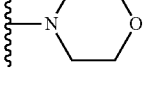 | N |
| 855 | H | 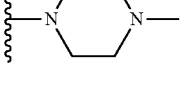 | N |
| 856 | H | 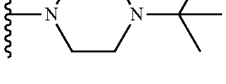 | N |

TABLE 5-continued
| Compound | R³ | R⁴ | X³ |
|---|---|---|---|
| 857 | H | 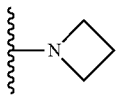 [SMILES: *N1CCC1] | N |
| 858 | H | 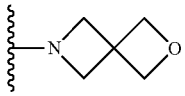 [SMILES: *N1CC2(COC2)C1] | N |
| 859 | H | 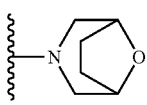 | N |
| 860 | H | —N(Et)Bn | N |
| 861 | H | H | N |
| 862 | —Cl | H | N |
| 863 | —Br | H | N |
| 864 | 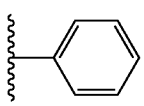 | H | N |
| 865 | —OMe | H | N |
| 866 | —Oi-Pr | H | N |
| 867 | —NHMe | H | N |
| 868 | —NHi-Pr | H | N |
| 869 | 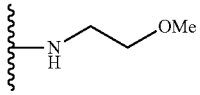 [SMILES: *NCCOC] | H | N |
| 870 | 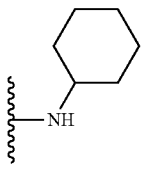 [SMILES: *NC1CCCCC1] | H | N |
| 871 | —N(CH₃)₂ | H | N |
| 872 | 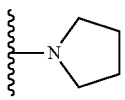 | H | N |
| 873 | 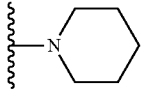 | H | N |
| 874 | 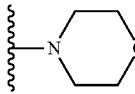 | H | N |
| 875 | 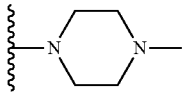 | H | N |
| 876 | 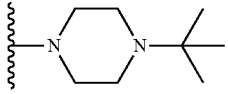 | H | N |

TABLE 5-continued
| Compound | R³ | R⁴ | X³ |
|---|---|---|---|
| 877 | 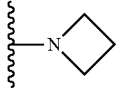 | H | N |
| 878 |  | H | N |
| 879 | 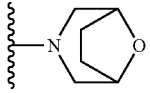 | H | N |
| 880 | —N(Et)Bn | H | N |
| 881 | —NHMe | —OMe | N |
| 882 | —NHMe | —Oi-Pr | N |
| 883 | —NHi-Pr | —OMe | N |
| 884 | —NHi-Pr | —Oi-Pr | N |
| 885 | 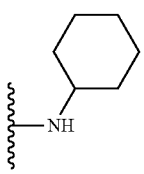 [SMILES: *NC1CCCCC1] | —OMe | N |
| 886 | 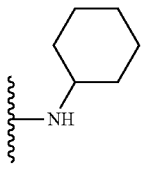 | —Oi-Pr | N |
| 887 | 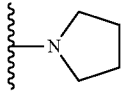 | —OMe | N |
| 888 | 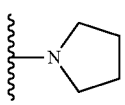 [SMILES: *N1CCCC1] | —Oi-Pr | N |
| 889 | 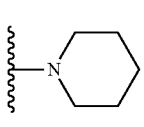 | —OMe | N |
| 890 | 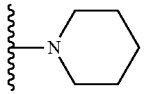 | —Oi-Pr | N |
| 891 | 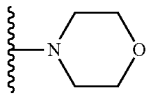 | —OMe | N |
| 892 | 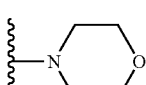 | —Oi-Pr | N |
| 893 | —NHMe | —NHMe | N |
| 894 | —NHMe | —NHi-Pr | N |
| 895 | —NHi-Pr | —NHMe | N |
| 896 | —NHi-Pr | —NHi-Pr | N |

TABLE 5-continued

| Compound | R³ | R⁴ | X³ |
|---|---|---|---|
| 897 | 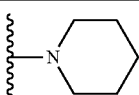 N-piperidinyl | —NHMe | N |
| 898 | 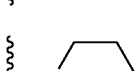 N-piperidinyl | —NHi-Pr | N |
| 899 | 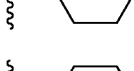 N-morpholinyl | —NHMe | N |
| 900 | 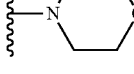 N-morpholinyl | —NHi-Pr | N |

In another embodiment of the invention, the compound of Formula I is represented by Formula XVIII or a pharmaceutically acceptable salt or ester thereof:

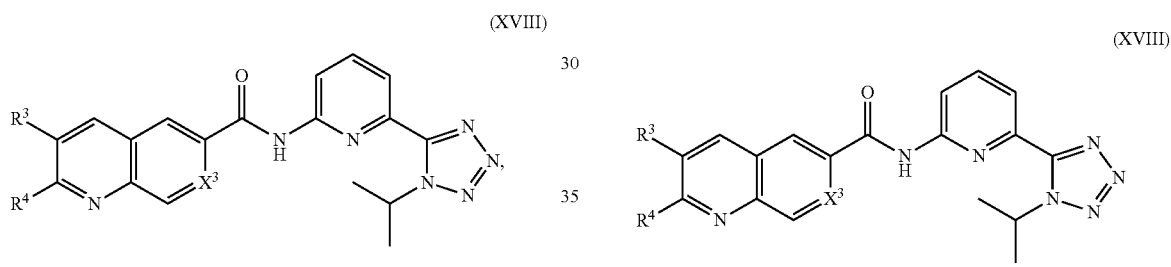

(XVIII)

wherein R³, R⁴, and X³ are as previously defined.

Representative compounds of the invention include, but are not limited to, the following compounds (compound 901 to compound 1080 in Table 6) according to Formula XVIII, and pharmaceutically acceptable salts thereof, wherein R³, R⁴, and X³ are delineated for each compound in Table 6.

TABLE 6

| Compound | R³ | R⁴ | X³ |
|---|---|---|---|
| 901 | H | H | C—H |
| 902 | H | —Cl | C—H |
| 903 | H | —Br | C—H |
| 904 | H | 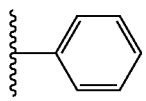 phenyl | C—H |
| 905 | H | —OMe | C—H |
| 906 | H | —Oi-Pr | C—H |
| 907 | H | —NHMe | C—H |
| 908 | H | —NHi-Pr | C—H |
| 909 | H | 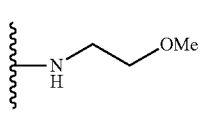 [SMILES: *NCCOC] —NH-CH₂CH₂-OMe | C—H |

TABLE 6-continued
| Compound | R³ | R⁴ | X³ |
|---|---|---|---|
| 910 | H | 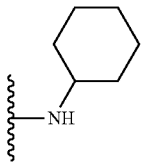 cyclohexyl-NH- | C—H |
| 911 | H | —N(CH₃)₂ | C—H |
| 912 | H | 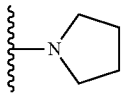 pyrrolidinyl | C—H |
| 913 | H | 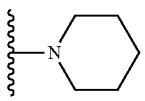 piperidinyl | C—H |
| 914 | H | 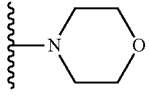 [SMILES: *N1CCOCC1] morpholinyl | C—H |
| 915 | H |  N-methylpiperazinyl | C—H |
| 916 | H | 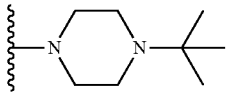 N-tert-butylpiperazinyl | C—H |
| 917 | H | 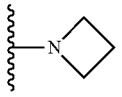 [SMILES: *N1CCC1] azetidinyl | C—H |
| 918 | H | 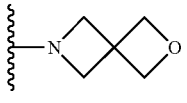 [SMILES: *N1CC2(COC2)C1] 2-oxa-6-azaspiro[3.3]heptanyl | C—H |
| 919 | H | 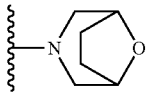 8-oxa-3-azabicyclo | C—H |
| 920 | H | —N(Et)Bn | C—H |
| 921 | H | H | C—H |
| 922 | —Cl | H | C—H |
| 923 | —Br | H | C—H |
| 924 | 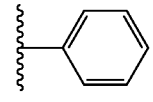 phenyl | H | C—H |
| 925 | —OMe | H | C—H |
| 926 | —Oi-Pr | H | C—H |
| 927 | —NHMe | H | C—H |
| 928 | —NHi-Pr | H | C—H |
| 929 | 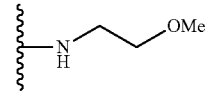 [SMILES: *NCCOC] —NH-CH₂CH₂-OMe | H | C—H |

TABLE 6-continued

| Compound | R³ | R⁴ | X³ |
|---|---|---|---|
| 930 | cyclohexyl-NH- | H | C—H |
| 931 | —N(CH₃)₂ | H | C—H |
| 932 | pyrrolidin-1-yl | H | C—H |
| 933 | piperidin-1-yl | H | C—H |
| 934 | morpholin-4-yl | H | C—H |
| 935 | 4-methylpiperazin-1-yl | H | C—H |
| 936 | 4-tert-butylpiperazin-1-yl | H | C—H |
| 937 | azetidin-1-yl | H | C—H |
| 938 | 2-oxa-6-azaspiro[3.3]heptan-6-yl | H | C—H |
| 939 | 8-oxa-3-azabicyclo[3.2.1]octan-3-yl | H | C—H |
| 940 | —N(Et)Bn | H | C—H |
| 941 | —NHMe | —OMe | C—H |
| 942 | —NHMe | —Oi-Pr | C—H |
| 943 | —NHi-Pr | —OMe | C—H |
| 944 | —NHi-Pr | —Oi-Pr | C—H |
| 945 | cyclohexyl-NH- | —OMe | C—H |
| 946 | cyclohexyl-NH- | —Oi-Pr | C—H |

TABLE 6-continued

| Compound | R³ | R⁴ | X³ |
| --- | --- | --- | --- |
| 947 | pyrrolidin-1-yl | —OMe | C—H |
| 948 | pyrrolidin-1-yl | —Oi-Pr | C—H |
| 949 | piperidin-1-yl | —OMe | C—H |
| 950 | piperidin-1-yl | —Oi-Pr | C—H |
| 951 | morpholin-4-yl | —OMe | C—H |
| 952 | morpholin-4-yl | —Oi-Pr | C—H |
| 953 | —NHMe | —NHMe | C—H |
| 954 | —NHMe | —NHi-Pr | C—H |
| 955 | —NHi-Pr | —NHMe | C—H |
| 956 | —NHi-Pr | —NHi-Pr | C—H |
| 957 | piperidin-1-yl | —NHMe | C—H |
| 958 | piperidin-1-yl | —NHi-Pr | C—H |
| 959 | morpholin-4-yl | —NHMe | C—H |
| 960 | morpholin-4-yl | —NHi-Pr | C—H |
| 961 | H | H | C—F |
| 962 | H | —Cl | C—F |
| 963 | H | —Br | C—F |
| 964 | H | phenyl | C—F |
| 965 | H | —OMe | C—F |
| 966 | H | —Oi-Pr | C—F |
| 967 | H | —NHMe | C—F |
| 968 | H | —NHi-Pr | C—F |

TABLE 6-continued
| Compound | R³ | R⁴ | X³ |
|---|---|---|---|
| 969 | H | 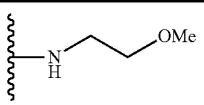 —NH—CH₂CH₂—OMe | C—F |
| 970 | H | 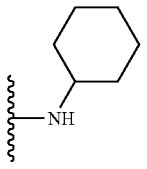 [SMILES: *NC1CCCCC1] —NH-cyclohexyl | C—F |
| 971 | H | —N(CH₃)₂ | C—F |
| 972 | H | 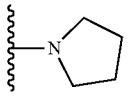 pyrrolidin-1-yl | C—F |
| 973 | H | 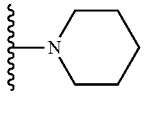 piperidin-1-yl | C—F |
| 974 | H | 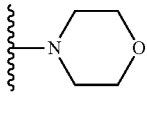 morpholin-4-yl | C—F |
| 975 | H | 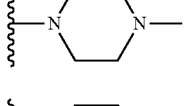 4-methylpiperazin-1-yl | C—F |
| 976 | H | 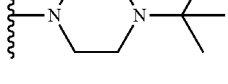 4-tert-butylpiperazin-1-yl | C—F |
| 977 | H | 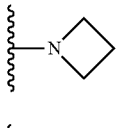 azetidin-1-yl | C—F |
| 978 | H | 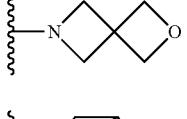 2-oxa-6-azaspiro[3.3]heptan-6-yl | C—F |
| 979 | H | 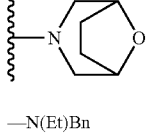 8-oxa-3-azabicyclo[3.2.1]octan-3-yl | C—F |
| 980 | H | —N(Et)Bn | C—F |
| 981 | H | H | C—F |
| 982 | —Cl | H | C—F |
| 983 | —Br | H | C—F |
| 984 | 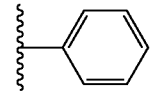 phenyl | H | C—F |
| 985 | —OMe | H | C—F |
| 986 | —Oi-Pr | H | C—F |
| 987 | —NHMe | H | C—F |
| 988 | —NHi-Pr | H | C—F |

TABLE 6-continued

| Compound | R³ | R⁴ | X³ |
|---|---|---|---|
| 989 | -NH-CH₂CH₂-OMe | H | C—F |
| 990 | -NH-cyclohexyl | H | C—F |
| 991 | —N(CH₃)₂ | H | C—F |
| 992 | -N-pyrrolidinyl | H | C—F |
| 993 | -N-piperidinyl | H | C—F |
| 994 | -N-morpholinyl | H | C—F |
| 995 | -N-(4-methylpiperazinyl) | H | C—F |
| 996 | -N-(4-tert-butylpiperazinyl) | H | C—F |
| 997 | -N-azetidinyl | H | C—F |
| 998 | -N-(2-oxa-6-azaspiro[3.3]heptanyl) | H | C—F |
| 999 | -N-(8-oxa-3-azabicyclo[3.2.1]octanyl) | H | C—F |
| 1000 | —N(Et)Bn | H | C—F |
| 1001 | —NHMe | —OMe | C—F |
| 1002 | —NHMe | —Oi-Pr | C—F |
| 1003 | —NHi-Pr | —OMe | C—F |
| 1004 | —NHi-Pr | —Oi-Pr | C—F |
| 1005 | -NH-cyclohexyl | —OMe | C—F |

TABLE 6-continued

| Compound | R³ | R⁴ | X³ |
|---|---|---|---|
| 1006 | cyclohexyl-NH- | —Oi-Pr | C—F |
| 1007 | pyrrolidin-1-yl | —OMe | C—F |
| 1008 | pyrrolidin-1-yl | —Oi-Pr | C—F |
| 1009 | piperidin-1-yl | —OMe | C—F |
| 1010 | piperidin-1-yl | —Oi-Pr | C—F |
| 1011 | morpholin-4-yl | —OMe | C—F |
| 1012 | morpholin-4-yl | —Oi-Pr | C—F |
| 1013 | —NHMe | —NHMe | C—F |
| 1014 | —NHMe | —NHi-Pr | C—F |
| 1015 | —NHi-Pr | —NHMe | C—F |
| 1016 | —NHi-Pr | —NHi-Pr | C—F |
| 1017 | piperidin-1-yl | —NHMe | C—F |
| 1018 | piperidin-1-yl | —NHi-Pr | C—F |
| 1019 | morpholin-4-yl | —NHMe | C—F |
| 1020 | morpholin-4-yl | —NHi-Pr | C—F |
| 1021 | H | H | N |
| 1022 | H | —Cl | N |
| 1023 | H | —Br | N |
| 1024 | H | phenyl | N |

TABLE 6-continued

| Compound | R³ | R⁴ | X³ |
|---|---|---|---|
| 1025 | H | —OMe | N |
| 1026 | H | —Oi-Pr | N |
| 1027 | H | —NHMe | N |
| 1028 | H | —NHi-Pr | N |
| 1029 | H | ![NH-CH2CH2-OMe] | N |
| 1030 | H | ![NH-cyclohexyl] | N |
| 1031 | H | —N(CH₃)₂ | N |
| 1032 | H | ![pyrrolidinyl] | N |
| 1033 | H | ![piperidinyl] | N |
| 1034 | H | ![morpholinyl] | N |
| 1035 | H | ![N-methylpiperazinyl] | N |
| 1036 | H | ![N-tert-butylpiperazinyl] | N |
| 1037 | H | ![azetidinyl] | N |
| 1038 | H | ![2-oxa-6-azaspiro[3.3]heptyl] | N |
| 1039 | H | ![8-oxa-3-azabicyclo[3.2.1]octyl] | N |
| 1040 | H | —N(Et)Bn | N |
| 1041 | H | H | N |
| 1042 | —Cl | H | N |
| 1043 | —Br | H | N |
| 1044 | H | | N |
| 1045 | —OMe | H | N |
| 1046 | —Oi-Pr | H | N |
| 1047 | —NHMe | H | N |
| 1048 | —NHi-Pr | H | N |

TABLE 6-continued

| Compound | R³ | R⁴ | X³ |
|---|---|---|---|
| 1049 | -NH-CH₂CH₂-OMe | H | N |
| 1050 | -NH-cyclohexyl | H | N |
| 1051 | —N(CH₃)₂ | H | N |
| 1052 | -N-pyrrolidinyl | H | N |
| 1053 | -N-piperidinyl | H | N |
| 1054 | -N-morpholinyl | H | N |
| 1055 | -N-(4-methylpiperazinyl) | H | N |
| 1056 | -N-(4-tert-butylpiperazinyl) | H | N |
| 1057 | -N-azetidinyl | H | N |
| 1058 | -N-(2-oxa-6-azaspiro[3.3]heptyl) | H | N |
| 1059 | -N-(8-oxa-3-azabicyclo[3.2.1]octyl) | H | N |
| 1060 | —N(Et)Bn | H | N |
| 1061 | —NHMe | —OMe | N |
| 1062 | —NHMe | —Oi-Pr | N |
| 1063 | —NHi-Pr | —OMe | N |
| 1064 | —NHi-Pr | —Oi-Pr | N |
| 1065 | -NH-cyclohexyl | —OMe | N |

TABLE 6-continued
| Compound | R³ | R⁴ | X³ |
|---|---|---|---|
| 1066 | 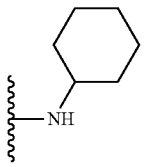 [SMILES: *NC1CCCCC1] cyclohexyl-NH- | —Oi-Pr | N |
| 1067 | 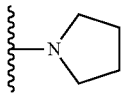 [SMILES: *N1CCCC1] pyrrolidin-1-yl | —OMe | N |
| 1068 | 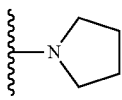 [SMILES: *N1CCCC1] pyrrolidin-1-yl | —Oi-Pr | N |
| 1069 | 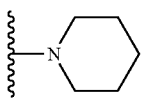 piperidin-1-yl | —OMe | N |
| 1070 | 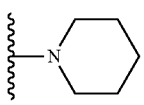 [SMILES: *N1CCCCC1] piperidin-1-yl | —Oi-Pr | N |
| 1071 | 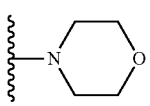 morpholin-4-yl | —OMe | N |
| 1072 | 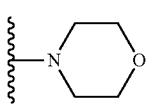 morpholin-4-yl | —Oi-Pr | N |
| 1073 | —NHMe | —NHMe | N |
| 1074 | —NHMe | —NHi-Pr | N |
| 1075 | —NHi-Pr | —NHMe | N |
| 1076 | —NHi-Pr | —NHi-Pr | N |
| 1077 | 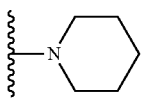 [SMILES: *N1CCCCC1] piperidin-1-yl | —NHMe | N |
| 1078 | 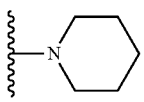 [SMILES: *N1CCCCC1] piperidin-1-yl | —NHi-Pr | N |
| 1079 | 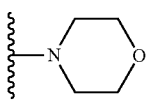 morpholin-4-yl | —NHMe | N |
| 1080 | 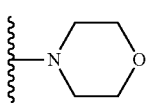 morpholin-4-yl | —NHi-Pr | N |

In certain embodiments, the compound of Formula I is represented by Formula XIX or a pharmaceutically acceptable salt or ester thereof:

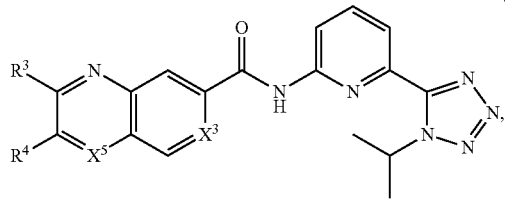
(XIX)

wherein $R^3$, $R^4$, $X^3$, and $X^5$ are as previously defined.

In certain embodiments, the compound of Formula I is represented by Formula XX or a pharmaceutically acceptable salt or ester thereof:

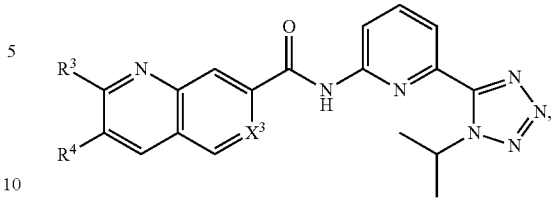
(XX)

wherein $R^3$, $R^4$, and $X^3$ are as previously defined.

Representative compounds of the invention include, but are not limited to, the following compounds (compound 1081 to compound 1260 in Table 7) according to Formula XX, and pharmaceutically acceptable salts thereof, wherein $R^3$, $R^4$, and $X^3$ are delineated for each compound in Table 7.

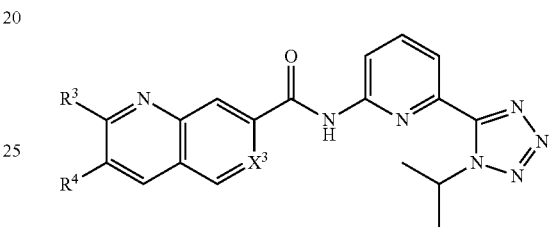
(XX)

TABLE 7

| Compound | $R^3$ | $R^4$ | $X^3$ |
|---|---|---|---|
| 1081 | H | H | C—H |
| 1082 | H | —Cl | C—H |
| 1083 | H | —Br | C—H |
| 1084 | H | ![phenyl] | C—H |
| 1085 | H | —OMe | C—H |
| 1086 | H | —Oi-Pr | C—H |
| 1087 | H | —NHMe | C—H |
| 1088 | H | —NHi-Pr | C—H |
| 1089 | H | —NH-CH₂CH₂-OMe | C—H |
| 1090 | H | —NH-cyclohexyl | C—H |
| 1091 | H | —N(CH₃)₂ | C—H |
| 1092 | H | —N-pyrrolidinyl | C—H |
| 1093 | H | —N-piperidinyl | C—H |

TABLE 7-continued
| Compound | R³ | R⁴ | X³ |
|---|---|---|---|
| 1094 | H | 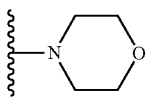 morpholine | C—H |
| 1095 | H |  N-methylpiperazine | C—H |
| 1096 | H | 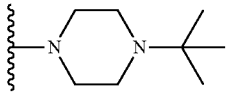 N-tert-butylpiperazine | C—H |
| 1097 | H | 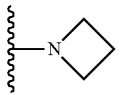 azetidine | C—H |
| 1098 | H | 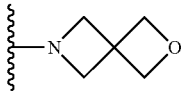 [SMILES: *N1CC2(COC2)C1] 2-oxa-6-azaspiro[3.3]heptane | C—H |
| 1099 | H | 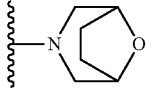 8-oxa-3-azabicyclo[3.2.1]octane | C—H |
| 1100 | H | —N(Et)Bn | C—H |
| 1101 | H | H | C—H |
| 1102 | —Cl | H | C—H |
| 1103 | —Br | H | C—H |
| 1104 | 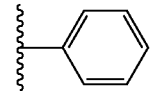 phenyl | H | C—H |
| 1105 | —OMe | H | C—H |
| 1106 | —Oi-Pr | H | C—H |
| 1107 | —NHMe | H | C—H |
| 1108 | —NHi-Pr | H | C—H |
| 1109 | 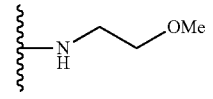 [SMILES: *NCCOC] —NH-CH₂CH₂-OMe | H | C—H |
| 1110 | 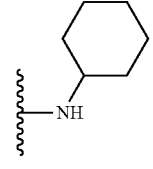 [SMILES: *NC1CCCCC1] cyclohexyl-NH | H | C—H |
| 1111 | —N(CH₃)₂ | H | C—H |
| 1112 | 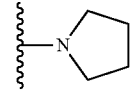 [SMILES: *N1CCCC1] pyrrolidine | H | C—H |
| 1113 | 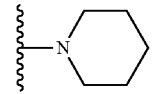 piperidine | H | C—H |

TABLE 7-continued
| Compound | R³ | R⁴ | X³ |
|---|---|---|---|
| 1114 | 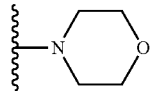 | H | C—H |
| 1115 | 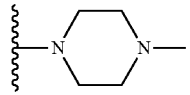 | H | C—H |
| 1116 | 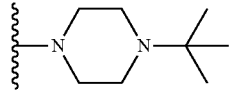 | H | C—H |
| 1117 | 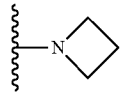 [SMILES: *N1CCC1] | H | C—H |
| 1118 |  | H | C—H |
| 1119 | 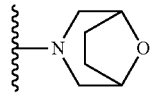 | H | C—H |
| 1120 | —N(Et)Bn | H | C—H |
| 1121 | —NHMe | —OMe | C—H |
| 1122 | —NHMe | —Oi-Pr | C—H |
| 1123 | —NHi-Pr | —OMe | C—H |
| 1124 | —NHi-Pr | —Oi-Pr | C—H |
| 1125 | 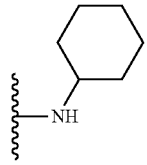 [SMILES: *NC1CCCCC1] | —OMe | C—H |
| 1126 | 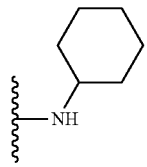 [SMILES: *NC1CCCCC1] | —Oi-Pr | C—H |
| 1127 | 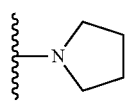 [SMILES: *N1CCCC1] | —OMe | C—H |
| 1128 | 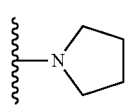 | —Oi-Pr | C—H |
| 1129 | 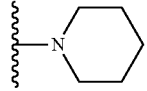 [SMILES: *N1CCCCC1] | —OMe | C—H |
| 1130 | 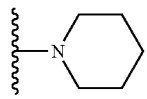 | —Oi-Pr | C—H |

TABLE 7-continued
| Compound | R³ | R⁴ | X³ |
|---|---|---|---|
| 1131 | 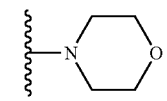 | —OMe | C—H |
| 1132 | 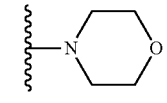 | —Oi-Pr | C—H |
| 1133 | —NHMe | —NHMe | C—H |
| 1134 | —NHMe | —NHi-Pr | C—H |
| 1135 | —NHi-Pr | —NHMe | C—H |
| 1136 | —NHi-Pr | —NHi-Pr | C—H |
| 1137 | 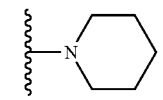 | —NHMe | C—H |
| 1138 | 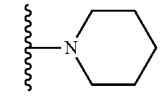 | —NHi-Pr | C—H |
| 1139 | 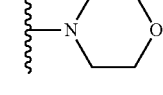 | —NHMe | C—H |
| 1140 | 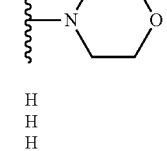 | —NHi-Pr | C—H |
| 1141 | H | H | C—F |
| 1142 | H | —Cl | C—F |
| 1143 | H | —Br | C—F |
| 1144 | H | 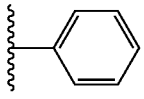 [SMILES: *c1ccccc1] | C—F |
| 1145 | H | —OMe | C—F |
| 1146 | H | —Oi-Pr | C—F |
| 1147 | H | —NHMe | C—F |
| 1148 | H | —NHi-Pr | C—F |
| 1149 | H | 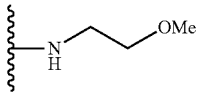 [SMILES: *NCCOC] | C—F |
| 1150 | H | 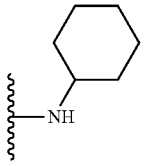 | C—F |
| 1151 | H | —N(CH₃)₂ | C—F |
| 1152 | H | 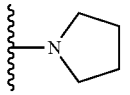 [SMILES: *N1CCCC1] | C—F |
| 1153 | H | 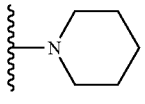 | C—F |

US 10,253,018 B2
135
136
TABLE 7-continued
| Compound | R³ | R⁴ | X³ |
|---|---|---|---|
| 1154 | H | 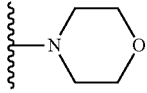 | C—F |
| 1155 | H | 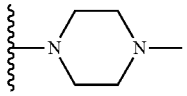 [SMILES: *N1CCN(C)CC1] | C—F |
| 1156 | H | 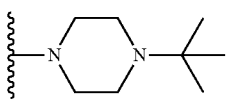 | C—F |
| 1157 | H | 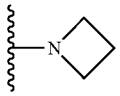 | C—F |
| 1158 | H |  | C—F |
| 1159 | H | 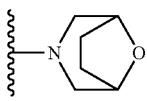 [SMILES: *N1CC2CCC(C1)O2] | C—F |
| 1160 | H | —N(Et)Bn | C—F |
| 1161 | H | H | C—F |
| 1162 | —Cl | H | C—F |
| 1163 | —Br | H | C—F |
| 1164 | 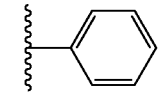 | H | C—F |
| 1165 | —OMe | H | C—F |
| 1166 | —Oi-Pr | H | C—F |
| 1167 | —NHMe | H | C—F |
| 1168 | —NHi-Pr | H | C—F |
| 1169 | 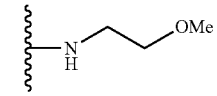 [SMILES: *NCCOC] | H | C—F |
| 1170 | 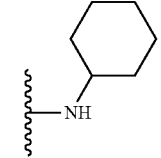 [SMILES: *NC1CCCCC1] | H | C—F |
| 1171 | —N(CH₃)₂ | H | C—F |
| 1172 | 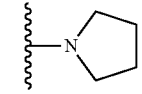 | H | C—F |
| 1173 | 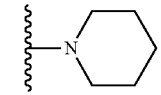 | H | C—F |

TABLE 7-continued
| Compound | R³ | R⁴ | X³ |
|---|---|---|---|
| 1174 | 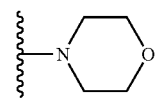 | H | C—F |
| 1175 | 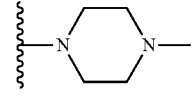 | H | C—F |
| 1176 | 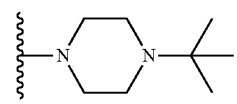 | H | C—F |
| 1177 | 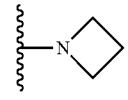 [SMILES: *N1CCC1] | H | C—F |
| 1178 | 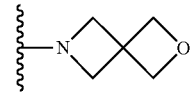 | H | C—F |
| 1179 | 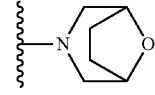 [SMILES: *N1CC2CCC(C1)O2] | H | C—F |
| 1180 | —N(Et)Bn | H | C—F |
| 1181 | —NHMe | —OMe | C—F |
| 1182 | —NHMe | —Oi-Pr | C—F |
| 1183 | —NHi-Pr | —OMe | C—F |
| 1184 | —NHi-Pr | —Oi-Pr | C—F |
| 1185 | 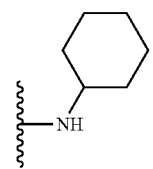 [SMILES: *NC1CCCCC1] | —OMe | C—F |
| 1186 | 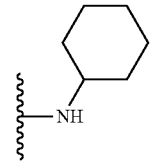 [SMILES: *NC1CCCCC1] | —Oi-Pr | C—F |
| 1187 | 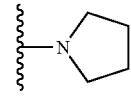 [SMILES: *N1CCCC1] | —OMe | C—F |
| 1188 | 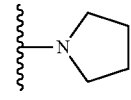 [SMILES: *N1CCCC1] | —Oi-Pr | C—F |
| 1189 | 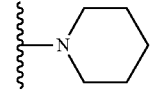 | —OMe | C—F |
| 1190 | 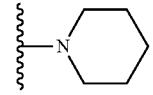 | —Oi-Pr | C—F |

TABLE 7-continued

| Compound | R³ | R⁴ | X³ |
|---|---|---|---|
| 1191 | morpholin-4-yl (N-linked) | —OMe | C—F |
| 1192 | morpholin-4-yl (N-linked) | —Oi-Pr | C—F |
| 1193 | —NHMe | —NHMe | C—F |
| 1194 | —NHMe | —NHi-Pr | C—F |
| 1195 | —NHi-Pr | —NHMe | C—F |
| 1196 | —NHi-Pr | —NHi-Pr | C—F |
| 1197 | piperidin-1-yl | —NHMe | C—F |
| 1198 | piperidin-1-yl | —NHi-Pr | C—F |
| 1199 | morpholin-4-yl (N-linked) | —NHMe | C—F |
| 1200 | morpholin-4-yl (N-linked) | —NHi-Pr | C—F |
| 1201 | H | H | N |
| 1202 | H | —Cl | N |
| 1203 | H | —Br | N |
| 1204 | H | phenyl | N |
| 1205 | H | —OMe | N |
| 1206 | H | —Oi-Pr | N |
| 1207 | H | —NHMe | N |
| 1208 | H | —NHi-Pr | N |
| 1209 | H | —NH-CH₂CH₂-OMe | N |
| 1210 | H | cyclohexyl-NH— | N |
| 1211 | H | —N(CH₃)₂ | N |
| 1212 | H | pyrrolidin-1-yl | N |
| 1213 | H | piperidin-1-yl | N |

TABLE 7-continued
| Compound | R³ | R⁴ | X³ |
|---|---|---|---|
| 1214 | H | 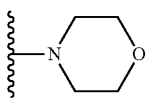 | N |
| 1215 | H | 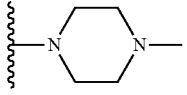 | N |
| 1216 | H | 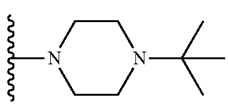 | N |
| 1217 | H | 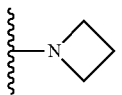 | N |
| 1218 | H | 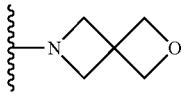 [SMILES: *N1CC2(COC2)C1] | N |
| 1219 | H | 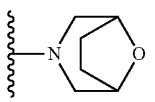 | N |
| 1220 | H | —N(Et)Bn | N |
| 1221 | H | H | N |
| 1222 | —Cl | H | N |
| 1223 | —Br | H | N |
| 1224 | 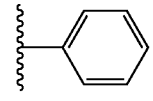 | H | N |
| 1225 | —OMe | H | N |
| 1226 | —Oi-Pr | H | N |
| 1227 | —NHMe | H | N |
| 1228 | —NHi-Pr | H | N |
| 1229 | 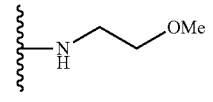 [SMILES: *NCCOC] | H | N |
| 1230 | 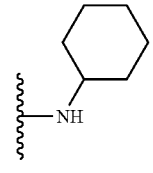 [SMILES: *NC1CCCCC1] | H | N |
| 1231 | —N(CH₃)₂ | H | N |
| 1232 | 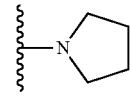 | H | N |
| 1233 | 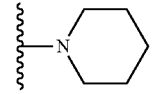 | H | N |

TABLE 7-continued
| Compound | R³ | R⁴ | X³ |
|---|---|---|---|
| 1234 | 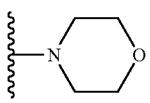 | H | N |
| 1235 | 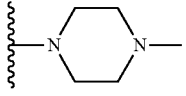 [SMILES: *N1CCN(C)CC1] | H | N |
| 1236 | 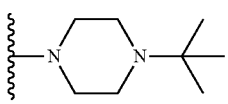 | H | N |
| 1237 | 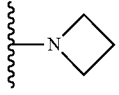 [SMILES: *N1CCC1] | H | N |
| 1238 | 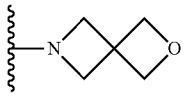 [SMILES: *N1CC2(COC2)C1] | H | N |
| 1239 | 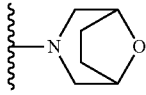 | H | N |
| 1240 | —N(Et)Bn | H | N |
| 1241 | —NHMe | —OMe | N |
| 1242 | —NHMe | —Oi-Pr | N |
| 1243 | —NHi-Pr | —OMe | N |
| 1244 | —NHi-Pr | —Oi-Pr | N |
| 1245 | 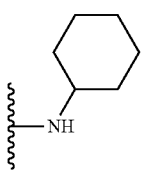 [SMILES: *NC1CCCCC1] | —OMe | N |
| 1246 | 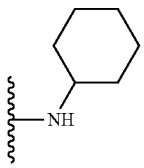 [SMILES: *NC1CCCCC1] | —Oi-Pr | N |
| 1247 | 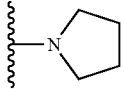 [SMILES: *N1CCCC1] | —OMe | N |
| 1248 | 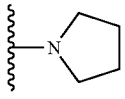 [SMILES: *N1CCCC1] | —Oi-Pr | N |
| 1249 | 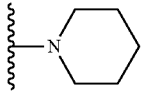 [SMILES: *N1CCCCC1] | —OMe | N |
| 1250 | 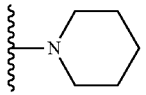 | —Oi-Pr | N |

TABLE 7-continued

| Compound | R³ | R⁴ | X³ |
|---|---|---|---|
| 1251 | 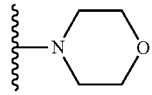 [SMILES: *N1CCOCC1] N-morpholine | —OMe | N |
| 1252 | N-morpholine | —Oi-Pr | N |
| 1253 | —NHMe | —NHMe | N |
| 1254 | —NHMe | —NHi-Pr | N |
| 1255 | —NHi-Pr | —NHMe | N |
| 1256 | —NHi-Pr | —NHi-Pr | N |
| 1257 | N-piperidine | —NHMe | N |
| 1258 | N-piperidine | —NHi-Pr | N |
| 1259 | N-morpholine | —NHMe | N |
| 1260 | N-morpholine | —NHi-Pr | N |

In certain embodiments, the compound of Formula I is represented by Formula XXI or a pharmaceutically acceptable salt or ester thereof:

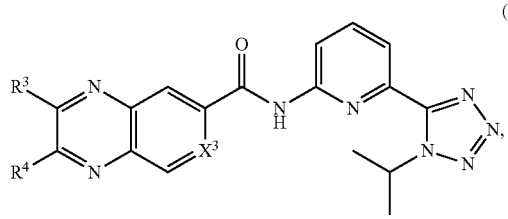

(XXI)

wherein R³, R⁴, and X³ are as previously defined.

Representative compounds of the invention include, but are not limited to, the following compounds (compound 1261 to compound 1440 in Table 8) according to Formula XXI, and pharmaceutically acceptable salts thereof, wherein R³, R⁴, and X³ are delineated for each compound in Table 8.

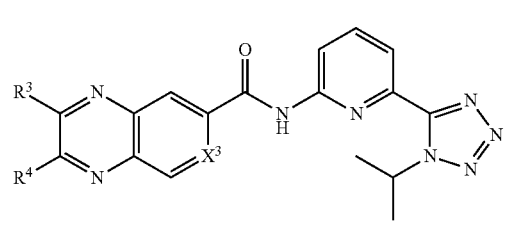

(XXI)

TABLE 8

| Compound | R³ | R⁴ | X³ |
|---|---|---|---|
| 1261 | H | H | C—H |
| 1262 | H | —Cl | C—H |
| 1263 | H | —Br | C—H |
| 1264 | H | phenyl | C—H |
| 1265 | H | OMe | C—H |
| 1266 | H | —Oi-Pr | C—H |
| 1267 | H | —NHMe | C—H |
| 1268 | H | —NHi-Pr | C—H |
| 1269 | H | —NH-CH₂CH₂-OMe | C—H |
| 1270 | H | —NH-cyclohexyl | C—H |
| 1271 | H | —N(CH₃)₂ | C—H |

TABLE 8-continued

| Compound | R³ | R⁴ | X³ |
|---|---|---|---|
| 1272 | H | 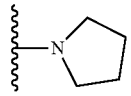 pyrrolidin-1-yl | C—H |
| 1273 | H | 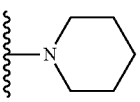 piperidin-1-yl | C—H |
| 1274 | H | 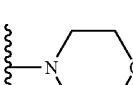 morpholin-4-yl | C—H |
| 1275 | H | 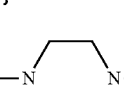 4-methylpiperazin-1-yl | C—H |
| 1276 | H | 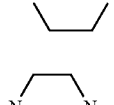 4-tert-butylpiperazin-1-yl | C—H |
| 1277 | H | 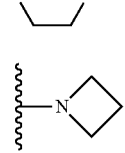 azetidin-1-yl | C—H |
| 1278 | H |  2-oxa-6-azaspiro[3.3]heptan-6-yl | C—H |
| 1279 | H | 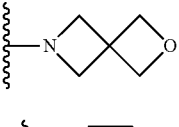 8-oxa-3-azabicyclo[3.2.1]octan-3-yl | C—H |
| 1280 | H | —N(Et)Bn | C—H |
| 1281 | H | H | C—H |
| 1282 | —Cl | H | C—H |
| 1283 | —Br | H | C—H |
| 1284 | 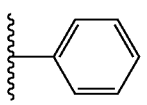 phenyl | H | C—H |
| 1285 | —OMe | H | C—H |
| 1286 | —Oi-Pr | H | C—H |
| 1287 | —NHMe | H | C—H |
| 1288 | —NHi-Pr | H | C—H |
| 1289 | 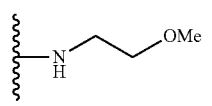 —NH(CH₂)₂OMe | H | C—H |
| 1290 | 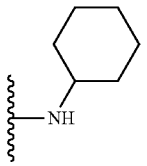 cyclohexylamino | H | C—H |
| 1291 | —N(CH₃)₂ | H | C—H |
| 1292 |  | H | C—H |
| 1293 |  | H | C—H |
| 1294 |  | H | C—H |
| 1295 |  | H | C—H |
| 1296 |  | H | C—H |
| 1297 |  | H | C—H |
| 1298 |  | H | C—H |
| 1299 |  | H | C—H |
| 1300 | —N(Et)Bn | H | C—H |
| 1301 | —NHMe | —OMe | C—H |
| 1302 | —NHMe | —Oi-Pr | C—H |
| 1303 | —NHi-Pr | —OMe | C—H |
| 1304 | —NHi-Pr | —Oi-Pr | C—H |
| 1305 | 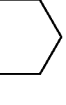 | —OMe | C—H |
| 1306 |  | —Oi-Pr | C—H |
| 1307 |  | —OMe | C—H |
| 1308 |  | —Oi-Pr | C—H |

TABLE 8-continued

| Compound | R³ | R⁴ | X³ |
|---|---|---|---|
| 1309 | piperidin-1-yl | —OMe | C—H |
| 1310 | piperidin-1-yl | —Oi-Pr | C—H |
| 1311 | morpholin-4-yl | —OMe | C—H |
| 1312 | morpholin-4-yl | —Oi-Pr | C—H |
| 1313 | —NHMe | —NHMe | C—H |
| 1314 | —NHMe | —NHi-Pr | C—H |
| 1315 | —NHi-Pr | —NHMe | C—H |
| 1316 | —NHi-Pr | —NHi-Pr | C—H |
| 1317 | piperidin-1-yl | —NHMe | C—H |
| 1318 | piperidin-1-yl | —NHi-Pr | C—H |
| 1319 | morpholin-4-yl | —NHMe | C—H |
| 1320 | morpholin-4-yl | —NHi-Pr | C—H |
| 1321 | H | H | C—F |
| 1322 | H | —Cl | C—F |
| 1323 | H | —Br | C—F |
| 1324 | H | phenyl | C—F |
| 1325 | H | —OMe | C—F |
| 1326 | H | —Oi-Pr | C—F |
| 1327 | H | —NHMe | C—F |
| 1328 | H | —NHi-Pr | C—F |
| 1329 | H | —NH-CH₂CH₂-OMe | C—F |
| 1330 | H | cyclohexyl-NH— | C—F |
| 1331 | H | —N(CH₃)₂ | C—F |
| 1332 | H | pyrrolidin-1-yl | C—F |
| 1333 | H | piperidin-1-yl | C—F |
| 1334 | H | morpholin-4-yl | C—F |
| 1335 | H | 4-methylpiperazin-1-yl | C—F |
| 1336 | H | 4-tert-butylpiperazin-1-yl | C—F |
| 1337 | H | azetidin-1-yl | C—F |
| 1338 | H | 2-oxa-6-azaspiro[3.3]heptan-6-yl | C—F |
| 1339 | H | 8-oxa-3-azabicyclo[3.2.1]octan-3-yl | C—F |
| 1340 | H | —N(Et)Bn | C—F |
| 1341 | H | H | C—F |
| 1342 | —Cl | H | C—F |
| 1343 | —Br | H | C—F |
| 1344 | phenyl | H | C—F |
| 1345 | —OMe | H | C—F |
| 1346 | —Oi-Pr | H | C—F |
| 1347 | —NHMe | H | C—F |
| 1348 | —NHi-Pr | H | C—F |
| 1349 | —NH-CH₂CH₂-OMe | H | C—F |
| 1350 | cyclohexyl-NH— | H | C—F |
| 1351 | —N(CH₃)₂ | H | C—F |

TABLE 8-continued

| Compound | R³ | R⁴ | X³ |
|---|---|---|---|
| 1352 | pyrrolidin-1-yl | H | C—F |
| 1353 | piperidin-1-yl | H | C—F |
| 1354 | morpholin-4-yl | H | C—F |
| 1355 | 4-methylpiperazin-1-yl | H | C—F |
| 1356 | 4-tert-butylpiperazin-1-yl | H | C—F |
| 1357 | azetidin-1-yl | H | C—F |
| 1358 | 2-oxa-6-azaspiro[3.3]heptan-6-yl | H | C—F |
| 1359 | 8-oxa-3-azabicyclo[3.2.1]octan-3-yl | H | C—F |
| 1360 | —N(Et)Bn | H | C—F |
| 1361 | —NHMe | —OMe | C—F |
| 1362 | —NHMe | —Oi-Pr | C—F |
| 1363 | —NHi-Pr | —OMe | C—F |
| 1364 | —NHi-Pr | —Oi-Pr | C—F |
| 1365 | cyclohexyl-NH— | —OMe | C—F |
| 1366 | cyclohexyl-NH— | —Oi-Pr | C—F |
| 1367 | pyrrolidin-1-yl | —OMe | C—F |
| 1368 | pyrrolidin-1-yl | —Oi-Pr | C—F |
| 1369 | piperidin-1-yl | —OMe | C—F |
| 1370 | piperidin-1-yl | —Oi-Pr | C—F |
| 1371 | morpholin-4-yl | —OMe | C—F |
| 1372 | morpholin-4-yl | —Oi-Pr | C—F |
| 1373 | —NHMe | —NHMe | C—F |
| 1374 | —NHMe | —NHi-Pr | C—F |
| 1375 | —NHi-Pr | —NHMe | C—F |
| 1376 | —NHi-Pr | —NHi-Pr | C—F |
| 1377 | piperidin-1-yl | —NHMe | C—F |
| 1378 | piperidin-1-yl | —NHi-Pr | C—F |
| 1379 | morpholin-4-yl | —NHMe | C—F |
| 1380 | morpholin-4-yl | —NHi-Pr | C—F |
| 1381 | H | H | N |
| 1382 | H | —Cl | N |
| 1383 | H | —Br | N |
| 1384 | H | phenyl | N |
| 1385 | H | —OMe | N |
| 1386 | H | —Oi-Pr | N |
| 1387 | H | —NHMe | N |
| 1388 | H | —NHi-Pr | N |
| 1389 | H | —NH-CH₂CH₂-OMe | N |
| 1390 | H | cyclohexyl-NH— | N |

TABLE 8-continued
| Compound | R³ | R⁴ | X³ |
|---|---|---|---|
| 1391 | H | —N(CH₃)₂ | N |
| 1392 | H | 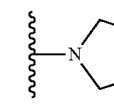 | N |
| 1393 | H | 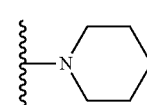 | N |
| 1394 | H | 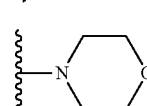 | N |
| 1395 | H | 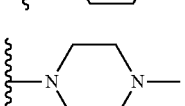 | N |
| 1396 | H | 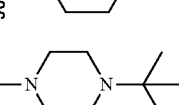 | N |
| 1397 | H | 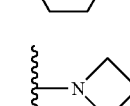 | N |
| 1398 | H | 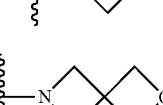 | N |
| 1399 | H | 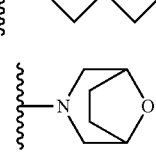 | N |
| 1400 | H | —N(Et)Bn | N |
| 1401 | H | H | N |
| 1402 | —Cl | H | N |
| 1403 | —Br | H | N |
| 1404 | 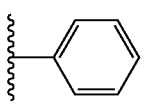 [SMILES: *c1ccccc1] | H | N |
| 1405 | —OMe | H | N |
| 1406 | —Oi-Pr | H | N |
| 1407 | —NHMe | H | N |
| 1408 | —NHi-Pr | H | N |
| 1409 | 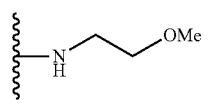 [SMILES: *NCCOC] | H | N |
| 1410 | 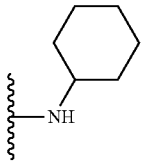 [SMILES: *NC1CCCCC1] | H | N |
| 1411 | —N(CH₃)₂ | H | N |
TABLE 8-continued
| Compound | R³ | R⁴ | X³ |
|---|---|---|---|
| 1412 |  | H | N |
| 1413 | 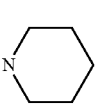 | H | N |
| 1414 | 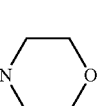 | H | N |
| 1415 | 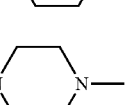 | H | N |
| 1416 | 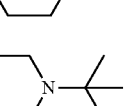 | H | N |
| 1417 | 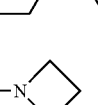 | H | N |
| 1418 | 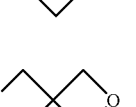 | H | N |
| 1419 |  | H | N |
| 1420 | —N(Et)Bn | H | N |
| 1421 | —NHMe | —OMe | N |
| 1422 | —NHMe | —Oi-Pr | N |
| 1423 | —NHi-Pr | —OMe | N |
| 1424 | —NHi-Pr | —Oi-Pr | N |
| 1425 | 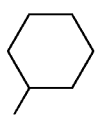 | —OMe | N |
| 1426 | 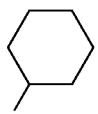 | —Oi-Pr | N |
| 1427 |  | —OMe | N |
| 1428 |  | —Oi-Pr | N |

TABLE 8-continued

| Compound | R³ | R⁴ | X³ |
|---|---|---|---|
| 1429 | 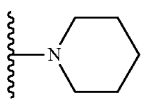 | —OMe | N |
| 1430 | 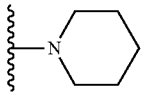 | —Oi-Pr | N |
| 1431 | 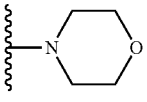 | —OMe | N |
| 1432 | 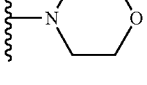 | —Oi-Pr | N |
| 1433 | —NHMe | —NHMe | N |
| 1434 | —NHMe | —NHi-Pr | N |
| 1435 | —NHi-Pr | —NHMe | N |
| 1436 | —NHi-Pr | —NHi-Pr | N |
| 1437 | 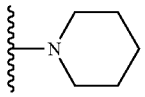 | —NHMe | N |
| 1438 | 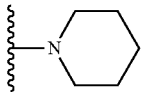 | —NHi-Pr | N |
| 1439 | 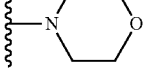 | —NHMe | N |
| 1440 | 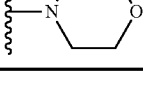 | —NHi-Pr | N. |

In certain embodiments, the present invention provides a method for the treatment of an ASK-1 mediated disease or condition in a subject in need thereof. The method comprises administering to the subject a therapeutically effective amount of a compound of Formula (I) or a pharmaceutically acceptable salt or ester thereof. The present invention also provides the use of a compound of Formula (I) for the preparation of a medicament for treatment of an ASK-1 mediated disease or condition.

In certain embodiments, the ASK-1 mediated disease or condition is an autoimmune disorder, a neurodegenerative disorder, an inflammatory disease, chronic kidney disease, renal disease, cardiovascular disease, a metabolic disease, or an acute or chronic liver disease.

In certain embodiments, the chronic liver disease is primary biliary cirrhosis (PBC), cerebrotendinous xanthomatosis (CTX), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, chronic viral hepatitis, alcoholic liver disease, nonalcoholic fatty liver disease (NAFLD), nonalcoholic steatohepatitis (NASH), liver transplant associated graft versus host disease, living donor transplant liver regeneration, congenital hepatic fibrosis, choledocholithiasis, granulomatous liver disease, intra- or extrahepatic malignancy, Sjogren's syndrome, Sarcoidosis, Wilson's disease, Gaucher's disease, hemochromatosis, or alpha 1-antitrypsin deficiency. In certain embodiments, the gastrointestinal disease is inflammatory bowel disease (IBD) (including Crohn's disease and ulcerative colitis), irritable bowel syndrome (IBS), bacterial overgrowth, malabsorption, post-radiation colitis, or microscopic colitis.

In certain embodiments, the renal disease is diabetic nephropathy, focal segmental glomerulosclerosis (FSGS), hypertensive nephrosclerosis, chronic glomerulonephritis, chronic transplant glomerulopathy, chronic interstitial nephritis, or polycystic kidney disease.

In certain embodiments, the cardiovascular disease is atherosclerosis, arteriosclerosis, reperfusion/ischemia in stroke, cardiac hypertrophy, respiratory diseases, heart attacks, myocardial ischemia.

In certain embodiments, the metabolic disease is insulin resistance, Type I and Type II diabetes, or obesity.

In certain embodiments, the chronic kidney disease is polycystic kidney disease, pyelonephritis, kidney fibrosis and glomerulonephritis.

Yet a further aspect of the present invention is a process of making any of the compounds delineated herein employing any of the synthetic means delineated herein.

DEFINITIONS

Listed below are definitions of various terms used to describe this invention. These definitions apply to the terms as they are used throughout this specification and claims, unless otherwise limited in specific instances, either individually or as part of a larger group.

The term "alkyl" as used herein, refers to saturated, straight- or branched-chain hydrocarbon radicals. "$C_1$-$C_3$ alkyl," "$C_1$-$C_6$ alkyl," "$C_1$-$C_{10}$ alkyl" "$C_2$-$C_4$ alkyl," or "$C_3$-$C_6$ alkyl," refer to alkyl groups containing from one to three, one to six, one to ten carbon atoms, 2 to 4 and 3 to 6 carbon atoms respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals.

The term "alkenyl" as used herein, refers to straight- or branched-chain hydrocarbon radicals having at least one carbon-carbon double bond by the removal of a single hydrogen atom. "$C_2$-$C_{10}$ alkenyl," "$C_2$-$C_4$ alkenyl," "$C_2$-$C_4$ alkenyl," or "$C_3$-$C_6$ alkenyl," refer to alkenyl groups containing from two to ten, two to eight, two to four or three to six carbon atoms respectively. Alkenyl groups include, but are not limited to, for example, ethenyl, propenyl, butenyl, 1-methyl-2-buten-1-yl, heptenyl, octenyl, and the like.

The term "alkynyl" as used herein, refers to straight- or branched-chain hydrocarbon radicals having at least one carbon-carbon triple bond by the removal of a single hydrogen atom. "$C_2$-$C_{10}$ alkynyl," "$C_2$-$C_4$ alkynyl," "$C_2$-$C_4$ alkynyl," or "$C_3$-$C_6$ alkynyl," refer to alkynyl groups containing from two to ten, two to eight, two to four or three to six carbon atoms respectively. Representative alkynyl groups include, but are not limited to, for example, ethynyl, 1-propynyl, 1-butynyl, heptynyl, octynyl, and the like.

The term "cycloalkyl", as used herein, refers to a monocyclic or polycyclic saturated carbocyclic ring or a bi- or tri-cyclic group fused, bridged or spiro system, and the carbon atoms may be optionally oxo-substituted or optionally substituted with exocyclic olefinic, iminic or oximic double bond. Preferred cycloalkyl groups include $C_3$-$C_{12}$ cycloalkyl, $C_3$-$C_6$ cycloalkyl, $C_3$-$C_8$ cycloalkyl and $C_4$-$C_7$ cycloalkyl. Examples of $C_3$-$C_{12}$ cycloalkyl include, but not limited to, cyclopropyl, cyclobutyl, cyclopentyl, cyclohexyl, cyclopentyl, 4-methylene-cyclohexyl, bicyclo [2.2.1]heptyl, bicyclo[3.1.0]hexyl, spiro[2.5]octyl, 3-methylenebicyclo[3.2.1]octyl, spiro[4.4]nonanyl, and the like.

The term "cycloalkenyl", as used herein, refers to monocyclic or polycyclic carbocyclic ring or a bi- or tri-cyclic group fused, bridged or spiro system having at least one carbon-carbon double bond and the carbon atoms may be optionally oxo-substituted or optionally substituted with exocyclic olefinic, iminic or oximic double bond. Preferred cycloalkenyl groups include $C_3$-$C_{12}$ cycloalkenyl, $C_3$-$C_8$ cycloalkenyl or $C_5$-$C_7$ cycloalkenyl groups. Examples of $C_3$-$C_{12}$ cycloalkenyl include, but not limited to, cyclopropenyl, cyclobutenyl, cyclopentenyl, cyclohexenyl, cycloheptenyl, cyclooctenyl, bicyclo[2.2.1]hept-2-enyl, bicyclo [3.1.0]hex-2-enyl, spiro[2.5]oct-4-enyl, spiro[4.4]non-1-enyl, bicyclo[4.2.1]non-3-en-9-yl, and the like.

The term "aryl," as used herein, refers to a mono- or polycyclic carbocyclic ring system comprising at least one aromatic ring, including, but not limited to, phenyl, naphthyl, tetrahydronaphthyl, indanyl, and indenyl. A polycyclic aryl is a polycyclic ring system that comprises at least one aromatic ring. Polycyclic aryls can comprise fused rings, covalently attached rings or a combination thereof.

The term "heteroaryl," as used herein, refers to a mono- or polycyclic aromatic radical having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isoxazolyl, thiadiazolyl, oxadiazolyl, thiophenyl, furanyl, quinolinyl, isoquinolinyl, benzimidazolyl, benzoxazolyl, quinoxalinyl. A polycyclic heteroaryl can comprise fused rings, covalently attached rings or a combination thereof.

In accordance with the invention, aromatic groups can be substituted or unsubstituted.

The term "bicyclic aryl" or "bicyclic heteroaryl" refers to a ring system consisting of two rings wherein at least one ring is aromatic; and the two rings can be fused or covalently attached.

As used herein, the term "arylalkyl" means a functional group wherein an alkylene chain is attached to an aryl group, e.g., —$CH_2CH_2$-phenyl. The term "substituted arylalkyl" means an arylalkyl functional group in which the aryl group is substituted. Similarly, the term "heteroarylalkyl" means a functional group wherein an alkylene chain is attached to a heteroaryl group. The term "substituted heteroarylalkyl" means a heteroarylalkyl functional group in which the heteroaryl group is substituted.

The term "alkylene" as used herein, refers to a diradical of a branched or unbranched saturated hydrocarbon chain, typically having from 1 to 20 carbon atoms (e.g. 1-10 carbon atoms, or 1, 2, 3, 4, 5, or 6 carbon atoms). This term is exemplified by groups such as methylene (—$CH_2$—), ethylene (—$CH_2CH_2$—), the propylene isomers (e.g., —$CH_2CH_2CH_2$— and —$CH(CH_3)CH_2$—), and the like.

The term "substituted" as used herein, refers to independent replacement of one, two, or three or more of the hydrogen atoms thereon with substituents including, but not limited to, deuterium, —F, —Cl, —Br, —I, —OH, protected hydroxy, —$NO_2$, —CN, —$NH_2$, $N_3$, protected amino, alkoxy, thioalkoxy, oxo, $C_1$-$C_{12}$-alkyl, $C_2$-$C_{12}$-alkenyl, $C_2$-$C_{12}$-alkynyl, -halo-$C_1$-$C_{12}$-alkyl, -halo-$C_2$-$C_{12}$-alkenyl, -halo-$C_2$-$C_{12}$-alkynyl, -halo-$C_3$-$C_{12}$-cycloalkyl, —NH—$C_1$-$C_{12}$-alkyl, —NH—$C_2$-$C_{12}$-alkenyl, —NH—$C_2$-$C_{12}$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)— $C_2$-$C_{12}$-alkynyl, —C(O)—$C_3$-$C_{12}$-cycloalkyl, —C(O)-aryl, —C(O)-heteroaryl, —C(O)-heterocycloalkyl, —$CONH_2$, —CONH— $C_1$-$C_{12}$-alkyl, —CONH—$C_2$-$C_{12}$-alkenyl, —CONH— $C_2$-$C_{12}$-alkynyl, —CONH—$C_3$-$C_{12}$-cycloalkyl, —CONH-aryl, —CONH— heteroaryl, —CONH-heterocycloalkyl, —$OCO_2$— $C_1$-$C_{12}$-alkyl, —$OCO_2$— $C_2$-$C_{12}$-alkenyl, —$OCO_2$— $C_2$-$C_{12}$-alkynyl, —$OCO_2$—$C_3$-$C_{12}$-cycloalkyl, —$OCO_2$-aryl, —$OCO_2$-heteroaryl, —$OCO_2$-heterocycloalkyl, —$OCONH_2$, —OCONH— $C_1$-$C_{12}$-alkyl, —OCONH— $C_2$-$C_{12}$-alkenyl, —OCONH— $C_2$-$C_{12}$-alkynyl, —OCONH—$C_3$-$C_{12}$-cycloalkyl, —OCONH— aryl, —OCONH— heteroaryl, —OCONH— heterocycloalkyl, —NHC(O)— $C_1$-$C_{12}$-alkyl, —NHC(O)—$C_2$-$C_{12}$-alkenyl, —NHC(O)—$C_2$-$C_{12}$-alkynyl, —NHC(O)—$C_3$-$C_{12}$-cycloalkyl, —NHC(O)-aryl, —NHC (O)-heteroaryl, —NHC(O)-heterocycloalkyl, —$NHCO_2$— $C_1$-$C_{12}$-alkyl, —$NHCO_2$— $C_2$-$C_{12}$-alkenyl, —$NHCO_2$— $C_2$-$C_{12}$-alkynyl, —$NHCO_2$— $C_3$-$C_{12}$-cycloalkyl, —$NHCO_2$-aryl, —$NHCO_2$— heteroaryl, —$NHCO_2$— heterocycloalkyl, —$NHC(O)NH_2$, —NHC(O)NH— $C_1$-$C_{12}$-alkyl, —NHC(O)NH—$C_2$-$C_{12}$-alkenyl, —NHC(O)NH— $C_2$-$C_{12}$-alkynyl, —NHC(O)NH—$C_3$-$C_{12}$-cycloalkyl, —NHC(O)NH-aryl, —NHC(O)NH-heteroaryl, —NHC(O) NH-heterocycloalkyl, $NHC(S)NH_2$, —NHC(S)NH— $C_1$-$C_{12}$-alkyl, —NHC(S)NH—$C_2$-$C_{12}$-alkenyl, —NHC(S) NH—$C_2$-$C_{12}$-alkynyl, —NHC(S)NH—$C_3$-$C_{12}$-cycloalkyl, —NHC(S)NH-aryl, —NHC(S)NH-heteroaryl, —NHC(S) NH-heterocycloalkyl, —$NHC(NH)NH_2$, —NHC(NH) NH— $C_1$-$C_{12}$-alkyl, —NHC(NH)NH—$C_2$-$C_{12}$-alkenyl, —NHC(NH)NH—$C_2$-$C_{12}$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)— $C_1$-$C_{12}$-alkyl, —NHC(NH)—$C_2$-$C_{12}$-alkenyl, —NHC (NH)—$C_2$-$C_{12}$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_3$-$C_{12}$-alkyl, —C(NH) NH—$C_2$-$C_{12}$-alkenyl, —C(NH)NH—$C_2$-$C_{12}$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_{12}$-alkenyl, —S(O)—$C_2$-$C_{12}$-alkynyl, —S(O)—$C_3$-$C_{12}$-cycloalkyl, —S(O)-aryl, —S(O)-heteroaryl, —S(O)-heterocycloalkyl —$SO_2NH_2$, —$SO_2$NH— $C_1$-$C_{12}$-alkyl, —$SO_2$NH— $C_2$-$C_{12}$-alkenyl, —$SO_2$NH— $C_2$-$C_{12}$-alkynyl, —$SO_2$NH— $C_3$-$C_{12}$-cycloalkyl, —$SO_2$NH— aryl, —$SO_2$NH— heteroaryl, —$SO_2$NH— heterocycloalkyl, —$NHSO_2$—$C_1$-$C_{12}$-alkyl, —$NHSO_2$—$C_2$-$C_{12}$-alkenyl, —$NHSO_2$—$C_2$-$C_{12}$-alkynyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_{12}$-alkenyl, —S—$C_2$-$C_{12}$-alkynyl, —S—$C_3$-$C_{12}$-cycloalkyl, —S-aryl, —S-heteroaryl, —S-heterocycloalkyl, methylthiomethyl, or -L'-R', wherein L' is $C_1$-$C_6$alkylene, $C_2$-$C_6$alkenylene or $C_2$-$C_6$alkynylene, and R' is aryl, heteroaryl, heterocyclic, $C_3$-$C_{12}$cycloalkyl or $C_3$-$C_{12}$cycloalkenyl. It is understood that the aryls, heteroaryls, alkyls, and the like can be further substituted. In some cases, each substituent in a substituted moiety is additionally optionally substituted with one or more groups, each group being independently selected from $C_1$-$C_6$-alkyl, —F, —Cl, —Br, —I, —OH, —$NO_2$, —CN, or —$NH_2$.

In accordance with the invention, any of the aryls, substituted aryls, heteroaryls and substituted heteroaryls described herein, can be any aromatic group. Aromatic groups can be substituted or unsubstituted.

It is understood that any alkyl, alkenyl, alkynyl, cycloalkyl and cycloalkenyl moiety described herein can also be an aliphatic group, an alicyclic group or a heterocyclic group. An "aliphatic group" is non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may be used in place of the alkyl, alkenyl, alkynyl, alkylene, alkenylene, and alkynylene groups described herein.

The term "alicyclic" as used herein, denotes a monovalent group derived from a monocyclic or polycyclic saturated carbocyclic ring compound by the removal of a single hydrogen atom. Examples include, but are not limited to, cyclopropyl, cyclobutyl, cyclopentyl, cyclohexyl, bicyclo[2.2.1]heptyl, and bicyclo[2.2.2]octyl. Such alicyclic groups may be further substituted.

As used herein, the term "alkoxy" employed alone or in combination with other terms means, unless otherwise stated, an alkyl group having the designated number of carbon atoms connected to the rest of the molecule via an oxygen atom, such as, for example, methoxy, ethoxy, 1-propoxy, 2-propoxy (isopropoxy) and the higher homologs and isomers. Preferred alkoxy are ($C_1$-$C_3$) alkoxy.

The term "aryloxy" refers to the group aryl-O— wherein the aryl group is as defined above, and includes optionally substituted aryl groups as also defined above. The term "arylthio" refers to the group R—S—, where R is as defined for aryl.

The terms "heterocyclic" or "heterocycloalkyl" can be used interchangeably and referred to a non-aromatic ring or a bi- or tri-cyclic group fused, bridged or spiro system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted or optionally substituted with exocyclic olefinic, iminic or oximic double bond. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, 2-azabicyclo[2.2.1]-heptyl, 8-azabicyclo[3.2.1]octyl, 5-azaspiro[2.5]octyl, 1-oxa-7-azaspiro[4.4]nonanyl, 7-oxooxepan-4-yl, and tetrahydrofuryl. Such heterocyclic groups may be further substituted. Heteroaryl or heterocyclic groups can be C-attached or N-attached (where possible).

It is understood that any alkyl, alkenyl, alkynyl, cycloalkyl, heterocyclic and cycloalkenyl moiety described herein can also be an aliphatic group or an alicyclic group.

It will be apparent that in various embodiments of the invention, the substituted or unsubstituted alkyl, alkenyl, alkynyl, cycloalkyl, cycloalkenyl, cycloalkynyl, arylalkyl, heteroarylalkyl, and heterocycloalkyl are intended to be monovalent or divalent. Thus, alkylene, alkenylene, and alkynylene, cycloaklylene, cycloalkenylene, cycloalkynylene, arylalkylene, heteroarylalkylene and heterocycloalkylene groups are to be included in the above definitions, and are applicable to provide the Formulas herein with proper valency.

The terms "halo" and "halogen," as used herein, refer to an atom selected from fluorine, chlorine, bromine and iodine.

The term "optionally substituted", as used herein, means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

The term "hydrogen" includes hydrogen and deuterium. In addition, the recitation of an atom includes other isotopes of that atom so long as the resulting compound is pharmaceutically acceptable.

In certain embodiments, the compounds of each formula herein are defined to include isotopically labelled compounds. An "isotopically labelled compound" is a compound in which at least one atomic position is enriched in a specific isotope of the designated element to a level which is significantly greater than the natural abundance of that isotope. For example, one or more hydrogen atom positions in a compound can be enriched with deuterium to a level which is significantly greater than the natural abundance of deuterium, for example, enrichment to a level of at least 1%, preferably at least 20% or at least 50%. Such a deuterated compound may, for example, be metabolized more slowly than its non-deuterated analog, and therefore exhibit a longer half-life when administered to a subject. Such compounds can synthesize using methods known in the art, for example by employing deuterated starting materials. Unless stated to the contrary, isotopically labelled compounds are pharmaceutically acceptable.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art.

Berge, et al. describes pharmaceutically acceptable salts in detail in J. Pharmaceutical Sciences, 66: 1-19 (1977). The salts can be prepared in situ during the final isolation and purification of the compounds of the invention, or separately by reaction of the free base function with a suitable organic acid. Examples of pharmaceutically acceptable salts include, but are not limited to, nontoxic acid addition salts e.g., salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, esters of $C_1$-$C_6$-alkanoic acids, such as acetate, propionate, butyrate and pivalate esters.

The term "hydroxy activating group," as used herein, refers to a labile chemical moiety which is known in the art to activate a hydroxyl group so that it will depart during synthetic procedures such as in a substitution or an elimination reaction. Examples of hydroxyl activating group include, but not limited to, mesylate, tosylate, triflate, p-nitrobenzoate, phosphonate and the like.

The term "activated hydroxyl," as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, *Protective Groups in Organic Synthesis,* 3rd edition, John Wiley & Sons, New York (1999). Examples of hydroxyl protecting groups include benzyloxycarbonyl, 4-methoxybenzyloxycarbonyl, tert-butoxy-carbonyl, isopropoxycarbonyl, diphenylmethoxycarbonyl, 2,2,2-trichloroethoxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, allyl, benzyl, triphenyl-methyl (trityl), methoxymethyl, methylthiomethyl, benzyloxymethyl, 2-(trimethylsilyl)-ethoxymethyl, methanesulfonyl, trimethylsilyl, triisopropylsilyl, and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group," as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery,* (Drugs and the Pharmaceutical Sciences; Volume 53), Marcel Dekker, Inc., New York (1992) and in "Prodrugs of Alcohols and Phenols" by S. S. Dhareshwar and V. J. Stella, in *Prodrugs Challenges and Rewards Part-*2, (Biotechnology: Pharmaceutical Aspects), edited by V. J. Stella, et al, Springer and AAPSPress, 2007, pp 31-99.

The term "amino" as used herein, refers to the group —$NH_2$.

The term "substituted amino" as used herein, refers to the group —NRR where each R is independently selected from the group consisting of hydrogen, alkyl, cycloalkyl, aryl, heteroaryl and heterocycloalkyl provided that both R groups are not hydrogen, or a group —Y—Z, in which Y is optionally substituted alkylene and Z is alkenyl, cycloalkenyl, or alkynyl.

The term "amino protecting group" as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, *Protective Groups in Organic Synthesis,* 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound, which is convertible in vivo by metabolic means (e.g. by hydrolysis) to afford any compound delineated by the Formulae of the instant invention. Various forms of prodrugs are known in the art, for example, as discussed in Bundgaard, (ed.), *Design of Prodrugs*, Elsevier (1985); Widder, et al. (ed.), *Methods in Enzymology*, Vol. 4, Academic Press (1985); Krogsgaard-Larsen, et al., (ed). "Design and Application of Prodrugs, *Textbook of Drug Design and Development*, Chapter 5, 113-191 (1991); Bundgaard, et al., *Journal of Drug Deliver Reviews*, 8:1-38(1992); Bundgaard, J. of *Pharmaceutical Sciences*, 77:285 et seq. (1988); Higuchi and Stella (eds.) Prodrugs as Novel Drug Delivery Systems, *American Chemical Society* (1975); and Bernard Testa & Joachim Mayer, "Hydrolysis In Drug And Prodrug Metabolism: Chemistry, Biochemistry And Enzymology," John Wiley and Sons, Ltd. (2002).

The term "treating", as used herein, means relieving, lessening, reducing, eliminating, modulating, or ameliorating, i.e. causing regression of the disease state or condition. Treating can also include inhibiting, i.e. arresting the development, of an existing disease state or condition, and relieving or ameliorating, i.e. causing regression of an existing disease state or condition, for example when the disease state or condition may already be present.

The term "preventing", as used herein means, to completely or almost completely stop a disease state or condition, from occurring in a patient or subject, especially when the patient or subject is predisposed to such or at risk of contracting a disease state or condition.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvates" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar to or comparable in function and appearance to the reference compound.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, N Y, 1986.

The terms "protogenic organic solvent" or "protic solvent" as used herein, refer to a solvent that tends to provide protons, such as an alcohol, for example, methanol, ethanol, propanol, isopropanol, butanol, t-butanol, and the like. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, N Y, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. Additionally, the various synthetic steps may be performed in an alternate sequence or order to give the desired compounds. In addition, the solvents, temperatures, reaction durations, etc. delineated herein are for purposes of illustration only and variation of the reaction conditions can produce the desired isoxazole products of the present invention. Synthetic chemistry transformations and protecting group methodologies (protection and deprotection) useful in synthesizing the compounds described herein include, for example, those described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. *Fieser and M. Fieser, Fieser and Fieser's Reagents for Organic Synthesis*, John Wiley and Sons (1994); and L. Paquette, ed., *Encyclopedia of Reagents for Organic Synthesis*, John Wiley and Sons (1995).

The compounds of this invention may be modified by appending various functionalities via synthetic means delineated herein to enhance selective biological properties. Such modifications include those which increase biological penetration into a given biological system (e.g., blood, lymphatic system, central nervous system), increase oral availability, increase solubility to allow administration by injection, alter metabolism and alter rate of excretion.

PHARMACEUTICAL COMPOSITIONS

The pharmaceutical compositions of the present invention comprise a therapeutically effective amount of a compound of the present invention Formulated together with one or more pharmaceutically acceptable carriers. As used herein, the term "pharmaceutically acceptable carrier" means a non-toxic, inert solid, semi-solid or liquid filler, diluent, encapsulating material or Formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the Formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the Formulation may be adjusted with pharmaceutically acceptable acids, bases or buffers to enhance the stability of the Formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable Formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable Formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragées, capsules, pills, and granules can be prepared with coatings and shells such as enteric coatings, release controlling coatings and other coatings well known in the pharmaceutical Formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic Formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Unless otherwise defined, all technical and scientific terms used herein are accorded the meaning commonly known to one with ordinary skill in the art. All publications, patents, published patent applications, and other references mentioned herein are hereby incorporated by reference in their entirety.

ABBREVIATIONS

Abbreviations which have been used in the descriptions of the schemes and the examples that follow are:
Alloc for allyloxycarbonyl;
Alloc-Cl for allyl chloroformate;
ASK1 for apoptosis signal-regulating kinase 1;
ATP for adenosine triphosphate;
BOP—Cl for bis(2-oxo-3-oxazolidinyl)phosphinic chloride;
Cbz for benzyloxycarbonyl;
Cbz-Cl for benzyl chloroformate;
CDI for carbonyldiimidazole;
$(COCl)_2$ for oxalyl chloride;
DBU for 1,8-diazabicycloundec-7-ene;
DCC for N,N-dicyclohexylcarbodiimide;
1,2-DCE for 1,2-dichloroethane;
DCM for dichloromethane;
DEAD for diethyl azidocarboxylate;
DIAD for diisopropyl azidocarboxylate;
DIPEA or Hunig's base or i-Pr2NEt for N,N-diisopropylethylamine;
DMAc for N,N-dimethylacetamide;
DMAP for N,N-dimethylaminopyridine;
DMEDA for N,N'-dimethylethylenediamine;
DMF for N,N-dimethyl formamide;
EDC for 1-(3-diethylaminopropyl)-3-ethylcarbodiimide hydrochloride;
EGTA for ethylene glycol-bis(2-aminoethylether)-N,N, N',N'-tetraacetic acid;
ESI for electrospray ionization;
$Et_3N$ or TEA for triethylamine;
EtOAc for ethyl acetate;
Ghosez's Reagent for 1-chloro-N,N,2-trimethyl-1-propenylamine;
HATU for 1-[bis(dimethylamino)methylene]-1H-1,2,3-triazolo[4,5-b]pyridinium 3-oxid hexafluorophosphate;
HBTU for N,N,N',N'-tetramethyl-O-(1H-benzotriazol-1-yl)uronium hexafluorophosphate;
HEPES for 4-(2-Hydroxyethyl)piperazine-1-ethanesulfonic acid, N-(2-Hydroxyethyl)piperazine-N'-(2-ethanesulfonic acid);
$IC_{50}$ for half maximal inhibitory concentration;
KOt-Bu for potassium tert-butoxide;
LCMS for liquid chromatography-mass spectrometry;
$Me_4Phen$ for 3,4,7,8-tetramethyl-1,10-phenanthroline;
MeCN for acetonitrile;
m/z for mass-to-charge ratio;
NaOt-Bu for sodium tert-butoxide;
NMP for 1-methyl-2-pyrrolidinone;
NMR for nuclear magnetic resonance spectroscopy;
OMs for methanesulfonate;

OTf for trifluoromethanesulfonate;
OTs for para-toluenesulfonate;
$Pd_2(dba)_3$ for tris(dibenzylideneacetone)dipalladium(0);
$Pd(OAc)_2$ for palladium(II) acetate;
$Pd(PPh_3)_4$ for tetrakis(triphenylphosphine)palladium(0);
PhMe for toluene;
$P(o\text{-tolyl})_3$ for tri(o-tolyl)phosphine;
$PPh_3$ for triphenylphosphine;
PyAOP for 7-azabenzotriazol-1-yloxy)tripyrrolidinophosphonium hexafluorophosphate;
PyBOP for benzotriazol-1-yl-oxytripyrrolidinophosphonium hexafluorophosphate;
rac-BINAP for (+)-2,2'-bis(diphenylphosphino)-1,1'-binaphthalene;
STK3 for serine/threonine-protein kinase 3;
THF for tetrahydrofuran.

Synthetic Methods

The compounds and processes of the present invention will be better understood in connection with the following synthetic schemes that illustrate the methods by which the compounds of the invention may be prepared, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

As shown in Scheme 1, compounds of Formula (I) are prepared from a compound of Formula (1-1) wherein $R^3$, $R^4$, $X^3$, $X^4$, and $X^5$ are as previously defined, and wherein $R^{11}$ is methyl or ethyl. Thus, the compound of Formula (1-1) is hydrolyzed to afford a compound of Formula (1-2) using a suitable hydroxide source such as, but not limited to, NaOH or LiOH. The compound of Formula (1-2) is reacted with a suitable chlorinating reagent such as, but not limited to, oxalyl chloride in combination with a catalytic quantity of DMF, thionyl chloride, or Ghosez's reagent to afford a compound of Formula (1-3). The reaction solvent can be, but is not limited to, THF or DCM. The reaction temperature is from −20° C. to 40° C. For the preparation of compounds of Formula (1-4), see US 2014/0018370. The compound of Formula (1-3) is reacted with a compound of Formula (1-4), wherein $X^1$, $X^2$, $R^1$ and $R^2$ are as previously defined, to afford a compound of Formula (I) using a suitable base such as, but not limited to, $Et_3N$, DMAP, pyridine, or DIPEA. The reaction solvent can be, but is not limited to, THF, DCM, pyridine and toluene. The reaction temperature is from −20° C. to 40° C. Alternatively, the compound of Formula (1-2) is reacted with a compound of Formula (1-4) to afford a compound of Formula (I) using a suitable coupling reagent such as, but not limited to, BOP—$C_1$, CDI, DCC, EDC, HATU, PyAOP or PyBOP in the presence of a suitable base such as, but not limited to, $Et_3N$ or DIPEA. The reaction solvent can be, but is not limited to, THF, DCM and DMF. The reaction temperature is from −20° C. to 40° C. In certain embodiments of Formula (I), wherein $R^3$ or $R^4$ are —$C_1$ or —Br, a compound of Formula (I) may be further reacted with a suitable combination of reagents to afford alternative compounds of Formula (I). The reagent combinations can be, but are not limited to:

$R^3B(OH)_2$ or $R^4B(OH)_2$, wherein $R^3$ and $R^4$ are as previously defined, in the presence of a suitable palladium(0) catalyst such as, but not limited to, $Pd(PPh_3)_4$. The reaction is also run in the presence of a suitable base, such as, but not limited to, $Cs_2CO_3$. The reaction solvent can be, but is not limited to, toluene or 1,4-dioxane.

$HN(R^7)(R^8)$ or $HOR^7$, wherein $R^7$ and $R^8$ are as previously defined, in combination with a suitable base, palladium catalyst, ligand, and solvent. The base can be, but is not limited to, $K_3PO_4$, NaOt-Bu or KOt-Bu. The palladium catalyst can be, but is not limited to, $Pd(OAc)_2$, $Pd(PPh_3)_4$ or $Pd_2(dba)_3$. The ligand can be, but is not limited to, $P(o\text{-tolyl})_3$ or (2-biphenyl)di-tert-butylphosphine. The solvent can be, but is not limited to, toluene or THF.

$HN(R^7)(R^8)$ or $HOR^7$, wherein $R^7$ and $R^8$ are as previously defined, in combination with a suitable base, copper catalyst, ligand, and solvent. The base can be, but is not limited to, $K_3PO_4$ or $Cs_2CO_3$. The copper catalyst can be, but is not limited to, CuI or CuBr. The ligand can be, but is not limited to, $Me_4Phen$, DMEDA, or ethylene glycol. The solvent can be, but is not limited to, toluene or THF.

$HN(R^7)(R^8)$, wherein $R^7$ and $R^8$ are as previously defined, in combination with a suitable base, such as, but not limited to, $Et_3N$, DIPEA, or $Cs_2CO_3$. The reaction solvent can be, but is not limited to, EtOH, DMF, DME, DMAc, or NMP.

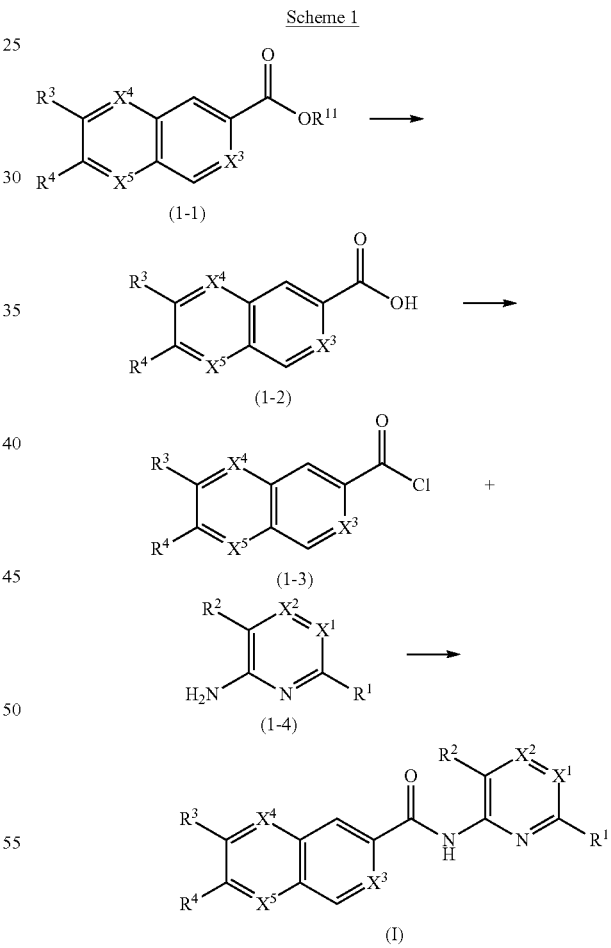

Scheme 1

As shown in Scheme 2, novel analogs of the compound of Formula (2-6) are prepared from the compound of Formula (2-1), wherein $X^3$ is as previously defined. Thus, the compound of Formula (2-1) is reacted with a suitable azidocarboxylate such as, but not limited to, DEAD or DIAD in the presence of a suitable phosphine such as, but not limited to, $PPh_3$ to afford a compound of Formula (2-2). The reaction solvent can be, but is not limited to, MeOH or DCM. The reaction temperature is from −20° C. to 40° C. A compound of Formula (2-2) may be reacted with a suitable combination of reagents to afford compounds of Formula (2-3). The reagent combinations may be, but are not limited to:

$R^3B(OH)_2$ or $R^4B(OH)_2$, wherein $R^3$ and $R^4$ are as previously defined, in the presence of a suitable palladium(0) catalyst such as, but not limited to, $Pd(PPh_3)_4$. The reaction is also run in the presence of a suitable base, such as, but not limited to, $Cs_2CO_3$. The reaction solvent can be, but is not limited to, toluene or 1,4-dioxane.

$HN(R^7)(R^8)$ or $HOR^7$, wherein $R^7$ and $R^8$ are as previously defined, in combination with a suitable base, palladium catalyst, ligand, and solvent. The base can be, but is not limited to, $K_3PO_4$, NaOt-Bu or KOt-Bu. The palladium catalyst can be, but is not limited to, $Pd(OAc)_2$, $Pd(PPh_3)_4$ or $Pd_2(dba)_3$. The ligand can be, but is not limited to, rac-BINAP, $P(o-tolyl)_3$, or (2-biphenyl)di-tert-butylphosphine. The solvent can be, but is not limited to, toluene or THF.

$HN(R^7)(R^8)$ or $HOR^7$, wherein $R^7$ and $R^8$ are as previously defined, in combination with a suitable base, copper catalyst, ligand, and solvent. The base can be, but is not limited to, $K_3PO_4$ or $Cs_2CO_3$. The copper catalyst can be, but is not limited to, CuI or CuBr. The ligand can be, but is not limited to, $Me_4$Phen, DMEDA, or ethylene glycol. The solvent can be, but is not limited to, toluene or THF.

$HN(R^7)(R^8)$, wherein $R^7$ and $R^8$ are as previously defined, in combination with a suitable base, such as, but not limited to, $Et_3N$, DIPEA, or $Cs_2CO_3$. The reaction solvent can be, but is not limited to, EtOH, DMF, DME, DMAc, or NMP.

The compound of Formula (2-3) is hydrolyzed to afford a compound of Formula (2-4) using a suitable hydroxide source such as, but not limited to, NaOH or LiOH. The compound of Formula (2-4) is reacted with a suitable chlorinating reagent such as, but not limited to, oxalyl chloride in combination with a catalytic quantity of DMF, thionyl chloride, or Ghosez's reagent to afford a compound of Formula (2-5). The reaction solvent can be, but is not limited to, THF or DCM. The reaction temperature is from −20° C. to 40° C. For the preparation of compounds of Formula (1-4), see US 2014/0018370. The compound of Formula (2-5) is reacted with a compound of Formula (1-4), wherein $X^1$, $X^2$, $R^1$ and $R^2$ are as previously defined, to afford a compound of Formula (2-6) using a suitable base such as, but not limited to, $Et_3N$, DMAP, pyridine, or DIPEA. The reaction solvent can be, but is not limited to, THF, DCM, pyridine and toluene. The reaction temperature is from −20° C. to 40° C. Alternatively, the compound of Formula (2-4) is reacted with a compound of Formula (1-4) to afford a compound of Formula (2-6) using a suitable coupling reagent such as, but not limited to, BOP—$C_1$, CDI, DCC, EDC, HATU, PyAOP or PyBOP in the presence of a suitable base such as, but not limited to, $Et_3N$ or DIPEA. The reaction solvent can be, but is not limited to, THF, DCM and DMF. The reaction temperature is from −20° C. to 40° C.

Scheme 2

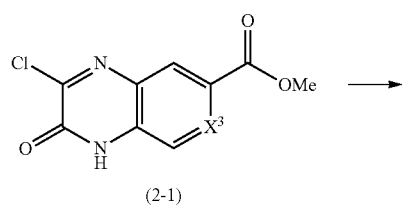

(2-1)

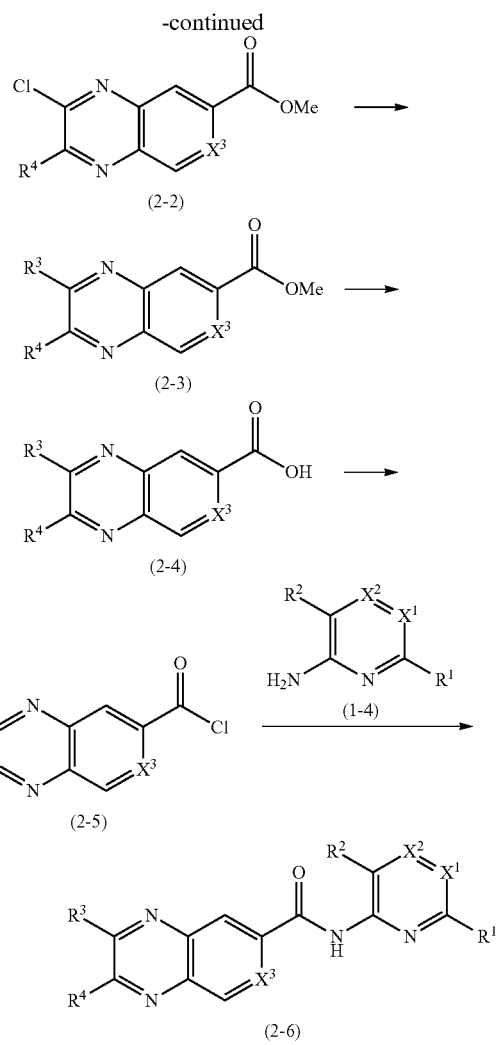

As shown in Scheme 2, novel analogs of the compound of Formula (2-3) can alternatively be prepared from the compound of Formula (2-1), wherein $X^3$ is as previously defined. Thus, the compound of Formula (2-1) is reacted with a suitable combination of reagents to afford compounds of Formula (3-1). The reagent combinations may be, but are not limited to: $R^3B(OH)_2$ or $R^4B(OH)_2$, wherein $R^3$ and $R^4$ are as previously defined, in the presence of a suitable palladium (0) catalyst such as, but not limited to, $Pd(PPh_3)_4$. The reaction is also run in the presence of a suitable base, such as, but not limited to, $Cs_2CO_3$. The reaction solvent can be, but is not limited to, toluene or 1,4-dioxane.

$HN(R^7)(R^8)$ or $HOR^7$, wherein $R^7$ and $R^8$ are as previously defined, in combination with a suitable base, palladium catalyst, ligand, and solvent. The base can be, but is not limited to, $K_3PO_4$, NaOt-Bu or KOt-Bu. The palladium catalyst can be, but is not limited to, $Pd(OAc)_2$, $Pd(PPh_3)_4$ or $Pd_2(dba)_3$. The ligand can be, but is not limited to, rac-BINAP, $P(o-tolyl)_3$, or (2-biphenyl)di-tert-butylphosphine. The solvent can be, but is not limited to, toluene or THF.

$HN(R^7)(R^8)$ or $HOR^7$, wherein $R^7$ and $R^8$ are as previously defined, in combination with a suitable base, copper catalyst, ligand, and solvent. The base can be, but is not limited to, $K_3PO_4$ or $Cs_2CO_3$. The copper catalyst can be, but is not limited to, CuI or CuBr. The ligand can be, but is not limited to, Me₄Phen, DMEDA, or ethylene glycol. The solvent can be, but is not limited to, toluene or THF.

HN(R⁷)(R⁸), wherein R⁷ and R⁸ are as previously defined, in combination with a suitable base, such as, but not limited to, Et₃N, DIPEA, or Cs₂CO₃. The reaction solvent can be, but is not limited to, EtOH, DMF, DME, DMAc, or NMP.

The compound of Formula (3-1) is reacted with a suitable chlorinating reagent such as, but not limited to, phosphorus (V) oxychloride in the presence of a suitable base such as, but not limited to, N,N-dimethylaniline to afford a compound of Formula (3-2). The reaction solvent can be, but is not limited to, toluene. The reaction temperature is from 20° C. to 110° C. The compound of Formula (3-2) is reacted with a suitable combination of reagents to afford compounds of Formula (2-3). The reagent combinations may be, but are not limited to:

R³B(OH)₂ or R⁴B(OH)₂, wherein R³ and R⁴ are as previously defined, in the presence of a suitable palladium(0) catalyst such as, but not limited to, Pd(PPh₃)₄. The reaction is also run in the presence of a suitable base, such as, but not limited to, Cs₂CO₃. The reaction solvent can be, but is not limited to, toluene or 1,4-dioxane.

HN(R⁷)(R⁸) or HOR⁷, wherein R⁷ and R⁸ are as previously defined, in combination with a suitable base, palladium catalyst, ligand, and solvent. The base can be, but is not limited to, K₃PO₄, NaOt-Bu or KOt-Bu. The palladium catalyst can be, but is not limited to, Pd(OAc)₂, Pd(PPh₃)₄ or Pd₂(dba)₃. The ligand can be, but is not limited to, rac-BINAP, P(o-tolyl)₃, or (2-biphenyl)di-tert-butylphosphine. The solvent can be, but is not limited to, toluene or THF.

HN(R⁷)(R⁸) or HOR⁷, wherein R⁷ and R⁸ are as previously defined, in combination with a suitable base, copper catalyst, ligand, and solvent. The base can be, but is not limited to, K₃PO₄ or Cs₂CO₃. The copper catalyst can be, but is not limited to, CuI or CuBr. The ligand can be, but is not limited to, Me₄Phen, DMEDA, or ethylene glycol. The solvent can be, but is not limited to, toluene or THF.

HN(R⁷)(R⁸), wherein R⁷ and R⁸ are as previously defined, in combination with a suitable base, such as, but not limited to, Et₃N, DIPEA, or Cs₂CO₃. The reaction solvent can be, but is not limited to, EtOH, DMF, DME, DMAc, or NMP.

A compound of Formula (2-3) may be utilized as previously described in Scheme 2 to afford a compound of Formula (2-6).

Scheme 3

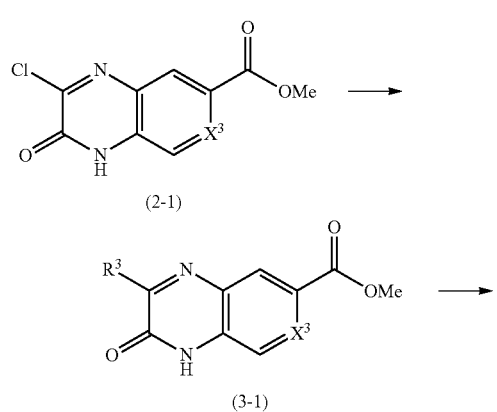

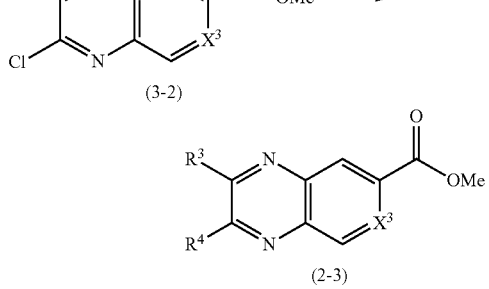

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, Formulations and/or methods of the invention may be made without departing from the spirit of the invention and the scope of the appended claims.

Example 1

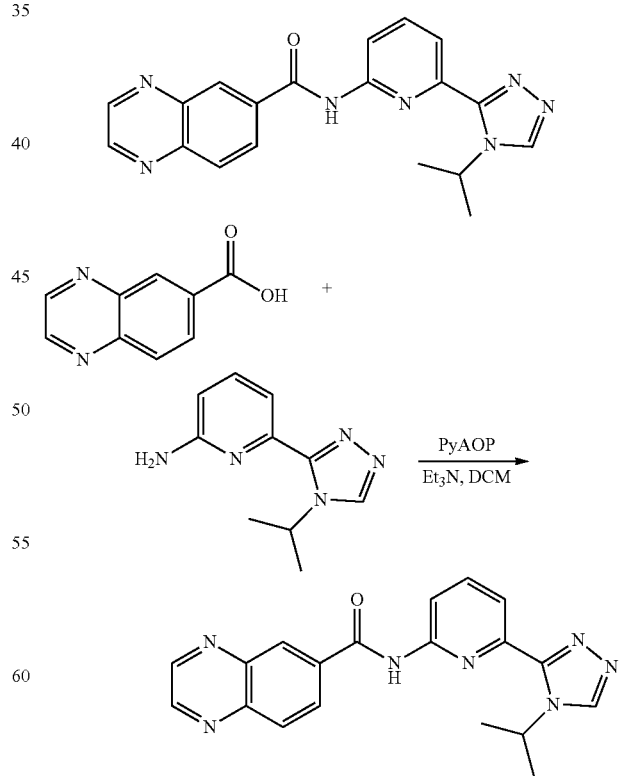

PyAOP (308 mg, 0.59 mmol, 1.2 eq) was added to a suspension of quinoxaline-6-carboxylic acid (94 mg, 0.54 mmol, 1.1 eq) in DCM (2.0 mL). 6-(4-Isopropyl-4H-1,2,4-triazol-3-yl)pyridin-2-amine (100 mg, 0.49 mmol, 1.0 eq) and Et₃N (0.16 mL, 1.13 mmol, 2.3 eq) were added and the reaction was stirred overnight. The reaction was partitioned between EtOAc and H₂O. The layers were separated and the organic layer was washed with sat. NaHCO₃, 10% citric acid, and brine. The organic layer was dried (MgSO4), filtered, and concentrated under reduced pressure. The resultant orange gum was purified by column chromatography eluting with DCM/MeOH (0% MeOH→8% MeOH) to afford Example 1 (23.7 mg, 0.07 mmol, 13%) as a colorless amorphous solid: LCMS (ESI) m/z 360.15 (M+1).

Example 3

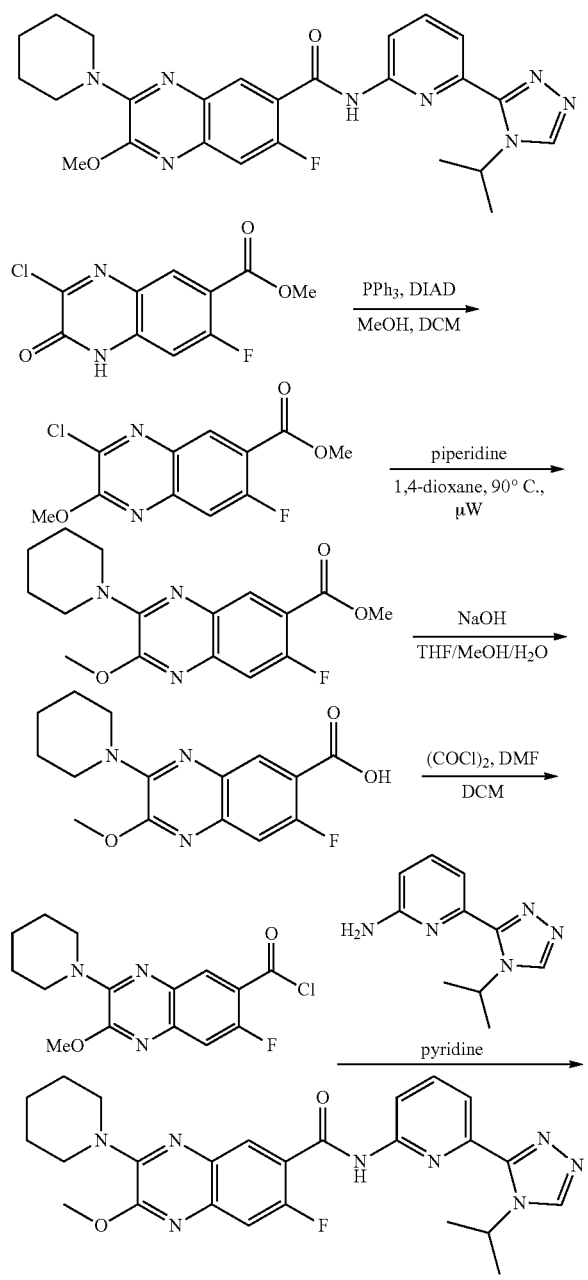

Methanol (20 µL, 0.487 mmol, 2.5 eq), triphenylphosphine (102 mg, 0.390 mmol, 2.0 eq), and DIAD (76 µL, 0.390 mmol, 2.0 eq) were added to a solution of methyl 3-chloro-7-fluoro-2-oxo-1,2-dihydroquinoxaline-6-carboxylate (50 mg, 0.195 mmol, 1.0 eq), prepared according to US 2012/119046, in DCM (mL) and the reaction was stirred overnight. The reaction was quenched with MeOH and concentrated under reduced pressure. The resultant residue was purified by column chromatography eluting with hexanes/EtOAc (0% EtOAc→25% EtOAc) to afford methyl 3-chloro-7-fluoro-2-methoxyquinoxaline-6-carboxylate that still contained some DIAD (42.7 mg) as a yellow solid. This material was used directly in the next step.

A mixture of methyl 3-chloro-7-fluoro-2-methoxyquinoxaline-6-carboxylate (40 mg, 0.148 mmol, 1.0 eq) and piperidine (44 µL, 0.443 mmol, 3.0 eq) in 1,4-dioxane (0.74 mL) was heated at 90° C. in a microwave reactor for 15 minutes. The reaction was concentrated under reduced pressure. The resultant yellow solid was purified by column chromatography eluting with hexanes/EtOAc (0% EtOAc→30% EtOAc) to afford methyl 7-fluoro-2-methoxy-3-(piperidin-1-yl)quinoxaline-6-carboxylate (18.4 mg, 0.058 mmol, 39%) as a pale yellow solid.

Sodium hydroxide (33.8 mg, 0.85 mmol, 15.0 eq) was added to a suspension of methyl 7-fluoro-2-methoxy-3-(piperidin-1-yl)quinoxaline-6-carboxylate (18 mg, 0.056 mmol, 1.0 eq) in MeOH (0.38 mL), THF (0.38 ml), and H₂O (0.38 mL), and the reaction was stirred overnight. The reaction was acidified to pH-3 with 1.0 M HCl and extracted with EtOAc. The organic layer was dried (MgSO4), filtered, and concentrated under reduced pressure to afford 7-fluoro-2-methoxy-3-(piperidin-1-yl)quinoxaline-6-carboxylic acid as a pale yellow solid that was used in the next step without purification.

Oxalyl chloride (8.8 µL, 0.10 mmol, 1.8 eq) was added dropwise to a mixture of 7-fluoro-2-methoxy-3-(piperidin-1-yl)quinoxaline-6-carboxylic acid (17 mg, 0.056 mmol, 1.0 eq) and DMF (1 drop) in DCM (0.2 mL). The reaction was stirred for 2 hrs. The reaction was concentrated under reduced pressure to give a yellow residue. The crude compound, 7-fluoro-2-methoxy-3-(piperidin-1-yl)quinoxaline-6-carbonyl chloride, was used in the next step without purification.

A solution of 6-(4-isopropyl-4H-1,2,4-triazol-3-yl)pyridin-2-amine (10.4 mg, 0.051 mmol, 1.0 eq) in pyridine (0.2 mL) was added to 7-fluoro-2-methoxy-3-(piperidin-1-yl)quinoxaline-6-carbonyl chloride (18 mg, 0.056 mmol, 1.1 eq) and the reaction was stirred overnight. The reaction was concentrated under reduced pressure. The resultant brown residue was purified by column chromatography eluting with DCM/MeOH (0% MeOH→5% MeOH) to afford Example 3 (7.9 mg, 0.016 mmol, 32%) as a pale yellow solid: LCMS (ESI) m/z 491.21 (M+1).

Example 8

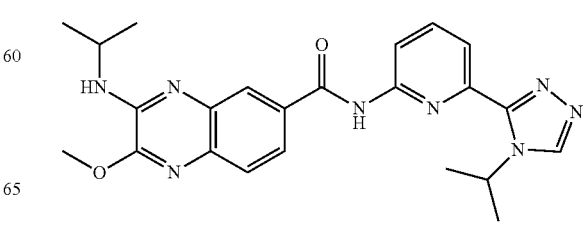

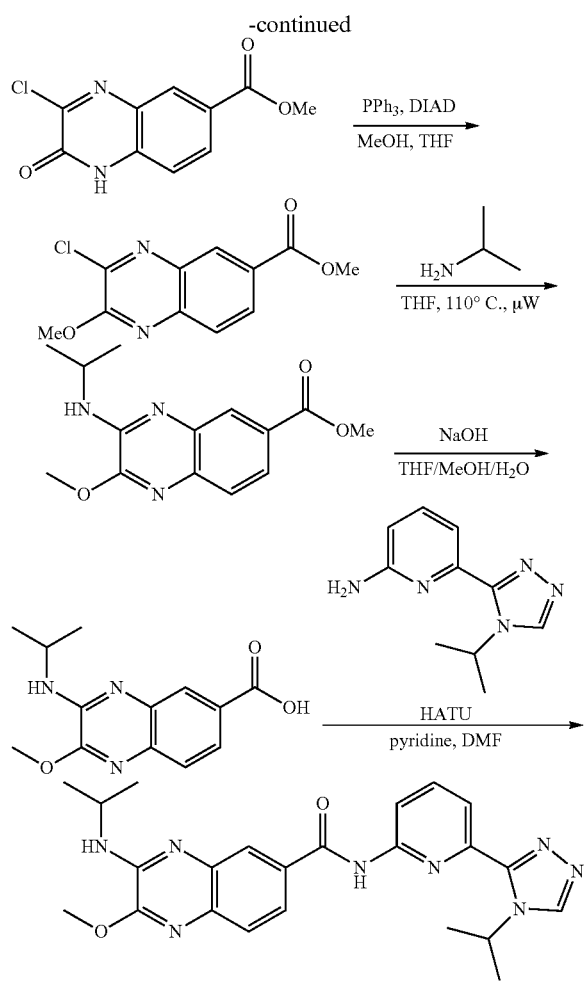

Methanol (116 µL, 2.87 mmol, 2.5 eq), triphenylphosphine (602 mg, 2.30 mmol, 2.0 eq), and DIAD (447 µL, 2.30 mmol, 2.0 eq) were added to a solution of methyl 3-chloro-2-oxo-1,2-dihydroquinoxaline-6-carboxylate (274 mg, 1.15 mmol, 1.0 eq), prepared according to US 2012/094462, in TH (5.7 mL) and the reaction was stirred for 5 hrs. The reaction was quenched with MeOH and concentrated under reduced pressure. The resultant residue was dissolved in DCM and washed with water. The organic layer was dried ($Na_2SO_4$), filtered, and concentrated under reduced pressure. The resultant orange gum was purified by column chromatography eluting with hexanes/EtOAc (0% EtOAc→5020% EtOAc) to afford methyl 3-chloro-2-methoxyquinoxaline-6-carboxylate that still contained some DIAD (293 mg, 1.16 mmol, 101%) as a yellow gum. This material was used directly in the next step.

A mixture of methyl 3-chloro-2-methoxyquinoxaline-6-carboxylate (50 mg, 0.2 mmol, 1.0 eq) and isopropylamine (0.15 mL, 1.8 mmol, 9.0 eq) in THF (0.99 mL) was heated at 110° C. in a microwave reactor for 15 minutes. The reaction was concentrated under reduced pressure. The resultant residue was purified by column chromatography eluting with hexanes/EtOAc (0% EtOAc→20% EtOAc) to afford methyl 3-(isopropylamino)-2-methoxyquinoxaline-6-carboxylate (15 mg, 0.054 mmol, 28%) as a yellow amorphous solid: LCMS (ESI) m/z 276.11 (M+1).

Sodium hydroxide (0.55 mL of a 1.0 M solution in $H_2O$, 0.55 mmol, 10.0 eq) was added to a solution of methyl 3-(isopropylamino)-2-methoxyquinoxaline-6-carboxylate (15 mg, 0.054 mmol, 1.0 eq) in MeOH (0.5 mL) and THF (0.5 ml) and the reaction was stirred overnight. The reaction was acidified to pH-3 with 1.0 M HCl and extracted with EtOAc. The organic layer was dried ($Na_2SO_4$), filtered, and concentrated under reduced pressure to afford 3-(isopropylamino)-2-methoxyquinoxaline-6-carboxylic acid as a white solid (12 mg, 0.046 mmol, 84%): LCMS (ESI) m/z 262.10 (M+1).

HATU (26.2 mg, 0.069 mmol, 1.5 eq) and 6-(4-isopropyl-4H-1,2,4-triazol-3-yl)pyridin-2-amine (14.0 mg, 0.069 mmol, 1.5 eq) was added to a solution of 3-(isopropylamino)-2-methoxyquinoxaline-6-carboxylic acid (12 mg, 0.046 mmol, 1.0 eq) in DMF (0.23 mL) and pyridine (0.23 mL) and the reaction was heated at 70° C. overnight. The reaction was partitioned between EtOAc and $H_2O$. The layers were separated, and the organic layer was dried (MgSO4), filtered, and concentrated under reduced pressure. The residue was purified by column chromatography eluting with DCM/MeOH (0% MeOH→10% MeOH) to afford Example 8 (1.7 mg, 0.004 mmol, 8%): LCMS (ESI) m/z 447.21 (M+1).

Examples 2, 4, 5, 6, and 7 were prepared following a similar protocol as shown in Example 8.

Example 9

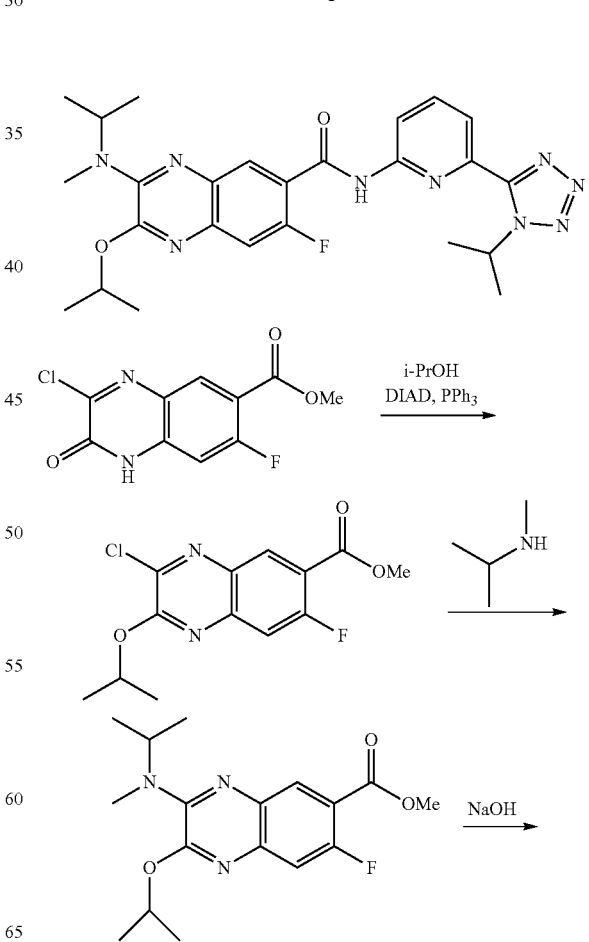

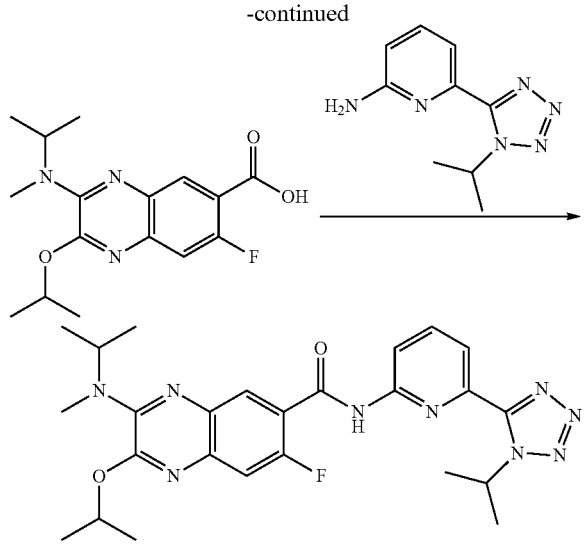

Methyl 3-chloro-7-fluoro-2-oxo-1,2-dihydroquinoxaline-6-carboxylate (50 mg, 0.195 mmol) was dissolved in CH$_2$Cl$_2$ (974 μl). Triphenylphosphine (56.2 mg, 0.214 mmol), i-PrOH (16.51 μl, 0.214 mmol) and DIAD (41.7 μl, 0.214 mmol) was added. The mixture was stirred at rt for 30 min, and purified on silica gel column with 0-20% EtOAc/hexane to afford methyl 3-chloro-7-fluoro-2-isopropoxyquinoxaline-6-carboxylate (32 mg, 0.107 mmol, 55.0% yield) as colorless oil.

In a microwave vial methyl 3-chloro-7-fluoro-2-isopropoxyquinoxaline-6-carboxylate (31 mg, 0.104 mmol) was dissolved in 1,4-Dioxane (2 ml) and N-methylpropan-2-amine (0.108 ml, 1.038 mmol) was added. The vial was heated in microwave at 130° C. for 30 min. Solvent was removed in vacuo. The residue was dissolved in DCM and washed with 5% NaHCO$_3$. The organic layer was dried over Na$_2$SO$_4$, and concentrated in vacuo. Purification of the residue on 12 g of silica with 0-50% EtOAc/hexane provided methyl 7-fluoro-2-isopropoxy-3-(isopropyl(methyl)amino)quinoxaline-6-carboxylate (26 mg, 0.078 mmol, 74.7% yield).

To a solution of methyl 7-fluoro-2-isopropoxy-3-(isopropyl(methyl)amino)quinoxaline-6-carboxylate (26 mg, 0.078 mmol) in THF (517 μl), MeOH (517 μl) and water (517 μl) was added a 10 M aqueous solution of sodium hydroxide (155 μl, 1.550 mmol). The resulting mixture was stirred at rt for 2 h, quenched with 1 M HCl (1.6 mL), and extracted with EtOAc (2×). The combined organic layer was dried over Na$_2$SO$_4$, and concentrated in vacuo. The crude product of 7-fluoro-2-isopropoxy-3-(isopropyl(methyl)amino)quinoxaline-6-carboxylic acid (19 mg, 0.059 mmol, 76% yield) was used for next step.

To a suspension of 7-fluoro-2-isopropoxy-3-(isopropyl(methyl)amino)quinoxaline-6-carboxylic acid (19 mg, 0.059 mmol) in CH$_2$Cl$_2$ (296 μl) was added 1-chloro-N,N,2-trimethylprop-1-en-1-amine (8.60 μl, 0.065 mmol). The mixture was stirred at rt for 30 min and 6-(1-isopropyl-1H-tetrazol-5-yl)pyridin-2-amine (13.28 mg, 0.065 mmol) and pyridine (296 μl) was added. The resulting mixture was stirred at rt for 30 min, quenched with water, and extracted with EtOAc. Purification of the organic layer on silica gel with 0-50% acetone/hexane provided Example 9 (2.7 mg, 5.32 μmol, 9.00% yield) as a white solid.

Example 12, 14, 16, 17 were prepared following a similar protocol as shown in Example 9.

Example 10

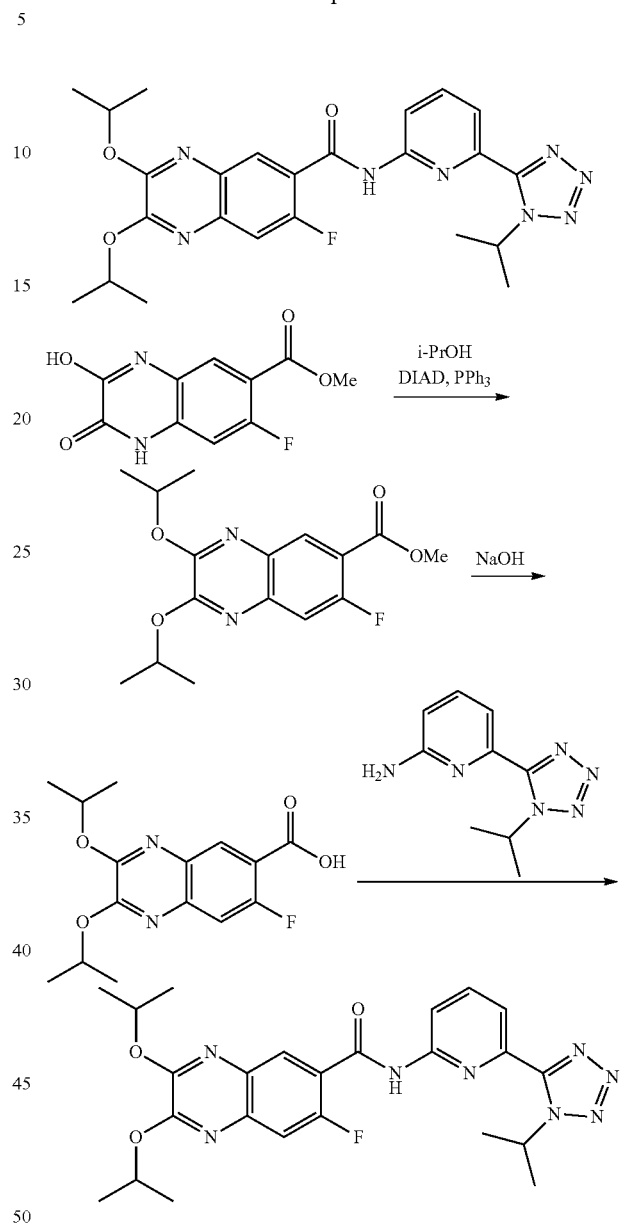

To a suspension of methyl 7-fluoro-3-hydroxy-2-oxo-1,2-dihydroquinoxaline-6-carboxylate (194 mg, 0.815 mmol) in CH$_2$Cl$_2$ (4073 μl) was added triphenylphosphine (641 mg, 2.444 mmol), i-PrOH (188 μl, 2.444 mmol) and DIAD (475 μl, 2.444 mmol). The mixture was stirred at rt for 1 h. Purification of the mixture on 20 g of silica gel column with 0-20% EtOAc/hexane afforded methyl 7-fluoro-2,3-diisopropoxyquinoxaline-6-carboxylate (100 mg, 0.310 mmol, 38.1% yield) as an oil.

To a solution of methyl 7-fluoro-2,3-diisopropoxyquinoxaline-6-carboxylate (100 mg, 0.310 mmol) in THF (2 ml), MeOH (2 ml) and water (1.4 ml) was added a 10 M aqueous solution of sodium hydroxide (0.620 ml, 6.20 mmol). The resulting mixture was stirred at rt for 2 h, quenched with 1 M HCl (6.2 mL), and extracted with EtOAc (2×). The combined organic layer was dried over Na$_2$SO$_4$, and concentrated in vacuo. Purification of the residue on 12 of silica with 0-50% acetone/hexane provided 7-fluoro-2,3-diisopropoxyquinoxaline-6-carboxylic acid (39 mg, 0.126 mmol, 40.8% yield).

To a suspension of 7-fluoro-2,3-diisopropoxyquinoxaline-6-carboxylic acid (18.5 mg, 0.060 mmol) in CH$_2$Cl$_2$ (0.25 ml) was added 1-chloro-N,N,2-trimethylprop-1-en-1-amine (8.73 µl, 0.066 mmol). The mixture was stirred at rt for 1 h and the clear solution was transferred to a solution of 6-(1-isopropyl-1H-tetrazol-5-yl)pyridin-2-amine (13.48 mg, 0.066 mmol) in pyridine (0.250 ml). The resulting mixture was stirred at rt for 30 min, quenched with water, and extracted with EtOAc. Desired product was precipitated from the organic layer during standing at rt. Example 10 (5 mg, 10.11 µmol, 16.85% yield) was obtained as a white solid.

Example 11

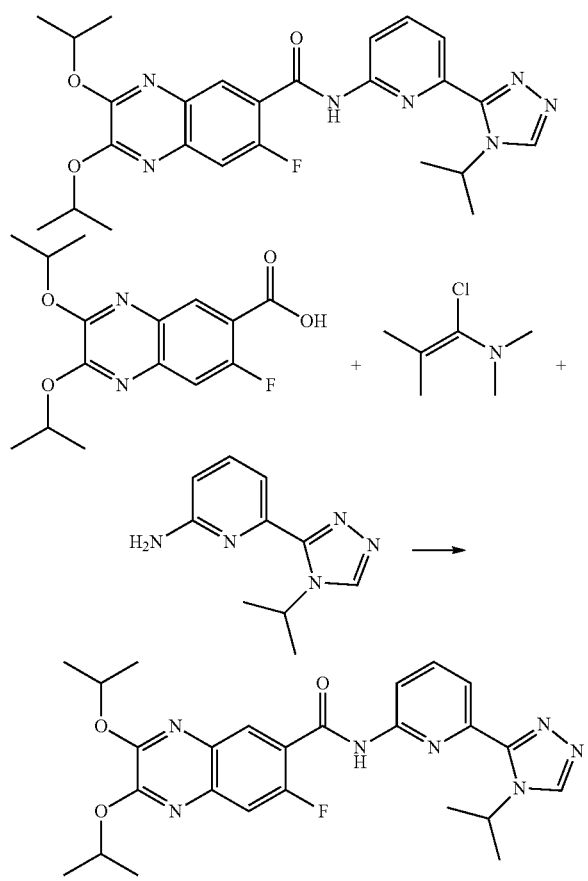

To a suspension of 7-fluoro-2,3-diisopropoxyquinoxaline-6-carboxylic acid (18.5 mg, 0.060 mmol) in CH$_2$Cl$_2$ (0.25 ml) was added 1-chloro-N,N,2-trimethylprop-1-en-1-amine (8.73 µl, 0.066 mmol). The mixture was stirred at rt for 1 h and the clear solution was transferred to a solution of 6-(4-isopropyl-4H-1,2,4-triazol-3-yl)pyridin-2-amine (13.42 mg, 0.066 mmol) in pyridine (0.250 ml). The resulting mixture was stirred at rt for 30 min, quenched with water, and extracted with EtOAc. Purification of the organic layer on 12 g of silica gel with 0-50% acetone/hexane provided Example 11 (15 mg, 0.030 mmol, 50.7% yield) as a white solid.

Example 13

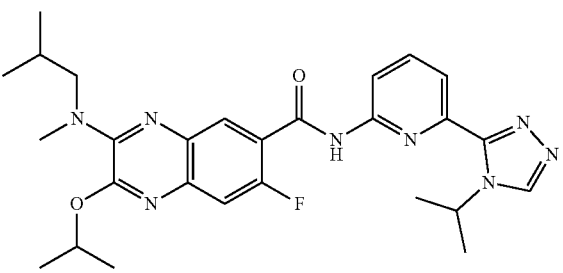

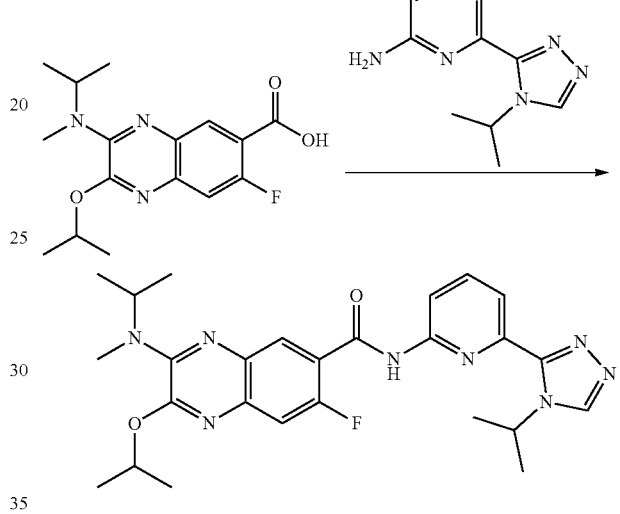

To a suspension of 7-fluoro-2-isopropoxy-3-(isopropyl(methyl)amino)quinoxaline-6-carboxylic acid (50 mg, 0.15 mmol) in CH$_2$Cl$_2$ (1.5 mL) was added 1-chloro-N,N,2-trimethylprop-1-en-1-amine (35 µl, 0.26 mmol). The mixture was stirred at rt for 1 h and concentrated in vacuo. The residue was re-dissolved in 0.75 mL of pyridine and added to a solution of 6-(4-isopropyl-4H-1,2,4-triazol-3-yl)pyridin-2-amine (30.5 mg, 0.150 mmol) in pyridine (0.75 mL). The mixture was stirred at rt for 30 min, quenched with water, and extracted with EtOAc (3×). The combined organic layer was dried over Na$_2$SO$_4$, and concentrated in vacuo. Purification of the residue on 20 g of silica with 0-50% acetone/hexane and 0-10% MeOH/DCM provided Example 13 (35 mg, 0.067 mmol, 44.8% yield). Example 15 was prepared following a similar protocol as shown in Example 13.

Example 18

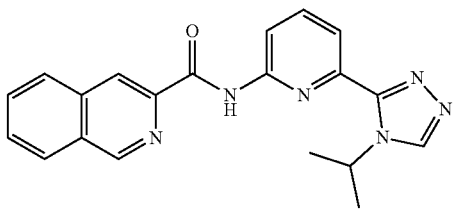

-continued

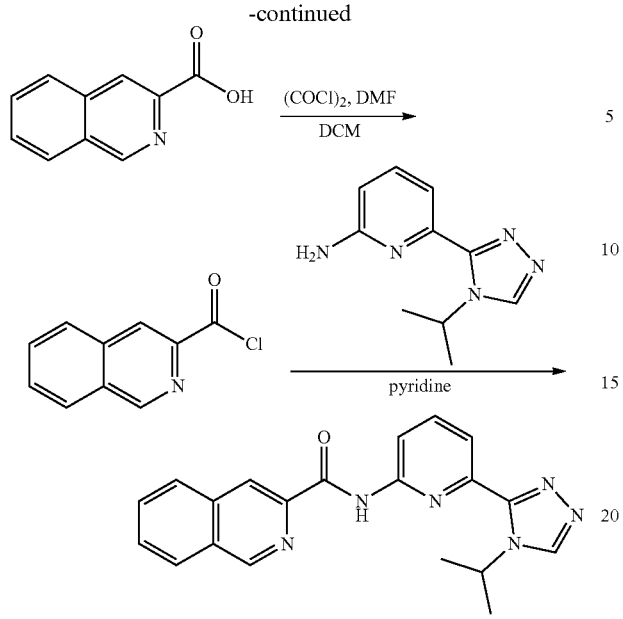

Oxalyl chloride (91 μL, 1.04 mmol, 1.8 eq) was added dropwise to a mixture of isoquinoline-3-carboxylic acid (100 mg, 0.58 mmol, 1.0 eq) and DMF (5 μL, 0.06 mmol, 0.1 eq) in DCM (1.7 mL). The reaction was stirred for 2 hrs. The reaction was concentrated under reduced pressure to give a yellow residue of isoquinoline-3-carbonyl chloride, which was used in the next step without purification.

A solution of 6-(4-isopropyl-4H-1,2,4-triazol-3-yl)pyridin-2-amine (107 mg, 0.53 mmol, 1.0 eq) in pyridine (1.5 mL) was added to isoquinoline-3-carbonyl chloride (111 mg, 0.58 mmol, 1.1 eq) and the reaction was stirred overnight. The reaction was concentrated under reduced pressure. The resultant brown residue was purified by column chromatography eluting with DCM/MeOH (0% MeOH→10% MeOH) to afford Example 18 (106 mg, 0.30 mmol, 56%) as a pink solid: LCMS (ESI) m/z 359.14 (M+1).

Example 19

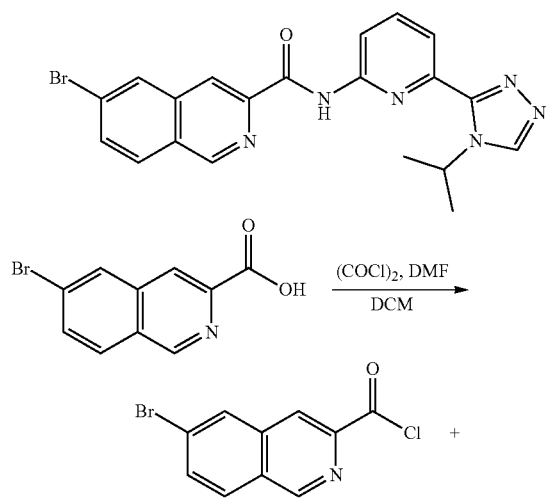

-continued

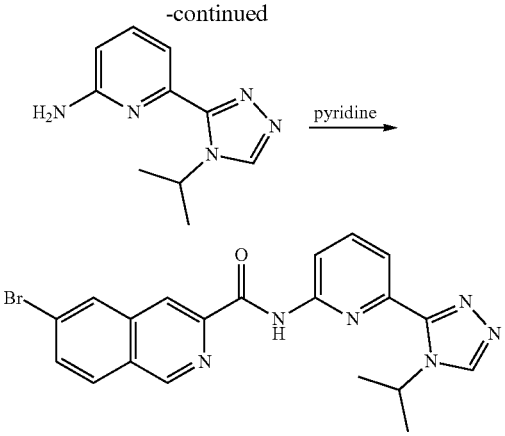

To a mixture of 6-bromoisoquinoline-3-carboxylic acid (1 g, 4.0 mmol) in DCM (11.3 ml) and DMF (31 μl, 0.40 mmol) was charged oxalyl chloride (0.59 ml, 6.74 mmol), and the mixture was stirred for 1 h. The reaction was concentrated and the residue was dissolved in pyridine (11.4 mL) and split into two portions.

A solution of crude acid chloride (538 mg, 2.0 mmol) in pyridine (5.7 mL) was added to 6-(4-isopropyl-4H-1,2,4-triazol-3-yl)pyridin-2-amine (404 mg, 2.0 mmol) and the reaction stirred for 72 h. The reaction was concentrated under reduced pressure and resultant brown residue was purified by column chromatography eluting with CH₂Cl₂/MeOH (0% MeOH→5% MeOH) to give Example 19 (328 mg, 0.75 mmol, 38% yield) as a tan solid.

Example 20

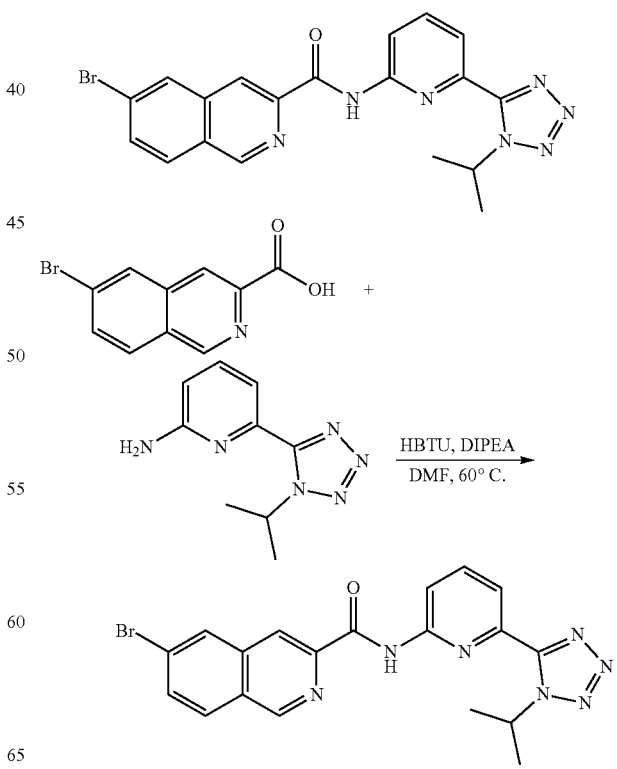

HBTU (54.2 mg, 0.14 mmol) and DIPEA (0.104 mL, 0.60 mmol) were added to a suspension of 6-bromoisoquinoline-3-carboxylic acid (30 mg, 0.12 mmol) in DMF (0.24 mL) and the homogeneous reaction was stirred for 10 min at rt. 6-(1-Isopropyl-1H-tetrazol-5-yl)pyridin-2-amine (48.6 mg, 0.24 mmol) was added and the reaction was stirred for 16 hr at 60° C. The reaction was quenched with H₂O and diluted with EtOAc. The layers were separated and the organic layer was washed with 1:1 H₂O/brine, sat. NaHCO₃, 10% citric acid, and brine. The organic layer was dried (MgSO4), filtered, and concentrated under reduced pressure. The resultant orange oil was purified by column chromatography eluting with CH₂Cl₂/MeOH (0% MeOH→3% MeOH) to give Example 20 (5.2 mg, 0.012 mmol, 10% yield) as a tan solid.

Example 21

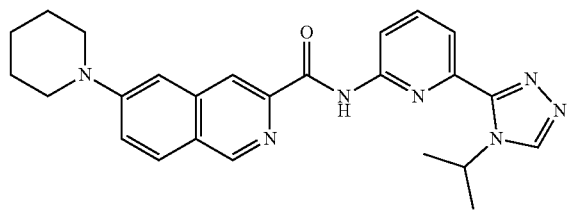

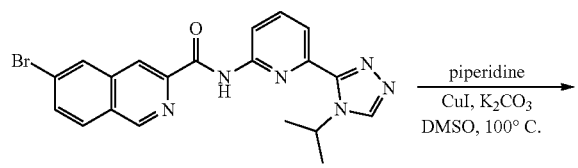

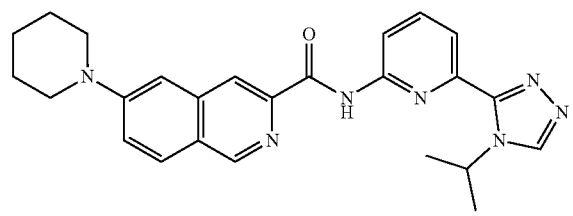

A mixture of 6-bromo-N-(6-(4-isopropyl-4H-1,2,4-triazol-3-yl)pyridin-2-yl)isoquinoline-3-carboxamide (50 mg, 0.11 mmol), K₂CO₃ (32 mg, 0.23 mmol), copper(I) iodide (11 mg, 0.06 mmol), and piperidine (0.06 mL, 0.57 mmol) in DMSO (0.1 mL) were heated at 100° C. for 16 hrs. The reaction was diluted with EtOAc and filtered through celite, rinsing with EtOAc. Water was added to the filtrate, and the layers separated. The aqueous layer was extracted with EtOAc (2×3 mL). The combined organic layers were dried (MgSO4), filtered, and concentrated under reduced pressure. The resultant brown residue was purified by column chromatography eluting with CH₂Cl₂/MeOH (0% MeOH→5% MeOH) to give Example 21 (5.2 mg, 0.012 mmol, 10% yield) as an orange residue.

Example 22

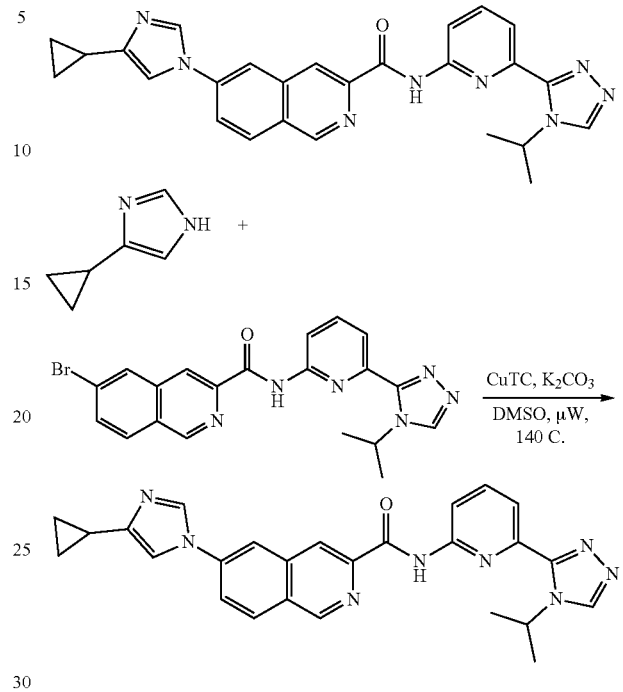

A mixture of 6-bromo-N-(6-(4-isopropyl-4H-1,2,4-triazol-3-yl)pyridin-2-yl)isoquinoline-3-carboxamide (30 mg, 0.07 mmol), 4-cyclopropyl-1H-imidazole (9.0 mg, 0.08 mmol), K₂CO₃ (19 mg, 0.14 mmol), and copper(I)-thiophene-2-carboxylate (6.5 mg, 0.034 mmol) in DMSO (0.34 mL) were combined in a microwave vial. The vial was purged with nitrogen and the reaction heated at 140° C. in the microwave for 2 h. The reaction was diluted with EtOAc and H₂O, and the mixture was filtered to remove a brown solid. The layers were separated and the organic layer was washed with H₂O (2×) and brine. The combined organic layers were dried (MgSO4), filtered, and concentrated under reduced pressure. The resultant brown gum was purified by column chromatography eluting with CH₂Cl₂/MeOH (0% MeOH→8% MeOH) to give Example 22 (3.8 mg, 8.2 μmol, 12% yield) as a yellow gum.

Example 23

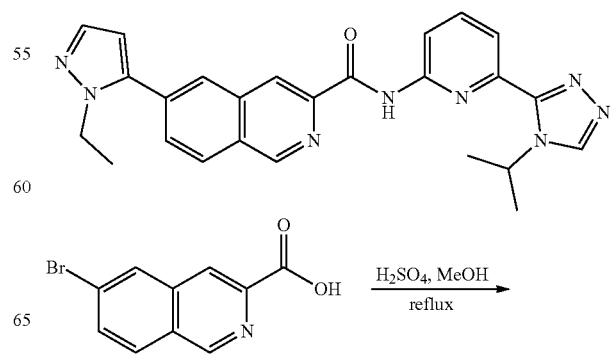

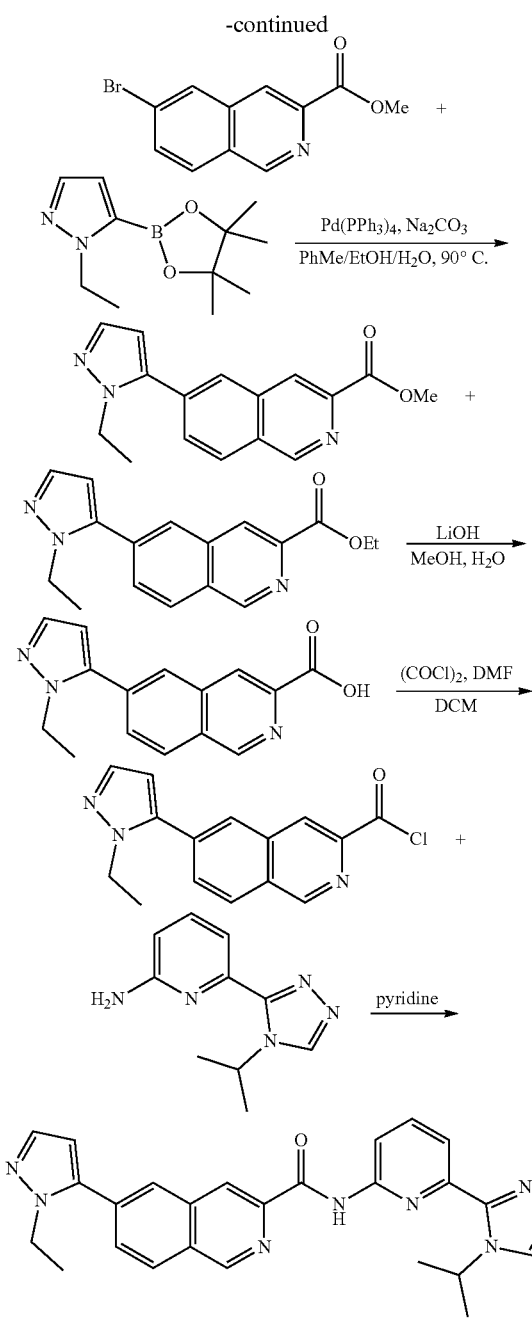

A mixture of 6-bromoisoquinoline-3-carboxylic acid (2 g, 7.9 mmol) and H$_2$SO$_4$ (1 ml, 18.8 mmol) in MeOH (20 mL) was heated at reflux for 72 h. The reaction was concentrated under reduced pressure and the resulant residue was partitioned between EtOAc and sat. NaHCO$_3$. The layers were separated and the organic layer was washed with sat. NaHCO$_3$ and brine. The organic layer was dried (MgSO4), filtered, and concentrated under reduced pressure to give methyl 6-bromoisoquinoline-3-carboxylate (1.8 g, 6.8 mmol, 85% yield) as a white solid: LCMS (m/z) 265.97 [M+H]+; $^1$H NMR (400 MHz, Chloroform-d) δ 9.32 (t, J=0.9 Hz, 1H), 8.52 (d, J=1.1 Hz, 1H), 8.16 (d, J=1.8 Hz, 1H), 7.94 (dt, J=8.7, 0.7 Hz, 1H), 7.84 (dd, J=8.7, 1.8 Hz, 1H), 4.07 (s, 3H).

Na$_2$CO$_3$ (0.38 mL of a 2M solution in H$_2$O, 0.75 mmol) was added to a mixture of 1-ethyl-5-(4,4,5,5-tetramethyl-1,3,2-dioxaborolan-2-yl)-1H-pyrazole (92 mg, 0.41 mmol), methyl 6-bromoisoquinoline-3-carboxylate (100 mg, 0.38 mmol), and Pd(Ph$_3$P)$_4$ (43 mg, 0.04 mmol) in Toluene (1.6 mL)/EtOH (0.3 mL) and the reaction was heated at 90° C. for 16 hrs. The reaction was quenched with H$_2$O and diluted with EtOAc. The layers were separated and the aqueous layer was extracted with EtOAc (2×). The combined organic layers were dried (MgSO4), filtered, and concentrated under reduced pressure. The resultant orange oil was purified by column chromatography eluting with CH$_2$Cl$_2$/MeOH (0% MeOH→5% MeOH) to give 67 mg of a mixture of methyl 6-(1-ethyl-1H-pyrazol-5-yl)isoquinoline-3-carboxylate and ethyl 6-(1-ethyl-1H-pyrazol-5-yl)isoquinoline-3-carboxylate; LCMS (m/z) 282.12 [M+H]+ and 296.13 [M+H]+. LiOH (10 mg, 0.24 mmol) in H$_2$O (0.64 mL) was added to a solution of 6-(1-ethyl-1H-pyrazol-5-yl)isoquinoline-3-carboxylate and ethyl 6-(1-ethyl-1H-pyrazol-5-yl)isoquinoline-3-carboxylate (67 mg) in MeOH (0.95=mL) and the reaction was stirred for 1 h. The reaction was neutralized with 2 M HCl and extracted with EtOAc (3×). The combined organic layers were dried (MgSO4), filtered, and concentrated under reduced pressure. The resultant clear gum was purified by column chromatography eluting with CH$_2$Cl$_2$/MeOH (0% MeOH→15% MeOH) to give 6-(1-ethyl-1H-pyrazol-5-yl)isoquinoline-3-carboxylic acid (18.6 mg, 0.07 mmol, 29% yield) as a white solid; LCMS (m/z) 268.08 [M+H]+.

Oxalyl chloride (10 µl, 0.12 mmol) was added to a solution of 6-(1-ethyl-1H-pyrazol-5-yl)isoquinoline-3-carboxylic acid (18.6 mg, 0.07 mmol) and DMF (1.0 µl, 0.014 mmol) in DCM (0.2 mL) and the reaction was stirred for 1 hr. The reaction was concentrated under reduced pressure and used directly in the next step.

A solution of 6-(4-isopropyl-4H-1,2,4-triazol-3-yl)pyridin-2-amine (15 mg, 0.07 mmol) in pyridine (0.60 mL) was added to crude 6-(1-ethyl-1H-pyrazol-5-yl)isoquinoline-3-carbonyl chloride (20 mg, 0.07 mmol) and the reaction was stirred overnight. The reaction was concentrated under reduced pressure. The resultant yellow residue was purified by column chromatography eluting with CH$_2$Cl$_2$/MeOH (0% MeOH→5% MeOH) to give Example 23 (12.1 mg, 0.03 mmol, 38% yield).

Example 34

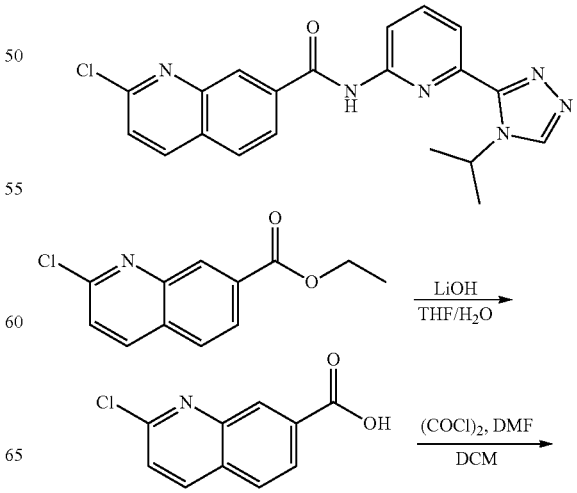

-continued

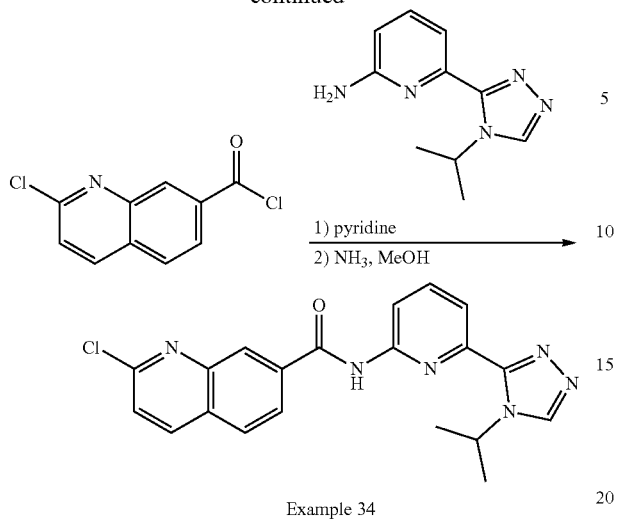

Example 34

Lithium hydroxide (8.5 mL of a 1.0 M solution in H$_2$O, 8.5 mmol, 2.0 eq) was added to a solution of ethyl 2-chloroquinoline-7-carboxylate (1.0 g, 4.2 mmol, 1.0 eq) in THF (12.5 mL) and the reaction was stirred overnight. The reaction was concentrated under reduced pressure. The resultant aqueous solution was made acidic (pH ~6) with 1.0 M aqueous HCl. The resultant precipitate was filtered to afford 2-chloroquinoline-7-carboxylic acid (700 mg, 3.4 mmol, 79%) as a colorless solid.

Oxalyl chloride (0.29 mL, 3.28 mmol, 1.7 eq) was added dropwise to a mixture of 2-chloroquinoline-7-carboxylic acid (400 mg, 1.93 mmol, 1.0 eq) and DMF (15 μL, 0.19 mmol, 0.1 eq) in DCM (5.5 mL). The reaction was stirred for 2 hrs. The reaction was concentrated under reduced pressure to give a yellow residue. The crude compound, 2-chloroquinoline-7-carbonyl chloride, was used in the next step without purification.

A solution of 6-(4-isopropyl-4H-1,2,4-triazol-3-yl)pyridin-2-amine (356 mg, 1.75 mmol, 1.0 eq) in pyridine (4.6 mL) was added to 2-chloroquinoline-7-carbonyl chloride (436 mg, 1.93 mmol, 1.1 eq) and the reaction was stirred overnight. The reaction was concentrated under reduced pressure. The resultant brown gum was dissolved in 7N NH$_3$ in MeOH (13.7 mL) and stirred for 3 hrs. The reaction was concentrated under reduced pressure. The resultant brown gum was purified by column chromatography eluting with DCM/MeOH (0% MeOH→10% MeOH) to afford Example 34 (586 mg, 1.49 mmol, 85%) as a pale yellow amorphous solid: LCMS (ESI) m/z 393.11 (M+1).

Example 33

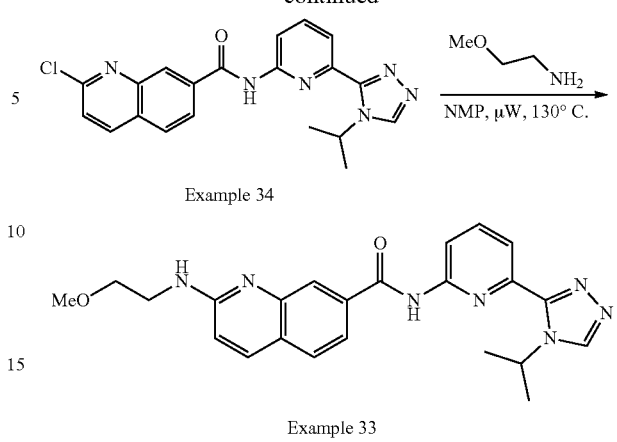

Example 33

A mixture of Example 34 (25 mg, 0.06 mmol, 1.0 eq) in NMP (0.2 mL) and 2-methoxyethan-1-amine (0.2 mL) was heated at 130° C. in a microwave reactor for 60 minutes. The reaction was quenched with sat. NaHCO$_3$ and diluted with EtOAc. The layers were separated and the organic layer was washed with H$_2$O (2×). The organic layer was dried (MgSO4), filtered, and concentrated under reduced pressure. The resultant pale yellow residue was purified by column chromatography eluting with DCM/MeOH (0% MeOH→12% MeOH) to afford Example 33 (18.7 mg, 0.04 mmol, 68%) as a colorless amorphous solid: LCMS (ESI) m/z 432.22 (M+1).

Examples 24-32 were prepared following the same protocol as shown in Example 33.

Example 35

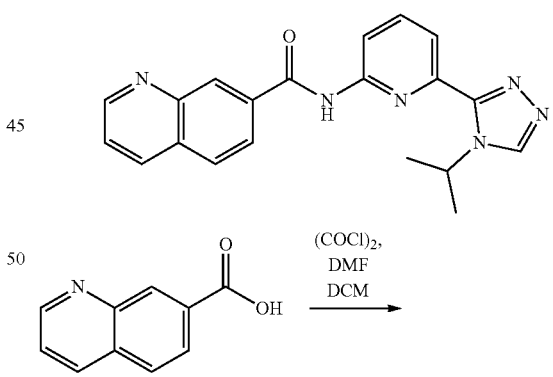

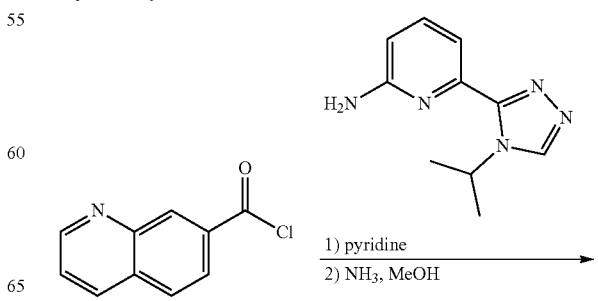

-continued

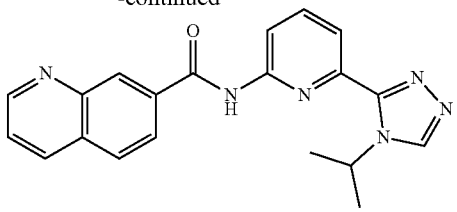

Oxalyl chloride (42 µL, 0.47 mmol, 1.7 eq) was added dropwise to a mixture of quinoline-7-carboxylic acid (48 mg, 0.28 mmol, 1.0 eq) and DMF (2 µL, 0.03 mmol, 0.1 eq) in DCM (0.7 mL). The reaction was stirred for 2 hrs. The reaction was concentrated under reduced pressure to give a yellow residue. The crude product, quinoline-7-carbonyl chloride, was used in the next step without purification.

A solution of 6-(4-isopropyl-4H-1,2,4-triazol-3-yl)pyridin-2-amine (51.6 mg, 0.25 mmol, 1.0 eq) in pyridine (0.67 mL) was added to quinoline-7-carbonyl chloride (55.1 mg, 0.29 mmol, 1.1 eq) and the reaction was stirred overnight. The reaction was concentrated under reduced pressure. The resultant brown residue was dissolved in 7N $NH_3$ in MeOH (2 mL) and stirred for 3 hrs. The reaction was concentrated under reduced pressure. The resultant yellow residue was purified by column chromatography eluting with DCM/MeOH (0% MeOH→8% MeOH) to afford Example 35 (34.9 mg, 0.10 mmol, 38%) as a colorless amorphous solid: LCMS (ESI) m/z 359.15 (M+1).

Example 36

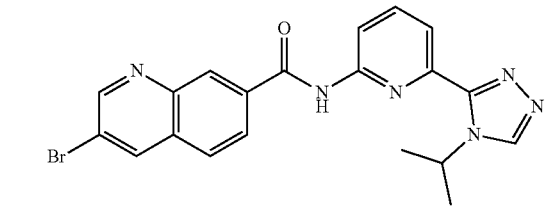

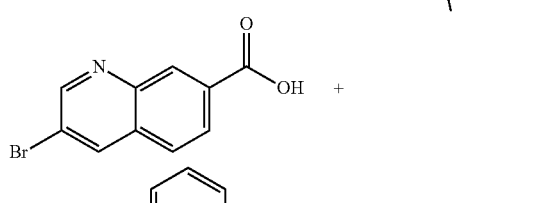

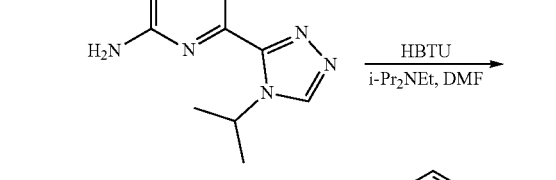

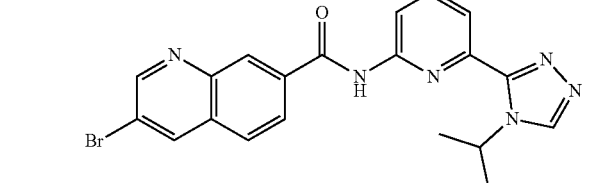

HBTU (451 mg, 1.2 mmol, 1.2 eq) was added to a solution of 3-bromoquinoline-7-carboxylic acid (250 mg, 1.0 mmol, 1.0 eq) and Hunig's base (0.87 mL, 5.0 mmol, 5.0 eq) in DMF (3.0 mL) and the reaction was stirred for 10 min at room temperature. 6-(4-Isopropyl-4H-1,2,4-triazol-3-yl)pyridin-2-amine (1-6) (222 mg, 1.1 mmol, 1.1 eq) was added and the resultant suspension was heated at 60° C. overnight. The reaction was partitioned between EtOAc and $H_2O$. The layers were separated and the organic layer was washed with sat. $NaHCO_3$, 10% citric acid, and brine. The organic layer was dried (MgSO4), filtered, and concentrated under reduced pressure. The resultant brown gum was purified by column chromatography eluting with DCM/MeOH (0% MeOH→8% MeOH) to afford pure compound 36 (82 mg, 0.19 mmol, 19%) as a brown amorphous solid: LCMS (ESI) m/z 437.06 (M+1).

Example 37

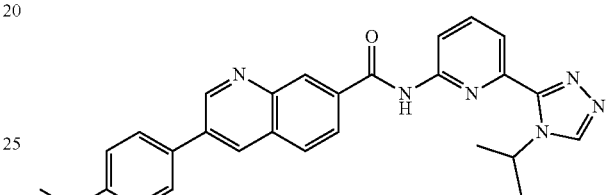

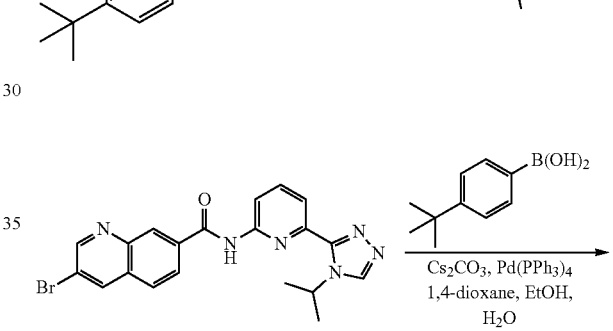

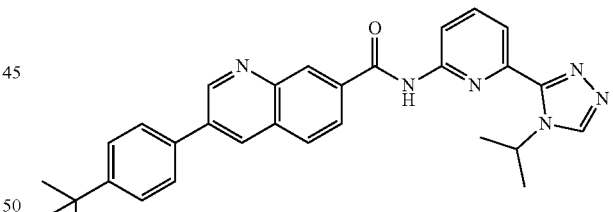

A mixture of Example 36 (18 mg, 0.04 mmol, 1.0 eq), (4-(tert-butyl)phenyl)boronic acid (11 mg, 0.06 mmol, 1.5 eq), $Cs_2CO_3$ (26.8 mg, 0.08 mmol, 2.0 eq), and $Pd(PPh_3)_4$ (2.4 mg, 2.06 µmol, 0.05 eq) in 1,4-dioxane (1.5 mL)/EtOH (0.19 mL)/$H_2O$ (0.37 mL) was sparged with $N_2$ for 5 min. The reaction was heated at 80° C. overnight. The reaction was partitioned between $H_2O$/brine and EtOAc. The layers were separated and the aqueous layer was extracted with EtOAc (2×). The combined organic layers were dried (MgSO4), filtered, and concentrated under reduced pressure. The resultant yellow residue was purified by column chromatography eluting with DCM/MeOH (0% MeOH→5% MeOH) to afford Example 37 (15.6 mg, 0.03 mmol, 77%) as a yellow solid: LCMS (ESI) m/z 491.25 (M+1).

Example 38

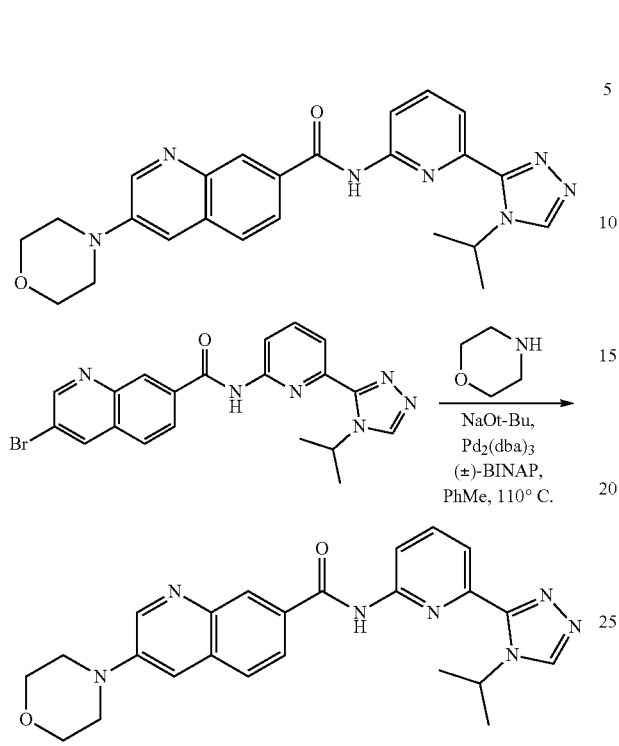

A mixture of Example 36 (18 mg, 0.04 mmol, 1.0 eq), sodium tert-butoxide (5.9 mg, 0.06 mmol, 1.5 eq), morpholine (4.3 μL, 0.05 mmol, 1.2 eq), Pd$_2$(dba)$_3$ (1.9 mg, 2.06 μmol, 0.05 eq), and rac-BINAP (3.8 mg, 6.17 μmol, 0.15 eq) in toluene (0.41 mL) was heated at 110° C. overnight. The reaction was partitioned between H$_2$O and EtOAc. The layers were separated and the aqueous layer was extracted with EtOAc (2×). The combined organic layers were dried (MgSO4), filtered, and concentrated under reduced pressure. The resultant yellow residue was purified by column chromatography eluting with DCM/MeOH (0% MeOH→8% MeOH) to afford Example 38 (3.4 mg, 7.67 μmol, 19%) as a yellow residue: LCMS (ESI) m/z 444.21 (M+1).

Example 39

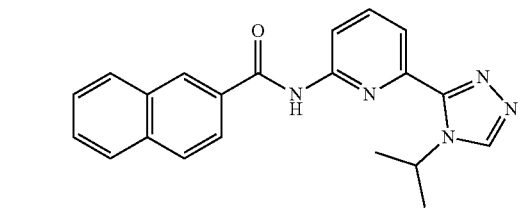

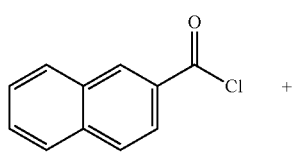

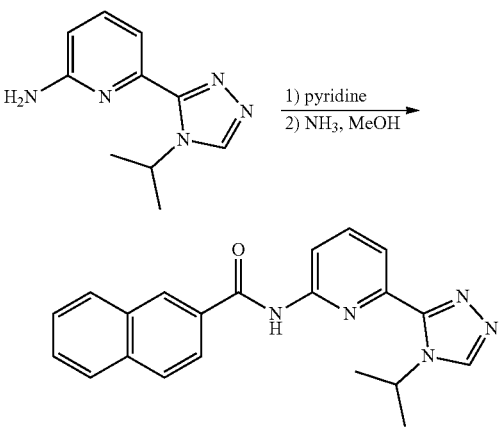

2-naphthoyl chloride (50 mg, 0.26 mmol, 1.1 eq) was added to a solution of 6-(4-isopropyl-4H-1,2,4-triazol-3-yl)pyridin-2-amine (48.4 mg, 0.24 mmol, 1.0 eq), prepared according to US 2014/0018370, in pyridine (0.67 mL) and the reaction was stirred overnight. The reaction was concentrated under reduced pressure. The resultant brown residue was dissolved in 7N NH$_3$ in MeOH (2 mL) and stirred for 3 hrs. The reaction was concentrated under reduced pressure. The resultant brown residue was purified by column chromatography eluting with DCM/MeOH (0% MeOH→5% MeOH) to afford Example 39 (63.6 mg, 0.18 mmol, 75%) as a colorless amorphous solid: LCMS (ESI) m/z 358.15 (M+1).

Example 40

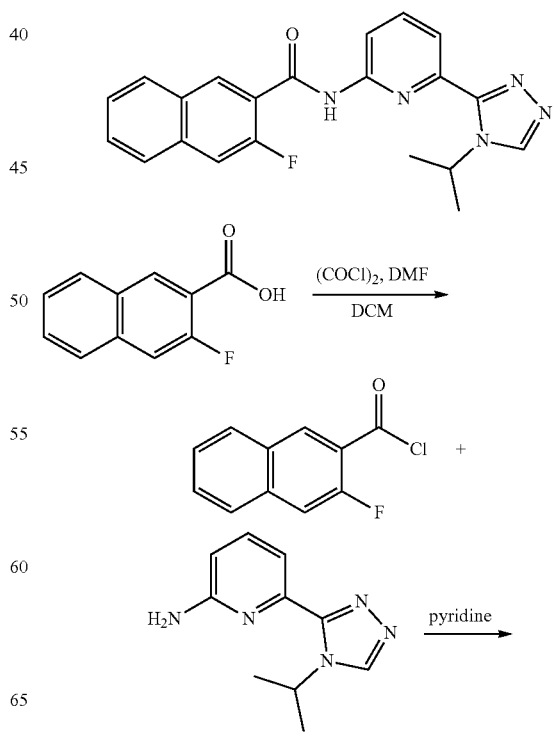

-continued

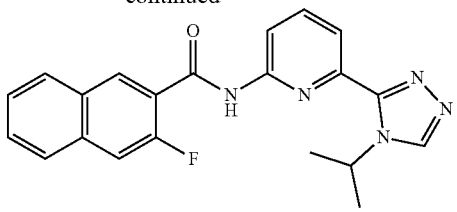

To a mixture of 3-fluoro-2-naphthoic acid (100 mg, 0.53 mmol) in DCM (1.5 mL) and DMF (4.07 µL, 0.053 mmol) was charged oxalyl chloride (78 µL, 0.89 mmol) and the mixture was stirred for 1 hr. The reaction was concentrated under reduced pressure to give an orange gum.

A solution of 6-(4-isopropyl-4H-1,2,4-triazol-3-yl)pyridin-2-amine (53.5 mg, 0.26 mmol) in pyridine (750 µl) was added to crude 3-fluoro-2-naphthoyl chloride (55 mg, 0.26 mmol) and the reaction was stirred overnight. The reaction was concentrated under reduced pressure and the resultant orange residue was purified by column chromatography eluting with $CH_2Cl_2$/MeOH (0% MeOH→10% MeOH) to give Example 40 (89 mg, 0.24 mmol, 90% yield) as a pale yellow solid.

Example 41 was prepared according to the procedure for the synthesis of Example 40.

| Example | Structure | LC-MS [M + H]+ unless otherwise noted | H-NMR |
|---|---|---|---|
| 1 | 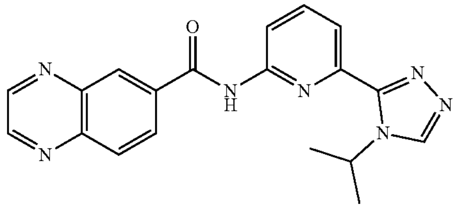 [SMILES: CC(C)n1cnnc1-c1cccc(NC(=O)c2ccc3nccnc3c2)n1] | 360.15 | 1H NMR (400 MHz, DMSO-d6) δ 11.16 (s, 1H), 9.12-9.07 (m, 2H), 8.88 (s, 1H), 8.76 (d, J = 2.0 Hz, 1H), 8.36 (dd, J = 8.8, 2.0 Hz, 1H), 8.29-8.22 (comp, 2H), 8.06 (t, J = 8.0 Hz, 1H), 7.91 (dd, J = 7.7, 0.9 Hz, 1H), 5.75 (hept, J = 2.6 Hz, 1H), 1.46 (d, J = 6.6 Hz, 6H) |
| 2 | 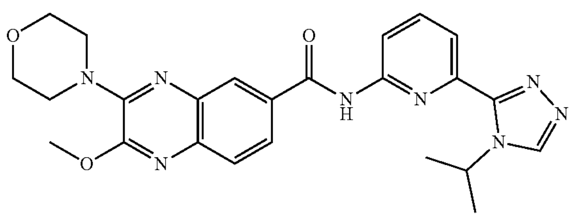 [SMILES: COc1nc2ccc(C(=O)Nc3cccc(-c4nncn4C(C)C)n3)cc2nc1N1CCOCC1] | 475.21 | 1H NMR (400 MHz, Chloroform-d) δ 8.56-8.41 (m, 3H), 8.09-7.89 (m, 4H), 7.35 (d, J = 8.7 Hz, 1H), 5.57 (hept, J = 6.7 Hz, 1H), 4.07 (t, J = 4.7 Hz, 4H), 3.88 (dd, J = 5.6, 3.9 Hz, 4H), 3.74 (s, 3H), 1.58 (d, J = 6.7 Hz, 6H) |
| 3 | 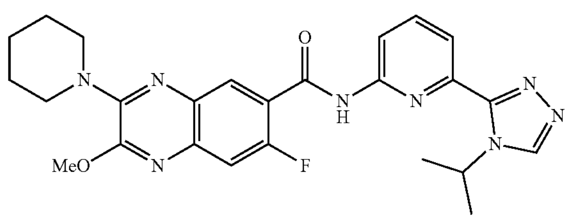 [SMILES: COc1nc2cc(F)c(C(=O)Nc3cccc(-c4nncn4C(C)C)n3)cc2nc1N1CCCCC1] | 491.21 | 1H NMR (500 MHz, DMSO-d6) δ 10.78 (d, J = 2.0 Hz, 1H), 8.86 (s, 1H), 8.21 (dd, J = 8.3, 0.9 Hz, 1H), 8.03 (t, J = 8.0 Hz, 1H), 7.89 (dd, J = 7.6, 0.9 Hz, 1H), 7.73 (d, J = 7.3 Hz, 1H), 7.45 (d, J = 12.2 Hz, 1H), 5.67 (hept, J = 6.6 Hz, 1H), 3.89-3.80 (comp, 4H), 3.59 (s, 3H), 1.64-1.59 (comp, 6H), 1.44 (d, J = 6.7 Hz, 6H) |
| 4 | 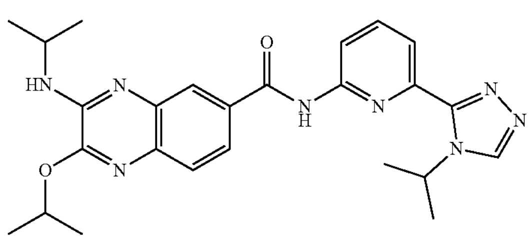 [SMILES: CC(C)Nc1nc2cc(C(=O)Nc3cccc(-c4nncn4C(C)C)n3)ccc2nc1OC(C)C] | 475.24 | 1H NMR (400 MHz, Chloroform-d) δ 8.58 (s, 1H), 8.50 (dd, J = 8.3, 0.9 Hz, 1H), 8.40 (s, 1H), 8.20 (s, 1H), 8.05 (dd, J = 7.7, 1.0 Hz, 1H), 8.00-7.87 (m, 2H), 7.75 (d, J = 8.4 Hz, 1H), 5.64 (pd, J = 6.4, 2.7 Hz, 2H), 5.50 (d, J = 7.6 Hz, 1H), 4.52-4.42 (m, 1H), 1.60 (d, J = 6.7 Hz, 7H), 1.50 (d, J = 6.2 Hz, 6H), 1.38 (d, J = 6.5 Hz, 6H) |
| 5 | 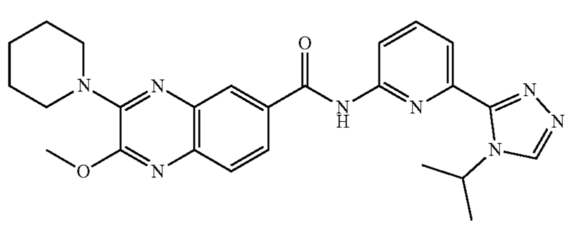 [SMILES: COc1nc2ccc(C(=O)Nc3cccc(-c4nncn4C(C)C)n3)cc2nc1N1CCCCC1] | 473.23 | 1H NMR (400 MHz, Chloroform-d) δ 8.55 (s, 1H), 8.47 (d, J = 8.2 Hz, 1H), 8.40 (s, 1H), 8.03 (dd, J = 4.9, 2.8 Hz, 2H), 7.99-7.84 (m, 2H), 7.35-7.26 (m, 1H), 5.60 (h, J = 6.8 Hz, 1H), 3.98 (t, J = 4.3 Hz, 4H), 3.72 (s, 3H), 1.75 (br s, 6H), 1.58 (d, J = 6.7 Hz, 6H) |

-continued

| Example | Structure | LC-MS [M + H]+ unless otherwise noted | H-NMR |
|---|---|---|---|
| 6 | 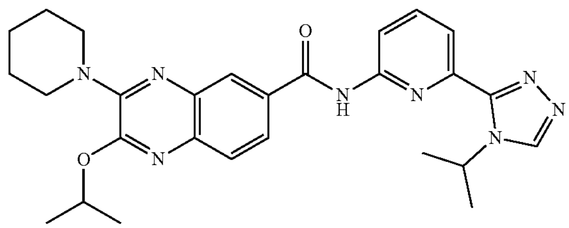 [SMILES: CC(C)Oc1nc2ccc(C(=O)Nc3cccc(-c4nncn4C(C)C)n3)cc2nc1N1CCCCC1] | 501.26 | ¹H NMR (400 MHz, Chloroform-d) δ 8.49 (s, 1H), 8.40 (dd, J = 8.3, 0.9 Hz, 1H), 8.30 (s, 1H), 8.10 (d, J = 2.1 Hz, 1H), 7.95 (dd, J = 7.6, 1.0 Hz, 1H), 7.89-7.80 (m, 2H), 7.66 (d, J = 8.5 Hz, 1H), 5.53 (pd, J = 6.4, 2.0 Hz, 2H), 3.64 (t, J = 4.7 Hz, 4H), 1.49 (d, J = 6.7 Hz, 6H), 1.41 (d, J = 6.2 Hz, 6H) |
| 7 | 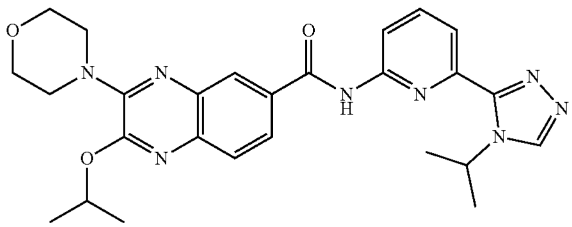 [SMILES: CC(C)Oc1nc2ccc(C(=O)Nc3cccc(-c4nncn4C(C)C)n3)cc2nc1N1CCOCC1] | 503.24 | ¹H NMR (400 MHz, Chloroform-d) δ 8.46 (s, 1H), 8.45-8.33 (m, 2H), 8.16 (d, J = 2.0 Hz, 1H), 7.97 (dd, J = 7.6, 0.9 Hz, 1H), 7.94-7.83 (m, 2H), 7.71 (d, J = 8.5 Hz, 1H), 5.54 (m, 2H), 3.82 (dd, J = 5.6, 3.4 Hz, 4H), 3.73 (dd, J = 5.6, 3.5 Hz, 4H), 1.51 (d, J = 6.7 Hz, 6H), 1.41 (d, J = 6.2 Hz, 6H) |
| 8 | 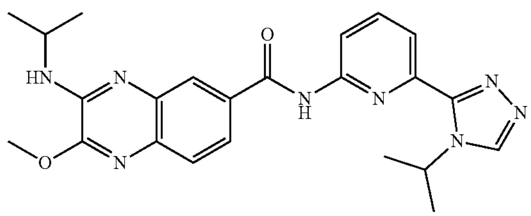 [SMILES: COc1nc2ccc(C(=O)Nc3cccc(-c4nncn4C(C)C)n3)cc2nc1NC(C)C] | 447.21 | ¹H NMR (400 MHz, Chloroform-d) δ 8.57-8.45 (m, 2H), 8.42 (s, 1H), 8.19-8.14 (m, 1H), 8.06 (dd, J = 7.7, 1.0 Hz, 1H), 8.00-7.89 (m, 2H), 7.38 (d, J = 8.7 Hz, 1H), 6.51 (d, J = 8.2 Hz, 1H), 5.64 (p, J = 6.7 Hz, 1H), 4.49-4.39 (m, 1H), 3.79 (s, 3H), 1.60 (d, J = 6.7 Hz, 6H), 1.38 (d, J = 6.5 Hz, 6H) |
| 9 | 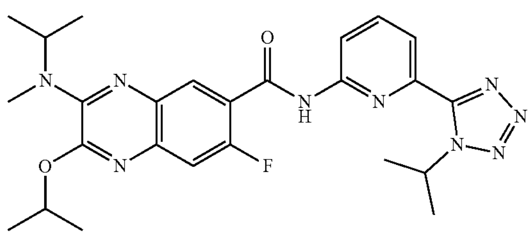 [SMILES: CC(C)Oc1nc2cc(F)c(C(=O)Nc3cccc(-c4nnnn4C(C)C)n3)cc2nc1N(C)C(C)C] | 508.25 | ¹H NMR (500 MHz, Chloroform-d) δ 9.16 (d, J = 16.3 Hz, 1H), 8.52 (dd, J = 8.4, 0.9 Hz, 1H), 8.44 (d, J = 8.2 Hz, 1H), 8.01 (dd, J = 7.6, 1.0 Hz, 1H), 7.91 (t, J = 8.0 Hz, 1H), 7.31 (d, J = 13.4 Hz, 1H), 5.70 (h, J = 6.7 Hz, 1H), 5.55-5.43 (m, 1H), 4.74 (h, J = 6.7 Hz, 1H), 2.99 (s, 3H), 1.66 (dd, J = 6.7, 2.4 Hz, 6H), 1.46-1.36 (m, 6H), 1.20 (d, J = 6.7 Hz, 6H) |
| 10 | 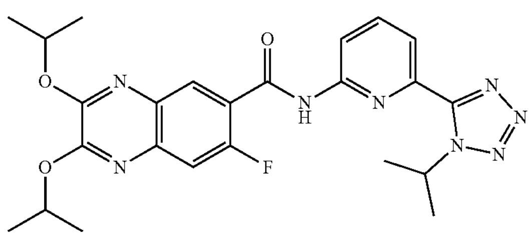 [SMILES: CC(C)Oc1nc2cc(F)c(C(=O)Nc3cccc(-c4nnnn4C(C)C)n3)cc2nc1OC(C)C] | 495.23 | ¹H NMR (400 MHz, DMSO-d₆) δ 11.19 (s, 1H), 8.35 (dd, J = 8.4, 0.9 Hz, 1H), 8.16 (t, J = 8.0 Hz, 1H), 8.08-7.99 (m, 2H), 7.66 (d, J = 11.0 Hz, 1H), 6.04 (m, 1H), 5.49 (m, 2H), 1.55 (d, J = 6.6 Hz, 6H), 1.42 (m, 12H) |
| 11 | 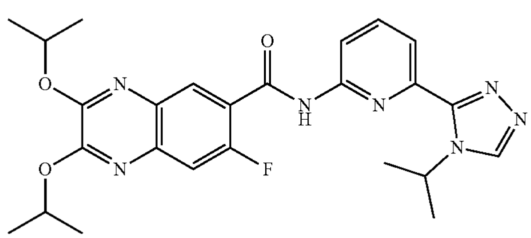 [SMILES: CC(C)Oc1nc2cc(F)c(C(=O)Nc3cccc(-c4nncn4C(C)C)n3)cc2nc1OC(C)C] | 494.22 | ¹H NMR (500 MHz, DMSO-d₆) δ 11.00 (s, 1H), 8.87 (s, 1H), 8.24 (dd, J = 8.3, 0.9 Hz, 1H), 8.09-8.01 (m, 2H), 7.91 (dd, J = 7.6, 0.9 Hz, 1H), 7.64 (d, J = 11.0 Hz, 1H), 5.68 (p, J = 6.6 Hz, 1H), 5.49 (m, 2H), 1.46-1.39 (m, 18H) |

-continued

| Example | Structure | LC-MS [M + H]+ unless otherwise noted | H-NMR |
|---|---|---|---|
| 12 | 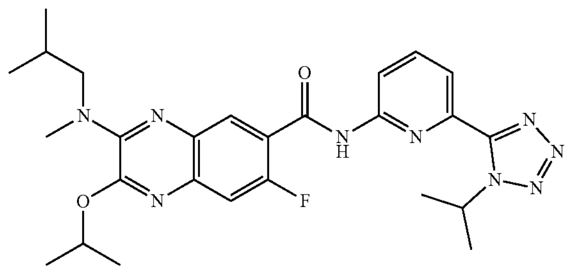 [SMILES: CC(C)CN(C)c1nc2cc(C(=O)Nc3cccc(-c4nnnn4C(C)C)n3)c(F)cc2nc1OC(C)C] | 522.27 | ¹H NMR (400 MHz, DMSO-d₆) δ 11.10 (s, 1H), 8.34 (dd, J = 8.4, 0.9 Hz, 1H), 8.20-8.10 (m, 1H), 8.08-7.98 (m, 1H), 7.88 (d, J = 7.3 Hz, 1H), 7.50 (d, J = 11.1 Hz, 1H), 6.05 (p, J = 6.5 Hz, 1H), 5.62-5.47 (m, 1H), 3.62 (d, J = 7.5 Hz, 2H), 3.19 (s, 3H), 1.55 (d, J = 6.6 Hz, 6H), 1.47-1.38 (m, 7H), 0.87 (d, J = 6.7 Hz, 6H) |
| 13 | 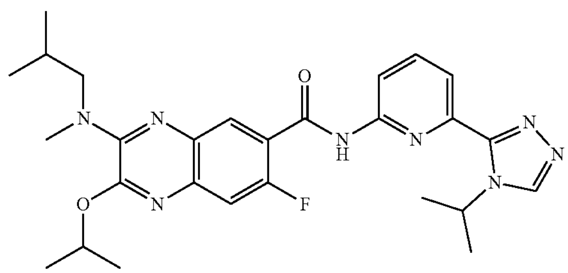 [SMILES: CC(C)CN(C)c1nc2cc(C(=O)Nc3cccc(-c4nncn4C(C)C)n3)c(F)cc2nc1OC(C)C] | 521.27 | ¹H NMR (400 MHz, DMSO-d₆) δ 10.92 (s, 1H), 8.87 (d, J = 1.6 Hz, 1H), 8.24 (dt, J = 8.3, 1.7 Hz, 1H), 8.04 (t, J = 8.0 Hz, 1H), 7.95-7.83 (m, 2H), 7.48 (d, J = 11.1 Hz, 1H), 5.69 (p, J = 6.7 Hz, 1H), 5.62-5.47 (m, 1H), 3.61 (d, J = 7.5 Hz, 2H), 3.19 (s, 3H), 2.05 (m, 1H), 1.43 (m, 12H), 0.87 (d, J = 6.7 Hz, 6H) |
| 14 | 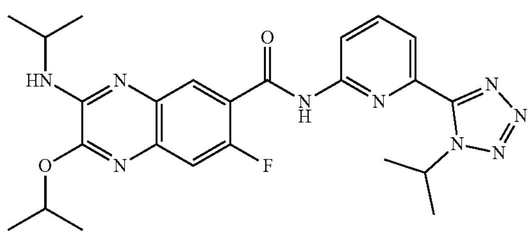 [SMILES: CC(C)Nc1nc2cc(C(=O)Nc3cccc(-c4nnnn4C(C)C)n3)c(F)cc2nc1OC(C)C] | 494.23 | ¹H NMR (400 MHz, Chloroform-d) δ 9.27 (d, J = 16.8 Hz, 1H), 8.62 (dd, J = 8.4, 1.0 Hz, 1H), 8.48 (d, J = 8.4 Hz, 1H), 8.11 (dd, J = 7.7, 1.0 Hz, 1H), 8.01 (t, J = 8.0 Hz, 1H), 7.41 (d, J = 13.5 Hz, 1H), 5.79 (h, J = 6.6 Hz, 1H), 5.61 (p, J = 6.2 Hz, 1H), 5.39 (d, J = 7.6 Hz, 1H), 4.49-4.35 (m, 1H), 1.76 (dd, J = 6.6, 1.8 Hz, 6H), 1.49 (d, J = 1.7 Hz, 6H), 1.37 (dd, J = 6.4, 1.7 Hz, 6H) |
| 15 | 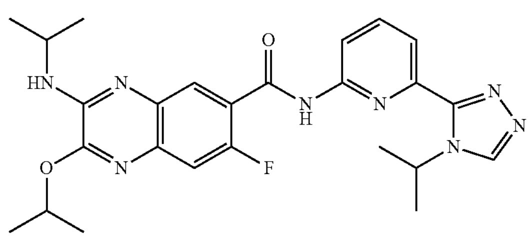 [SMILES: CC(C)Nc1nc2cc(C(=O)Nc3cccc(-c4nncn4C(C)C)n3)c(F)cc2nc1OC(C)C] | 493.24 | ¹H NMR (400 MHz, DMSO-d₆) δ 10.89 (s, 1H), 8.87 (s, 1H), 8.24 (dd, J = 8.3, 1.0 Hz, 1H), 8.04 (t, J = 8.0 Hz, 1H), 7.90 (dd, J = 7.7, 0.9 Hz, 1H), 7.81 (d, J = 7.3 Hz, 1H), 7.45 (d, J = 11.2 Hz, 1H), 6.87 (d, J = 8.0 Hz, 1H), 5.69 (h, J = 6.9 Hz, 1H), 5.50 (p, J = 6.2 Hz, 1H), 4.42-4.28 (m, 1H), 1.47-1.40 (m, 12H), 1.26 (d, J = 6.5 Hz, 6H) |
| 16 | 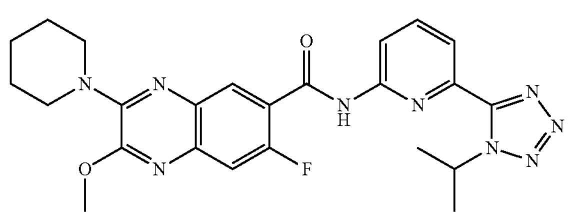 [SMILES: COc1nc2cc(F)c(C(=O)Nc3cccc(-c4nnnn4C(C)C)n3)cc2nc1N1CCCCC1] | 492.22 | ¹H NMR (400 MHz, Chloroform-d) δ 9.16 (d, J = 13.7 Hz, 1H), 8.92 (d, J = 7.9 Hz, 1H), 8.61 (d, J = 8.4 Hz, 1H), 8.12 (d, J = 7.6 Hz, 1H), 8.01 (t, J = 7.9 Hz, 1H), 7.51 (dd, J = 12.7, 1.3 Hz, 1H), 5.82 (p, J = 6.6 Hz, 1H), 4.20 (d, J = 1.4 Hz, 3H), 3.89 (d, J = 5.8 Hz, 4H), 1.80-1.60 (m, 12H) |
| 17 | 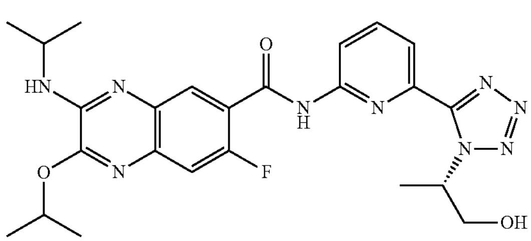 [SMILES: CC(C)Nc1nc2cc(C(=O)Nc3cccc(-c4nnnn4[C@@H](C)CO)n3)c(F)cc2nc1OC(C)C] | 510.23 | ¹H NMR (400 MHz, Chloroform-d) δ 9.24 (d, J = 17.1 Hz, 1H), 8.51 (dd, J = 8.4, 0.9 Hz, 1H), 8.45 (d, J = 8.3 Hz, 1H), 8.11 (dd, J = 7.6, 0.9 Hz, 1H), 8.00 (t, J = 8.0 Hz, 1H), 7.39 (d, J = 13.5 Hz, 1H), 5.77 (td, J = 7.1, 4.4 Hz, 1H), 5.59 (p, J = 6.2 Hz, 1H), 5.37 (d, J = 7.7 Hz, 1H), 4.39 (dt, J = 13.5, 6.7 Hz, 1H), 4.10-4.21 (comp, 2H), 1.72 (d, J = 6.8 Hz, 3H), 1.47 (d, J = 6.2 Hz, 6H), 1.34 (d, J = 6.5 Hz, 6H) |

-continued

| Example | Structure | LC-MS [M + H]+ unless otherwise noted | H-NMR |
|---|---|---|---|
| 18 | 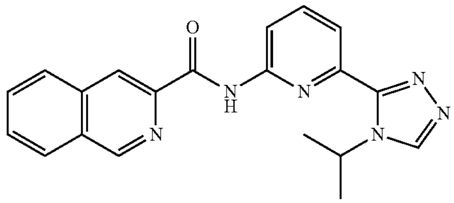 [SMILES: CC(C)n1cnnc1-c1cccc(NC(=O)c2cc3ccccc3cn2)n1] | 359.14 | ¹H NMR (400 MHz, DMSO-d₆) δ 10.80 (s, 1H), 9.51 (d, J = 0.9 Hz, 1H), 8.92 (s, 1H), 8.81 (s, 1H), 8.41 (dd, J = 8.3, 0.8 Hz, 1H), 8.31 (td, J = 7.2, 6.6, 1.2 Hz, 2H), 8.11 (t, J = 8.0 Hz, 1H), 7.95 (ddd, J = 8.3, 6.9, 1.4 Hz, 1H), 7.91-7.87 (comp, 2H), 5.51 (hept, J = 6.7 Hz, 1H), 1.53 (d, J = 6.7 Hz, 6H) |
| 19 | 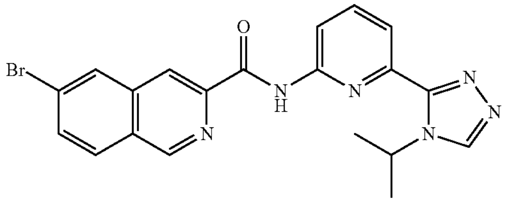 [SMILES: CC(C)n1cnnc1-c1cccc(NC(=O)c2cc3cc(Br)ccc3cn2)n1] | 437.06 | ¹H NMR (400 MHz, DMSO-d₆) δ 10.78 (s, 1H), 9.53 (s, 1H), 8.91 (s, 1H), 8.78 (s, 1H), 8.63 (d, J = 1.9 Hz, 1H), 8.39 (dd, J = 8.3, 0.9 Hz, 1H), 8.28 (d, J = 8.8 Hz, 1H), 8.11 (t, J = 8.0 Hz, 1H), 8.02 (dd, J = 8.7, 2.0 Hz, 1H), 7.90 (dd, J = 7.7, 0.9 Hz, 1H), 5.51 (hept, J = 6.5 Hz, 1H), 1.52 (d, J = 6.7 Hz, 6H) |
| 20 | 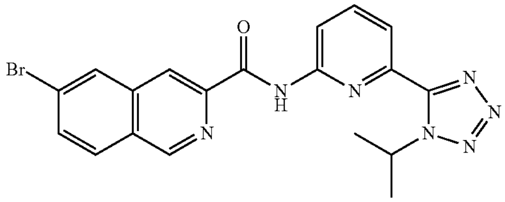 [SMILES: CC(C)n1nnnc1-c1cccc(NC(=O)c2cc3cc(Br)ccc3cn2)n1] | 438.05 | ¹H NMR (400 MHz, DMSO-d₆) δ 10.96 (s, 1H), 9.55 (s, 1H), 8.80 (s, 1H), 8.64 (d, J = 1.8 Hz, 1H), 8.48 (dd, J = 8.4, 0.9 Hz, 1H), 8.29 (d, J = 8.7 Hz, 1H), 8.20 (t, J = 8.0 Hz, 1H), 8.02 (td, J = 8.2, 7.4, 1.4 Hz, 2H), 5.91 (p, J = 6.6 Hz, 1H), 1.63 (d, J = 6.6 Hz, 6H) |
| 21 | 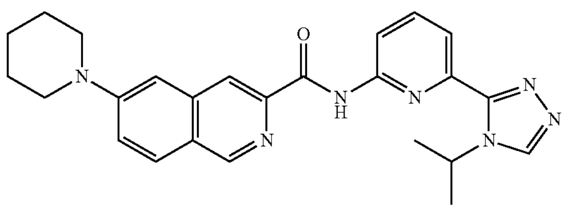 [SMILES: CC(C)n1cnnc1-c1cccc(NC(=O)c2cc3cc(N4CCCCC4)ccc3cn2)n1] | 442.22 | No Data |
| 22 | 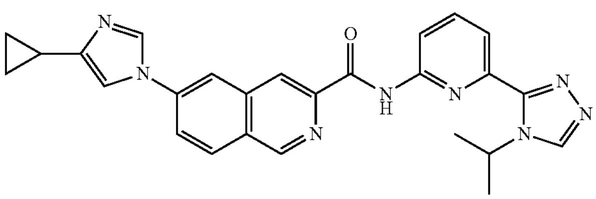 [SMILES: CC(C)n1cnnc1-c1cccc(NC(=O)c2cc3cc(-n4cnc(C5CC5)c4)ccc3cn2)n1] | 465.21 | ¹H NMR (400 MHz, DMSO-d₆) δ 10.80 (s, 1H), 9.51 (s, 1H), 8.92 (s, 1H), 8.75 (s, 1H), 8.53 (d, J = 2.2 Hz, 1H), 8.47-8.37 (compz, 3H), 8.21 (dd, J = 8.9, 2.2 Hz, 1H), 8.11 (t, J = 8.0 Hz, 1H), 7.94-7.89 (m, 1H), 7.75 (d, J = 1.4 Hz, 1H), 5.60-5.46 (m, 1H), 1.78 (tt, J = 8.3, 5.0 Hz, 2H), 1.53 (d, J = 6.7 Hz, 6H), 0.77-0.72 (m, 2H), 0.64-0.55 (m, 2H) |
| 23 | 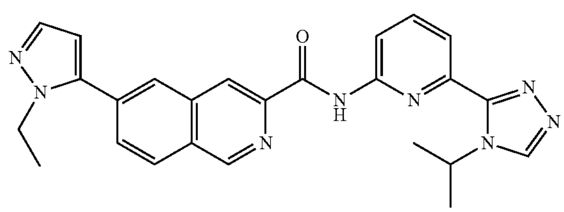 [SMILES: CCn1nccc1-c1ccc2cnc(C(=O)Nc3cccc(-c4nncn4C(C)C)n3)cc2c1] | 453.20 | No Data |
| 24 | 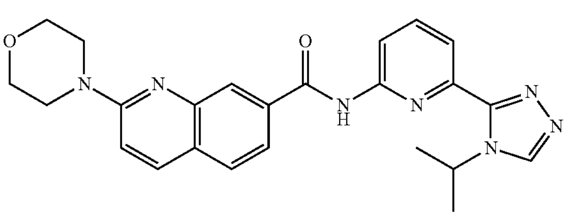 [SMILES: CC(C)n1cnnc1-c1cccc(NC(=O)c2ccc3ccc(N4CCOCC4)nc3c2)n1] | 444.20 | ¹H NMR (400 MHz, DMSO-d₆) δ 10.93 (s, 1H), 8.87 (s, 1H), 8.23-8.12 (comp, 3H), 8.03 (t, J = 8.0 Hz, 1H), 7.93-7.84 (comp, 2H), 7.75 (dd, J = 8.3, 1.8 Hz, 1H), 7.38 (d, J = 9.2 Hz, 1H), 5.87-5.73 (m, 1H), 3.80-3.67 (comp, 8H), 1.45 (d, J = 6.7 Hz, 6H) |

| Example | Structure | LC-MS [M + H]+ unless otherwise noted | H-NMR |
|---|---|---|---|
| 25 | 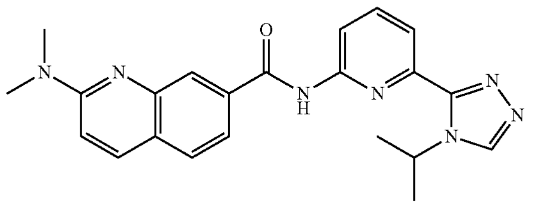 [SMILES: CC(C)n1cnnc1-c1cccc(NC(=O)c2ccc3ccc(N(C)C)nc3c2)n1] | 402.21 | ¹H NMR (400 MHz, DMSO-$d_6$) δ 10.91 (s, 1H), 8.87 (s, 1H), 8.22-8.17 (m, 2H), 8.10 (dd, J = 9.3, 0.7 Hz, 1H), 8.02 (dd, J = 7.6, 7.7 Hz, 1H), 7.88 (dd, J = 7.6, 0.9 Hz, 1H), 7.83 (d, J = 8.3 Hz, 1H), 7.69 (dd, J = 8.2, 1.7 Hz, 1H), 7.22 (d, J = 9.2 Hz, 1H), 5.80 (hept, J = 6.7 Hz, 1H), 3.20 (s, 6H), 1.45 (d, J = 6.6 Hz, 6H) |
| 26 | 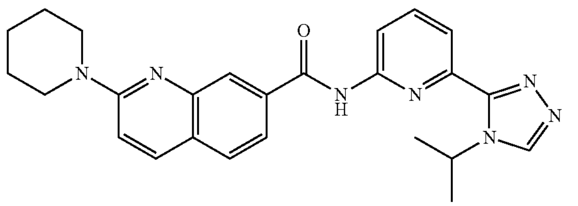 [SMILES: CC(C)n1cnnc1-c1cccc(NC(=O)c2ccc3ccc(N4CCCCC4)nc3c2)n1] | 442.22 | ¹H NMR (400 MHz, DMSO-$d_6$) δ 10.90 (s, 1H), 8.87 (s, 1H), 8.19 (dd, J = 8.4, 0.9 Hz, 1H), 8.17 (d, J = 1.7 Hz, 1H), 8.09 (d, J = 9.2 Hz, 1H), 8.02 (t, J = 8.0 Hz, 1H), 7.88 (dd, J = 7.6, 0.9 Hz, 1H), 7.82 (d, J = 8.3 Hz, 1H), 7.70 (dd, J = 8.3, 1.7 Hz, 1H), 7.36 (d, J = 9.3 Hz, 1H), 5.86-5.73 (m, 1H), 3.75 (t, J = 5.4 Hz, 4H), 1.71-1.63 (m, 2H), 1.63-1.55 (m, 4H), 1.45 (d, J = 6.7 Hz, 6H) |
| 27 | 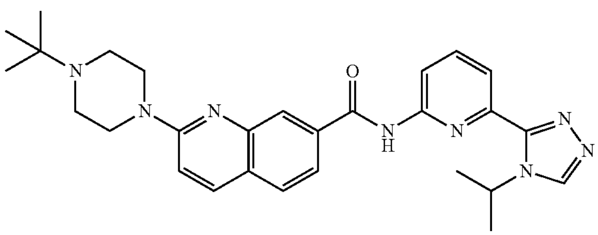 [SMILES: CC(C)n1cnnc1-c1cccc(NC(=O)c2ccc3ccc(N4CCN(C(C)(C)C)CC4)nc3c2)n1] | 499.33 | ¹H NMR (400 MHz, DMSO-$d_6$) δ 10.92 (s, 1H), 8.87 (s, 1H), 8.23-8.17 (comp, 2H), 8.12 (d, J = 9.2 Hz, 1H), 8.03 (t, J = 8.0 Hz, 1H), 7.88 (dd, J = 7.7, 0.9 Hz, 1H), 7.84 (d, J = 8.3 Hz, 1H), 7.72 (dd, J = 8.3, 1.7 Hz, 1H), 7.36 (d, J = 9.2 Hz, 1H), 5.80 (hept, J = 6.8 Hz, 1H), 3.70 (t, J = 4.9 Hz, 4H), 2.62 (t, J = 4.9 Hz, 4H), 1.45 (d, J = 6.7 Hz, 6H), 1.05 (s, 9H) |
| 28 | 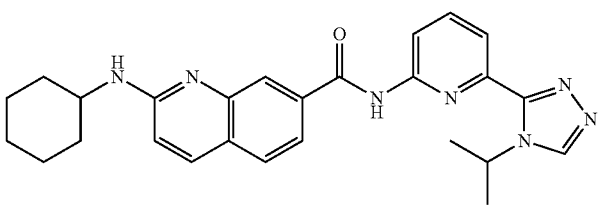 [SMILES: CC(C)n1cnnc1-c1cccc(NC(=O)c2ccc3ccc(NC4CCCCC4)nc3c2)n1] | 456.27 | ¹H NMR (400 MHz, DMSO-$d_6$) δ 10.89 (s, 1H), 8.87 (s, 1H), 8.18 (dd, J = 8.3, 0.9 Hz, 1H), 8.10 (d, J = 1.7 Hz, 1H), 8.05-7.97 (m, 1H), 7.92-7.84 (comp, 2H), 7.73 (d, J = 8.1 Hz, 1H), 7.64 (dd, J = 8.2, 1.8 Hz, 1H), 7.08 (d, J = 7.7 Hz, 1H), 6.85 (d, J = 9.0 Hz, 1H), 5.86-5.77 (m, 1H), 4.09-3.91 (m, J = 11.7 Hz, 2H), 2.03-1.95 (comp, 2H), 1.84-1.69 (comp, 2H), 1.66-1.59 (m, 1H), 1.48-1.42 (comp, 7H), 1.42-1.12 (comp, 4H) |
| 29 | 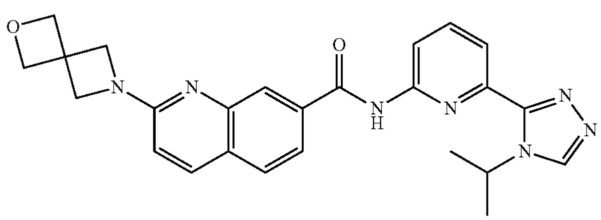 [SMILES: CC(C)n1cnnc1-c1cccc(NC(=O)c2ccc3ccc(N4CC5(COC5)C4)nc3c2)n1] | 456.22 | ¹H NMR (400 MHz, DMSO-$d_6$) δ 10.89 (s, 1H), 8.87 (s, 1H), 8.27 (d, J = 1.8 Hz, 1H), 8.19 (dd, J = 8.4, 0.9 Hz, 1H), 8.12 (d, J = 8.9 Hz, 1H), 8.02 (t, J = 8.0 Hz, 1H), 7.89 (dd, J = 7.6, 0.9 Hz, 1H), 7.86 (d, J = 8.3 Hz, 1H), 7.74 (dd, J = 8.3, 1.8 Hz, 1H), 6.85 (d, J = 8.9 Hz, 1H), 5.80 (hept, J = 6.7 Hz, 1H), 4.76 (s, 4H), 4.30 (s, 4H), 1.46 (d, J = 6.7 Hz, 6H) |
| 30 | 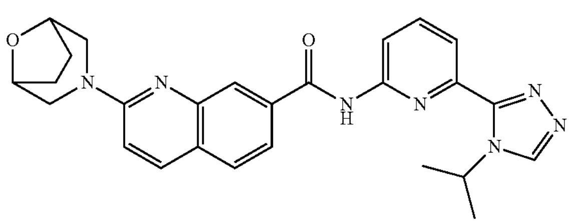 [SMILES: CC(C)n1cnnc1-c1cccc(NC(=O)c2ccc3ccc(N4CC5CCC(C4)O5)nc3c2)n1] | 470.22 | No Data |
| 31 | 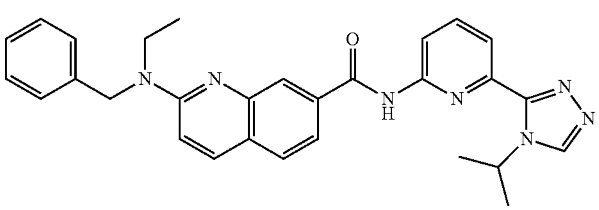 [SMILES: CCN(Cc1ccccc1)c1ccc2ccc(C(=O)Nc3cccc(-c4nncn4C(C)C)n3)cc2n1] | 492.24 | ¹H NMR (400 MHz, DMSO-$d_6$) δ 10.91 (s, 1H), 8.86 (s, 1H), 8.18 (dd, J = 8.3, 0.7 Hz, 1H), 8.16 (d, J = 1.7 Hz, 1H), 8.09 (d, J = 9.2 Hz, 1H), 8.02 (t, J = 8.0 Hz, 1H), 7.87 (dd, J = 7.6, 0.9 Hz, 1H), 7.82 (d, J = 8.2 Hz, 1H), 7.69 (dd, J = 8.2, 1.8 Hz, 1H), 7.34-7.30 (comp, 5H), 7.28-7.20 (m, 1H), 7.16 (d, J = 9.2 Hz, 1H), 5.83-5.76 (m, 1H), 4.94 (s, 2H), 3.71 (q, J = 7.0 Hz, 2H), 1.44 (d, J = 6.6 Hz, 6H), 1.19 (t, J = 7.0 Hz, 3H) |

-continued

| Example | Structure | LC-MS [M + H]+ unless otherwise noted | H-NMR |
|---|---|---|---|
| 32 | 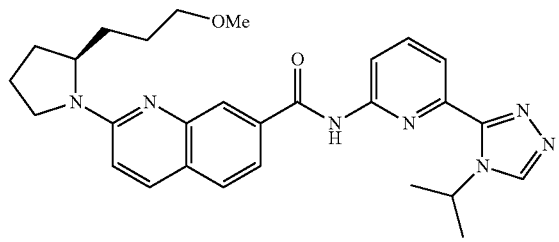 [SMILES: COCCC[C@@H]1CCCN1c1ccc2ccc(C(=O)Nc3cccc(-c4nncn4C(C)C)n3)cc2n1] | 472.27 [M − CH₂ + 1] | ¹H NMR (400 MHz, DMSO-d₆) δ 10.93 (s, 1H), 8.87 (s, 1H), 8.19 (dd, J = 8.3, 0.9 Hz, 1H), 8.17 (d, J = 1.7 Hz, 1H), 8.09 (d, J = 9.1 Hz, 1H), 8.03 (t, J = 8.0 Hz, 1H), 7.88 (dd, J = 7.6, 0.9 Hz, 1H), 7.83 (d, J = 8.3 Hz, 1H), 7.69 (dd, J = 8.3, 1.8 Hz, 1H), 7.06 (d, J = 9.1 Hz, 1H), 5.85-5.76 (m, 1H), 4.40 (br s, 1H), 3.71-3.56 (m, 2H), 3.52-3.41 (m, 2H), 3.37 (dd, J = 9.3, 7.7 Hz, 2H), 3.31 (s, 3H), 2.16-1.91 (comp, 4H), 1.45 (d, J = 6.6 Hz, 6H) |
| 33 | 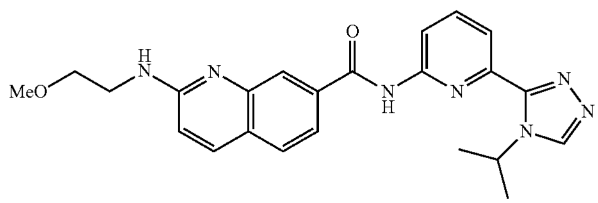 [SMILES: COCCNc1ccc2ccc(C(=O)Nc3cccc(-c4nncn4C(C)C)n3)cc2n1] | 432.22 | ¹H NMR (400 MHz, DMSO-d₆) δ 10.88 (s, 1H), 8.87 (s, 1H), 8.19 (dd, J = 8.3, 0.9 Hz, 1H), 8.14 (d, J = 1.7 Hz, 1H), 8.02 (t, J = 7.9 Hz, 1H), 7.93 (d, J = 8.9 Hz, 1H), 7.88 (dd, J = 7.6, 0.9 Hz, 1H), 7.76 (d, J = 8.2 Hz, 1H), 7.67 (dd, J = 8.2, 1.8 Hz, 1H), 7.30 (t, J = 5.3 Hz, 1H), 6.92 (d, J = 8.9 Hz, 1H), 5.81 (hept, J = 6.7 Hz, 1H), 3.67-3.52 (comp, 4H), 3.31 (s, 3H), 1.45 (d, J = 6.7 Hz, 6H) |
| 34 | 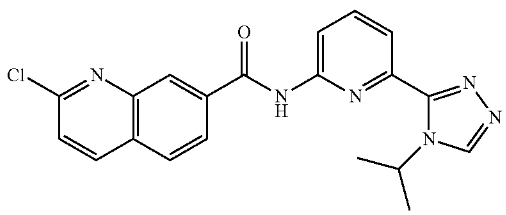 [SMILES: CC(C)n1cnnc1-c1cccc(NC(=O)c2ccc3ccc(Cl)nc3c2)n1] | 393.11 | ¹H NMR (400 MHz, DMSO-d₆) δ 11.06 (s, 1H), 8.88 (s, 1H), 8.61 (dd, J = 1.8, 0.8 Hz, 1H), 8.58 (dd, J = 8.7, 0.7 Hz, 1H), 8.25-8.21 (comp, 2H), 8.15 (dd, J = 8.5, 1.7 Hz, 1H), 8.06 (dd, J = 8.3, 7.7 Hz, 1H), 7.91 (dd, J = 7.7, 0.9 Hz, 1H), 7.75 (d, J = 8.6 Hz, 1H), 5.83-5.76 (m, 1H), 1.46 (d, J = 6.6 Hz, 6H) |
| 35 | 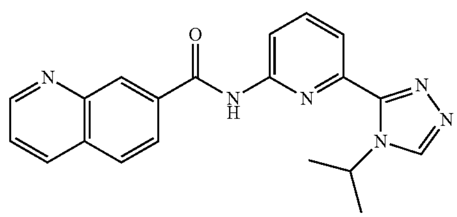 [SMILES: CC(C)n1cnnc1-c1cccc(NC(=O)c2ccc3cccnc3c2)n1] | 359.15 | ¹H NMR (500 MHz, DMSO-d₆) δ 11.07 (s, 1H), 9.04 (dd, J = 4.2, 1.7 Hz, 1H), 8.88 (s, 1H), 8.70-8.66 (m, 1H), 8.49 (ddd, J = 8.4, 1.7, 0.8 Hz, 1H), 8.24 (dd, J = 8.3, 0.9 Hz, 1H), 8.16 (d, J = 8.5 Hz, 1H), 8.11 (dd, J = 8.5, 1.8 Hz, 1H), 8.08-8.02 (m, 1H), 7.91 (dd, J = 7.6, 0.9 Hz, 1H), 7.68 (dd, J = 8.3, 4.2 Hz, 1H), 5.83-5.76 (m, 1H), 1.46 (d, J = 6.7 Hz, 6H) |
| 36 | 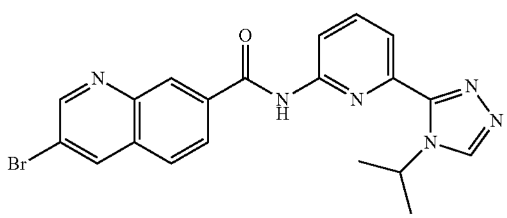 [SMILES: CC(C)n1cnnc1-c1cccc(NC(=O)c2ccc3cc(Br)cnc3c2)n1] | 439.06 | ¹H NMR (400 MHz, DMSO-d₆) δ 11.10 (s, 1H), 9.10 (d, J = 2.3 Hz, 1H), 8.89-8.87 (comp, 2H), 8.68 (d, J = 1.4 Hz, 1H), 8.23 (dd, J = 8.3, 0.9 Hz, 1H), 8.19-8.11 (comp, 2H), 8.05 (t, J = 8.0 Hz, 1H), 7.90 (dd, J = 7.6, 0.9 Hz, 1H), 5.83-5.70 (m, 1H), 1.45 (d, J = 6.7 Hz, 6H) |
| 37 | 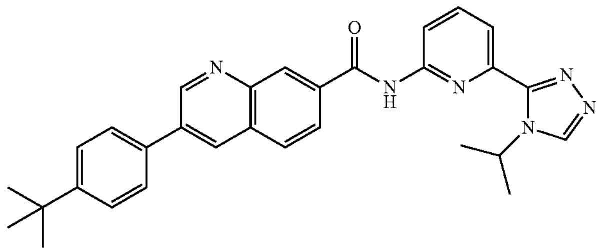 [SMILES: CC(C)n1cnnc1-c1cccc(NC(=O)c2ccc3cc(-c4ccc(C(C)(C)C)cc4)cnc3c2)n1] | 491.25 | ¹H NMR (500 MHz, DMSO-d₆) δ 11.09 (s, 1H), 9.40 (d, J = 2.3 Hz, 1H), 8.89 (s, 1H), 8.74 (dd, J = 11.1, 2.2 Hz, 1H), 8.26 (dd, J = 8.3, 0.9 Hz, 1H), 8.22 (d, J = 8.6 Hz, 1H), 8.16 (dd, J = 8.4, 1.8 Hz, 1H), 8.07 (t, J = 8.0 Hz, 1H), 7.91 (dd, J = 7.8, 0.9 Hz, 1H), 7.90-7.88 (m, 2H), 7.67-7.56 (m, 2H), 5.83-5.75 (m, 1H), 1.47 (d, J = 6.7 Hz, 6H), 1.36 (s, 9H) |

-continued

| Example | Structure | LC-MS [M + H]+ unless otherwise noted | H-NMR |
|---|---|---|---|
| 38 | 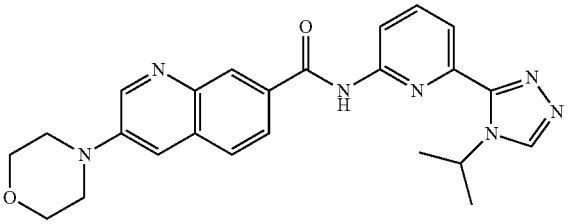 [SMILES: CC(C)n1cnnc1-c1cccc(NC(=O)c2ccc3cc(N4CCOCC4)cnc3c2)n1] | 444.21 | — |
| 39 | 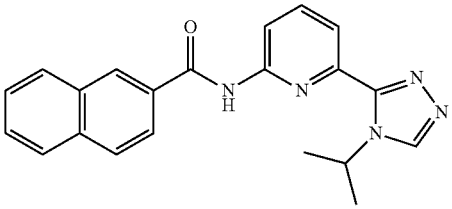 [SMILES: CC(C)n1cnnc1-c1cccc(NC(=O)c2ccc3ccccc3c2)n1] | 358.17 | $^1$H NMR (500 MHz, DMSO-$d_6$) δ 10.93 (s, 1H), 8.87 (s, 1H), 8.62 (s, 1H), 8.23 (dd, J = 8.3, 0.9 Hz, 1H), 8.12 (dd, J = 7.9, 1.6 Hz, 1H), 8.10-8.06 (m, 1H), 8.05-8.00 (comp, 3H), 7.88 (dd, J = 7.6, 0.9 Hz, 1H), 7.70-7.62 (comp, 2H), 5.76-5.70 (m, 1H), 1.45 (d, J = 6.7 Hz, 6H) |
| 40 | 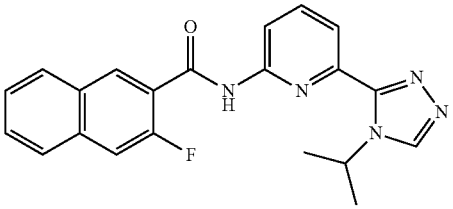 [SMILES: CC(C)n1cnnc1-c1cccc(NC(=O)c2cc3ccccc3cc2F)n1] | 376.14 | $^1$H NMR (500 MHz, DMSO-$d_6$) δ 11.04 (s, 1H), 8.86 (s, 1H), 8.40 (d, J = 7.1 Hz, 1H), 8.26 (d, J = 8.7 Hz, 1H), 8.12 (d, J = 8.1 Hz, 1H), 8.06 (t, J = 8.0 Hz, 1H), 7.99 (d, J = 7.8 Hz, 1H), 7.92 (dd, J = 7.8, 0.9 Hz, 1H), 7.89 (d, J = 11.6 Hz, 1H), 7.70-7.65 (m, 1H), 7.59 (ddd, J = 8.1, 6.7, 1.2 Hz, 1H), 5.68 (p, J = 6.6 Hz, 1H), 1.42 (d, J = 6.7 Hz, 6H) |
| 41 | 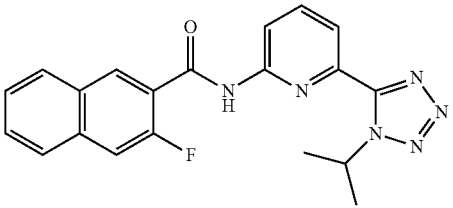 [SMILES: CC(C)n1nnnc1-c1cccc(NC(=O)c2cc3ccccc3cc2F)n1] | 377.13 | $^1$H NMR (400 MHz, DMSO-$d_6$) δ 11.22 (s, 1H), 8.41 (d, J = 7.1 Hz, 1H), 8.37 (d, J = 8.3 Hz, 1H), 8.20-8.10 (comp, 2H), 8.04-7.99 (comp, 2H), 7.91 (d, J = 11.5 Hz, 1H), 7.68 (t, J = 7.5 Hz, 1H), 7.60 (t, J = 7.5 Hz, 1H), 6.04 (hept, J = 6.8 Hz, 1H), 1.54 (d, J = 6.6 Hz, 6H) |

Assays
HTRF® KinEASE™ Assay
ASK1 was purchased from Thermofisher (Catalogue # PV4011), ATP was purchased from Sigma (Catalogue # A7699), HTRF® KinEASE™ Assay System was obtained from Cisbio (Bedford, Mass.). ½ Area plate was purchased from Perkin Elmer (Catalogue # #6005560). HTRF® KinEASE™-STK is a generic method for measuring serine/threonine kinase activities using a time-resolved fluorescence resonance energy transfer (TR-FRET) immunoassay. The $IC_{50}$ value for each compound was determined in the presence of compound (various concentration from 0 to 10 μM) and a fixed amount of ATP and peptide substrates. The test compound, 1 uM STK3 peptide substrate, and 5 nM of ASK1 kinase are incubated with kinase reaction buffer containing 50 mM HEPES pH 7.5, 0.01% BRIJ-35, 10 mM MgCl2, and 1 mM EGTA for 30 minutes. 100 uM ATP is added to start kinase reaction and incubated for 3 hours. The STK3-antibody labeled with $Eu^{3+}$-Cryptate and 125 nM streptavidin-XL665 are mixed in a single addition with stop reagents provided by the Cisbio kit used to stop the kinase reaction. Fluorescence is detected using an Envision Multilabeled 2014 reader from PerkinElmer. The Fluorescence is measured at 615 nm (Cryptate) and 665 nm (XL665) and a ratio of 665 nm/615 nm is calculated for each well. The resulting TR-FRET is proportional to the phosphorylation level. Staurosporine was used as the positive control. $IC_{50}$ was determined by XLfit 5.3. By using above method, the inhibition of ASK1 was evaluated for the example of the compounds of Formula (I), shown in table 11:

TABLE 11

| Example | $IC_{50}$ |
|---|---|
| 1 | D |
| 2 | D |
| 3 | C |
| 4 | C |
| 5 | D |
| 6 | E |
| 7 | D |
| 8 | D |
| 9 | E |
| 10 | E |
| 11 | D |
| 12 | E |
| 13 | D |
| 14 | E |

TABLE 11-continued

| Example | IC$_{50}$ |
|---|---|
| 15 | C |
| 16 | D |
| 17 | E |
| 18 | B |
| 19 | B |
| 20 | E |
| 21 | B |
| 22 | B |
| 23 | C |
| 24 | D |
| 25 | E |
| 26 | C |
| 27 | E |
| 28 | E |
| 29 | E |
| 30 | D |
| 31 | E |
| 32 | C |
| 33 | C |
| 34 | D |
| 35 | E |
| 36 | D |
| 37 | E |
| 38 | C |
| 39 | D |
| 40 | D |
| 41 | E |

A = IC$_{50}$ < 1 nM;
B = 1 nM < IC$_{50}$ < 10 nM;
C = 10 nM < IC$_{50}$ < 100 nM;
D = 100 nM < IC$_{50}$ < 1 μM;
E = IC$_{50}$ > 1 μM (A=IC$_{50}$<1 nM; B=1 nM<IC$_{50}$<10 nM; C=10 nM<IC$_{50}$<100 nM; D=100 nM<IC$_{50}$<1 μM; E=IC$_{50}$>1 μM)

While this invention has been particularly shown and described with references to preferred embodiments thereof, it will be understood by those skilled in the art that various changes in form and details may be made therein without departing from the scope of the invention encompassed by the appended claims.

What is claimed:

1. A compound represented by Formula I, or a pharmaceutically acceptable salt or ester thereof:

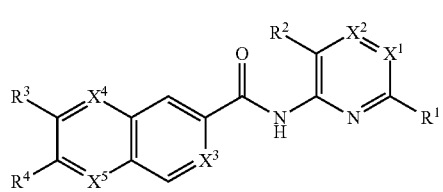

(I)

wherein;

$X^1$, $X^2$, $X^4$, and $X^5$ are each independently $C(R^9)$ or N;

$X^3$ is $C(R^{10})$ or N, in which $R^{10}$ is selected from the group consisting of hydrogen, optionally substituted —$C_1$-$C_8$ alkyl, optionally substituted —$C_1$-$C_8$ alkoxy and halogen;

$R^1$ is selected from

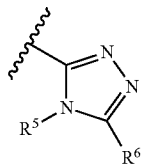

and

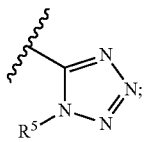

wherein $R^5$ is selected from the group consisting of:
1) Hydrogen;
2) Substituted or unsubstituted —$C_1$-$C_8$ alkyl;
3) Substituted or unsubstituted —$C_2$-$C_8$ alkenyl;
4) Substituted or unsubstituted —$C_2$-$C_8$ alkynyl;
5) Substituted or unsubstituted —$C_3$-$C_8$ cycloalkyl;
6) Substituted or unsubstituted aryl;
7) Substituted or unsubstituted arylalkyl;
8) Substituted or unsubstituted 3- to 8 membered heterocycloalkyl;
9) Substituted or unsubstituted heteroaryl; and
10) Substituted or unsubstituted heteroarylalkyl;

$R^2$, $R^6$, and $R^9$ are each independently selected from the group consisting of:
1) Hydrogen;
2) Halogen;
3) —$NO_2$;
4) Cyano;
5) Substituted or unsubstituted —$C_1$-$C_8$ alkyl;
6) Substituted or unsubstituted —$C_2$-$C_8$ alkenyl;
7) Substituted or unsubstituted —$C_2$-$C_8$ alkynyl;
8) Substituted or unsubstituted —$C_3$-$C_8$ cycloalkyl;
9) Substituted or unsubstituted aryl;
10) Substituted or unsubstituted arylalkyl;
11) Substituted or unsubstituted 3- to 8-membered heterocycloalkyl;
12) Substituted or unsubstituted heteroaryl;
13) Substituted or unsubstituted heteroarylalkyl;
14) —$N(R^7)(R^8)$;
15) —$S(O)_2N(R^7)(R^8)$;
16) —$N(R^7)C(O)R^8$; and
17) —$N(R^7)S(O)_2R^8$;

$R^3$ and $R^4$ are independently selected from the group consisting of:
1) Hydrogen;
2) Halogen;
3) Substituted or unsubstituted —$C_1$-$C_8$ alkyl;
4) Substituted or unsubstituted —$C_2$-$C_8$ alkenyl;
5) Substituted or unsubstituted —$C_2$-$C_8$ alkynyl;
6) Substituted or unsubstituted —$C_3$-$C_8$ cycloalkyl;
7) Substituted or unsubstituted aryl;
8) Substituted or unsubstituted arylalkyl;
9) Substituted or unsubstituted 3- to 8-membered heterocycloalkyl;
10) Substituted or unsubstituted 3- to 8-membered heterocycloalkyl-alkyl;
11) Substituted or unsubstituted heteroaryl;
12) Substituted or unsubstituted heteroarylalkyl;

13) —N($R^7$)($R^8$); and
14) —O$R^7$;
   wherein $R^7$ and $R^8$ are independently selected from the group consisting of hydrogen, —$C_1$-$C_8$ alkyl, —$C_1$-$C_8$ alkenyl, —$C_1$-$C_8$ alkynyl, —$C_3$-$C_8$ cycloalkyl, aryl, heterocycloalkyl, heteroaryl, and heteroarylalkyl, wherein each —$C_1$-$C_8$ alkyl, —$C_1$-$C_8$ alkenyl, —$C_1$-$C_8$ alkynyl, —$C_3$-$C_8$ cycloalkyl, aryl, heterocycloalkyl, heteroaryl, and heteroarylalkyl is optionally substituted with 1-3 substituents independently selected from halo, alkyl, —$C_3$-$C_8$ cycloalkyl, alkylamino, dialkylamino, alkylC(O)NH—, arylC(O)NH—, heteroarylC(O)NH—, —CN, alkoxy, —$CF_3$, aryl, and heteroaryl; alternatively, $R^7$ and $R^8$ are taken together with the nitrogen atom to which they are attached to form an optionally substituted heterocyclic.

2. The compound of claim 1, represented by one of Formulas IIa~IIh or a pharmaceutically acceptable salt thereof:

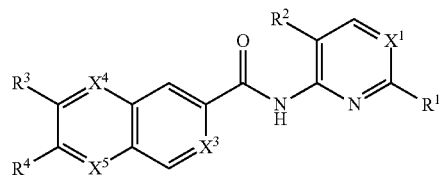
(IIa)

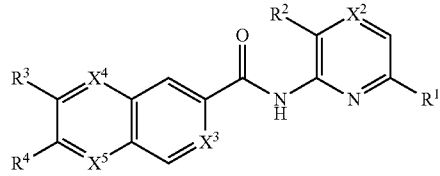
(IIb)

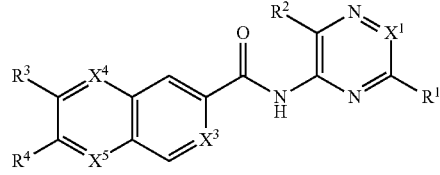
(IIc)

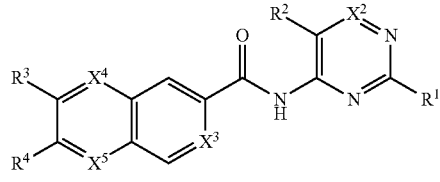
(IId)

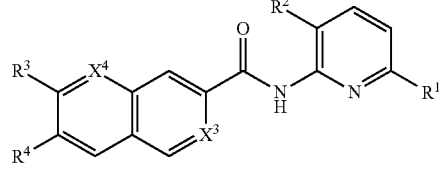
(IIe)

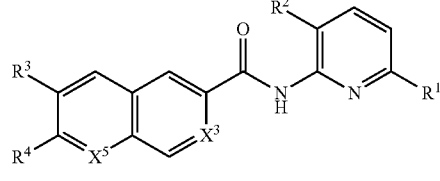
(IIf)

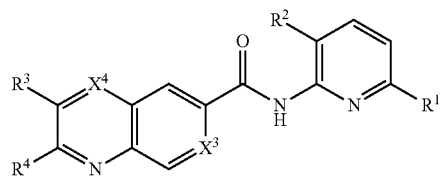
(IIg)

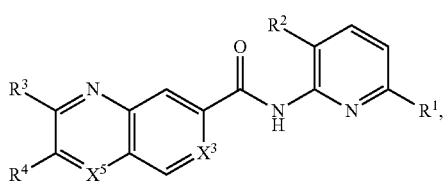
(IIh)

wherein $R^1$, $R^2$, $R^3$, $R^4$, $X^1$, $X^2$, $X^3$, $X^4$, and $X^5$ are as defined in claim 1.

3. The compound of claim 1, represented by one of Formulas IIIa~IIIh, or a pharmaceutically acceptable salt thereof:

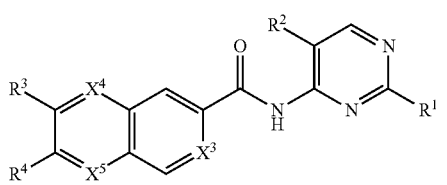
(IIIa)

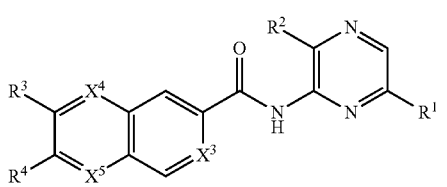
(IIIb)

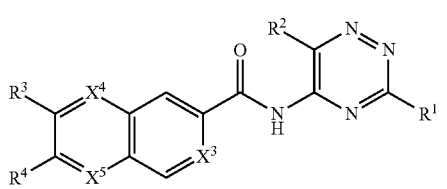
(IIIc)

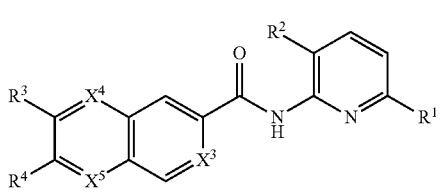
(IIId)

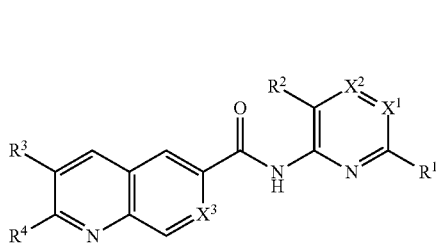
(IIIe)

-continued

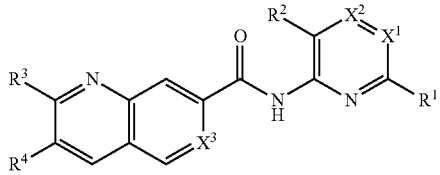
(IIIf)

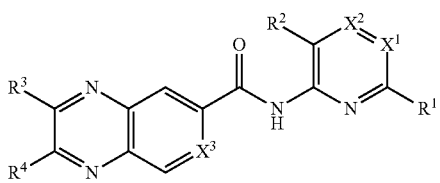
(IIIg)

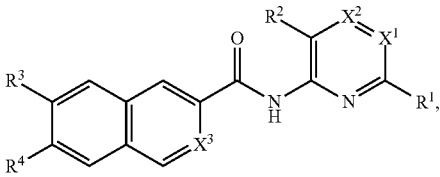
(IIIh)

wherein $R^1$, $R^2$, $R^3$, $R^4$, $X^1$, $X^2$, $X^3$, $X^4$, and $X^5$ are as defined in claim 1.

4. The compound of claim 1, represented by Formula IV or a pharmaceutically acceptable salt thereof:

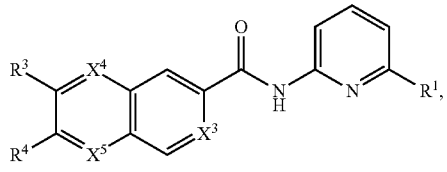
(IV)

wherein $R^1$, $R^3$, $R^4$, $X^3$, $X^4$, and $X^5$ are as defined in claim 1.

5. The compound of claim 1, represented by Formula V or a pharmaceutically acceptable salt thereof:

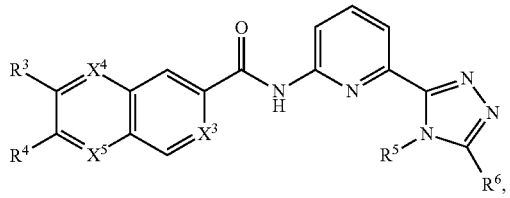
(V)

wherein $R^3$, $R^4$, $R^5$, $R^6$, $X^3$, $X^4$, and $X^5$ are as defined in claim 1.

6. The compound of claim 1, represented by Formula VI or a pharmaceutically acceptable salt thereof:

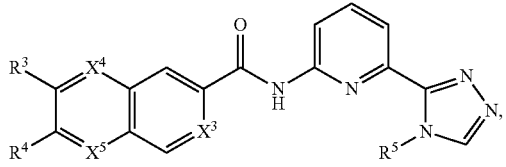
(VI)

wherein $R^3$, $R^4$, $R^5$, $X^3$, $X^4$, and $X^5$ are as defined in claim 1.

7. The compound of claim 1, represented by Formula VII or a pharmaceutically acceptable salt thereof:

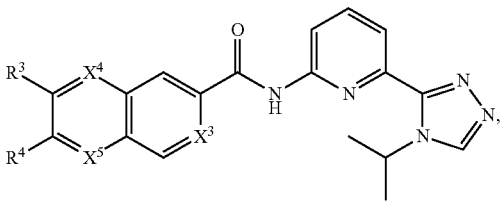
(VII)

wherein $R^3$, $R^4$, $X^3$, $X^4$, and $X^5$ are as defined in claim 1.

8. The compound of claim 1, represented by Formula VIII or a pharmaceutically acceptable salt thereof:

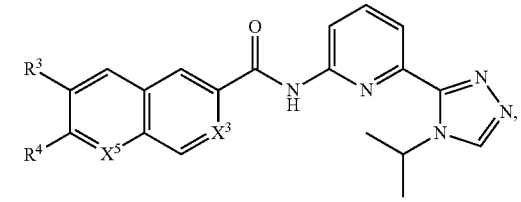
(VIII)

wherein $R^3$, $R^4$, $X^3$, and $X^5$ are as defined in claim 1.

9. The compound of claim 1, which is selected from compounds of Formula IX or a pharmaceutically acceptable salt thereof:

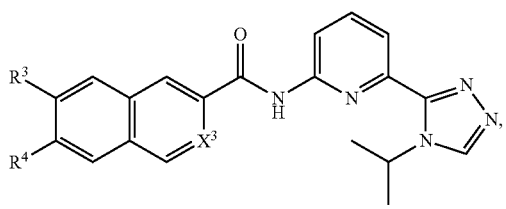
(IX)

wherein $R^3$, $R^4$ and $X^3$ are delineated for each compound in Table 1:

TABLE 1

| Compound | $R^3$ | $R^4$ | $X^3$ |
|---|---|---|---|
| 1 | H | H | C—H |
| 2 | H | —Cl | C—H |

TABLE 1-continued

| Compound | R³ | R⁴ | X³ |
|---|---|---|---|
| 3 | H | —Br | C—H |
| 4 | H | phenyl | C—H |
| 5 | H | —OMe | C—H |
| 6 | H | —Oi-Pr | C—H |
| 7 | H | —NHMe | C—H |
| 8 | H | —NHi-Pr | C—H |
| 9 | H | —NH-CH₂CH₂-OMe | C—H |
| 10 | H | cyclohexyl-NH— | C—H |
| 11 | H | —N(CH₃)₂ | C—H |
| 12 | H | pyrrolidin-1-yl | C—H |
| 13 | H | piperidin-1-yl | C—H |
| 14 | H | morpholin-4-yl | C—H |
| 15 | H | 4-methylpiperazin-1-yl | C—H |
| 16 | H | 4-tert-butylpiperazin-1-yl | C—H |
| 17 | H | azetidin-1-yl | C—H |
| 18 | H | 2-oxa-6-azaspiro[3.3]heptan-6-yl | C—H |
| 19 | H | 8-oxa-3-azabicyclo[3.2.1]octan-3-yl | C—H |
| 20 | H | —N(Et)Bn | C—H |
| 21 | H | H | C—H |
| 22 | —Cl | H | C—H |
| 23 | —Br | H | C—H |
| 24 | phenyl | H | C—H |
| 25 | —OMe | H | C—H |
| 26 | —Oi-Pr | H | C—H |
| 27 | —NHMe | H | C—H |
| 28 | —NHi-Pr | H | C—H |
| 29 | —NH-CH₂CH₂-OMe | H | C—H |
| 30 | cyclohexyl-NH— | H | C—H |
| 31 | —N(CH₃)₂ | H | C—H |
| 32 | pyrrolidin-1-yl | H | C—H |
| 33 | piperidin-1-yl | H | C—H |
| 34 | morpholin-4-yl | H | C—H |
| 35 | 4-methylpiperazin-1-yl | H | C—H |
| 36 | 4-tert-butylpiperazin-1-yl | H | C—H |
| 37 | azetidin-1-yl | H | C—H |
| 38 | 2-oxa-6-azaspiro[3.3]heptan-6-yl | H | C—H |
| 39 | 8-oxa-3-azabicyclo[3.2.1]octan-3-yl | H | C—H |
| 40 | —N(Et)Bn | H | C—H |
| 41 | —NHMe | —OMe | C—H |
| 42 | —NHMe | —Oi-Pr | C—H |
| 43 | —NHi-Pr | —OMe | C—H |
| 44 | —NHi-Pr | —Oi-Pr | C—H |

TABLE 1-continued

| Compound | R³ | R⁴ | X³ |
|---|---|---|---|
| 45 | cyclohexyl-NH- | —OMe | C—H |
| 46 | cyclohexyl-NH- | —Oi-Pr | C—H |
| 47 | pyrrolidin-1-yl | —OMe | C—H |
| 48 | pyrrolidin-1-yl | —Oi-Pr | C—H |
| 49 | piperidin-1-yl | —OMe | C—H |
| 50 | piperidin-1-yl | —Oi-Pr | C—H |
| 51 | morpholin-4-yl | —OMe | C—H |
| 52 | morpholin-4-yl | —Oi-Pr | C—H |
| 53 | —NHMe | —NHMe | C—H |
| 54 | —NHMe | —NHi-Pr | C—H |
| 55 | —NHi-Pr | —NHMe | C—H |
| 56 | —NHi-Pr | —NHi-Pr | C—H |
| 57 | piperidin-1-yl | —NHMe | C—H |
| 58 | piperidin-1-yl | —NHi-Pr | C—H |
| 59 | morpholin-4-yl | —NHMe | C—H |
| 60 | morpholin-4-yl | —NHi-Pr | C—H |
| 61 | H | H | C—F |
| 62 | H | —Cl | C—F |
| 63 | H | —Br | C—F |
| 64 | H | phenyl | C—F |
| 65 | H | —OMe | C—F |
| 66 | H | —Oi-Pr | C—F |
| 67 | H | —NHMe | C—F |
| 68 | H | —NHi-Pr | C—F |
| 69 | H | —NH-CH₂CH₂-OMe | C—F |
| 70 | H | cyclohexyl-NH- | C—F |
| 71 | H | —N(CH₃)₂ | C—F |
| 72 | H | pyrrolidin-1-yl | C—F |
| 73 | H | piperidin-1-yl | C—F |
| 74 | H | morpholin-4-yl | C—F |
| 75 | H | 4-methylpiperazin-1-yl | C—F |
| 76 | H | 4-tert-butylpiperazin-1-yl | C—F |
| 77 | H | azetidin-1-yl | C—F |
| 78 | H | 2-oxa-6-azaspiro[3.3]heptan-6-yl | C—F |
| 79 | H | 8-oxa-3-azabicyclo[3.2.1]octan-3-yl | C—F |
| 80 | H | —N(Et)Bn | C—F |
| 81 | H | H | C—F |
| 82 | —Cl | H | C—F |

TABLE 1-continued
| Compound | R³ | R⁴ | X³ |
|---|---|---|---|
| 83 | —Br | H | C—F |
| 84 | 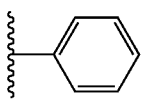 [SMILES: *c1ccccc1] | H | C—F |
| 85 | —OMe | H | C—F |
| 86 | —Oi-Pr | H | C—F |
| 87 | —NHMe | H | C—F |
| 88 | —NHi-Pr | H | C—F |
| 89 | 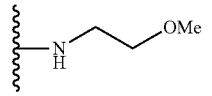 | H | C—F |
| 90 | 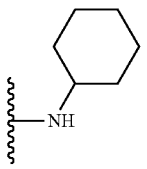 [SMILES: *NC1CCCCC1] | H | C—F |
| 91 | —N(CH₃)₂ | H | C—F |
| 92 | 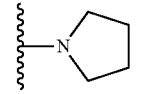 [SMILES: *N1CCCC1] | H | C—F |
| 93 | 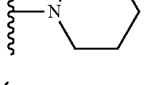 | H | C—F |
| 94 | 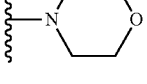 | H | C—F |
| 95 | 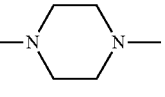 | H | C—F |
| 96 | 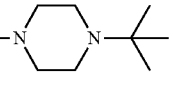 | H | C—F |
| 97 | 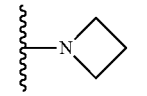 | H | C—F |
| 98 | 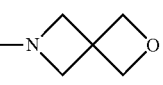 | H | C—F |
| 99 | 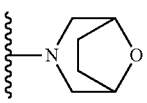 | H | C—F |
| 100 | —N(Et)Bn | H | C—F |
| 101 | —NHMe | —OMe | C—F |
| 102 | —NHMe | —Oi-Pr | C—F |
| 103 | —NHi-Pr | —OMe | C—F |
| 104 | —NHi-Pr | —Oi-Pr | C—F |
| 105 | 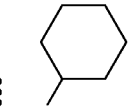 | —OMe | C—F |
| 106 | 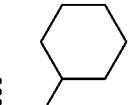 | —Oi-Pr | C—F |
| 107 | 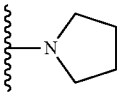 | —OMe | C—F |
| 108 | 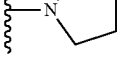 | —Oi-Pr | C—F |
| 109 | 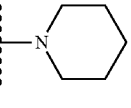 | —OMe | C—F |
| 110 | 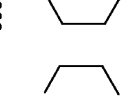 | —Oi-Pr | C—F |
| 111 | 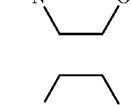 | —OMe | C—F |
| 112 | 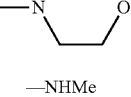 | —Oi-Pr | C—F |
| 113 | —NHMe | —NHMe | C—F |
| 114 | —NHMe | —NHi-Pr | C—F |
| 115 | —NHi-Pr | —NHMe | C—F |
| 116 | —NHi-Pr | —NHi-Pr | C—F |
| 117 | 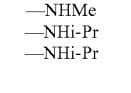 | —NHMe | C—F |
| 118 | 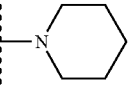 | —NHi-Pr | C—F |
| 119 | 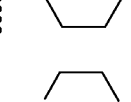 | —NHMe | C—F |
| 120 | 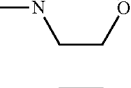 | —NHi-Pr | C—F |

TABLE 1-continued

| Compound | R³ | R⁴ | X³ |
|---|---|---|---|
| 121 | H | H | N |
| 122 | H | —Cl | N |
| 123 | H | —Br | N |
| 124 | H | phenyl | N |
| 125 | H | —OMe | N |
| 126 | H | —Oi-Pr | N |
| 127 | H | —NHMe | N |
| 128 | H | —NHi-Pr | N |
| 129 | H | —NH-CH₂CH₂-OMe | N |
| 130 | H | cyclohexyl-NH— | N |
| 131 | H | —N(CH₃)₂ | N |
| 132 | H | pyrrolidin-1-yl | N |
| 133 | H | piperidin-1-yl | N |
| 134 | H | morpholin-4-yl | N |
| 135 | H | 4-methylpiperazin-1-yl | N |
| 136 | H | 4-tert-butylpiperazin-1-yl | N |
| 137 | H | azetidin-1-yl | N |
| 138 | H | 2-oxa-6-azaspiro[3.3]heptan-6-yl | N |
| 139 | H | 8-oxa-3-azabicyclo[3.2.1]octan-3-yl | N |
| 140 | H | —N(Et)Bn | N |
| 141 | H | H | N |
| 142 | —Cl | H | N |

TABLE 1-continued

| Compound | R³ | R⁴ | X³ |
|---|---|---|---|
| 143 | —Br | H | N |
| 144 | phenyl | H | N |
| 145 | —OMe | H | N |
| 146 | —Oi-Pr | H | N |
| 147 | —NHMe | H | N |
| 148 | —NHi-Pr | H | N |
| 149 | —NH-CH₂CH₂-OMe | H | N |
| 150 | cyclohexyl-NH— | H | N |
| 151 | —N(CH₃)₂ | H | N |
| 152 | pyrrolidin-1-yl | H | N |
| 153 | piperidin-1-yl | H | N |
| 154 | morpholin-4-yl | H | N |
| 155 | 4-methylpiperazin-1-yl | H | N |
| 156 | 4-tert-butylpiperazin-1-yl | H | N |
| 157 | azetidin-1-yl | H | N |
| 158 | 2-oxa-6-azaspiro[3.3]heptan-6-yl | H | N |
| 159 | 8-oxa-3-azabicyclo[3.2.1]octan-3-yl | H | N |
| 160 | —N(Et)Bn | H | N |
| 161 | —NHMe | —OMe | N |
| 162 | —NHMe | —Oi-Pr | N |
| 163 | —NHi-Pr | —OMe | N |
| 164 | —NHi-Pr | —Oi-Pr | N |

TABLE 1-continued

| Compound | R³ | R⁴ | X³ |
|---|---|---|---|
| 165 | cyclohexyl-NH- | —OMe | N |
| 166 | cyclohexyl-NH- | —Oi-Pr | N |
| 167 | pyrrolidin-1-yl | —OMe | N |
| 168 | pyrrolidin-1-yl | —Oi-Pr | N |
| 169 | piperidin-1-yl | —OMe | N |
| 170 | piperidin-1-yl | —Oi-Pr | N |
| 171 | morpholin-4-yl | —OMe | N |
| 172 | morpholin-4-yl | —Oi-Pr | N |
| 173 | —NHMe | —NHMe | N |
| 174 | —NHMe | —NHi-Pr | N |
| 175 | —NHi-Pr | —NHMe | N |
| 176 | —NHi-Pr | —NHi-Pr | N |
| 177 | piperidin-1-yl | —NHMe | N |
| 178 | piperidin-1-yl | —NHi-Pr | N |
| 179 | morpholin-4-yl | —NHMe | N |
| 180 | morpholin-4-yl | —NHi-Pr | N. |

10. The compound of claim 1, which is selected from compounds of Formula X or a pharmaceutically acceptable salt thereof:

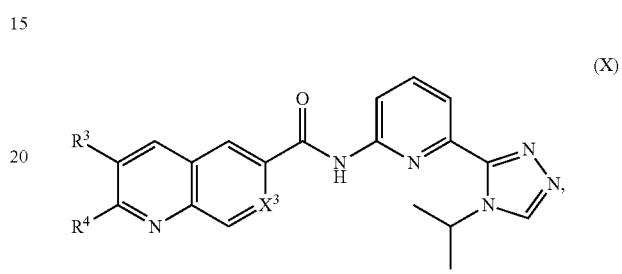

wherein R³, R⁴ and X³ are delineated for each compound in Table 2:

TABLE 2

| Compound | R³ | R⁴ | X³ |
|---|---|---|---|
| 181 | H | H | C—H |
| 182 | H | —Cl | C—H |
| 183 | H | —Br | C—H |
| 184 | H | phenyl | C—H |
| 185 | H | —OMe | C—H |
| 186 | H | —Oi-Pr | C—H |
| 187 | H | —NHMe | C—H |
| 188 | H | —NHi-Pr | C—H |
| 189 | H | —NH-CH₂CH₂-OMe | C—H |
| 190 | H | cyclohexyl-NH- | C—H |
| 191 | H | —N(CH₃)₂ | C—H |
| 192 | H | pyrrolidin-1-yl | C—H |
| 193 | H | piperidin-1-yl | C—H |

TABLE 2-continued

| Compound | R³ | R⁴ | X³ |
|---|---|---|---|
| 194 | H |  morpholine | C—H |
| 195 | H | N-methylpiperazine | C—H |
| 196 | H | N-tert-butylpiperazine | C—H |
| 197 | H | azetidine | C—H |
| 198 | H | 2-oxa-6-azaspiro[3.3]heptane | C—H |
| 199 | H | 8-oxa-3-azabicyclo[3.2.1]octane | C—H |
| 200 | H | —N(Et)Bn | C—H |
| 201 | H | H | C—H |
| 202 | —Cl | H | C—H |
| 203 | —Br | H | C—H |
| 204 | phenyl | H | C—H |
| 205 | —OMe | H | C—H |
| 206 | —Oi-Pr | H | C—H |
| 207 | —NHMe | H | C—H |
| 208 | —NHi-Pr | H | C—H |
| 209 | —NHCH₂CH₂OMe | H | C—H |
| 210 | cyclohexyl-NH— | H | C—H |
| 211 | —N(CH₃)₂ | H | C—H |
| 212 | pyrrolidine | H | C—H |
| 213 | piperidine | H | C—H |

TABLE 2-continued

| Compound | R³ | R⁴ | X³ |
|---|---|---|---|
| 214 | morpholine | H | C—H |
| 215 | N-methylpiperazine | H | C—H |
| 216 | N-tert-butylpiperazine | H | C—H |
| 217 | azetidine | H | C—H |
| 218 | 2-oxa-6-azaspiro[3.3]heptane | H | C—H |
| 219 | 8-oxa-3-azabicyclo[3.2.1]octane | H | C—H |
| 220 | —N(Et)Bn | H | C—H |
| 221 | —NHMe | —OMe | C—H |
| 222 | —NHMe | —Oi-Pr | C—H |
| 223 | —NHi-Pr | —OMe | C—H |
| 224 | —NHi-Pr | —Oi-Pr | C—H |
| 225 | cyclohexyl-NH— | —OMe | C—H |
| 226 | cyclohexyl-NH— | —Oi-Pr | C—H |
| 227 | pyrrolidine | —OMe | C—H |
| 228 | pyrrolidine | —Oi-Pr | C—H |
| 229 | piperidine | —OMe | C—H |
| 230 | piperidine | —Oi-Pr | C—H |

TABLE 2-continued

| Compound | R³ | R⁴ | X³ |
|---|---|---|---|
| 231 | 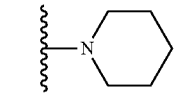 [SMILES: *N1CCCCC1] N-morpholine | —OMe | C—H |
| 232 | N-morpholine | —Oi-Pr | C—H |
| 233 | —NHMe | —NHMe | C—H |
| 234 | —NHMe | —NHi-Pr | C—H |
| 235 | —NHi-Pr | —NHMe | C—H |
| 236 | —NHi-Pr | —NHi-Pr | C—H |
| 237 | N-piperidine | —NHMe | C—H |
| 238 | N-piperidine | —NHi-Pr | C—H |
| 239 | N-morpholine | —NHMe | C—H |
| 240 | N-morpholine | —NHi-Pr | C—H |
| 241 | H | H | C—F |
| 242 | H | —Cl | C—F |
| 243 | H | —Br | C—F |
| 244 | H | phenyl | C—F |
| 245 | H | —OMe | C—F |
| 246 | H | —Oi-Pr | C—F |
| 247 | H | —NHMe | C—F |
| 248 | H | —NHi-Pr | C—F |
| 249 | H | —NH-CH₂CH₂-OMe | C—F |
| 250 | H | —NH-cyclohexyl | C—F |
| 251 | H | —N(CH₃)₂ | C—F |
| 252 | H | N-pyrrolidine | C—F |
| 253 | H | N-piperidine | C—F |
| 254 | H | N-morpholine | C—F |
| 255 | H | N-methylpiperazine | C—F |
| 256 | H | N-(4-tert-butyl)piperazine | C—F |
| 257 | H | N-azetidine | C—F |
| 258 | H | N-(2-oxa-6-azaspiro[3.3]heptane) | C—F |
| 259 | H | N-(8-oxa-3-azabicyclo[3.2.1]octane) | C—F |
| 260 | H | —N(Et)Bn | C—F |
| 261 | H | H | C—F |
| 262 | —Cl | H | C—F |
| 263 | —Br | H | C—F |
| 264 | phenyl | H | C—F |
| 265 | —OMe | H | C—F |
| 266 | —Oi-Pr | H | C—F |
| 267 | —NHMe | H | C—F |
| 268 | —NHi-Pr | H | C—F |
| 269 | —NH-CH₂CH₂-OMe | H | C—F |
| 270 | —NH-cyclohexyl | H | C—F |
| 271 | —N(CH₃)₂ | H | C—F |
| 272 | N-pyrrolidine | H | C—F |

TABLE 2-continued

| Compound | R³ | R⁴ | X³ |
|---|---|---|---|
| 273 | piperidin-1-yl | H | C—F |
| 274 | morpholin-4-yl | H | C—F |
| 275 | 4-methylpiperazin-1-yl | H | C—F |
| 276 | 4-tert-butylpiperazin-1-yl | H | C—F |
| 277 | azetidin-1-yl | H | C—F |
| 278 | 2-oxa-6-azaspiro[3.3]hept-6-yl | H | C—F |
| 279 | 3-oxa-8-azabicyclo[3.2.1]oct-8-yl | H | C—F |
| 280 | —N(Et)Bn | H | C—F |
| 281 | —NHMe | —OMe | C—F |
| 282 | —NHMe | —Oi-Pr | C—F |
| 283 | —NHi-Pr | —OMe | C—F |
| 284 | —NHi-Pr | —Oi-Pr | C—F |
| 285 | cyclohexyl-NH— | —OMe | C—F |
| 286 | cyclohexyl-NH— | —Oi-Pr | C—F |
| 287 | pyrrolidin-1-yl | —OMe | C—F |
| 288 | pyrrolidin-1-yl | —Oi-Pr | C—F |
| 289 | piperidin-1-yl | —OMe | C—F |
| 290 | piperidin-1-yl | —Oi-Pr | C—F |
| 291 | morpholin-4-yl | —OMe | C—F |
| 292 | morpholin-4-yl | —Oi-Pr | C—F |
| 293 | —NHMe | —NHMe | C—F |
| 294 | —NHMe | —NHi-Pr | C—F |
| 295 | —NHi-Pr | —NHMe | C—F |
| 296 | —NHi-Pr | —NHi-Pr | C—F |
| 297 | piperidin-1-yl | —NHMe | C—F |
| 298 | piperidin-1-yl | —NHi-Pr | C—F |
| 299 | morpholin-4-yl | —NHMe | C—F |
| 300 | morpholin-4-yl | —NHi-Pr | C—F |
| 301 | H | H | N |
| 302 | H | —Cl | N |
| 303 | H | —Br | N |
| 304 | H | phenyl | N |
| 305 | H | —OMe | N |
| 306 | H | —Oi-Pr | N |
| 307 | H | —NHMe | N |
| 308 | H | —NHi-Pr | N |
| 309 | H | —NH-CH₂CH₂-OMe | N |
| 310 | H | cyclohexyl-NH— | N |
| 311 | H | —N(CH₃)₂ | N |

TABLE 2-continued
| Compound | R³ | R⁴ | X³ |
|---|---|---|---|
| 312 | H | 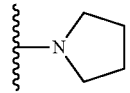 [SMILES: *N1CCCC1] | N |
| 313 | H | 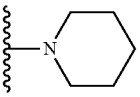 | N |
| 314 | H | 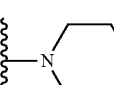 | N |
| 315 | H | 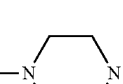 | N |
| 316 | H | 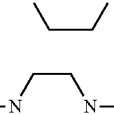 | N |
| 317 | H | 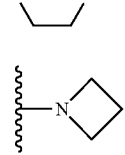 | N |
| 318 | H |  | N |
| 319 | H | 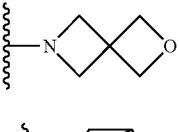 | N |
| 320 | H | —N(Et)Bn | N |
| 321 | H | H | N |
| 322 | —Cl | H | N |
| 323 | —Br | H | N |
| 324 | 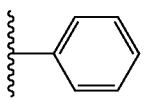 [SMILES: *c1ccccc1] | H | N |
| 325 | —OMe | H | N |
| 326 | —Oi-Pr | H | N |
| 327 | —NHMe | H | N |
| 328 | —NHi-Pr | H | N |
| 329 | 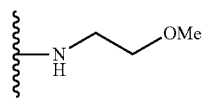 | H | N |
| 330 | 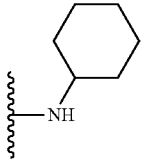 [SMILES: *NC1CCCCC1] | H | N |
| 331 | —N(CH₃)₂ | H | N |
TABLE 2-continued
| Compound | R³ | R⁴ | X³ |
|---|---|---|---|
| 332 | 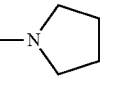 | H | N |
| 333 | 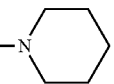 | H | N |
| 334 | 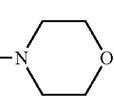 | H | N |
| 335 | 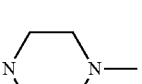 | H | N |
| 336 | 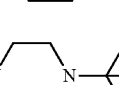 | H | N |
| 337 | 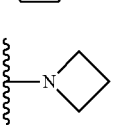 | H | N |
| 338 |  | H | N |
| 339 |  | H | N |
| 340 | —N(Et)Bn | H | N |
| 341 | —NHMe | —OMe | N |
| 342 | —NHMe | —Oi-Pr | N |
| 343 | —NHi-Pr | —OMe | N |
| 344 | —NHi-Pr | —Oi-Pr | N |
| 345 | 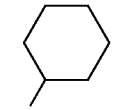 | —OMe | N |
| 346 | 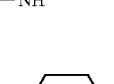 | —Oi-Pr | N |
| 347 | 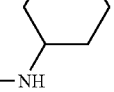 | —OMe | N |
| 348 |  | —Oi-Pr | N |

TABLE 2-continued

| Compound | R³ | R⁴ | X³ |
|---|---|---|---|
| 349 | piperidinyl | —OMe | N |
| 350 | piperidinyl | —Oi-Pr | N |
| 351 | morpholinyl | —OMe | N |
| 352 | morpholinyl | —Oi-Pr | N |
| 353 | —NHMe | —NHMe | N |
| 354 | —NHMe | —NHi-Pr | N |
| 355 | —NHi-Pr | —NHMe | N |
| 356 | —NHi-Pr | —NHi-Pr | N |
| 357 | piperidinyl | —NHMe | N |
| 358 | piperidinyl | —NHi-Pr | N |
| 359 | morpholinyl | —NHMe | N |
| 360 | morpholinyl | —NHi-Pr | N. |

11. The compound of claim 1, represented by Formula XI or a pharmaceutically acceptable salt thereof:

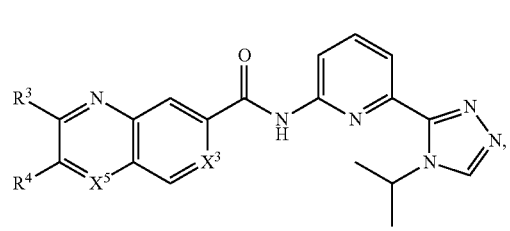

(XI)

wherein R³, R⁴, X³, and X⁵ are as defined in claim 1.

12. The compound of claim 1, which is selected from compounds of Formula XII or a pharmaceutically acceptable salt thereof:

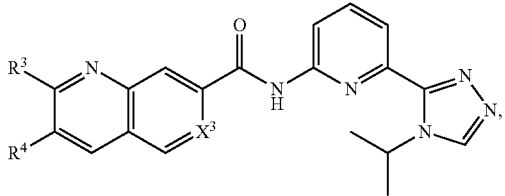

(XII)

wherein R³, R⁴ and X³ are delineated for each compound in Table 3:

TABLE 3

| Compound | R³ | R⁴ | X³ |
|---|---|---|---|
| 361 | H | H | C—H |
| 362 | H | —Cl | C—H |
| 363 | H | —Br | C—H |
| 364 | H | 4-tert-butylphenyl | C—H |
| 365 | H | —OMe | C—H |
| 366 | H | —Oi-Pr | C—H |
| 367 | H | —NHMe | C—H |
| 368 | H | —NHi-Pr | C—H |
| 369 | H | —NHCH₂CH₂OMe | C—H |
| 370 | H | cyclohexyl-NH— | C—H |
| 371 | H | —N(CH₃)₂ | C—H |
| 372 | H | pyrrolidinyl | C—H |
| 373 | H | piperidinyl | C—H |
| 374 | H | morpholinyl | C—H |
| 375 | H | 4-methylpiperazinyl | C—H |
| 376 | H | 4-tert-butylpiperazinyl | C—H |

TABLE 3-continued

| Compound | R³ | R⁴ | X³ |
|---|---|---|---|
| 377 | H | azetidinyl | C—H |
| 378 | H | 2-oxa-6-azaspiro[3.3]heptyl | C—H |
| 379 | H | 8-oxa-3-azabicyclo[3.2.1]octyl | C—H |
| 380 | H | —N(Et)Bn | C—H |
| 381 | H | H | C—H |
| 382 | —Cl | H | C—H |
| 383 | —Br | H | C—H |
| 384 | phenyl | H | C—H |
| 385 | —OMe | H | C—H |
| 386 | —Oi-Pr | H | C—H |
| 387 | —NHMe | H | C—H |
| 388 | —NHi-Pr | H | C—H |
| 389 | —NH-CH₂CH₂-OMe | H | C—H |
| 390 | cyclohexyl-NH— | H | C—H |
| 391 | —N(CH₃)₂ | H | C—H |
| 392 | 2-(methoxymethyl)pyrrolidin-1-yl | H | C—H |
| 393 | piperidin-1-yl | H | C—H |
| 394 | morpholin-4-yl | H | C—H |
| 395 | 4-methylpiperazin-1-yl | H | C—H |
| 396 | 4-tert-butylpiperazin-1-yl | H | C—H |
| 397 | azetidinyl | H | C—H |
| 398 | 2-oxa-6-azaspiro[3.3]heptyl | H | C—H |
| 399 | 8-oxa-3-azabicyclo[3.2.1]octyl | H | C—H |
| 400 | —N(Et)Bn | H | C—H |
| 401 | —NHMe | —OMe | C—H |
| 402 | —NHMe | —Oi-Pr | C—H |
| 403 | —Nhi-Pr | —OMe | C—H |
| 404 | —Nhi-Pr | —Oi-Pr | C—H |
| 405 | cyclohexyl-NH— | —OMe | C—H |
| 406 | cyclohexyl-NH— | —Oi-Pr | C—H |
| 407 | pyrrolidin-1-yl | OMe | C—H |
| 408 | pyrrolidin-1-yl | —Oi-Pr | C—H |
| 409 | piperidin-1-yl | —OMe | C—H |
| 410 | piperidin-1-yl | —Oi-Pr | C—H |
| 411 | morpholin-4-yl | —OMe | C—H |
| 412 | morpholin-4-yl | —Oi-Pr | C—H |
| 413 | —NHMe | —NHMe | C—H |
| 414 | —NHMe | —NHi-Pr | C—H |
| 415 | —Nhi-Pr | —NHMe | C—H |
| 416 | —Nhi-Pr | —NHi-Pr | C—H |

TABLE 3-continued

| Compound | R³ | R⁴ | X³ |
|---|---|---|---|
| 417 | piperidin-1-yl | —NHMe | C—H |
| 418 | piperidin-1-yl | —NHi-Pr | C—H |
| 419 | morpholin-4-yl | —NHMe | C—H |
| 420 | morpholin-4-yl | —NHi-Pr | C—H |
| 421 | H | H | C—F |
| 422 | H | —Cl | C—F |
| 423 | H | —Br | C—F |
| 424 | H | phenyl | C—F |
| 425 | H | —OMe | C—F |
| 426 | H | —Oi-Pr | C—F |
| 427 | H | —NHMe | C—F |
| 428 | H | —NHi-Pr | C—F |
| 429 | H | —NH-CH₂CH₂-OMe | C—F |
| 430 | H | —NH-cyclohexyl | C—F |
| 431 | H | —N(CH₃)₂ | C—F |
| 432 | H | pyrrolidin-1-yl | C—F |
| 433 | H | piperidin-1-yl | C—F |
| 434 | H | morpholin-4-yl | C—F |
| 435 | H | 4-methylpiperazin-1-yl | C—F |
| 436 | H | 4-tert-butylpiperazin-1-yl | C—F |
| 437 | H | azetidin-1-yl | C—F |
| 438 | H | 2-oxa-6-azaspiro[3.3]heptan-6-yl | C—F |
| 439 | H | 8-oxa-3-azabicyclo[3.2.1]octan-3-yl | C—F |
| 440 | H | —N(Et)Bn | C—F |
| 441 | H | H | C—F |
| 442 | —Cl | H | C—F |
| 443 | —Br | H | C—F |
| 444 | phenyl | H | C—F |
| 445 | —OMe | H | C—F |
| 446 | —Oi-Pr | H | C—F |
| 447 | —NHMe | H | C—F |
| 448 | —NHi-Pr | H | C—F |
| 449 | —NH-CH₂CH₂-OMe | H | C—F |
| 450 | —NH-cyclohexyl | H | C—F |
| 451 | —N(CH₃)₂ | H | C—F |
| 452 | pyrrolidin-1-yl | H | C—F |
| 453 | piperidin-1-yl | H | C—F |
| 454 | morpholin-4-yl | H | C—F |
| 455 | 4-methylpiperazin-1-yl | H | C—F |

TABLE 3-continued

| Compound | R³ | R⁴ | X³ |
|---|---|---|---|
| 456 | N-piperazine-N-t-Bu | H | C—F |
| 457 | N-azetidine | H | C—F |
| 458 | N-2-oxa-6-azaspiro[3.3]heptane | H | C—F |
| 459 | N-8-oxa-3-azabicyclo[3.2.1] | H | C—F |
| 460 | —N(Et)Bn | H | C—F |
| 461 | —NHMe | —OMe | C—F |
| 462 | —NHMe | —Oi-Pr | C—F |
| 463 | —NHi-Pr | —OMe | C—F |
| 464 | —NHi-Pr | —Oi-Pr | C—F |
| 465 | cyclohexyl-NH— | —OMe | C—F |
| 466 | cyclohexyl-NH— | —Oi-Pr | C—F |
| 467 | N-pyrrolidine | —OMe | C—F |
| 468 | N-pyrrolidine | —Oi-Pr | C—F |
| 469 | N-piperidine | —OMe | C—F |
| 470 | N-piperidine | —Oi-Pr | C—F |
| 471 | N-morpholine | —OMe | C—F |
| 472 | N-morpholine | —Oi-Pr | C—F |
| 473 | —NHMe | —NHMe | C—F |
| 474 | —NHMe | —NHi-Pr | C—F |
| 475 | —NHi-Pr | —NHMe | C—F |
| 476 | —Nhi-Pr | —Nhi-Pr | C—F |
| 477 | N-piperidine | —NHMe | C—F |
| 478 | N-piperidine | —NHi-Pr | C—F |
| 479 | N-morpholine | —NHMe | C—F |
| 480 | N-morpholine | —NHi-Pr | C—F |
| 481 | H | H | N |
| 482 | H | —Cl | N |
| 483 | H | —Br | N |
| 484 | H | phenyl | N |
| 485 | H | —OMe | N |
| 486 | H | —Oi-Pr | N |
| 487 | H | —NHMe | N |
| 488 | H | —NHi-Pr | N |
| 489 | H | —NH-CH₂CH₂-OMe | N |
| 490 | H | cyclohexyl-NH— | N |
| 491 | H | —N(CH₃)₂ | N |
| 492 | H | N-pyrrolidine | N |
| 493 | H | N-piperidine | N |
| 494 | H | N-morpholine | N |

TABLE 3-continued

| Compound | R³ | R⁴ | X³ |
|---|---|---|---|
| 495 | H | *N-piperazinyl-N'-methyl* | N |
| 496 | H | *N-piperazinyl-N'-tert-butyl* | N |
| 497 | H | *N-azetidinyl* | N |
| 498 | H | *2-oxa-6-azaspiro[3.3]heptanyl* | N |
| 499 | H | *3-oxa-8-azabicyclo[3.2.1]octanyl* | N |
| 500 | H | —N(Et)Bn | N |
| 501 | H | H | N |
| 502 | —Cl | H | N |
| 503 | —Br | H | N |
| 504 | *phenyl* | H | N |
| 505 | —OMe | H | N |
| 506 | —Oi-Pr | H | N |
| 507 | —NHMe | H | N |
| 508 | —NHi-Pr | H | N |
| 509 | *—NHCH₂CH₂OMe* | H | N |
| 510 | *cyclohexyl-NH—* | H | N |
| 511 | —N(CH₃)₂ | H | N |
| 512 | *N-pyrrolidinyl* | H | N |
| 513 | *N-piperidinyl* | H | N |
| 514 | *N-morpholinyl* | H | N |

TABLE 3-continued

| Compound | R³ | R⁴ | X³ |
|---|---|---|---|
| 515 | *N-piperazinyl-N'-methyl* | H | N |
| 516 | *N-piperazinyl-N'-tert-butyl* | H | N |
| 517 | *N-azetidinyl* | H | N |
| 518 | *2-oxa-6-azaspiro[3.3]heptanyl* | H | N |
| 519 | *3-oxa-8-azabicyclo[3.2.1]octanyl* | H | N |
| 520 | —N(Et)Bn | H | N |
| 521 | —NHMe | —OMe | N |
| 522 | —NHMe | —Oi-Pr | N |
| 523 | —NHi-Pr | —OMe | N |
| 524 | —NHi-Pr | —Oi-Pr | N |
| 525 | *cyclohexyl-NH—* | —OMe | N |
| 526 | *cyclohexyl-NH—* | —Oi-Pr | N |
| 527 | *N-pyrrolidinyl* | —OMe | N |
| 528 | *N-pyrrolidinyl* | —Oi-Pr | N |
| 529 | *N-piperidinyl* | —OMe | N |
| 530 | *N-piperidinyl* | —Oi-Pr | N |
| 531 | *N-piperidinyl* | —OMe | N |

TABLE 3-continued

| Compound | R³ | R⁴ | X³ |
|---|---|---|---|
| 532 | N-morpholine | —Oi-Pr | N |
| 533 | —NHMe | —NHMe | N |
| 534 | —NHMe | —NHi-Pr | N |
| 535 | —NHi-Pr | —NHMe | N |
| 536 | —NHi-Pr | —NHi-Pr | N |
| 537 | N-piperidine | —NHMe | N |
| 538 | N-piperidine | —NHi-Pr | N |
| 539 | N-morpholine | —NHMe | N |
| 540 | N-morpholine | —NHi-Pr | N. |

13. The compound of claim 1, which is selected from compounds of Formula XIII or a pharmaceutically acceptable salt thereof:

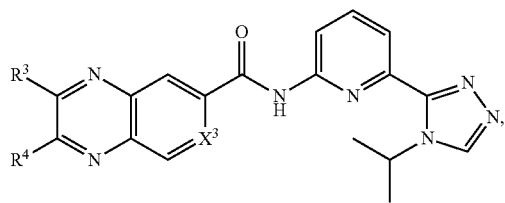

(XIII)

wherein R³, R⁴ and X³ are delineated for each compound in Table 4:

TABLE 4

| Compound | R³ | R⁴ | X³ |
|---|---|---|---|
| 541 | H | H | C—H |
| 542 | H | —Cl | C—H |
| 543 | H | —Br | C—H |
| 544 | H | phenyl | C—H |
| 545 | H | —OMe | C—H |
| 546 | H | —Oi-Pr | C—H |
| 547 | H | —NHMe | C—H |
| 548 | H | —NHi-Pr | C—H |
| 549 | H | —NH-CH₂CH₂-OMe | C—H |
| 550 | H | —NH-cyclohexyl | C—H |
| 551 | H | —N(CH₃)₂ | C—H |
| 552 | H | N-pyrrolidine | C—H |
| 553 | H | N-piperidine | C—H |
| 554 | H | N-morpholine | C—H |
| 555 | H | N-methylpiperazine | C—H |
| 556 | H | N-(4-tert-butyl)piperazine | C—H |
| 557 | H | N-azetidine | C—H |
| 558 | H | 2-oxa-6-azaspiro[3.3]heptane | C—H |
| 559 | H | 8-oxa-3-azabicyclo[3.2.1]octane | C—H |
| 560 | H | —N(Et)Bn | C—H |
| 561 | H | H | C—H |
| 562 | —Cl | H | C—H |
| 563 | —Br | H | C—H |
| 564 | phenyl | H | C—H |
| 565 | —OMe | H | C—H |
| 566 | —Oi-Pr | H | C—H |
| 567 | —NHMe | H | C—H |
| 568 | —NHi-Pr | H | C—H |

TABLE 4-continued

| Compound | R³ | R⁴ | X³ |
|---|---|---|---|
| 569 | ~NH-CH₂CH₂-OMe | H | C—H |
| 570 | ~NH-cyclohexyl | H | C—H |
| 571 | —N(CH₃)₂ | H | C—H |
| 572 | ~N-pyrrolidinyl | H | C—H |
| 573 | ~N-piperidinyl | H | C—H |
| 574 | ~N-morpholinyl | H | C—H |
| 575 | ~N-(4-methylpiperazinyl) | H | C—H |
| 576 | ~N-(4-tert-butylpiperazinyl) | H | C—H |
| 577 | ~N-azetidinyl | H | C—H |
| 578 | ~N-(2-oxa-6-azaspiro[3.3]heptyl) | H | C—H |
| 579 | ~N-(8-oxa-3-azabicyclo[3.2.1]octyl) | H | C—H |
| 580 | —N(Et)Bn | H | C—H |
| 581 | —NHMe | —OMe | C—H |
| 582 | —NHMe | —Oi-Pr | C—H |
| 583 | —NHi-Pr | —OMe | C—H |
| 584 | —NHi-Pr | —Oi-Pr | C—H |
| 585 | ~NH-cyclohexyl | —OMe | C—H |
| 586 | ~NH-cyclohexyl | —Oi-Pr | C—H |
| 587 | ~N-pyrrolidinyl | —OMe | C—H |
| 588 | ~N-pyrrolidinyl | —Oi-Pr | C—H |
| 589 | ~N-piperidinyl | —OMe | C—H |
| 590 | ~N-piperidinyl | —Oi-Pr | C—H |
| 591 | ~N-morpholinyl | —OMe | C—H |
| 592 | ~N-morpholinyl | —Oi-Pr | C—H |
| 593 | —NHMe | —NHMe | C—H |
| 594 | —NHMe | —NHi-Pr | C—H |
| 595 | —NHi-Pr | —NHMe | C—H |
| 596 | —NHi-Pr | —NHi-Pr | C—H |
| 597 | ~N-piperidinyl | —NHMe | C—H |
| 598 | ~N-piperidinyl | —NHi-Pr | C—H |
| 599 | ~N-morpholinyl | —NHMe | C—H |
| 600 | ~N-morpholinyl | —NHi-Pr | C—H |
| 601 | H | H | C—F |
| 602 | H | —Cl | C—F |
| 603 | H | —Br | C—F |
| 604 | H | ~phenyl | C—F |

TABLE 4-continued

| Compound | R³ | R⁴ | X³ |
|---|---|---|---|
| 605 | H | —OMe | C—F |
| 606 | H | —Oi-Pr | C—F |
| 607 | H | —NHMe | C—F |
| 608 | H | —NHi-Pr | C—F |
| 609 | H | —NH-CH₂CH₂-OMe | C—F |
| 610 | H | —NH-cyclohexyl | C—F |
| 611 | H | —N(CH₃)₂ | C—F |
| 612 | H | pyrrolidin-1-yl | C—F |
| 613 | H | piperidin-1-yl | C—F |
| 614 | H | morpholin-4-yl | C—F |
| 615 | H | 4-methylpiperazin-1-yl | C—F |
| 616 | H | 4-tert-butylpiperazin-1-yl | C—F |
| 617 | H | azetidin-1-yl | C—F |
| 618 | H | 2-oxa-6-azaspiro[3.3]heptan-6-yl | C—F |
| 619 | H | 8-oxa-3-azabicyclo[3.2.1]octan-3-yl | C—F |
| 620 | H | —N(Et)Bn | C—F |
| 621 | H | H | C—F |
| 622 | —Cl | H | C—F |
| 623 | —Br | H | C—F |
| 624 | phenyl | H | C—F |
| 625 | —OMe | H | C—F |
| 626 | —Oi-Pr | H | C—F |
| 627 | —NHMe | H | C—F |
| 628 | —NHi-Pr | H | C—F |
| 629 | —NH-CH₂CH₂-OMe | H | C—F |
| 630 | —NH-cyclohexyl | H | C—F |
| 631 | —N(CH₃)₂ | H | C—F |
| 632 | pyrrolidin-1-yl | H | C—F |
| 633 | piperidin-1-yl | H | C—F |
| 634 | morpholin-4-yl | H | C—F |
| 635 | 4-methylpiperazin-1-yl | H | C—F |
| 636 | 4-tert-butylpiperazin-1-yl | H | C—F |
| 637 | azetidin-1-yl | H | C—F |
| 638 | 2-oxa-6-azaspiro[3.3]heptan-6-yl | H | C—F |
| 639 | 8-oxa-3-azabicyclo[3.2.1]octan-3-yl | H | C—F |
| 640 | —N(Et)Bn | H | C—F |
| 641 | —NHMe | —OMe | C—F |
| 642 | —NHMe | —Oi-Pr | C—F |
| 643 | —NHi-Pr | —OMe | C—F |
| 644 | —NHi-Pr | —Oi-Pr | C—F |
| 645 | —NH-cyclohexyl | —OMe | C—F |

TABLE 4-continued
| Compound | R³ | R⁴ | X³ |
|---|---|---|---|
| 646 | 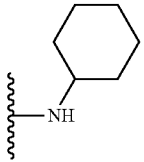 [SMILES: *NC1CCCCC1] | —Oi-Pr | C—F |
| 647 | 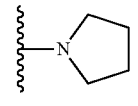 | —OMe | C—F |
| 648 | 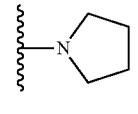 [SMILES: *N1CCCC1] | —Oi-Pr | C—F |
| 649 | 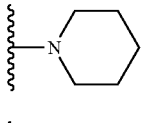 | —OMe | C—F |
| 650 | 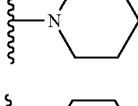 | —Oi-Pr | C—F |
| 651 | 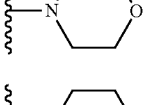 | —OMe | C—F |
| 652 | 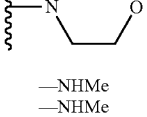 | —Oi-Pr | C—F |
| 653 | —NHMe | —NHMe | C—F |
| 654 | —NHMe | —NHi-Pr | C—F |
| 655 | —NHi-Pr | —NHMe | C—F |
| 656 | —NHi-Pr | —NHi-Pr | C—F |
| 657 | 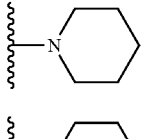 | —NHMe | C—F |
| 658 | 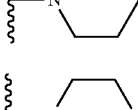 | —NHi-Pr | C—F |
| 659 | 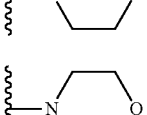 | —NHMe | C—F |
| 660 | 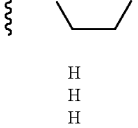 | —NHi-Pr | C—F |
| 661 | H | H | N |
| 662 | H | —Cl | N |
| 663 | H | —Br | N |
| 664 | H | 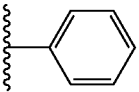 | N |
| 665 | H | —OMe | N |
| 666 | H | —Oi-Pr | N |
| 667 | H | —NHMe | N |
| 668 | H | —NHi-Pr | N |
| 669 | H | 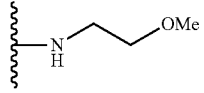 [SMILES: *NCCOC] | N |
| 670 | H | 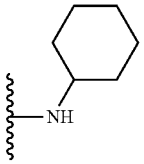 | N |
| 671 | H | —N(CH₃)₂ | N |
| 672 | H | 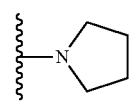 [SMILES: *N1CCCC1] | N |
| 673 | H | 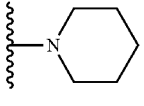 | N |
| 674 | H | 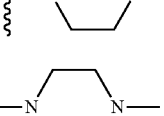 | N |
| 675 | H | 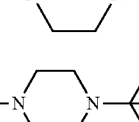 | N |
| 676 | H | 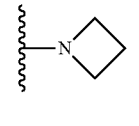 [SMILES: *N1CCC1] | N |
| 677 | H |  | N |
| 678 | H | 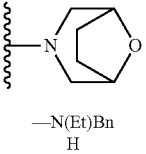 | N |
| 679 | H | 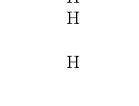 | N |
| 680 | H | —N(Et)Bn | N |
| 681 | H | H | N |
| 682 | —Cl | H | N |
| 683 | —Br | H | N |
| 684 | 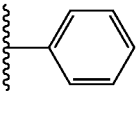 | H | N |
| 685 | —OMe | H | N |
| 686 | —Oi-Pr | H | N |

TABLE 4-continued

| Compound | R³ | R⁴ | X³ |
|---|---|---|---|
| 687 | —NHMe | H | N |
| 688 | —NHi-Pr | H | N |
| 689 | —NH-CH₂CH₂-OMe | H | N |
| 690 | cyclohexyl-NH— | H | N |
| 691 | —N(CH₃)₂ | H | N |
| 692 | pyrrolidin-1-yl | H | N |
| 693 | piperidin-1-yl | H | N |
| 694 | morpholin-4-yl | H | N |
| 695 | 4-methylpiperazin-1-yl | H | N |
| 696 | 4-tert-butylpiperazin-1-yl | H | N |
| 697 | azetidin-1-yl | H | N |
| 698 | 2-oxa-6-azaspiro[3.3]heptan-6-yl | H | N |
| 699 | 8-oxa-3-azabicyclo[3.2.1]octan-3-yl | H | N |
| 700 | —N(Et)Bn | H | N |
| 701 | —NHMe | —OMe | N |
| 702 | —NHMe | —Oi-Pr | N |
| 703 | —NHi-Pr | —OMe | N |
| 704 | —NHi-Pr | —Oi-Pr | N |
| 705 | cyclohexyl-NH— | —OMe | N |
| 706 | cyclohexyl-NH— | —Oi-Pr | N |
| 707 | pyrrolidin-1-yl | —OMe | N |
| 708 | pyrrolidin-1-yl | —Oi-Pr | N |
| 709 | piperidin-1-yl | —OMe | N |
| 710 | piperidin-1-yl | —Oi-Pr | N |
| 711 | morpholin-4-yl | —OMe | N |
| 712 | morpholin-4-yl | —Oi-Pr | N |
| 713 | —NHMe | —NHMe | N |
| 714 | —NHMe | —NHi-Pr | N |
| 715 | —NHi-Pr | —NHMe | N |
| 716 | —NHi-Pr | —NHi-Pr | N |
| 717 | piperidin-1-yl | —NHMe | N |
| 718 | piperidin-1-yl | —NHi-Pr | N |
| 719 | morpholin-4-yl | —NHMe | N |
| 720 | morpholin-4-yl | —NHi-Pr | N. |

14. The compound of claim 1, represented by Formula XIV or a pharmaceutically acceptable salt thereof:

(XIV)

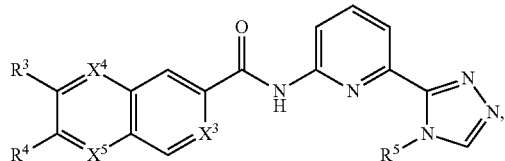

wherein $R^3$, $R^4$, $R^5$, $X^3$, $X^4$, and $X^5$ are as defined in claim 1.

15. The compound of claim 1, represented by Formula XV or a pharmaceutically acceptable salt thereof:

(XV)

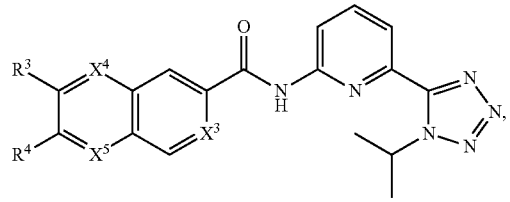

wherein $R^3$, $R^4$, $X^3$, $X^4$, and $X^5$ are as defined in claim 1.

16. The compound of claim 1, represented by Formula XVI or a pharmaceutically acceptable salt thereof:

(XVI)

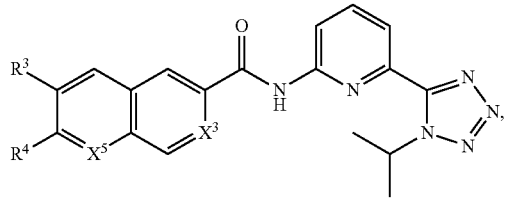

wherein $R^3$, $R^4$, $X^3$, and $X^5$ are as defined in claim 1.

17. The compound of claim 1, which is selected from compounds of Formula XVII or a pharmaceutically acceptable salt thereof:

(XVII)

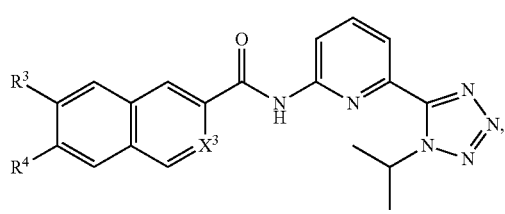

wherein $R^3$, $R^4$ and $X^3$ are delineated for each compound in Table 5:

TABLE 5

| Compound | $R^3$ | $R^4$ | $X^3$ |
|---|---|---|---|
| 721 | H | H | C—H |
| 722 | H | —Cl | C—H |
| 723 | H | —Br | C—H |
| 724 | H | phenyl | C—H |
| 725 | H | —OMe | C—H |
| 726 | H | —Oi-Pr | C—H |
| 727 | H | —NHMe | C—H |
| 728 | H | —NHi-Pr | C—H |
| 729 | H | —NH-CH₂CH₂-OMe | C—H |
| 730 | H | cyclohexyl-NH— | C—H |
| 731 | H | —N(CH₃)₂ | C—H |
| 732 | H | pyrrolidin-1-yl | C—H |
| 733 | H | piperidin-1-yl | C—H |
| 734 | H | morpholin-4-yl | C—H |
| 735 | H | 4-methylpiperazin-1-yl | C—H |
| 736 | H | 4-tert-butylpiperazin-1-yl | C—H |
| 737 | H | azetidin-1-yl | C—H |
| 738 | H | 2-oxa-6-azaspiro[3.3]heptan-6-yl | C—H |
| 739 | H | 8-oxa-3-azabicyclo[3.2.1]octan-3-yl | C—H |
| 740 | H | —N(Et)Bn | C—H |
| 741 | H | H | C—H |
| 742 | —Cl | H | C—H |
| 743 | —Br | H | C—H |

TABLE 5-continued

| Compound | R³ | R⁴ | X³ |
|---|---|---|---|
| 744 | phenyl | H | C—H |
| 745 | OMe | H | C—H |
| 746 | —Oi-Pr | H | C—H |
| 747 | —NHMe | H | C—H |
| 748 | —NHi-Pr | H | C—H |
| 749 | —NH-CH₂CH₂-OMe | H | C—H |
| 750 | cyclohexyl-NH— | H | C—H |
| 751 | —N(CH₃)₂ | H | C—H |
| 752 | pyrrolidin-1-yl | H | C—H |
| 753 | piperidin-1-yl | H | C—H |
| 754 | morpholin-4-yl | H | C—H |
| 755 | 4-methylpiperazin-1-yl | H | C—H |
| 756 | 4-tert-butylpiperazin-1-yl | H | C—H |
| 757 | azetidin-1-yl | H | C—H |
| 758 | 2-oxa-6-azaspiro[3.3]heptan-6-yl | H | C—H |
| 759 | 8-oxa-3-azabicyclo[3.2.1]octan-3-yl | H | C—H |
| 760 | —N(Et)Bn | H | C—H |
| 761 | —NHMe | OMe | C—H |
| 762 | —NHMe | —Oi-Pr | C—H |
| 763 | —NHi-Pr | OMe | C—H |
| 764 | —Nhi-Pr | —Oi-Pr | C—H |
| 765 | cyclohexyl-NH— | OMe | C—H |
| 766 | cyclohexyl-NH— | —Oi-Pr | C—H |
| 767 | pyrrolidin-1-yl | OMe | C—H |
| 768 | pyrrolidin-1-yl | —Oi-Pr | C—H |
| 769 | piperidin-1-yl | OMe | C—H |
| 770 | piperidin-1-yl | —Oi-Pr | C—H |
| 771 | morpholin-4-yl | OMe | C—H |
| 772 | morpholin-4-yl | —Oi-Pr | C—H |
| 773 | —NHMe | —NHMe | C—H |
| 774 | —NHMe | —NHi-Pr | C—H |
| 775 | —Nhi-Pr | —NHMe | C—H |
| 776 | —Nhi-Pr | —NHi-Pr | C—H |
| 777 | piperidin-1-yl | —NHMe | C—H |
| 778 | piperidin-1-yl | —NHi-Pr | C—H |
| 779 | morpholin-4-yl | —NHMe | C—H |
| 780 | morpholin-4-yl | —NHi-Pr | C—H |

TABLE 5-continued
| Compound | R³ | R⁴ | X³ |
|---|---|---|---|
| 781 | H | H | C—F |
| 782 | H | —Cl | C—F |
| 783 | H | —Br | C—F |
| 784 | H | 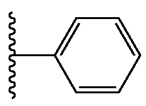 | C—F |
| 785 | H | OMe | C—F |
| 786 | H | —Oi-Pr | C—F |
| 787 | H | —NHMe | C—F |
| 788 | H | —Nhi-Pr | C—F |
| 789 | H | 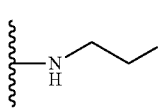 | C—F |
| 790 | H | 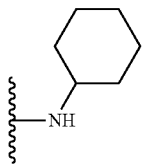 [SMILES: *NC1CCCCC1] | C—F |
| 791 | H | —N(CH₃)₂ | C—F |
| 792 | H | 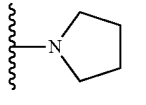 [SMILES: *N1CCCC1] | C—F |
| 793 | H | 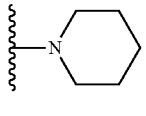 | C—F |
| 794 | H | 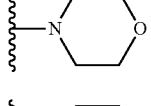 | C—F |
| 795 | H | 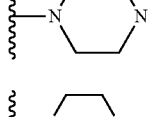 | C—F |
| 796 | H | 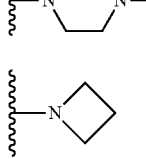 | C—F |
| 797 | H |  | C—F |
| 798 | H | 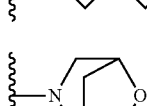 | C—F |
| 799 | H | 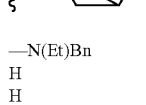 | C—F |
| 800 | H | —N(Et)Bn | C—F |
| 801 | H | H | C—F |
| 802 | —Cl | H | C—F |
TABLE 5-continued
| Compound | R³ | R⁴ | X³ |
|---|---|---|---|
| 803 | —Br | H | C—F |
| 804 | 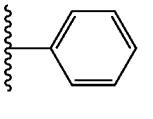 | H | C—F |
| 805 | OMe | H | C—F |
| 806 | —Oi-Pr | H | C—F |
| 807 | —NHMe | H | C—F |
| 808 | —NHi-Pr | H | C—F |
| 809 | 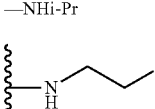 | H | C—F |
| 810 | 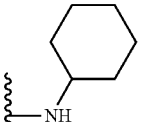 | H | C—F |
| 811 | —N(CH₃)₂ | H | C—F |
| 812 | 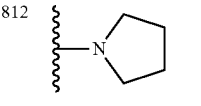 | H | C—F |
| 813 | 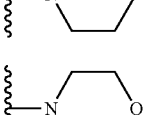 | H | C—F |
| 814 | 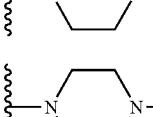 | H | C—F |
| 815 | 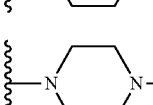 | H | C—F |
| 816 | 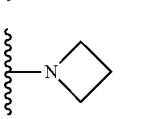 | H | C—F |
| 817 | 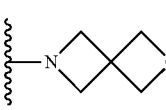 | H | C—F |
| 818 | 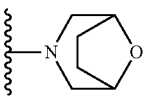 | H | C—F |
| 819 | 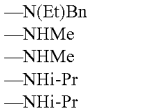 | H | C—F |
| 820 | —N(Et)Bn | H | C—F |
| 821 | —NHMe | —OMe | C—F |
| 822 | —NHMe | —Oi-Pr | C—F |
| 823 | —NHi-Pr | —OMe | C—F |
| 824 | —NHi-Pr | —Oi-Pr | C—F |

TABLE 5-continued
| Compound | R³ | R⁴ | X³ |
|---|---|---|---|
| 825 | 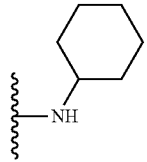 [SMILES: *NC1CCCCC1] | —OMe | C—F |
| 826 | 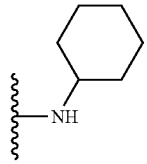 [SMILES: *NC1CCCCC1] | —Oi-Pr | C—F |
| 827 | 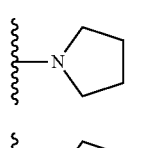 | —OMe | C—F |
| 828 | 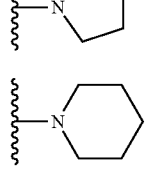 | —Oi-Pr | C—F |
| 829 | 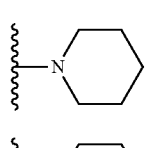 | —OMe | C—F |
| 830 | 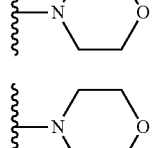 | —Oi-Pr | C—F |
| 831 | 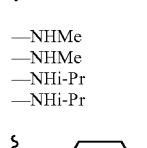 | —OMe | C—F |
| 832 | 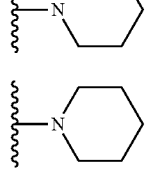 | —Oi-Pr | C—F |
| 833 | —NHMe | —NHMe | C—F |
| 834 | —NHMe | —NHi-Pr | C—F |
| 835 | —NHi-Pr | —NHMe | C—F |
| 836 | —NHi-Pr | —NHi-Pr | C—F |
| 837 | 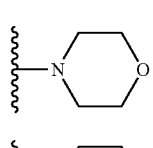 | —NHMe | C—F |
| 838 | 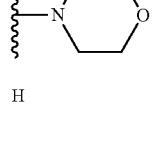 | —NHi-Pr | C—F |
| 839 |  | —NHMe | C—F |
| 840 | 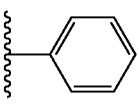 [SMILES: *c1ccccc1] | —NHi-Pr | C—F |
| 841 | H | H | N |
TABLE 5-continued
| Compound | R³ | R⁴ | X³ |
|---|---|---|---|
| 842 | H | —Cl | N |
| 843 | H | —Br | N |
| 844 | H | 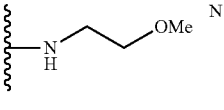 | N |
| 845 | H | OMe | N |
| 846 | H | —Oi-Pr | N |
| 847 | H | —NHMe | N |
| 848 | H | —NHi-Pr | N |
| 849 | H | 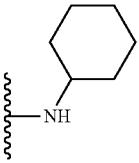 | N |
| 850 | H | 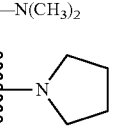 | N |
| 851 | H | —N(CH₃)₂ | N |
| 852 | H | 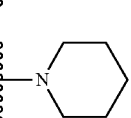 | N |
| 853 | H | 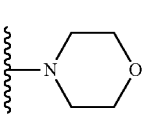 | N |
| 854 | H | 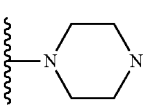 | N |
| 855 | H | 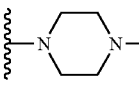 | N |
| 856 | H | 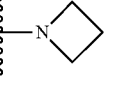 | N |
| 857 | H | 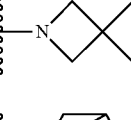 | N |
| 858 | H | 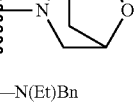 | N |
| 859 | H |  | N |
| 860 | H | —N(Et)Bn | N |
| 861 | H | H | N |
| 862 | —Cl | H | N |
| 863 | —Br | H | N |

TABLE 5-continued

| Compound | R³ | R⁴ | X³ |
|---|---|---|---|
| 864 | phenyl | H | N |
| 865 | OMe | H | N |
| 866 | —Oi-Pr | H | N |
| 867 | —NHMe | H | N |
| 868 | —NHi-Pr | H | N |
| 869 | —NH-CH₂CH₂-OMe | H | N |
| 870 | cyclohexyl-NH— | H | N |
| 871 | —N(CH₃)₂ | H | N |
| 872 | pyrrolidin-1-yl | H | N |
| 873 | piperidin-1-yl | H | N |
| 874 | morpholin-4-yl | H | N |
| 875 | 4-methylpiperazin-1-yl | H | N |
| 876 | 4-tert-butylpiperazin-1-yl | H | N |
| 877 | azetidin-1-yl | H | N |
| 878 | 2-oxa-6-azaspiro[3.3]heptan-6-yl | H | N |
| 879 | 8-oxa-3-azabicyclo[3.2.1]octan-3-yl | H | N |
| 880 | —N(Et)Bn | H | N |
| 881 | —NHMe | OMe | N |
| 882 | —NHMe | —Oi-Pr | N |
| 883 | —NHi-Pr | OMe | N |
| 884 | —NHi-Pr | —Oi-Pr | N |

TABLE 5-continued

| Compound | R³ | R⁴ | X³ |
|---|---|---|---|
| 885 | cyclohexyl-NH— | OMe | N |
| 886 | cyclohexyl-NH— | —Oi-Pr | N |
| 887 | pyrrolidin-1-yl | OMe | N |
| 888 | pyrrolidin-1-yl | —Oi-Pr | N |
| 889 | piperidin-1-yl | OMe | N |
| 890 | piperidin-1-yl | —Oi-Pr | N |
| 891 | morpholin-4-yl | OMe | N |
| 892 | morpholin-4-yl | —Oi-Pr | N |
| 893 | —NHMe | —NHMe | N |
| 894 | —NHMe | —NHi-Pr | N |
| 895 | —NHi-Pr | —NHMe | N |
| 896 | —NHi-Pr | —NHi-Pr | N |
| 897 | piperidin-1-yl | —NHMe | N |
| 898 | piperidin-1-yl | —NHi-Pr | N |
| 899 | morpholin-4-yl | —NHMe | N |
| 900 | morpholin-4-yl | —NHi-Pr | N. |

18. The compound of claim 1, which is selected from compounds of Formula XVIII or a pharmaceutically acceptable salt thereof:

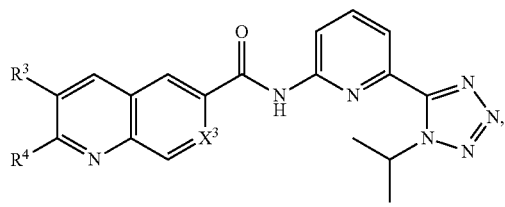

(XVIII)

wherein $R^3$, $R^4$ and $X^3$ are delineated for each compound in Table 6:

TABLE 6

| Compound | $R^3$ | $R^4$ | $X^3$ |
|---|---|---|---|
| 901 | H | H | C—H |
| 902 | H | —Cl | C—H |
| 903 | H | —Br | C—H |
| 904 | H | phenyl | C—H |
| 905 | H | —OMe | C—H |
| 906 | H | —Oi-Pr | C—H |
| 907 | H | —NHMe | C—H |
| 908 | H | —NHi-Pr | C—H |
| 909 | H | —NH-CH2CH2-OMe | C—H |
| 910 | H | cyclohexyl-NH— | C—H |
| 911 | H | —N(CH3)2 | C—H |
| 912 | H | pyrrolidinyl | C—H |
| 913 | H | piperidinyl | C—H |
| 914 | H | morpholinyl | C—H |
| 915 | H | 4-methylpiperazinyl | C—H |
| 916 | H | 4-tert-butylpiperazinyl | C—H |
| 917 | H | azetidinyl | C—H |
| 918 | H | 2-oxa-6-azaspiro[3.3]heptyl | C—H |
| 919 | H | 8-oxa-3-azabicyclo[3.2.1]octyl | C—H |
| 920 | H | —N(Et)Bn | C—H |
| 921 | H | H | C—H |
| 922 | —Cl | H | C—H |
| 923 | —Br | H | C—H |
| 924 | phenyl | H | C—H |
| 925 | —OMe | H | C—H |
| 926 | —Oi-Pr | H | C—H |
| 927 | —NHMe | H | C—H |
| 928 | —NHi-Pr | H | C—H |
| 929 | —NH-CH2CH2-OMe | H | C—H |
| 930 | cyclohexyl-NH— | H | C—H |
| 931 | —N(CH3)2 | H | C—H |
| 932 | pyrrolidinyl | H | C—H |
| 933 | piperidinyl | H | C—H |
| 934 | morpholinyl | H | C—H |
| 935 | 4-methylpiperazinyl | H | C—H |

TABLE 6-continued

| Compound | R³ | R⁴ | X³ |
|---|---|---|---|
| 936 | 4-tert-butylpiperazin-1-yl | H | C—H |
| 937 | azetidin-1-yl | H | C—H |
| 938 | 2-oxa-6-azaspiro[3.3]heptan-6-yl | H | C—H |
| 939 | 8-oxa-3-azabicyclo[3.2.1]octan-3-yl | H | C—H |
| 940 | —N(Et)Bn | H | C—H |
| 941 | —NHMe | —OMe | C—H |
| 942 | —NHMe | —Oi-Pr | C—H |
| 943 | —NHi-Pr | —OMe | C—H |
| 944 | —NHi-Pr | —Oi-Pr | C—H |
| 945 | cyclohexyl-NH— | —OMe | C—H |
| 946 | cyclohexyl-NH— | —Oi-Pr | C—H |
| 947 | pyrrolidin-1-yl | —OMe | C—H |
| 948 | pyrrolidin-1-yl | —Oi-Pr | C—H |
| 949 | piperidin-1-yl | —OMe | C—H |
| 950 | piperidin-1-yl | —Oi-Pr | C—H |
| 951 | morpholin-4-yl | —OMe | C—H |
| 952 | morpholin-4-yl | —Oi-Pr | C—H |
| 953 | —NHMe | —NHMe | C—H |
| 954 | —NHMe | —NHi-Pr | C—H |
| 955 | —NHi-Pr | —NHMe | C—H |
| 956 | —NHi-Pr | —NHi-Pr | C—H |
| 957 | piperidin-1-yl | —NHMe | C—H |
| 958 | piperidin-1-yl | —NHi-Pr | C—H |
| 959 | morpholin-4-yl | —NHMe | C—H |
| 960 | morpholin-4-yl | —NHi-Pr | C—H |
| 961 | H | H | C—F |
| 962 | H | —Cl | C—F |
| 963 | H | —Br | C—F |
| 964 | H | phenyl | C—F |
| 965 | H | —OMe | C—F |
| 966 | H | —Oi-Pr | C—F |
| 967 | H | —NHMe | C—F |
| 968 | H | —NHi-Pr | C—F |
| 969 | H | —NH-CH₂CH₂-OMe | C—F |
| 970 | H | cyclohexyl-NH— | C—F |
| 971 | H | —N(CH₃)₂ | C—F |
| 972 | H | pyrrolidin-1-yl | C—F |
| 973 | H | piperidin-1-yl | C—F |
| 974 | H | morpholin-4-yl | C—F |

TABLE 6-continued
| Compound | R³ | R⁴ | X³ |
|---|---|---|---|
| 975 | H | 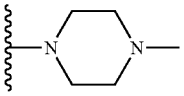 [SMILES: *N1CCN(C)CC1] | C—F |
| 976 | H | 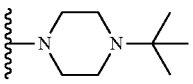 [SMILES: *N1CCN(C(C)(C)C)CC1] | C—F |
| 977 | H | 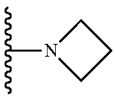 [SMILES: *N1CCC1] | C—F |
| 978 | H |  | C—F |
| 979 | H | 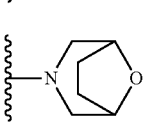 | C—F |
| 980 | H | —N(Et)Bn | C—F |
| 981 | H | H | C—F |
| 982 | —Cl | H | C—F |
| 983 | —Br | H | C—F |
| 984 | 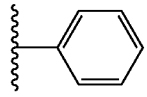 | H | C—F |
| 985 | —OMe | H | C—F |
| 986 | —Oi-Pr | H | C—F |
| 987 | —NHMe | H | C—F |
| 988 | —NHi-Pr | H | C—F |
| 989 | 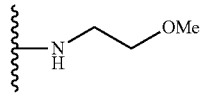 [SMILES: *NCCOC] | H | C—F |
| 990 | 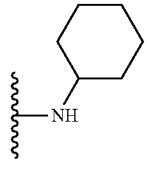 [SMILES: *NC1CCCCC1] | H | C—F |
| 991 | —N(CH₃)₂ | H | C—F |
| 992 | 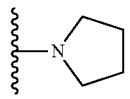 | H | C—F |
| 993 | 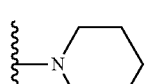 | H | C—F |
| 994 | 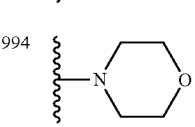 | H | C—F |
TABLE 6-continued
| Compound | R³ | R⁴ | X³ |
|---|---|---|---|
| 995 | 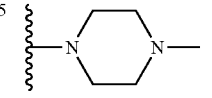 | H | C—F |
| 996 | 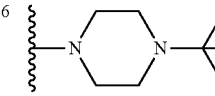 | H | C—F |
| 997 | 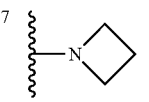 | H | C—F |
| 998 |  | H | C—F |
| 999 | 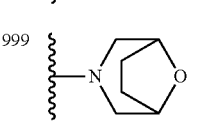 | H | C—F |
| 1000 | —N(Et)Bn | H | C—F |
| 1001 | —NHMe | —OMe | C—F |
| 1002 | —NHMe | —Oi-Pr | C—F |
| 1003 | —NHi-Pr | —OMe | C—F |
| 1004 | —NHi-Pr | —Oi-Pr | C—F |
| 1005 | 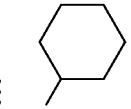 | —OMe | C—F |
| 1006 | 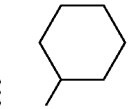 | —Oi-Pr | C—F |
| 1007 | 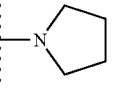 | —OMe | C—F |
| 1008 | 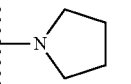 | —Oi-Pr | C—F |
| 1009 | 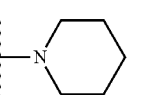 | —OMe | C—F |
| 1010 | 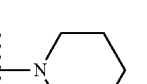 | —Oi-Pr | C—F |
| 1011 | 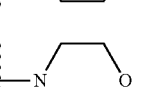 | —OMe | C—F |

TABLE 6-continued

| Compound | R³ | R⁴ | X³ |
|---|---|---|---|
| 1012 | N-morpholinyl | —Oi-Pr | C—F |
| 1013 | —NHMe | —NHMe | C—F |
| 1014 | —NHMe | —NHi-Pr | C—F |
| 1015 | —NHi-Pr | —NHMe | C—F |
| 1016 | —NHi-Pr | —NHi-Pr | C—F |
| 1017 | N-piperidinyl | —NHMe | C—F |
| 1018 | N-piperidinyl | —NHi-Pr | C—F |
| 1019 | N-morpholinyl | —NHMe | C—F |
| 1020 | N-morpholinyl | —NHi-Pr | C—F |
| 1021 | H | H | N |
| 1022 | H | —Cl | N |
| 1023 | H | —Br | N |
| 1024 | H | phenyl | N |
| 1025 | H | —OMe | N |
| 1026 | H | —Oi-Pr | N |
| 1027 | H | —NHMe | N |
| 1028 | H | —NHi-Pr | N |
| 1029 | H | —NH-CH₂CH₂-OMe | N |
| 1030 | H | —NH-cyclohexyl | N |
| 1031 | H | —N(CH₃)₂ | N |
| 1032 | H | N-pyrrolidinyl | N |
| 1033 | H | N-piperidinyl | N |

TABLE 6-continued

| Compound | R³ | R⁴ | X³ |
|---|---|---|---|
| 1034 | H | N-morpholinyl | N |
| 1035 | H | N-methylpiperazinyl | N |
| 1036 | H | N-(t-butyl)piperazinyl | N |
| 1037 | H | N-azetidinyl | N |
| 1038 | H | 2-oxa-6-azaspiro[3.3]heptan-6-yl | N |
| 1039 | H | 8-oxa-3-azabicyclo[3.2.1]octan-3-yl | N |
| 1040 | H | —N(Et)Bn | N |
| 1041 | H | H | N |
| 1042 | —Cl | H | N |
| 1043 | —Br | H | N |
| 1044 | phenyl | H | N |
| 1045 | —OMe | H | N |
| 1046 | —Oi-Pr | H | N |
| 1047 | —NHMe | H | N |
| 1048 | —NHi-Pr | H | N |
| 1049 | —NH-CH₂CH₂-OMe | H | N |
| 1050 | —NH-cyclohexyl | H | N |
| 1051 | —N(CH₃)₂ | H | N |
| 1052 | N-pyrrolidinyl | H | N |
| 1053 | N-piperidinyl | H | N |

TABLE 6-continued

| Compound | R³ | R⁴ | X³ |
|---|---|---|---|
| 1054 | N-morpholinyl | H | N |
| 1055 | 4-methylpiperazin-1-yl | H | N |
| 1056 | 4-tert-butylpiperazin-1-yl | H | N |
| 1057 | azetidin-1-yl | H | N |
| 1058 | 2-oxa-6-azaspiro[3.3]heptan-6-yl | H | N |
| 1059 | 8-oxa-3-azabicyclo[3.2.1]octan-3-yl | H | N |
| 1060 | —N(Et)Bn | H | N |
| 1061 | —NHMe | —OMe | N |
| 1062 | —NHMe | —Oi-Pr | N |
| 1063 | —NHi-Pr | —OMe | N |
| 1064 | —NHi-Pr | —Oi-Pr | N |
| 1065 | cyclohexyl-NH— | —OMe | N |
| 1066 | cyclohexyl-NH— | —Oi-Pr | N |
| 1067 | pyrrolidin-1-yl | —OMe | N |
| 1068 | pyrrolidin-1-yl | —Oi-Pr | N |
| 1069 | piperidin-1-yl | —OMe | N |
| 1070 | piperidin-1-yl | —Oi-Pr | N |
| 1071 | morpholin-4-yl | —OMe | N |
| 1072 | morpholin-4-yl | —Oi-Pr | N |
| 1073 | —NHMe | —NHMe | N |
| 1074 | —NHMe | —NHi-Pr | N |
| 1075 | —NHi-Pr | —NHMe | N |
| 1076 | —NHi-Pr | —NHi-Pr | N |
| 1077 | piperidin-1-yl | —NHMe | N |
| 1078 | piperidin-1-yl | —NHi-Pr | N |
| 1079 | morpholin-4-yl | —NHMe | N |
| 1080 | morpholin-4-yl | —NHi-Pr | N. |

19. The compound of claim 1, represented by Formula XIX or a pharmaceutically acceptable salt thereof:

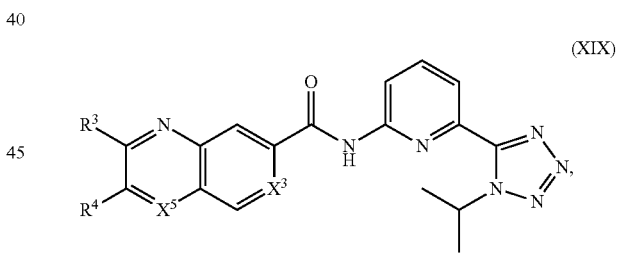

(XIX)

wherein R³, R⁴, X³, and X⁵ are as defined in claim 1.

20. The compound of claim 1, which is selected from compounds of Formula XX or a pharmaceutically acceptable salt thereof:

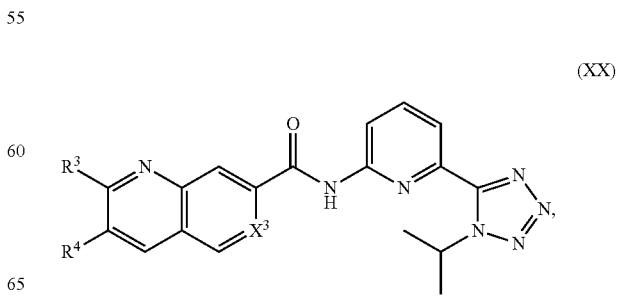

(XX)

wherein R³, R⁴ and X³ are delineated for each compound in Table 7:

TABLE 7

| Compound | R³ | R⁴ | X³ |
|---|---|---|---|
| 1081 | H | H | C—H |
| 1082 | H | —Cl | C—H |
| 1083 | H | —Br | C—H |
| 1084 | H | phenyl | C—H |
| 1085 | H | —OMe | C—H |
| 1086 | H | —Oi-Pr | C—H |
| 1087 | H | —NHMe | C—H |
| 1088 | H | —NHi-Pr | C—H |
| 1089 | H | —NH-CH₂CH₂-OMe | C—H |
| 1090 | H | —NH-cyclohexyl | C—H |
| 1091 | H | —N(CH₃)₂ | C—H |
| 1092 | H | pyrrolidin-1-yl | C—H |
| 1093 | H | piperidin-1-yl | C—H |
| 1094 | H | morpholin-4-yl | C—H |
| 1095 | H | 4-methylpiperazin-1-yl | C—H |
| 1096 | H | 4-tert-butylpiperazin-1-yl | C—H |
| 1097 | H | azetidin-1-yl | C—H |
| 1098 | H | 2-oxa-6-azaspiro[3.3]heptan-6-yl | C—H |
| 1099 | H | 8-oxa-3-azabicyclo[3.2.1]octan-3-yl | C—H |
| 1100 | H | —N(Et)Bn | C—H |
| 1101 | H | H | C—H |
| 1102 | —Cl | H | C—H |
| 1103 | —Br | H | C—H |
| 1104 | phenyl | H | C—H |
| 1105 | OMe | H | C—H |
| 1106 | —Oi-Pr | H | C—H |
| 1107 | —NHMe | H | C—H |
| 1108 | —NHi-Pr | H | C—H |
| 1109 | —NH-CH₂CH₂-OMe | H | C—H |
| 1110 | —NH-cyclohexyl | H | C—H |
| 1111 | —N(CH₃)₂ | H | C—H |
| 1112 | pyrrolidin-1-yl | H | C—H |
| 1113 | piperidin-1-yl | H | C—H |
| 1114 | morpholin-4-yl | H | C—H |
| 1115 | 4-methylpiperazin-1-yl | H | C—H |
| 1116 | 4-tert-butylpiperazin-1-yl | H | C—H |
| 1117 | azetidin-1-yl | H | C—H |
| 1118 | 2-oxa-6-azaspiro[3.3]heptan-6-yl | H | C—H |
| 1119 | 8-oxa-3-azabicyclo[3.2.1]octan-3-yl | H | C—H |
| 1120 | —N(Et)Bn | H | C—H |
| 1121 | —NHMe | OMe | C—H |

TABLE 7-continued

| Compound | R³ | R⁴ | X³ |
|---|---|---|---|
| 1122 | —NHMe | —Oi-Pr | C—H |
| 1123 | —NHi-Pr | OMe | C—H |
| 1124 | —NHi-Pr | —Oi-Pr | C—H |
| 1125 | cyclohexyl-NH— | OMe | C—H |
| 1126 | cyclohexyl-NH— | —Oi-Pr | C—H |
| 1127 | pyrrolidin-1-yl | OMe | C—H |
| 1128 | pyrrolidin-1-yl | —Oi-Pr | C—H |
| 1129 | piperidin-1-yl | OMe | C—H |
| 1130 | piperidin-1-yl | —Oi-Pr | C—H |
| 1131 | morpholin-4-yl | OMe | C—H |
| 1132 | morpholin-4-yl | —Oi-Pr | C—H |
| 1133 | —NHMe | —NHMe | C—H |
| 1134 | —NHMe | —NHi-Pr | C—H |
| 1135 | —NHi-Pr | —NHMe | C—H |
| 1136 | —NHi-Pr | —NHi-Pr | C—H |
| 1137 | piperidin-1-yl | —NHMe | C—H |
| 1138 | piperidin-1-yl | —NHi-Pr | C—H |
| 1139 | morpholin-4-yl | —NHMe | C—H |
| 1140 | morpholin-4-yl | —NHi-Pr | C—H |
| 1141 | H | H | C—F |
| 1142 | H | —Cl | C—F |
| 1143 | H | —Br | C—F |
| 1144 | H | phenyl | C—F |
| 1145 | H | OMe | C—F |
| 1146 | H | —Oi-Pr | C—F |
| 1147 | H | —NHMe | C—F |
| 1148 | H | —NHi-Pr | C—F |
| 1149 | H | —NH-CH₂CH₂-OMe | C—F |
| 1150 | H | cyclohexyl-NH— | C—F |
| 1151 | H | —N(CH₃)₂ | C—F |
| 1152 | H | pyrrolidin-1-yl | C—F |
| 1153 | H | piperidin-1-yl | C—F |
| 1154 | H | morpholin-4-yl | C—F |
| 1155 | H | 4-methylpiperazin-1-yl | C—F |
| 1156 | H | 4-tert-butylpiperazin-1-yl | C—F |
| 1157 | H | azetidin-1-yl | C—F |
| 1158 | H | 2-oxa-6-azaspiro[3.3]heptan-6-yl | C—F |

TABLE 7-continued

| Compound | R³ | R⁴ | X³ |
|---|---|---|---|
| 1159 | H | N-bridged oxa-bicyclic | C—F |
| 1160 | H | —N(Et)Bn | C—F |
| 1161 | H | H | C—F |
| 1162 | —Cl | H | C—F |
| 1163 | —Br | H | C—F |
| 1164 | phenyl | H | C—F |
| 1165 | OMe | H | C—F |
| 1166 | —Oi-Pr | H | C—F |
| 1167 | —NHMe | H | C—F |
| 1168 | —NHi-Pr | H | C—F |
| 1169 | —NH-CH₂CH₂-OMe | H | C—F |
| 1170 | cyclohexyl-NH— | H | C—F |
| 1171 | —N(CH₃)₂ | H | C—F |
| 1172 | pyrrolidin-1-yl | H | C—F |
| 1173 | piperidin-1-yl | H | C—F |
| 1174 | morpholin-4-yl | H | C—F |
| 1175 | 4-methylpiperazin-1-yl | H | C—F |
| 1176 | 4-tert-butylpiperazin-1-yl | H | C—F |
| 1177 | azetidin-1-yl | H | C—F |
| 1178 | 2-oxa-6-azaspiro[3.3]heptan-6-yl | H | C—F |
| 1179 | N-bridged oxa-bicyclic | H | C—F |
| 1180 | —N(Et)Bn | H | C—F |
| 1181 | —NHMe | OMe | C—F |
| 1182 | —NHMe | —Oi-Pr | C—F |
| 1183 | —Nhi-Pr | OMe | C—F |
| 1184 | —Nhi-Pr | —Oi-Pr | C—F |
| 1185 | cyclohexyl-NH— | OMe | C—F |
| 1186 | cyclohexyl-NH— | —Oi-Pr | C—F |
| 1187 | pyrrolidin-1-yl | OMe | C—F |
| 1188 | pyrrolidin-1-yl | —Oi-Pr | C—F |
| 1189 | piperidin-1-yl | OMe | C—F |
| 1190 | piperidin-1-yl | —Oi-Pr | C—F |
| 1191 | morpholin-4-yl | OMe | C—F |
| 1192 | morpholin-4-yl | —Oi-Pr | C—F |
| 1193 | —NHMe | —NHMe | C—F |
| 1194 | —NHMe | —NHi-Pr | C—F |
| 1195 | —NHi-Pr | —NHMe | C—F |
| 1196 | —NHi-Pr | —NHi-Pr | C—F |
| 1197 | piperidin-1-yl | —NHMe | C—F |
| 1198 | piperidin-1-yl | —NHi-Pr | C—F |

TABLE 7-continued
| Compound | R³ | R⁴ | X³ |
|---|---|---|---|
| 1199 | 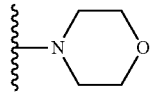 [SMILES: *N1CCOCC1] | —NHMe | C—F |
| 1200 | 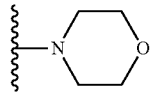 | —NHi-Pr | C—F |
| 1201 | H | H | N |
| 1202 | H | —Cl | N |
| 1203 | H | —Br | N |
| 1204 | H | 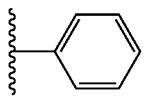 [SMILES: *c1ccccc1] | N |
| 1205 | H | OMe | N |
| 1206 | H | —Oi-Pr | N |
| 1207 | H | —NHMe | N |
| 1208 | H | —NHi-Pr | N |
| 1209 | H | 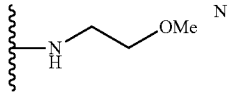 | N |
| 1210 | H | 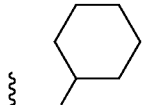 | N |
| 1211 | H | —N(CH₃)₂ | N |
| 1212 | H | 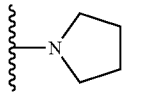 | N |
| 1213 | H | 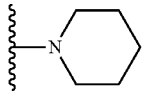 | N |
| 1214 | H | 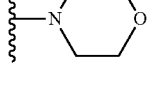 | N |
| 1215 | H | 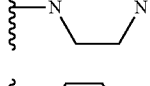 | N |
| 1216 | H | 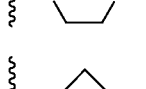 | N |
| 1217 | H | 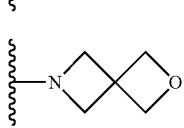 | N |
| 1218 | H |  | N |
TABLE 7-continued
| Compound | R³ | R⁴ | X³ |
|---|---|---|---|
| 1219 | H | 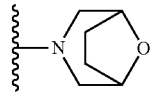 | N |
| 1220 | H | —N(Et)Bn | N |
| 1221 | H | H | N |
| 1222 | —Cl | H | N |
| 1223 | —Br | H | N |
| 1224 |  | H | N |
| 1225 | OMe | H | N |
| 1226 | —Oi-Pr | H | N |
| 1227 | —NHMe | H | N |
| 1228 | —NHi-Pr | H | N |
| 1229 |  | H | N |
| 1230 |  | H | N |
| 1231 | —N(CH₃)₂ | H | N |
| 1232 |  | H | N |
| 1233 |  | H | N |
| 1234 |  | H | N |
| 1235 |  | H | N |
| 1236 |  | H | N |
| 1237 |  | H | N |
| 1238 |  | H | N |

TABLE 7-continued

| Compound | R³ | R⁴ | X³ |
|---|---|---|---|
| 1239 | 8-oxa-3-azabicyclo[3.2.1]octan-3-yl | H | N |
| 1240 | —N(Et)Bn | H | N |
| 1241 | —NHMe | OMe | N |
| 1242 | —NHMe | —Oi-Pr | N |
| 1243 | —NHi-Pr | OMe | N |
| 1244 | —NHi-Pr | —Oi-Pr | N |
| 1245 | cyclohexyl-NH | OMe | N |
| 1246 | cyclohexyl-NH | —Oi-Pr | N |
| 1247 | pyrrolidin-1-yl | OMe | N |
| 1248 | pyrrolidin-1-yl | —Oi-Pr | N |
| 1249 | piperidin-1-yl | OMe | N |
| 1250 | piperidin-1-yl | —Oi-Pr | N |
| 1251 | morpholin-4-yl | OMe | N |
| 1252 | morpholin-4-yl | —Oi-Pr | N |
| 1253 | —NHMe | —NHMe | N |
| 1254 | —NHMe | —NHi-Pr | N |
| 1255 | —NHi-Pr | —NHMe | N |
| 1256 | —NHi-Pr | —NHi-Pr | N |
| 1257 | piperidin-1-yl | —NHMe | N |
| 1258 | piperidin-1-yl | —NHi-Pr | N |
| 1259 | morpholin-4-yl | —NHMe | N |
| 1260 | morpholin-4-yl | —NHi-Pr | N. |

21. The compound of claim 1, which is selected from compounds of Formula XXI or a pharmaceutically acceptable salt thereof:

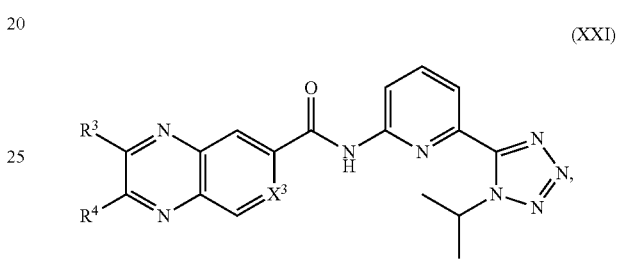

(XXI)

wherein R³, R⁴ and X³ are delineated for each compound in Table 8:

TABLE 8

| Compound | R³ | R⁴ | X³ |
|---|---|---|---|
| 1261 | H | H | C—H |
| 1262 | H | —Cl | C—H |
| 1263 | H | —Br | C—H |
| 1264 | H | phenyl | C—H |
| 1265 | H | OMe | C—H |
| 1266 | H | —Oi-Pr | C—H |
| 1267 | H | —NHMe | C—H |
| 1268 | H | —NHi-Pr | C—H |
| 1269 | H | —NH-CH₂CH₂-OMe | C—H |
| 1270 | H | cyclohexyl-NH | C—H |
| 1271 | H | —N(CH₃)₂ | C—H |
| 1272 | H | pyrrolidin-1-yl | C—H |

TABLE 8-continued
| Compound | R³ | R⁴ | X³ |
|---|---|---|---|
| 1273 | H | 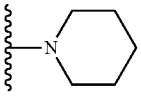 [SMILES: *N1CCCCC1] | C—H |
| 1274 | H | 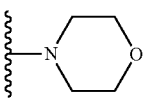 | C—H |
| 1275 | H | 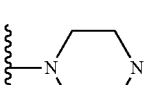 | C—H |
| 1276 | H | 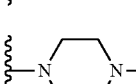 | C—H |
| 1277 | H | 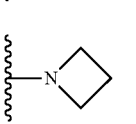 | C—H |
| 1278 | H |  | C—H |
| 1279 | H |  | C—H |
| 1280 | H | —N(Et)Bn | C—H |
| 1281 | H | H | C—H |
| 1282 | —Cl | H | C—H |
| 1283 | —Br | H | C—H |
| 1284 | 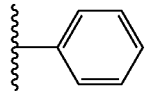 | H | C—H |
| 1285 | —OMe | H | C—H |
| 1286 | —Oi-Pr | H | C—H |
| 1287 | —NHMe | H | C—H |
| 1288 | —NHi-Pr | H | C—H |
| 1289 | 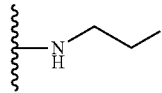 | H | C—H |
| 1290 | 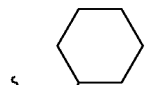 | H | C—H |
| 1291 | —N(CH₃)₂ | H | C—H |
| 1292 | 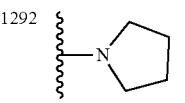 | H | C—H |
| 1293 |  | H | C—H |
| 1294 | 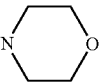 | H | C—H |
| 1295 | 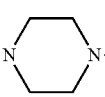 | H | C—H |
| 1296 | 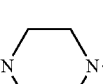 | H | C—H |
| 1297 | 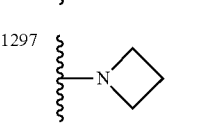 | H | C—H |
| 1298 |  | H | C—H |
| 1299 |  | H | C—H |
| 1300 | —N(Et)Bn | H | C—H |
| 1301 | —NHMe | —OMe | C—H |
| 1302 | —NHMe | —Oi-Pr | C—H |
| 1303 | —NHi-Pr | —OMe | C—H |
| 1304 | —NHi-Pr | —Oi-Pr | C—H |
| 1305 | 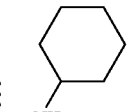 | —OMe | C—H |
| 1306 | 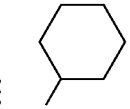 | —Oi-Pr | C—H |
| 1307 | 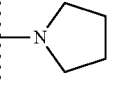 | —OMe | C—H |
| 1308 | 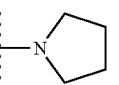 | —Oi-Pr | C—H |
| 1309 | 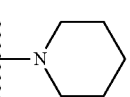 | —OMe | C—H |

TABLE 8-continued
| Compound | R³ | R⁴ | X³ |
|---|---|---|---|
| 1310 | 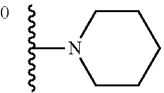 | —Oi-Pr | C—H |
| 1311 | 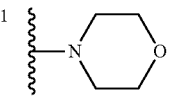 | —OMe | C—H |
| 1312 | 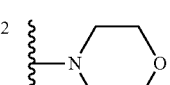 | —Oi-Pr | C—H |
| 1313 | —NHMe | —NHMe | C—H |
| 1314 | —NHMe | —NHi-Pr | C—H |
| 1315 | —NHi-Pr | —NHMe | C—H |
| 1316 | —NHi-Pr | —NHi-Pr | C—H |
| 1317 | 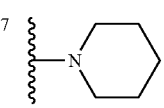 | —NHMe | C—H |
| 1318 | 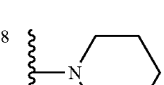 | —NHi-Pr | C—H |
| 1319 | 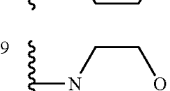 | —NHMe | C—H |
| 1320 | 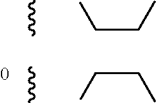 | —NHi-Pr | C—H |
| 1321 | H | H | C—F |
| 1322 | H | —Cl | C—F |
| 1323 | H | —Br | C—F |
| 1324 | H | 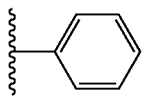 [SMILES: *c1ccccc1] | C—F |
| 1325 | H | —OMe | C—F |
| 1326 | H | —Oi-Pr | C—F |
| 1327 | H | —NHMe | C—F |
| 1328 | H | —NHi-Pr | C—F |
| 1329 | H | 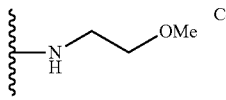 | C—F |
| 1330 | H | 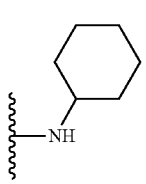 [SMILES: *NC1CCCCC1] | C—F |
| 1331 | H | —N(CH₃)₂ | C—F |
TABLE 8-continued
| Compound | R³ | R⁴ | X³ |
|---|---|---|---|
| 1332 | H | 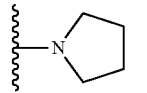 | C—F |
| 1333 | H | 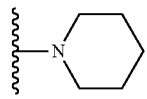 | C—F |
| 1334 | H | 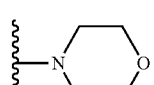 | C—F |
| 1335 | H | 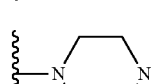 | C—F |
| 1336 | H | 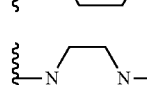 | C—F |
| 1337 | H | 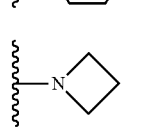 | C—F |
| 1338 | H |  | C—F |
| 1339 | H |  | C—F |
| 1340 | H | —N(Et)Bn | C—F |
| 1341 | H | H | C—F |
| 1342 | —Cl | H | C—F |
| 1343 | —Br | H | C—F |
| 1344 | 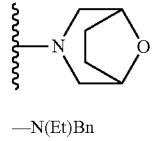 | H | C—F |
| 1345 | —OMe | H | C—F |
| 1346 | —Oi-Pr | H | C—F |
| 1347 | —NHMe | H | C—F |
| 1348 | —NHi-Pr | H | C—F |
| 1349 |  | H | C—F |
| 1350 |  | H | C—F |
| 1351 | —N(CH₃)₂ | H | C—F |

TABLE 8-continued

| Compound | R³ | R⁴ | X³ |
|---|---|---|---|
| 1352 | 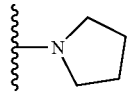 [SMILES: *N1CCCC1] pyrrolidine | H | C—F |
| 1353 | 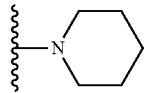 piperidine | H | C—F |
| 1354 | 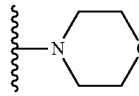 morpholine | H | C—F |
| 1355 | 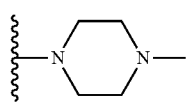 N-methylpiperazine | H | C—F |
| 1356 | 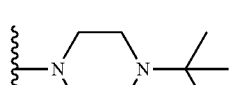 N-tert-butylpiperazine | H | C—F |
| 1357 | 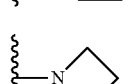 azetidine | H | C—F |
| 1358 | 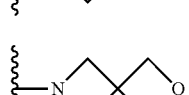 2-oxa-6-azaspiro[3.3]heptane | H | C—F |
| 1359 | 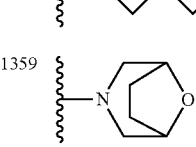 8-oxa-3-azabicyclo[3.2.1]octane | H | C—F |
| 1360 | —N(Et)Bn | H | C—F |
| 1361 | —NHMe | —OMe | C—F |
| 1362 | —NHMe | —Oi-Pr | C—F |
| 1363 | —NHi-Pr | —OMe | C—F |
| 1364 | —NHi-Pr | —Oi-Pr | C—F |
| 1365 | 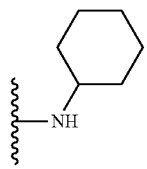 [SMILES: *NC1CCCCC1] cyclohexyl-NH | —OMe | C—F |
| 1366 | 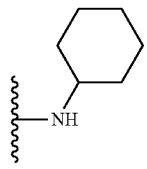 [SMILES: *NC1CCCCC1] cyclohexyl-NH | —Oi-Pr | C—F |
| 1367 | 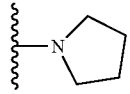 [SMILES: *N1CCCC1] pyrrolidine | —OMe | C—F |
| 1368 | 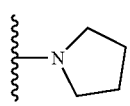 pyrrolidine | —Oi-Pr | C—F |
| 1369 |  piperidine | —OMe | C—F |
| 1370 |  piperidine | —Oi-Pr | C—F |
| 1371 |  morpholine | —OMe | C—F |
| 1372 | 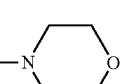 morpholine | —Oi-Pr | C—F |
| 1373 | —NHMe | —NHMe | C—F |
| 1374 | —NHMe | —NHi-Pr | C—F |
| 1375 | —NHi-Pr | —NHMe | C—F |
| 1376 | —NHi-Pr | —NHi-Pr | C—F |
| 1377 | 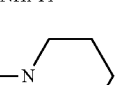 piperidine | —NHMe | C—F |
| 1378 | 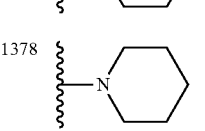 piperidine | —NHi-Pr | C—F |
| 1379 | 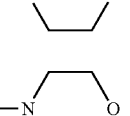 morpholine | —NHMe | C—F |
| 1380 | 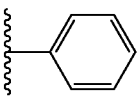 morpholine | —NHi-Pr | C—F |
| 1381 | H | H | N |
| 1382 | H | —Cl | N |
| 1383 | H | —Br | N |
| 1384 | H | 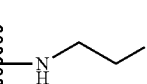 phenyl | N |
| 1385 | H | —OMe | N |
| 1386 | H | —Oi-Pr | N |
| 1387 | H | —NHMe | N |
| 1388 | H | —NHi-Pr | N |
| 1389 | H | —NH-CH₂CH₂-OMe | N |
| 1390 | H | 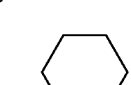 cyclohexyl-NH | N |

TABLE 8-continued

| Compound | R³ | R⁴ | X³ |
|---|---|---|---|
| 1391 | H | —N(CH₃)₂ | N |
| 1392 | H | pyrrolidin-1-yl | N |
| 1393 | H | piperidin-1-yl | N |
| 1394 | H | morpholin-4-yl | N |
| 1395 | H | 4-methylpiperazin-1-yl | N |
| 1396 | H | 4-tert-butylpiperazin-1-yl | N |
| 1397 | H | azetidin-1-yl | N |
| 1398 | H | 2-oxa-6-azaspiro[3.3]heptan-6-yl | N |
| 1399 | H | 8-oxa-3-azabicyclo[3.2.1]octan-3-yl | N |
| 1400 | H | —N(Et)Bn | N |
| 1401 | H | H | N |
| 1402 | —Cl | H | N |
| 1403 | —Br | H | N |
| 1404 | phenyl | H | N |
| 1405 | —OMe | H | N |
| 1406 | —Oi-Pr | H | N |
| 1407 | —NHMe | H | N |
| 1408 | —NHi-Pr | H | N |
| 1409 | —NH-CH₂CH₂-OMe | H | N |
| 1410 | cyclohexyl-NH— | H | N |
| 1411 | —N(CH₃)₂ | H | N |
| 1412 | pyrrolidin-1-yl | H | N |
| 1413 | piperidin-1-yl | H | N |
| 1414 | morpholin-4-yl | H | N |
| 1415 | 4-methylpiperazin-1-yl | H | N |
| 1416 | 4-tert-butylpiperazin-1-yl | H | N |
| 1417 | azetidin-1-yl | H | N |
| 1418 | 2-oxa-6-azaspiro[3.3]heptan-6-yl | H | N |
| 1419 | 8-oxa-3-azabicyclo[3.2.1]octan-3-yl | H | N |
| 1420 | —N(Et)Bn | H | N |
| 1421 | —NHMe | —OMe | N |
| 1422 | —NHMe | —Oi-Pr | N |
| 1423 | —NHi-Pr | —OMe | N |
| 1424 | —NHi-Pr | —Oi-Pr | N |
| 1425 | cyclohexyl-NH— | —OMe | N |
| 1426 | cyclohexyl-NH— | —Oi-Pr | N |
| 1427 | pyrrolidin-1-yl | —OMe | N |

TABLE 8-continued

| Compound | R³ | R⁴ | X³ |
|---|---|---|---|
| 1428 | 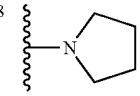 pyrrolidinyl | —Oi-Pr | N |
| 1429 | 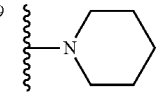 piperidinyl | —OMe | N |
| 1430 | 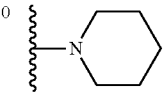 piperidinyl | —Oi-Pr | N |
| 1431 | 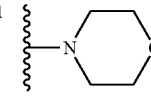 morpholinyl | —OMe | N |
| 1432 | 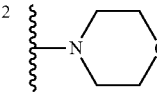 morpholinyl | —Oi-Pr | N |
| 1433 | —NHMe | —NHMe | N |
| 1434 | —NHMe | —NHi-Pr | N |
| 1435 | —NHi-Pr | —NHMe | N |
| 1436 | —NHi-Pr | —NHi-Pr | N |
| 1437 | 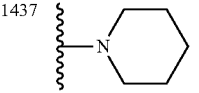 piperidinyl | —NHMe | N |
| 1438 |  piperidinyl | —NHi-Pr | N |
| 1439 | 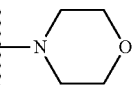 morpholinyl | —NHMe | N |
| 1440 | 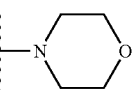 morpholinyl | —NHi-Pr | N. |

22. The compound of claim 1, selected from the compounds set forth below or a pharmaceutically acceptable salt thereof:

| Compound | Structure |
|---|---|
| 1 | 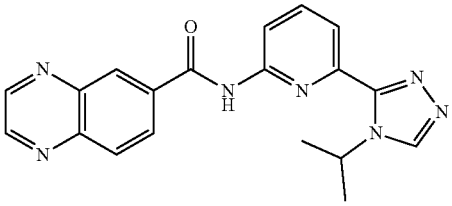 [SMILES: CC(C)n1cnnc1-c1cccc(NC(=O)c2ccc3nccnc3c2)n1] |
| 2 | 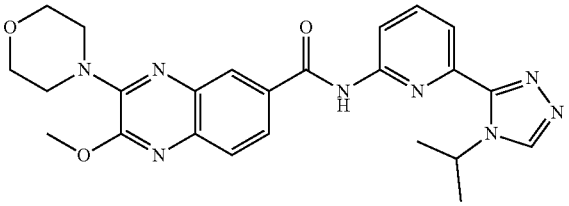 [SMILES: COc1nc2ccc(C(=O)Nc3cccc(-c4nncn4C(C)C)n3)cc2nc1N1CCOCC1] |
| 3 | 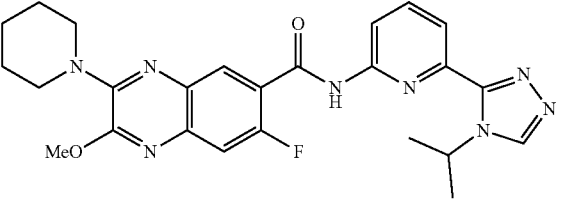 [SMILES: COc1nc2cc(F)c(C(=O)Nc3cccc(-c4nncn4C(C)C)n3)cc2nc1N1CCCCC1] |
| 4 | 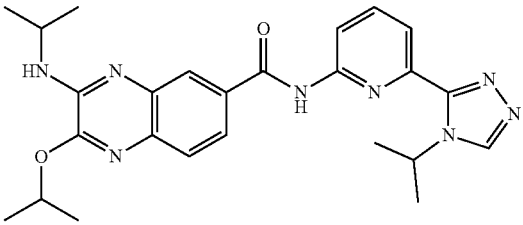 [SMILES: CC(C)Nc1nc2cc(C(=O)Nc3cccc(-c4nncn4C(C)C)n3)ccc2nc1OC(C)C] |

| Compound | Structure |
|---|---|
| 5 | 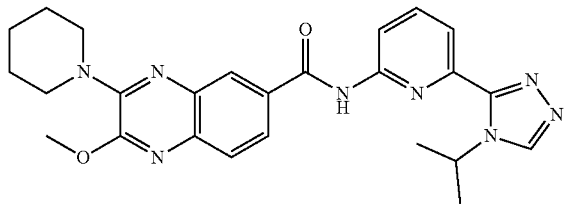 [SMILES: COc1nc2ccc(C(=O)Nc3cccc(-c4nncn4C(C)C)n3)cc2nc1N1CCCCC1] |
| 6 | 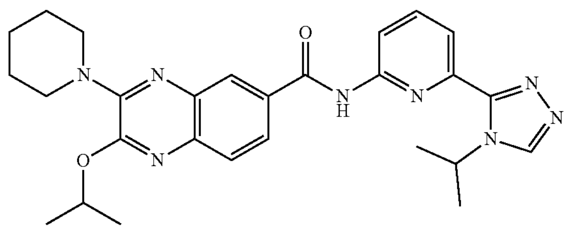 [SMILES: CC(C)Oc1nc2ccc(C(=O)Nc3cccc(-c4nncn4C(C)C)n3)cc2nc1N1CCCCC1] |
| 7 | 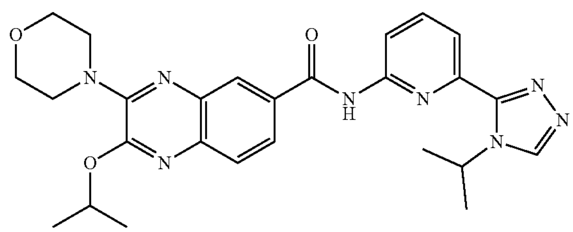 [SMILES: CC(C)Oc1nc2ccc(C(=O)Nc3cccc(-c4nncn4C(C)C)n3)cc2nc1N1CCOCC1] |
| 8 | 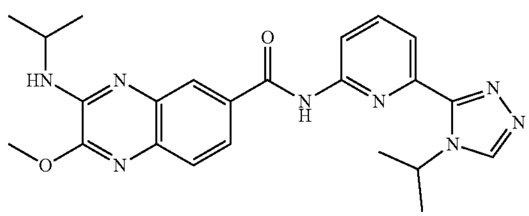 [SMILES: COc1nc2ccc(C(=O)Nc3cccc(-c4nncn4C(C)C)n3)cc2nc1NC(C)C] |
| 9 | 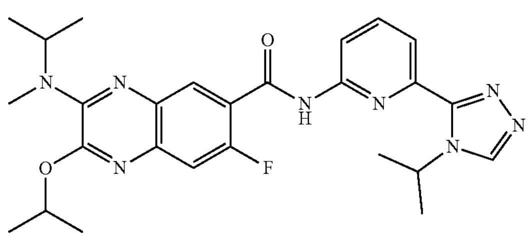 [SMILES: CC(C)Oc1nc2cc(F)c(C(=O)Nc3cccc(-c4nncn4C(C)C)n3)cc2nc1N(C)C(C)C] |
| 10 | 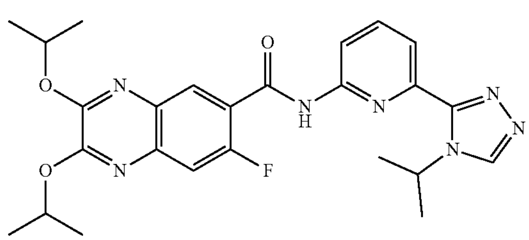 [SMILES: CC(C)Oc1nc2cc(F)c(C(=O)Nc3cccc(-c4nncn4C(C)C)n3)cc2nc1OC(C)C] |

-continued
| Compound | Structure |
|---|---|
| 11 | 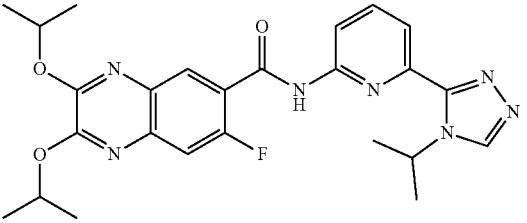 [SMILES: CC(C)Oc1nc2cc(F)c(C(=O)Nc3cccc(-c4nncn4C(C)C)n3)cc2nc1OC(C)C] |
| 12 | 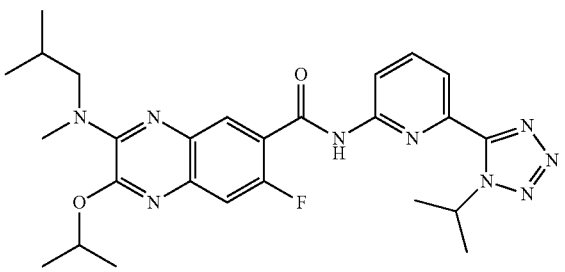 [SMILES: CC(C)CN(C)c1nc2cc(C(=O)Nc3cccc(-c4nnnn4C(C)C)n3)c(F)cc2nc1OC(C)C] |
| 13 | 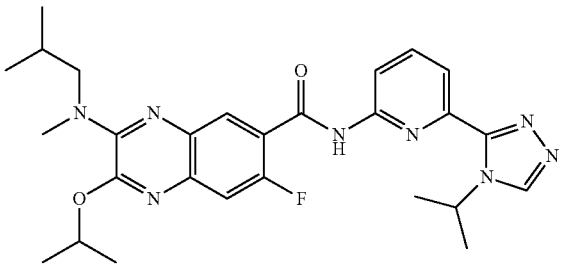 [SMILES: CC(C)CN(C)c1nc2cc(C(=O)Nc3cccc(-c4nncn4C(C)C)n3)c(F)cc2nc1OC(C)C] |
| 14 | 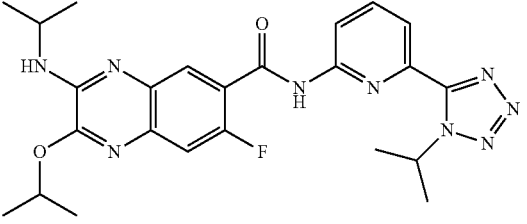 |
| 15 | 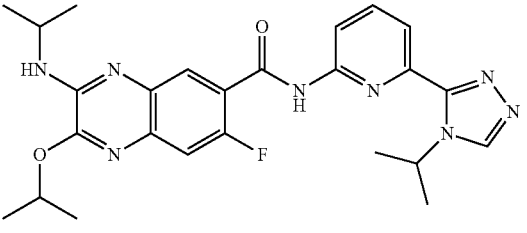 [SMILES: CC(C)Nc1nc2cc(C(=O)Nc3cccc(-c4nnnn4C(C)C)n3)c(F)cc2nc1OC(C)C] |
| 16 | 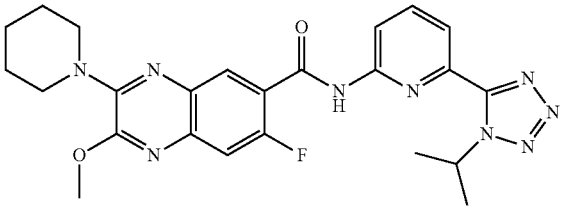 [SMILES: COc1nc2cc(F)c(C(=O)Nc3cccc(-c4nnnn4C(C)C)n3)cc2nc1N1CCCCC1] |

-continued

| Compound | Structure |
|---|---|
| 17 | 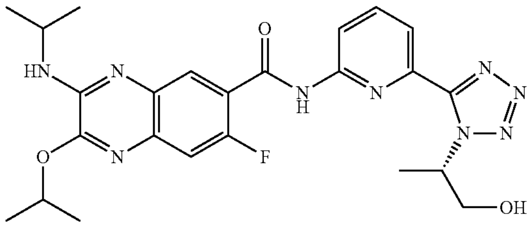 [SMILES: CC(C)Nc1nc2cc(C(=O)Nc3cccc(-c4nnnn4[C@@H](C)CO)n3)c(F)cc2nc1OC(C)C] |
| 18 | 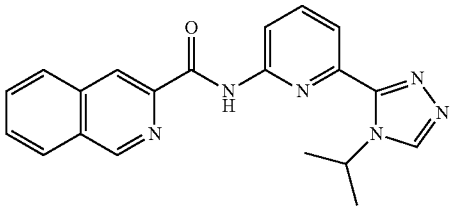 [SMILES: CC(C)n1cnnc1-c1cccc(NC(=O)c2cc3ccccc3cn2)n1] |
| 19 | 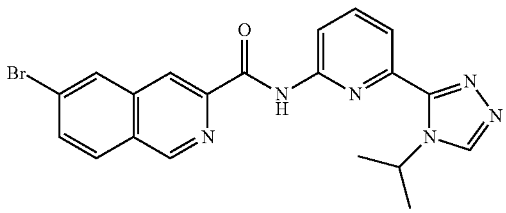 [SMILES: CC(C)n1cnnc1-c1cccc(NC(=O)c2cc3cc(Br)ccc3cn2)n1] |
| 20 | 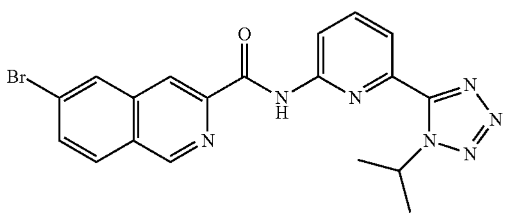 [SMILES: CC(C)n1nnnc1-c1cccc(NC(=O)c2cc3cc(Br)ccc3cn2)n1] |
| 21 | 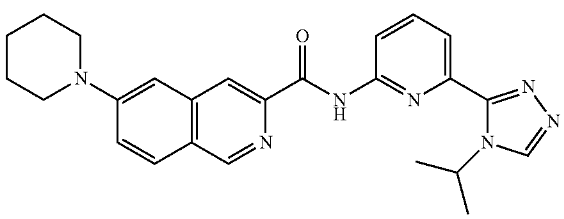 [SMILES: CC(C)n1cnnc1-c1cccc(NC(=O)c2cc3cc(N4CCCCC4)ccc3cn2)n1] |
| 22 | 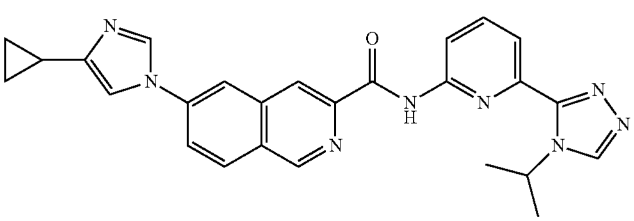 [SMILES: CC(C)n1cnnc1-c1cccc(NC(=O)c2cc3cc(-n4cnc(C5CC5)c4)ccc3cn2)n1] |
| 23 | 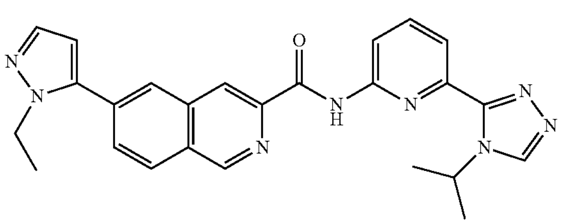 [SMILES: CCn1nccc1-c1ccc2cnc(C(=O)Nc3cccc(-c4nncn4C(C)C)n3)cc2c1] |

-continued
| Compound | Structure |
|---|---|
| 24 | 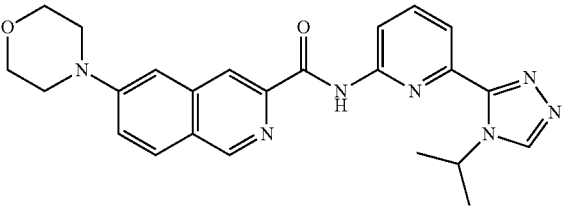 [SMILES: CC(C)n1cnnc1-c1cccc(NC(=O)c2cc3cc(N4CCOCC4)ccc3cn2)n1] |
| 25 | 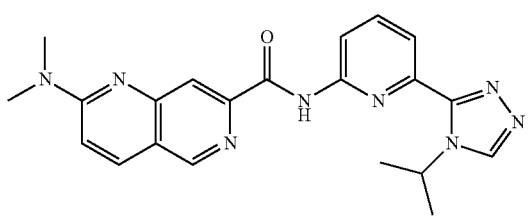 [SMILES: CC(C)n1cnnc1-c1cccc(NC(=O)c2cc3nc(N(C)C)ccc3cn2)n1] |
| 26 | 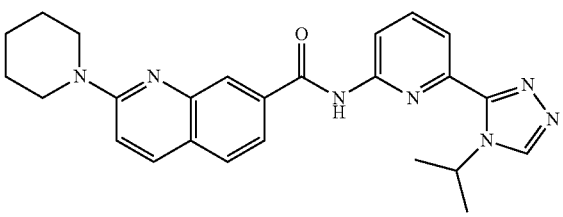 [SMILES: CC(C)n1cnnc1-c1cccc(NC(=O)c2ccc3ccc(N4CCCCC4)nc3c2)n1] |
| 27 | 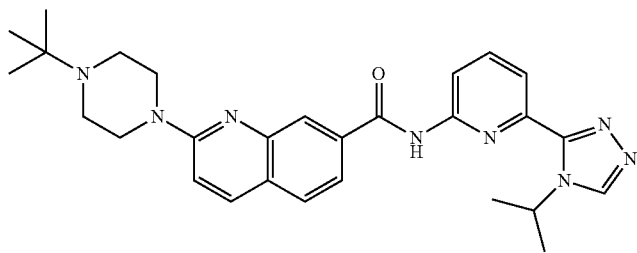 [SMILES: CC(C)n1cnnc1-c1cccc(NC(=O)c2ccc3ccc(N4CCN(C(C)(C)C)CC4)nc3c2)n1] |
| 28 | 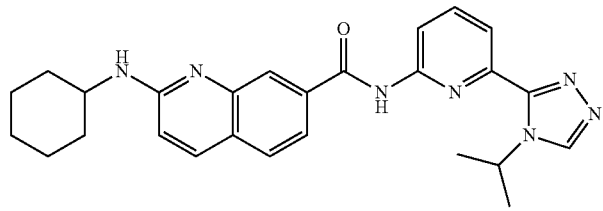 [SMILES: CC(C)n1cnnc1-c1cccc(NC(=O)c2ccc3ccc(NC4CCCCC4)nc3c2)n1] |
| 29 | 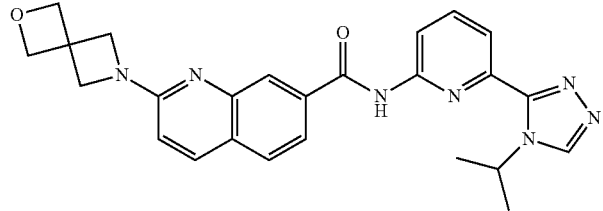 [SMILES: CC(C)n1cnnc1-c1cccc(NC(=O)c2ccc3ccc(N4CC5(COC5)C4)nc3c2)n1] |
| 30 | 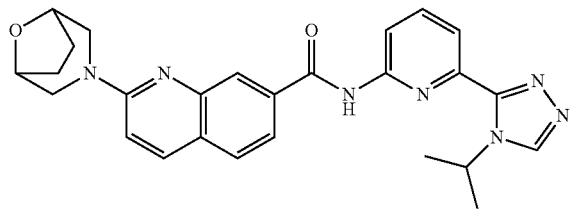 [SMILES: CC(C)n1cnnc1-c1cccc(NC(=O)c2ccc3ccc(N4CC5CCC(C4)O5)nc3c2)n1] |

| Compound | Structure |
|---|---|
| 31 | 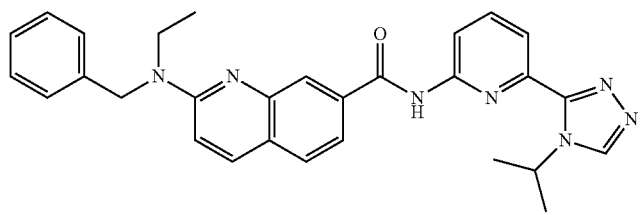 [SMILES: CCN(Cc1ccccc1)c1ccc2ccc(C(=O)Nc3cccc(-c4nncn4C(C)C)n3)cc2n1] |
| 32 | 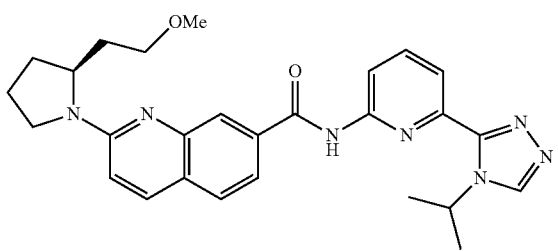 [SMILES: COCC[C@@H]1CCCN1c1ccc2ccc(C(=O)Nc3cccc(-c4nncn4C(C)C)n3)cc2n1] |
| 33 | 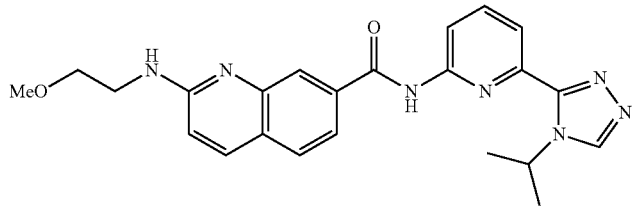 [SMILES: COCCNc1ccc2ccc(C(=O)Nc3cccc(-c4nncn4C(C)C)n3)cc2n1] |
| 34 | 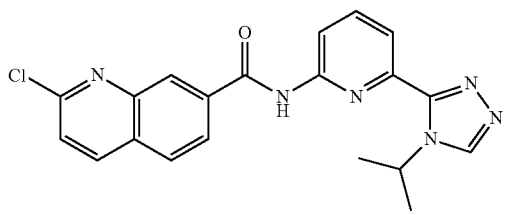 [SMILES: CC(C)n1cnnc1-c1cccc(NC(=O)c2ccc3ccc(Cl)nc3c2)n1] |
| 35 | 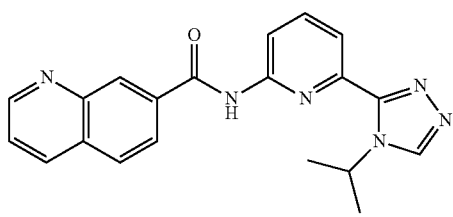 [SMILES: CC(C)n1cnnc1-c1cccc(NC(=O)c2ccc3cccnc3c2)n1] |
| 36 | 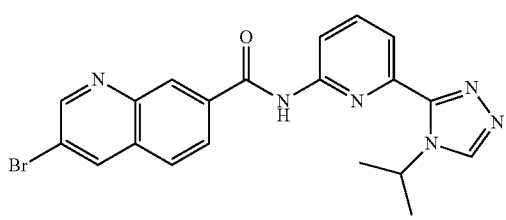 [SMILES: CC(C)n1cnnc1-c1cccc(NC(=O)c2ccc3cc(Br)cnc3c2)n1] |

-continued

| Compound | Structure |
|---|---|
| 37 | 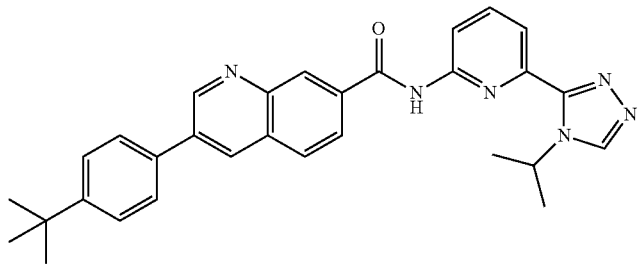 [SMILES: CC(C)n1cnnc1-c1cccc(NC(=O)c2ccc3cc(-c4ccc(C(C)(C)C)cc4)cnc3c2)n1] |
| 38 | 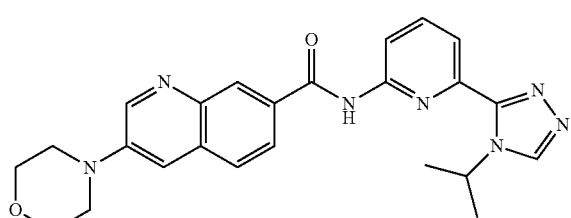 |
| 39 | 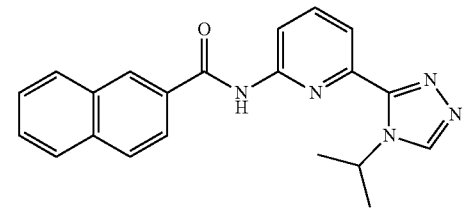 [SMILES: CC(C)n1cnnc1-c1cccc(NC(=O)c2ccc3ccccc3c2)n1] |
| 40 | 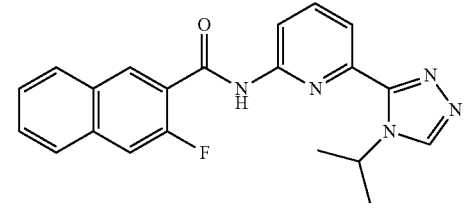 [SMILES: CC(C)n1cnnc1-c1cccc(NC(=O)c2cc3ccccc3cc2F)n1] |
| 41 | 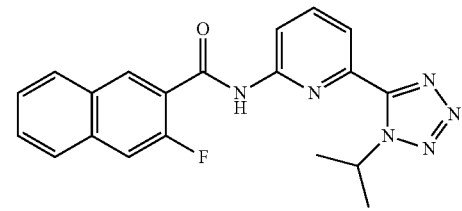 |

23. A pharmaceutical composition comprising a compound of claim 1 and a pharmaceutically acceptable excipient or carrier.

24. A method for the treatment of an ASK-1 mediated disease or condition in a subject in need thereof, comprising administering to the subject a therapeutically effective amount of a compound according to claim 1.

25. A method for treating a disease selected from the group consisting of glomerulonephritis, rheumatoid arthritis, systemic lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, Sjoegren's syndrome, syndromeischemia/reperfusion in stroke, heart attacks, myocardial ischemia, organ hypoxia, vascular hyperplasia, cardiac hypertrophy, hepatic ischemia, congestive heart failure, pathologic immune responses such as that caused by T cell activation, thrombin-induced platelet aggregation, osteoporosis, osteoarthritis, multiple myeloma-related bone disorder, Alzheimer's disease, Parkinson's disease, amyotrophic lateral sclerosis (ALS), epilepsy, seizures, Huntington's disease, polyglutamine diseases, traumatic brain injury, ischemic and hemorrhaging stroke, cerebral ischemias and neurodegenerative disease in a subject in need thereof, comprising administering to the subject a therapeutically effective amount of a compound according to claim 1.

26. A pharmaceutical composition comprising a compound according to claim 22 and a pharmaceutically acceptable carrier or excipient.

\* \* \* \* \*

UNITED STATES PATENT AND TRADEMARK OFFICE
CERTIFICATE OF CORRECTION

PATENT NO. : 10,253,018 B2
APPLICATION NO. : 15/988763
DATED : April 9, 2019
INVENTOR(S) : Guoqiang Wang et al.

Page 1 of 2

It is certified that error appears in the above-identified patent and that said Letters Patent is hereby corrected as shown below:

In the Claims

At Column 242

In Claim 12, Line 65, Compound 531, delete " 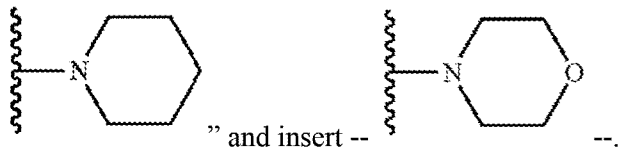 " and insert -- 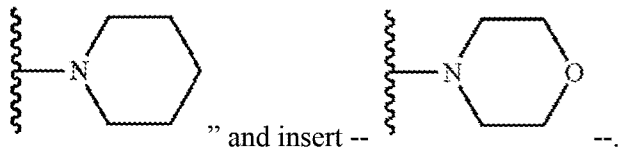 --.

At Columns 299 and 300

In Claim 22, Compound 24, delete " 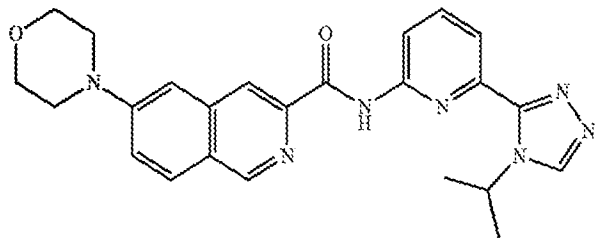 " and insert -- 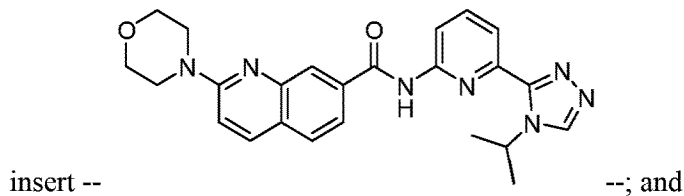 --; and Signed and Sealed this
Eighteenth Day of June, 2019

Andrei Iancu
*Director of the United States Patent and Trademark Office*

CERTIFICATE OF CORRECTION (continued)
U.S. Pat. No. 10,253,018 B2

In Claim 22, Compound 25, delete " 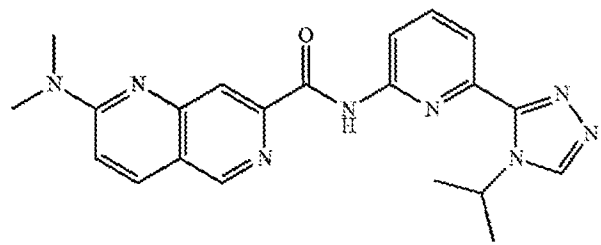 " and insert -- 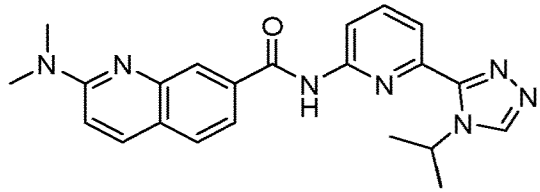 --.